(12) United States Patent
Salas Falgueras et al.

(10) Patent No.: US 12,188,057 B2
(45) Date of Patent: Jan. 7, 2025

(54) PRIMER-INDEPENDENT DNA POLYMERASES AND THEIR USE FOR DNA SYNTHESIS

(71) Applicants: CONSEJO SUPERIOR DE INVESTIGACIONES CIENTIFICAS (CSIC), Madrid (ES); INSTITUT PASTEUR, Paris (FR)

(72) Inventors: Margarita Salas Falgueras, Madrid (ES); Modesto Redrejo Rodriguez, Madrid (ES); Mart Krupovic, Paris (FR); Patrick Forterre, Paris (FR)

(73) Assignees: CONSEJO SUPERIOR DE INVESTIGACIONES CIENTIFICAS (CSIC), Madrid (ES); INSTITUT PASTEUR, Paris (FR)

( * ) Notice: Subject to any disclaimer, the term of this patent is extended or adjusted under 35 U.S.C. 154(b) by 715 days.

(21) Appl. No.: 16/756,812

(22) PCT Filed: Oct. 19, 2018

(86) PCT No.: PCT/EP2018/078737
§ 371 (c)(1),
(2) Date: Apr. 16, 2020

(87) PCT Pub. No.: WO2019/077119
PCT Pub. Date: Apr. 25, 2019

(65) Prior Publication Data
US 2020/0263151 A1 Aug. 20, 2020

(30) Foreign Application Priority Data
Oct. 20, 2017 (ES) .................. ES201731236

(51) Int. Cl.
*C12N 9/12* (2006.01)
*C12Q 1/6844* (2018.01)

(52) U.S. Cl.
CPC ......... *C12N 9/1252* (2013.01); *C12Q 1/6844* (2013.01); *C12Y 207/07007* (2013.01)

(58) Field of Classification Search
CPC ............... C12N 9/1252; C12Q 1/6844; C12Y 207/07007
USPC ...................................................... 435/6.12
See application file for complete search history.

(56) References Cited

FOREIGN PATENT DOCUMENTS

| EP | 2357225 A1 | 8/2011 |
|---|---|---|
| WO | WO2005/010032 A2 | 2/2005 |
| WO | WO2005/114221 A2 | 12/2005 |
| WO | WO 2014140309 A1 | 9/2014 |

OTHER PUBLICATIONS

Teng et al: Structural Assessment of the Effects of Amino Acid Substitutions on Protein Stability and Protein-Protein Interaction; International Journal of Computational Biology and Drug Design, vol. 3, No. 4, Author Manuscript, pp. 1-20 (Year: 2012).*
Altschul et al., "Basic Local Alignment Search Tool", Journal of Molecular Biology, Oct. 5, 1990, vol. 215 Issue 3, pp. 403-410.
Beck et al., "The archaeo-eukaryotic primase of plasmid pRN1 requires a helix bundle domain for faithful primer synthesis", Nucleic Acids Research, May 28, 2010, vol. 38, No. 19, pp. 6707-6718.
Devereux et al., "A comprehensive set of sequence analysis programs for the VAX", Nucleic Acids Research, Jan. 11, 1984, vol. 12 No. 1, pp. 387-395.
Gill et al., "A highly divergent archaeo-eukaryotic primase from the Thermococcus nautilus plasmid, pTN2", Nucleic Acids Research, Jan. 20, 2014, vol. 42, No. 6, pp. 3707-3719.
Higgins et al., "Fast and sensitive multiple sequence alignments on a microcomputer", Cabios Communications, Apr. 1, 1989, vol. 5 No. 2, pp. 151-153.
Kapitonov et al., "Self-synthesizing DNA transposons in eukaryotes", 4540-4545 Proceedings of the National Academy of Sciences of the United States of America, Mar. 21, 2006, vol. 103, No. 12.
Krupovic et al., "Self-synthesizing transposons: unexpected key players in the evolution of viruses and defense systems", Current Opinions in Microbiology, Jun. 2016; vol. 31, pp. 25-33.
Krupovic et al., "Conservation of major and minor jelly-roll capsid proteins in Polinton (Maverick) transposons suggests that they are bona fide viruses", Biology Direct, Apr. 29, 2014, vol. 9, No. 6.
Krupovic et al., "Casposons: a new superfamily of self-synthesizing DNA transposons at the origin of prokaryotic CRISPR-Cas immunity", BMC Biology, May 19, 2014, vol. 12, Article 36.
Krupovic et al., "Polintons: a hotbed of eukaryotic virus, transposon and plasmid evolution", Nature Reviews—Microbiology, vol. 13, Feb. 2015, pp. 105-115.
Martínez-Jiménez et al., "Alternative solutions and new scenarios for translesion DNA synthesisby human PrimPol", DNA Repair, Feb. 23, 2015, vol. 29 pp. 127-138.

(Continued)

Primary Examiner — Richard G Hutson
(74) Attorney, Agent, or Firm — WOMBLE BOND DICKINSON (US) LLP

(57) ABSTRACT

The present invention provides an isolated peptide of SEQ ID NO: 1 needed for primase active as well as new replicative DNA polymerase enzymes, preferably that of SEQ ID NO: 2, comprising said peptide. Thus, these DNA polymerases are endowed with priming activity and do not require externally provided primers for initiating and performing DNA amplification. These polymerases are able to carry out a faithful and processive de novo DNA synthesis of DNA templates in the absence of pre-synthetized primers. Therefore, these enzymes of the invention act both as primases and DNA polymerases. Furthermore, they show translesion synthesis capacity, so that they may be useful not only for whole-genome amplification but also for the amplification of damaged DNAs. The invention further refers to methods for amplifying templates DNAs using these enzymes.

11 Claims, 18 Drawing Sheets
Specification includes a Sequence Listing.

(56) References Cited

OTHER PUBLICATIONS

Picher et al., "TruePrime is a novel method for whole-genome amplification from single cells based on TthPrimPol", Nature Communications, Nov. 29, 2016, vol. 7 Article 13296.
Wilbur et al., "Rapid similarity searches of nucleic acid and protein data banks", Proceedings of the National Academy of Sciences of the United States of America, Feb. 1, 1983, vol. 80, No. 3, pp. 726-730.
Zhu et al., "Deep-sea vent phage DNA polymerase specifically initiates DNA synthesis in the absence of primers", Proceedings of the National Academy of Sciences of the United States of America, Mar. 6, 2017, vol. 114, No. 12, E2310-E2318.
Blasco et al., " Primer Terminus Stabilization at the φ29 DNA Polymerase Active Site: Mutational Analysis of Conserved Motif KXY", The Journal of Biological Chemistry, vol. 270, Feb. 10, 1995, No. 2735-2740.
Guilliam et al., "Survey and Summary Primase-polymerases are a functionally diverse superfamily of replication and repair enzymes", Nucleic Acids Research, Jun. 4, 2015, vol. 43, No. 14, pp. 6651-6664.
"Phage phi29 mutant DNA polymerase #28.", XP002787932, retrieved from EBI accession No. GSP:AZM07310, Database accession No. AZM07310, Sep. 29, 2011.
Jonathan Filée et al.: "Evolution of DNA Polymerase Families: Evidences for Multiple Gene Exchange Between Cellular and Viral Proteins", Journal of Molecular Evolution., vol. 54, No. 6, Jun. 1, 2002, pp. 763-773.

\* cited by examiner

SEQUENCE LISTING

```
<160> NUMBER OF SEQ ID NOS: 85

<210> SEQ ID NO 1
<211> LENGTH: 14
<212> TYPE: PRT
<213> ORGANISM: Artificial Sequence
<220> FEATURE:
<223> OTHER INFORMATION: Common conserved domain within the piPolBs
      described in the invention, needed for priming activity
<220> FEATURE:
<221> NAME/KEY: MISC_FEATURE
<222> LOCATION: (2)..(2)
<223> OTHER INFORMATION: A, H, K, T, D, Y, G or R
<220> FEATURE:
<221> NAME/KEY: MISC_FEATURE
<222> LOCATION: (3)..(10)
<223> OTHER INFORMATION: Any amino acid

<400> SEQUENCE: 1

Lys Xaa Xaa Xaa Xaa Xaa Xaa Xaa Xaa Xaa Lys Thr Arg Gly
1               5                   10

<210> SEQ ID NO 2
<211> LENGTH: 866
<212> TYPE: PRT
<213> ORGANISM: Escherichia coli

<400> SEQUENCE: 2

Met Ser Asn Asn Leu Gln Asp Ile Leu Ala Ala Ala Ser Gly Tyr Gln
1               5                   10                  15

Ser Val Thr Ser Glu Pro Ala Leu Asn Arg Lys Arg Pro Lys Thr Leu
            20                  25                  30

Asp Asp Tyr Pro Val Ile Pro Pro Ala Ser Lys Lys Val Ser Val Ile
```

```
                35                  40                  45
Ser Ser Asp Leu Thr Leu His Ile Gly Phe Asp Thr Glu Tyr Val Phe
 50                  55                  60
Asn Pro Glu Thr Arg Gln Asn Asp Ile Leu Ser Tyr Gln Ser Tyr Val
 65                  70                  75                  80
Val Leu Pro Asp Asn Thr Gly Ile Ser Asn Ile Ile Tyr Pro Pro Asp
                 85                  90                  95
Ser Gln Lys Lys Ser Arg Leu Ser Phe Lys Asp Phe Leu Cys Gln Thr
                100                 105                 110
Ile Thr Pro Leu Leu Glu Thr Gly Val Ile Thr Lys Trp Pro Gly Ile
                115                 120                 125
Ile Asn Ile Tyr Ala His Phe Ile Arg Ala Asp Ile Ala Ser Phe Ala
                130                 135                 140
Asn Phe Trp Ser Asp Tyr Lys Ile Leu Leu Lys Gly Ile Arg Gly Thr
145                 150                 155                 160
Val Ser Ser Phe Lys Asn Arg Tyr Gly Ile Asp Phe Asp Glu Gln Gln
                165                 170                 175
Glu Arg Arg Val Lys Thr Glu Gln Ile Met Phe Asp Lys Arg Thr Ser
                180                 185                 190
Pro Pro Arg Cys Ser Asn Val Ala Phe Ile Asp Thr Leu Leu Ile Thr
                195                 200                 205
Pro Gly Gly Met Gly Leu Ala Glu Cys Gly Glu Leu Leu Gly Leu Pro
                210                 215                 220
Lys Leu Thr Ile Pro Ala Pro Tyr Ser Ile Thr Asn Met Arg Glu Tyr
225                 230                 235                 240
Leu Leu Gly Asp Arg Ala Gly Phe Glu Ala Tyr Ala Leu Arg Asp Ala
                245                 250                 255
Glu Ile Ala Val Arg Tyr Ala Leu Gln Val Arg Asn Phe Cys Ala Arg
                260                 265                 270
Glu Leu Met Ile Asp Arg Val Pro Ala Thr Ile Gly Ala Met Ala Val
                275                 280                 285
Ser Arg Phe Thr Lys Thr Leu Lys Glu Asn Asn Met Ser Pro Glu Val
                290                 295                 300
Cys Leu Gly Thr His Ile Lys Thr Arg Glu Leu Trp Leu Thr Glu Lys
305                 310                 315                 320
Gln Ala Phe Arg Thr Ile Lys Asn Pro Ala Ser Val Pro Ser Arg Glu
                325                 330                 335
Leu Phe Glu Thr Phe Pro Ile Asn Cys Tyr His Gly Gly Arg Asn Glu
                340                 345                 350
Cys Phe Met Met Gly Val Thr Pro Ser Asp His Trp Tyr Asp Tyr Asp
                355                 360                 365
Leu Ala Gly Ala Tyr Thr Thr Gly Leu Leu Asp Ile Leu Thr Pro Asp
                370                 375                 380
Tyr Gly Asn Ile Arg Leu Ser Lys Asn Pro Asp Asp Tyr Cys Gly His
385                 390                 395                 400
Val Met Gly Phe Ala Leu Val Thr Phe Arg Phe Pro Glu Ser Val Pro
                405                 410                 415
Tyr Pro Ser Leu Pro Val Arg Thr Asp Gln Tyr Gly Leu Phe Phe Pro
                420                 425                 430
Leu Ser Gly Glu Ser Trp Ala Thr Ala Pro Glu Ile Glu Leu Ala Leu
                435                 440                 445
Ser Leu Gly Ala Glu Met Thr Ile His Asn Gly Ile Ile Val Pro Trp
                450                 455                 460
```

```
Ile Cys Asp Thr Ser Pro His Asn Ser Glu Ser Thr Ser Val Phe Leu
465                 470                 475                 480

Pro Phe Val Gln Gln Val Arg Glu Asn Arg Asn Arg His Ile Lys Gly
                485                 490                 495

Ser Leu Glu Glu Lys Phe Trp Lys Glu Ile Gly Asn Ser Leu Tyr Gly
            500                 505                 510

Lys Leu Ala Gln Gly Leu Arg Ala Lys Thr Ala Phe Asp Thr Ala Arg
            515                 520                 525

Gly Leu Asn Arg Ser Leu Pro Pro Ser Ser Val Thr Gln Pro Phe Phe
            530                 535                 540

Ala Ala His Val Thr Gly Phe Ile Arg Ala Val Val Gly Glu Leu Met
545                 550                 555                 560

Asn Ala Leu Pro Ser Asp Ser Ser Val Val Ser Val Thr Thr Asp Gly
                565                 570                 575

Phe Leu Thr Asn Cys Pro Leu Asp Lys Ile Asn Met Ser Gly Pro Leu
            580                 585                 590

Ser Ser Arg Phe Gln Ser Leu Cys Asp Ile Val Asp Pro Gly Ser Ser
            595                 600                 605

Met Leu Thr Cys Lys His Glu Val Ser Gln Leu Ile Ala Met Lys Thr
610                 615                 620

Arg Gly Gln Leu Thr Tyr Lys Ala Ile Gln Gly Lys Pro Val Val His
625                 630                 635                 640

Ala Arg Ala Gly Val Lys Pro Pro Ala Asp Ile Pro Arg Ser Asp Tyr
                645                 650                 655

Asn Asp Tyr Met Val Asp Leu Tyr Leu Asn Arg Leu Pro Gly Gln Thr
                660                 665                 670

Leu Ser Arg Ser Thr Leu Ile Ser Thr Arg Glu Met Trp Leu Ser Glu
            675                 680                 685

Ser Asp Leu Val Ser Arg Glu Gln Asp Ile Arg Leu Asn Leu Glu Phe
            690                 695                 700

Asp Phe Lys Arg Gln Pro Val Arg Pro Ala Met Asn Glu Gly His Leu
705                 710                 715                 720

Leu Met Phe Ser Arg Pro Trp Asp Asn Met Glu Glu Ala Leu Gln Gln
                725                 730                 735

Arg Ser Leu Phe Asp Asp Trp Arg Gln Thr His Thr Leu Lys Thr Leu
            740                 745                 750

Ala Asp Trp Asp Asp Trp Cys Asp Phe Leu Tyr Cys Arg Thr Val Phe
            755                 760                 765

Ser Asp Met Lys Leu Lys Val Gly Ser Lys Arg Ser Asp Ile Leu
            770                 775                 780

Val Arg Leu Phe Leu Arg Ala Leu Thr Gln Cys Gln Trp Gly Leu Met
785                 790                 795                 800

Leu Lys Asp Lys Lys Ser Tyr Ser Cys Lys Glu Val Ala Glu Trp Leu
                805                 810                 815

Thr Ser Glu Gly Tyr Ser Val Thr Thr Asp Val Lys Asn Ala Val
                820                 825                 830

Arg Ala Lys Ile Pro Gln Met Lys Phe Ser Ser Val Thr Pro Arg Met
            835                 840                 845

Lys Ser Leu Met Asp Ile Ile Ala Arg Lys Tyr Pro Thr Phe Cys Leu
            850                 855                 860

Pro Val
865
```

```
<210> SEQ ID NO 3
<211> LENGTH: 586
<212> TYPE: PRT
<213> ORGANISM: Artificial Sequence
<220> FEATURE:
<223> OTHER INFORMATION: Parental DNA pPolB of phi29 (SEQ ID NO: 6)
      comprising its KxY motif substituted by SEQ ID NO: 1
<220> FEATURE:
<221> NAME/KEY: MISC_FEATURE
<222> LOCATION: (499)..(499)
<223> OTHER INFORMATION: A, H, K, T, D, Y, G or R
<220> FEATURE:
<221> NAME/KEY: MISC_FEATURE
<222> LOCATION: (500)..(507)
<223> OTHER INFORMATION: Any amino acid

<400> SEQUENCE: 3
```

| | | | | | | | | | | | | | | |
|---|---|---|---|---|---|---|---|---|---|---|---|---|---|---|
| Met | Lys | His | Met | Pro | Arg | Lys | Met | Tyr | Ser | Cys | Asp | Phe | Glu | Thr | Thr |
| 1 | | | | 5 | | | | | 10 | | | | | 15 | |

| Thr | Lys | Val | Glu | Asp | Cys | Arg | Val | Trp | Ala | Tyr | Gly | Tyr | Met | Asn | Ile |
|---|---|---|---|---|---|---|---|---|---|---|---|---|---|---|---|
| | | | 20 | | | | | 25 | | | | | 30 | | |

| Glu | Asp | His | Ser | Glu | Tyr | Lys | Ile | Gly | Asn | Ser | Leu | Asp | Glu | Phe | Met |
|---|---|---|---|---|---|---|---|---|---|---|---|---|---|---|---|
| | | | 35 | | | | | 40 | | | | | 45 | | |

| Ala | Trp | Val | Leu | Lys | Val | Gln | Ala | Asp | Leu | Tyr | Phe | His | Asn | Leu | Lys |
|---|---|---|---|---|---|---|---|---|---|---|---|---|---|---|---|
| 50 | | | | | 55 | | | | | 60 | | | | | |

| Phe | Asp | Gly | Ala | Phe | Ile | Ile | Asn | Trp | Leu | Glu | Arg | Asn | Gly | Phe | Lys |
|---|---|---|---|---|---|---|---|---|---|---|---|---|---|---|---|
| 65 | | | | | 70 | | | | | 75 | | | | | 80 |

| Trp | Ser | Ala | Asp | Gly | Leu | Pro | Asn | Thr | Tyr | Asn | Thr | Ile | Ile | Ser | Arg |
|---|---|---|---|---|---|---|---|---|---|---|---|---|---|---|---|
| | | | | 85 | | | | | 90 | | | | | 95 | |

| Met | Gly | Gln | Trp | Tyr | Met | Ile | Asp | Ile | Cys | Leu | Gly | Tyr | Lys | Gly | Lys |
|---|---|---|---|---|---|---|---|---|---|---|---|---|---|---|---|
| | | | 100 | | | | | 105 | | | | | 110 | | |

| Arg | Lys | Ile | His | Thr | Val | Ile | Tyr | Asp | Ser | Leu | Lys | Lys | Leu | Pro | Phe |
|---|---|---|---|---|---|---|---|---|---|---|---|---|---|---|---|
| | | 115 | | | | | 120 | | | | | 125 | | | |

| Pro | Val | Lys | Lys | Ile | Ala | Lys | Asp | Phe | Lys | Leu | Thr | Val | Leu | Lys | Gly |
|---|---|---|---|---|---|---|---|---|---|---|---|---|---|---|---|
| | 130 | | | | | 135 | | | | | 140 | | | | |

| Asp | Ile | Asp | Tyr | His | Lys | Glu | Arg | Pro | Val | Gly | Tyr | Lys | Ile | Thr | Pro |
|---|---|---|---|---|---|---|---|---|---|---|---|---|---|---|---|
| 145 | | | | | 150 | | | | | 155 | | | | | 160 |

| Glu | Glu | Tyr | Ala | Tyr | Ile | Lys | Asn | Asp | Ile | Gln | Ile | Ile | Ala | Glu | Ala |
|---|---|---|---|---|---|---|---|---|---|---|---|---|---|---|---|
| | | | | 165 | | | | | 170 | | | | | 175 | |

| Leu | Leu | Ile | Gln | Phe | Lys | Gln | Gly | Leu | Asp | Arg | Met | Thr | Ala | Gly | Ser |
|---|---|---|---|---|---|---|---|---|---|---|---|---|---|---|---|
| | | | 180 | | | | | 185 | | | | | 190 | | |

| Asp | Ser | Leu | Lys | Gly | Phe | Lys | Asp | Ile | Ile | Thr | Thr | Lys | Lys | Phe | Lys |
|---|---|---|---|---|---|---|---|---|---|---|---|---|---|---|---|
| | | 195 | | | | | 200 | | | | | 205 | | | |

| Lys | Val | Phe | Pro | Thr | Leu | Ser | Leu | Gly | Leu | Asp | Lys | Glu | Val | Arg | Tyr |
|---|---|---|---|---|---|---|---|---|---|---|---|---|---|---|---|
| | 210 | | | | | 215 | | | | | 220 | | | | |

| Ala | Tyr | Arg | Gly | Gly | Phe | Thr | Trp | Leu | Asn | Asp | Arg | Phe | Lys | Glu | Lys |
|---|---|---|---|---|---|---|---|---|---|---|---|---|---|---|---|
| 225 | | | | | 230 | | | | | 235 | | | | | 240 |

| Glu | Ile | Gly | Glu | Gly | Met | Val | Phe | Asp | Val | Asn | Ser | Leu | Tyr | Pro | Ala |
|---|---|---|---|---|---|---|---|---|---|---|---|---|---|---|---|
| | | | | 245 | | | | | 250 | | | | | 255 | |

| Gln | Met | Tyr | Ser | Arg | Leu | Leu | Pro | Tyr | Gly | Glu | Pro | Ile | Val | Phe | Glu |
|---|---|---|---|---|---|---|---|---|---|---|---|---|---|---|---|
| | | | 260 | | | | | 265 | | | | | 270 | | |

| Gly | Lys | Tyr | Val | Trp | Asp | Glu | Asp | Tyr | Pro | Leu | His | Ile | Gln | His | Ile |
|---|---|---|---|---|---|---|---|---|---|---|---|---|---|---|---|
| | | 275 | | | | | 280 | | | | | 285 | | | |

| Arg | Cys | Glu | Phe | Glu | Leu | Lys | Glu | Gly | Tyr | Ile | Pro | Thr | Ile | Gln | Ile |
|---|---|---|---|---|---|---|---|---|---|---|---|---|---|---|---|
| | 290 | | | | | 295 | | | | | 300 | | | | |

| Lys | Arg | Ser | Arg | Phe | Tyr | Lys | Gly | Asn | Glu | Tyr | Leu | Lys | Ser | Ser | Gly |
|---|---|---|---|---|---|---|---|---|---|---|---|---|---|---|---|
| 305 | | | | | 310 | | | | | 315 | | | | | 320 |

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Xaa Xaa Xaa Xaa Xaa Xaa Xaa Xaa Lys Thr Arg Gly Ile
            500                 505                 510

Gln Asp Ile Tyr Met Lys Glu Val Asp Gly Lys Leu Val Glu Gly Ser
            515                 520                 525

Pro Asp Asp Tyr Thr Asp Ile Lys Phe Ser Val Lys Cys Ala Gly Met
530                 535                 540

Thr Asp Lys Ile Lys Lys Glu Val Thr Phe Glu Asn Phe Lys Val Gly
545                 550                 555                 560

Phe Ser Arg Lys Met Lys Pro Lys Pro Val Gln Val Pro Gly Gly Val
            565                 570                 575

Val Leu Val Asp Asp Thr Phe Thr Ile Lys
            580                 585

<210> SEQ ID NO 4
<211> LENGTH: 746
<212> TYPE: PRT
<213> ORGANISM: Artificial Sequence
<220> FEATURE:
<223> OTHER INFORMATION: Parental DNA pPolB of Bam35 (SEQ ID NO: 7)
      comprising its KxY motif substituted by SEQ ID NO: 1
<220> FEATURE:
<221> NAME/KEY: MISC_FEATURE
<222> LOCATION: (536)..(536)
<223> OTHER INFORMATION: A, H, K, T, D, Y, G or R
<220> FEATURE:
<221> NAME/KEY: MISC_FEATURE
<222> LOCATION: (537)..(544)
<223> OTHER INFORMATION: Any amino acid

<400> SEQUENCE: 4

Met Met Thr Thr Thr Asn Arg Lys Lys Arg Arg Glu Ile Lys Leu Phe
1               5                   10                  15

Thr Leu Asp Thr Glu Thr Arg Gly Leu Asp Gly Asp Val Phe Arg Ile
            20                  25                  30

Gly Leu Phe Asp Gly Lys Gln Tyr Tyr Thr Gly Tyr Thr Phe Ala Asp
        35                  40                  45

-continued

```
Val Leu Pro Val Phe Glu Lys Tyr Lys Ala Tyr Asp Cys His Val Tyr
     50                  55                  60
Ile His Asn Leu Asp Phe Asp Leu Ser Lys Ile Ile Ala Glu Leu Arg
 65                  70                  75                  80
Asp Tyr Ala Glu Pro Thr Phe Asn Asn Ser Leu Phe Ile Asn Gly Asn
                 85                  90                  95
Ile Val Thr Phe Thr Ala Ser His Ile Ile Leu His Asp Ser Phe Arg
                100                 105                 110
Leu Leu Pro Ser Ser Leu Glu Asn Leu Cys Arg Asp Phe Asp Leu Leu
             115                 120                 125
Glu Gly Gly Lys Met Asp Ile Val Asp Tyr Met Glu Glu Asn Asn Tyr
130                 135                 140
Gly Ile Tyr Asn Val Lys Asn Arg Lys Leu Asn Lys Arg Leu Thr Lys
145                 150                 155                 160
Gly Asn Phe Phe Thr Thr Val Asp Lys Asp Asp Pro Val Leu Cys Glu
                 165                 170                 175
Tyr Met Glu Tyr Asp Cys Arg Ser Leu Tyr Lys Ile Leu Glu Ile Val
                180                 185                 190
Ile Gly Leu Ser Lys Leu Glu Val Glu Gln Phe Ile Asn Cys Pro Thr
        195                 200                 205
Thr Ala Ser Leu Ala Lys Thr Val Tyr Lys Glu Gln Tyr Lys Lys Asp
210                 215                 220
Tyr Lys Val Ala Ile Ser Thr Lys Gln Tyr Asn His Lys Gln Ile Gly
225                 230                 235                 240
Lys Gly Leu Glu Ala Phe Ile Arg Lys Gly Tyr Tyr Gly Gly Arg Thr
                245                 250                 255
Glu Val Phe Thr Pro Arg Ile Glu Asn Gly Tyr His Tyr Asp Lys Asn
                260                 265                 270
Ser Leu Tyr Pro Tyr Val Met Lys Met Ala Glu Met Pro Val Gly Tyr
            275                 280                 285
Pro Asn Val Leu Asp Asn Glu Glu Ala Glu Leu Ser Phe Asp Leu Trp
290                 295                 300
Lys Arg Arg Lys Tyr Gly Ala Gly Phe Ile His Ala Lys Val His Val
305                 310                 315                 320
Pro Glu Asp Met Tyr Ile Pro Ile Leu Pro Lys Lys Asp Tyr Thr Gly
                325                 330                 335
Lys Leu Ile Phe Pro Val Gly Lys Ile Glu Gly Val Trp Thr Phe Pro
                340                 345                 350
Glu Leu Ala Leu Ala Glu Ala Glu Gly Cys Arg Ile Glu Lys Ile Glu
            355                 360                 365
Ser Gly Val Val Phe Lys Thr Ala Pro Val Phe Arg Glu Phe Ile
370                 375                 380
Ser Tyr Phe Glu Glu Ile Lys Asn Thr Ser Lys Gly Ala Lys Arg Ala
385                 390                 395                 400
Phe Ser Lys Leu Met Gln Asn Ala Leu Tyr Gly Lys Phe Ala Met Gln
                405                 410                 415
Arg Glu Arg Ile Met Tyr Ala Asp Ile Ser Glu Arg Asp Lys Leu Glu
                420                 425                 430
Ala Glu Gly His Thr Val Ser Glu Ile Ile Tyr Asp Met Asn Gly Ile
            435                 440                 445
Arg Met Glu Phe Leu Glu Tyr Asp Gly Tyr Ala Lys Ala Glu Tyr Ile
450                 455                 460
Gln Pro His Ile Ser Ala Tyr Ile Thr Ser Ile Ala Arg Ile Leu Leu
```

```
                465                 470                 475                 480
        Phe Lys Gly Leu Lys Tyr Ala His Glu Lys Gly Ile Leu Ala Tyr Cys
                        485                 490                 495

Asp Thr Asp Ser Cys Ala Thr Thr Lys Phe Pro Asp Lys Met Val
                        500                 505                 510

His Asp Lys Glu Tyr Gly Lys Trp Lys Leu Glu Gly Tyr Val Ile Glu
                        515                 520                 525

Gly Leu Tyr Phe Gln Pro Lys Xaa Xaa Xaa Xaa Xaa Xaa Xaa Xaa
                        530                 535                 540

Lys Thr Arg Gly Ala Glu Lys Ala Ile Asn Thr Asp Gly Glu Tyr Glu
        545                 550                 555                 560

Glu Val Leu Arg Met Lys Gly Val Pro Lys Trp Val Glu Glu Gln
                        565                 570                 575

Leu Asp Tyr Asn Thr Phe Lys Lys Trp Tyr Leu Gln Val Lys Arg Gly
                        580                 585                 590

Lys Ala Glu Ile Pro Ile Tyr Lys Gly Gly Glu Arg Val Gln Lys Phe
                        595                 600                 605

Leu Thr Lys Ser Lys Asn Asn Ile Glu Met Asn Glu Leu Ala Glu Met
                        610                 615                 620

His Lys Thr Ile Asn Phe Ala Arg Glu Gln Lys Arg Asn Ile Asp Leu
        625                 630                 635                 640

Asn Lys Asn Thr Thr Ser Pro Leu Val Arg Asn Asp Tyr Gly Glu Asn
                        645                 650                 655

Lys Asp Glu Lys Ser Glu Tyr Glu Phe Asp Glu Trp Tyr Glu Arg Leu
                        660                 665                 670

Glu Glu Phe Asn Asp Asp Met Asn Ala Val Glu Glu Leu Cys Met Lys
                        675                 680                 685

Phe Gly Lys Ile Gln Ile Pro Glu Lys Lys Gln Arg Lys Leu Tyr Gly
                        690                 695                 700

Leu Tyr Lys Glu Tyr Ser Ser Lys Ala Lys Ala Met Cys Phe Ser Asn
        705                 710                 715                 720

Glu Gly Leu Pro Ile Gln Asp Trp Cys Lys Lys Thr Gly Trp Asp Met
                        725                 730                 735

Lys Glu Leu Leu Gly Glu Leu Ser Phe Leu
                        740                 745

<210> SEQ ID NO 5
<211> LENGTH: 8
<212> TYPE: PRT
<213> ORGANISM: Artificial Sequence
<220> FEATURE:
<223> OTHER INFORMATION: X3-10 amino acid sequence within SEQ ID NO: 1

<400> SEQUENCE: 5

Glu Val Ser Gln Leu Ile Ala Met
1               5

<210> SEQ ID NO 6
<211> LENGTH: 575
<212> TYPE: PRT
<213> ORGANISM: Phage phi29

<400> SEQUENCE: 6

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30
```

```
Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asn Leu Lys
        50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                    100                 105                 110

Arg Lys Ile His Thr Val Ile Tyr Asp Ser Leu Lys Lys Leu Pro Phe
                115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                    165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Ile Thr Thr Lys Lys Phe Lys
                195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                    245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                    325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
            435                 440                 445
```

```
Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 7
<211> LENGTH: 735
<212> TYPE: PRT
<213> ORGANISM: Phage Bam35

<400> SEQUENCE: 7

Met Met Thr Thr Thr Asn Arg Lys Lys Arg Glu Ile Lys Leu Phe
1               5                   10                  15

Thr Leu Asp Thr Glu Thr Arg Gly Leu Asp Gly Asp Val Phe Arg Ile
            20                  25                  30

Gly Leu Phe Asp Gly Lys Gln Tyr Tyr Thr Gly Tyr Thr Phe Ala Asp
        35                  40                  45

Val Leu Pro Val Phe Glu Lys Tyr Lys Ala Tyr Asp Cys His Val Tyr
    50                  55                  60

Ile His Asn Leu Asp Phe Asp Leu Ser Lys Ile Ile Ala Glu Leu Arg
65                  70                  75                  80

Asp Tyr Ala Glu Pro Thr Phe Asn Asn Ser Leu Phe Ile Asn Gly Asn
                85                  90                  95

Ile Val Thr Phe Thr Ala Ser His Ile Ile Leu His Asp Ser Phe Arg
            100                 105                 110

Leu Leu Pro Ser Ser Leu Glu Asn Leu Cys Arg Asp Phe Asp Leu Leu
        115                 120                 125

Glu Gly Gly Lys Met Asp Ile Val Asp Tyr Met Glu Glu Asn Asn Tyr
130                 135                 140

Gly Ile Tyr Asn Val Lys Asn Arg Lys Leu Asn Lys Arg Leu Thr Lys
145                 150                 155                 160

Gly Asn Phe Phe Thr Thr Val Asp Lys Asp Pro Val Leu Cys Glu
                165                 170                 175

Tyr Met Glu Tyr Asp Cys Arg Ser Leu Tyr Lys Ile Leu Glu Ile Val
            180                 185                 190

Ile Gly Leu Ser Lys Leu Glu Val Glu Gln Phe Ile Asn Cys Pro Thr
        195                 200                 205

Thr Ala Ser Leu Ala Lys Thr Val Tyr Lys Gln Tyr Lys Lys Asp
    210                 215                 220

Tyr Lys Val Ala Ile Ser Thr Lys Gln Tyr Asn His Lys Gln Ile Gly
225                 230                 235                 240

Lys Gly Leu Glu Ala Phe Ile Arg Lys Gly Tyr Tyr Gly Gly Arg Thr
                245                 250                 255
```

```
Glu Val Phe Thr Pro Arg Ile Glu Asn Gly Tyr His Tyr Asp Lys Asn
            260                 265                 270

Ser Leu Tyr Pro Tyr Val Met Lys Met Ala Glu Met Pro Val Gly Tyr
            275                 280                 285

Pro Asn Val Leu Asp Asn Glu Glu Ala Glu Leu Ser Phe Asp Leu Trp
            290                 295                 300

Lys Arg Arg Lys Tyr Gly Ala Gly Phe Ile His Ala Lys Val His Val
305                 310                 315                 320

Pro Glu Asp Met Tyr Ile Pro Ile Leu Pro Lys Lys Asp Tyr Thr Gly
            325                 330                 335

Lys Leu Ile Phe Pro Val Gly Lys Ile Glu Gly Val Trp Thr Phe Pro
            340                 345                 350

Glu Leu Ala Leu Ala Glu Ala Glu Gly Cys Arg Ile Glu Lys Ile Glu
            355                 360                 365

Ser Gly Val Val Phe Glu Lys Thr Ala Pro Val Phe Arg Glu Phe Ile
    370                 375                 380

Ser Tyr Phe Glu Glu Ile Lys Asn Thr Ser Lys Gly Ala Lys Arg Ala
385                 390                 395                 400

Phe Ser Lys Leu Met Gln Asn Ala Leu Tyr Gly Lys Phe Ala Met Gln
            405                 410                 415

Arg Glu Arg Ile Met Tyr Ala Asp Ile Ser Glu Arg Asp Lys Leu Glu
            420                 425                 430

Ala Glu Gly His Thr Val Ser Glu Ile Ile Tyr Asp Met Asn Gly Ile
            435                 440                 445

Arg Met Glu Phe Leu Glu Tyr Asp Gly Tyr Ala Lys Ala Glu Tyr Ile
            450                 455                 460

Gln Pro His Ile Ser Ala Tyr Ile Thr Ser Ile Ala Arg Ile Leu Leu
465                 470                 475                 480

Phe Lys Gly Leu Lys Tyr Ala His Glu Lys Gly Ile Leu Ala Tyr Cys
            485                 490                 495

Asp Thr Asp Ser Cys Ala Thr Thr Thr Lys Phe Pro Asp Lys Met Val
            500                 505                 510

His Asp Lys Glu Tyr Gly Lys Trp Lys Leu Glu Gly Tyr Val Ile Glu
            515                 520                 525

Gly Leu Tyr Phe Gln Pro Lys Met Tyr Ala Glu Lys Ala Ile Asn Thr
            530                 535                 540

Asp Gly Glu Tyr Glu Glu Val Leu Arg Met Lys Gly Val Pro Lys Trp
545                 550                 555                 560

Val Val Glu Glu Gln Leu Asp Tyr Asn Thr Phe Lys Lys Trp Tyr Leu
            565                 570                 575

Gln Val Lys Arg Gly Lys Ala Glu Ile Pro Ile Tyr Lys Gly Gly Glu
            580                 585                 590

Arg Val Gln Lys Phe Leu Thr Lys Ser Lys Asn Asn Ile Glu Met Asn
            595                 600                 605

Glu Leu Ala Glu Met His Lys Thr Ile Asn Phe Ala Arg Glu Gln Lys
            610                 615                 620

Arg Asn Ile Asp Leu Asn Lys Asn Thr Thr Ser Pro Leu Val Arg Asn
625                 630                 635                 640

Asp Tyr Gly Glu Asn Lys Asp Glu Lys Ser Glu Tyr Glu Phe Asp Glu
            645                 650                 655

Trp Tyr Glu Arg Leu Glu Glu Phe Asn Asp Asp Met Asn Ala Val Glu
            660                 665                 670
```

```
Glu Leu Cys Met Lys Phe Gly Lys Ile Gln Ile Pro Glu Lys Lys Gln
            675                 680                 685

Arg Lys Leu Tyr Gly Leu Tyr Lys Glu Tyr Ser Ser Lys Ala Lys Ala
        690                 695                 700

Met Cys Phe Ser Asn Glu Gly Leu Pro Ile Gln Asp Trp Cys Lys Lys
705                 710                 715                 720

Thr Gly Trp Asp Met Lys Glu Leu Leu Gly Glu Leu Ser Phe Leu
                725                 730                 735

<210> SEQ ID NO 8
<211> LENGTH: 965
<212> TYPE: PRT
<213> ORGANISM: Acidithiobacillus caldus SM-1

<400> SEQUENCE: 8

Met Arg Gly Pro Val Pro Arg Gln Gly Gly Glu Gly Thr Val Ala
1               5                   10                  15

Ile Leu Ala Met Thr Leu His Glu Ala Ser Cys Ser Ala Val Gly Ile
                20                  25                  30

Gln Pro Gln Pro Cys Thr Ala Thr Ala Ala Ile Ala Glu Pro Ser Cys
            35                  40                  45

Pro Ala Leu Leu Pro Glu Pro Thr Ala Ala Val Thr Gln Pro Gln Arg
        50                  55                  60

Asp Ala Pro Cys Gln Asp Leu Ser Asn Ala Asn Thr Ala Val Pro Phe
65                  70                  75                  80

Ser Ser Tyr Arg Phe Glu Ser Gln Met Glu Thr Glu Phe Gly Pro Leu
                85                  90                  95

Arg Leu Tyr Val Phe Arg Gly Gln Lys Ala Lys Glu Ser Ile Gln Val
            100                 105                 110

Asp Asp Glu Tyr Thr Ser Asp Tyr Ser Gln His Ile Asp Asn Thr Ser
        115                 120                 125

Thr Ser Ala Gly Val Ile Thr Ser Met Gly Pro Asp Glu Gly Ile Asp
130                 135                 140

Thr Asn Gly Asn Asp Gln Thr Arg Leu Val Val Ala Leu Asp Ala Glu
145                 150                 155                 160

Trp Gln Glu Ser Glu Gly Gln Ala Gly Gly Glu Thr Gln Lys Arg Lys
                165                 170                 175

Ile Leu Cys Leu Gln Ala Ala Thr Arg Phe Arg Asp Gly Thr Arg Val
            180                 185                 190

Val Cys Leu Leu Tyr Leu Arg Ser Arg Arg Pro Ser Gln Gly Gln
        195                 200                 205

Phe Leu Gln Leu Leu Trp Gly Gln Trp Gln Arg Leu Gly Leu Val Pro
210                 215                 220

Ala Leu Val Tyr Arg Pro Lys Pro Lys Pro Thr Ser Asp Ser Thr Asp
225                 230                 235                 240

Arg Lys Cys Cys Thr Ala Val Lys Thr Gln Ala Leu Leu Tyr Leu Val
                245                 250                 255

Gly His Tyr Gly Ile Val Asp Asn Thr Ser Phe Tyr Asn Arg Arg Lys
            260                 265                 270

Ile Val Gln Asn Ala Asp Ala Val Arg Arg Thr Ile Val Ser Val Gln
        275                 280                 285

Tyr Pro Thr Ser Val Tyr Phe Tyr Asp Arg Gly Arg Arg Ala Lys
    290                 295                 300

Val Thr Val Phe Tyr Arg Asp Thr Met Leu Leu Ser Pro Ser Gly Ser
305                 310                 315                 320
```

```
Ser Leu Glu Met Leu Gly Asp Ala Leu Asp Phe Pro Lys Ile Gln Leu
            325                 330                 335

Pro Glu Gly Tyr Lys Lys Ser Asp Met Arg Gln Phe Leu Lys Glu Lys
            340                 345                 350

Pro Leu Gln Phe Glu Glu Tyr Ala Ala Thr Asp Ala Leu Ile Ala Leu
            355                 360                 365

Glu Trp Ile Phe Arg Asn Ser Trp Gly Arg Glu Val Pro Ile Thr Leu
    370                 375                 380

Gly Gly Glu Gly Ala Arg Leu Phe Arg Asp His Ile Met Thr Ala Arg
385                 390                 395                 400

Gly Trp Thr Ile Asp Glu Phe Asp Phe His Leu Arg Gly Leu Ala Arg
                405                 410                 415

Lys Ile Ile Asp Thr Gly Glu Gly Lys Arg Ile Lys Lys Lys Glu Pro
                420                 425                 430

Arg Ser Asn Thr Thr Thr Leu Ile Ala Arg Ala Thr Glu Ser Tyr Tyr
            435                 440                 445

Gly Gly Arg Asn Glu Cys Ile Leu Ser Gly Ile His His Gly Pro Trp
            450                 455                 460

Tyr Asp Phe Asp Ile Ala Gly Ala Tyr Pro Ala Ala Met Ser Leu Ile
465                 470                 475                 480

Pro Asp Pro Asp Tyr Asp Gln Pro Arg Ile Thr Leu Leu Pro Gly Pro
                485                 490                 495

Leu Pro Arg Glu Met Ile Arg Pro Glu Met Leu Leu Phe Ala His Val
            500                 505                 510

Ser Phe Thr Phe Pro Asp Glu Ile Arg Tyr Pro Cys Leu Pro Ile Lys
            515                 520                 525

Asp Ser Ser Gly Arg Gly Leu Ile Phe Pro Arg Ser Gly Glu Thr Trp
530                 535                 540

Ala Ala Ala Pro Glu Leu Trp Leu Ala Gln Arg Trp Gly Ala Glu Ile
545                 550                 555                 560

Thr Leu Leu Glu Pro Thr Glu Ile Ile Pro Thr Arg Asn Thr Phe Ser
                565                 570                 575

Leu Ala Asp Gly Met Arg Ala Met Val Gln Glu Arg Glu Arg Leu Lys
            580                 585                 590

Ser Arg Phe Gly Lys Lys Ser Ile Glu Gln Thr Arg Gln Lys Glu Met
            595                 600                 605

Asn Asn Ser Val Tyr Gly Lys Leu Ala Gln Gly Leu Ser Gly Lys Arg
            610                 615                 620

Ser Tyr Ser Pro Arg Ala Asp Arg Thr Glu Val Gly Pro Ser Ile
625                 630                 635                 640

Leu Thr Cys Ala Pro Leu Ala Ala Leu Thr Thr Ala Trp Val Arg Ala
                645                 650                 655

Leu Val Ser Ala Met Met Gln Ser Leu His Val Ala Gly Tyr Arg Val
            660                 665                 670

Ala Ser Val Thr Thr Asp Gly Phe Leu Cys Asp Ala His Ser Leu Asp
            675                 680                 685

Gly Leu Thr Thr Trp Gly Ile Ala Glu Ala Phe Ile Asp Gly Arg Lys
            690                 695                 700

Arg Leu Gly Leu Asp Ser Asn Leu Trp Glu Leu Lys His Ala Ala Gln
705                 710                 715                 720

Ser Leu Val Met Met Lys Thr Arg Gly Gly Tyr Gly Leu Gly Arg Val
                725                 730                 735
```

```
Gly Asp Leu Pro Leu Pro Ile Ala Arg Ala Gly Tyr Lys Ser Ser Gln
            740                 745                 750

Glu Asp Thr Ser Glu Ala Leu Ala Arg Val Tyr Leu Glu Arg Arg Gly
        755                 760                 765

Arg Val Val Thr Glu Glu Val Arg Leu Pro Thr Met Arg Glu Tyr Val
    770                 775                 780

Arg His Glu Ala Asp Gly Thr Gly Arg Ile Gln Arg Lys Glu Leu Ser
785                 790                 795                 800

Leu Asp Tyr Asp Phe Lys Arg Cys Pro Gln Lys Ile Trp Thr Glu Thr
            805                 810                 815

Ile Val Ile Gln Gly Gln Ser Tyr Glu His Val Ser Phe Asp Ser Val
        820                 825                 830

Pro Trp Gly Ser Ile Asp Glu Phe Thr Asn Ala Arg Glu Val Ile Asp
            835                 840                 845

Gln His His Asp Thr Pro Leu Lys Ser Glu Ser Asp Leu Lys Gln Ala
        850                 855                 860

Leu Leu Arg Val Glu Arg His Thr Ala Val Lys Ser Val Gly Leu Arg
865                 870                 875                 880

Val Asn Asn Val Ala Ile Ser Gly Ala Val Ser Val Leu Arg Gly
            885                 890                 895

Leu Arg Ala Gly Gly Ile Ser Ala Pro Trp Phe Asp Pro Asp Val Thr
            900                 905                 910

Ser Gly Lys Thr Val Leu Glu Arg Val Gly Ala Val Phe Gly Val Lys
            915                 920                 925

Leu Ser Thr Asn Asp Trp Lys Asn Ala Gly Arg Lys Glu Arg Gln Lys
            930                 935                 940

Gln Gly Trp Ser Leu Ile Gly Phe Asp Arg Glu Val Ala Ala Leu Glu
945                 950                 955                 960

Leu Thr Glu Lys Thr
            965

<210> SEQ ID NO 9
<211> LENGTH: 864
<212> TYPE: PRT
<213> ORGANISM: Colwellia sp. MT41

<400> SEQUENCE: 9

Met Phe Asn Glu Asp Glu Gly Tyr Pro Ser Ile Thr Ser Glu Thr Gln
1               5                   10                  15

Leu Ser Tyr Glu Glu Pro Ser Ser Val Ala Val Pro Ile Pro Phe Asp
            20                  25                  30

Glu Asn Lys Leu Asn Thr Tyr Gly Ser Ser Ala Gln Asn Lys Ser Gln
        35                  40                  45

Arg Glu Lys Lys Val Pro Ile Gln Met Arg Pro Val Leu Gly Phe Asp
    50                  55                  60

Thr Glu Tyr His Arg Ser Ser Asp Asn Thr Tyr Asn Val Ile Leu Ser
65                  70                  75                  80

Tyr Gln Ser Tyr Leu Phe Asn Pro Val Asn Gly Arg Ser Cys Lys Ala
                85                  90                  95

Val Phe Tyr Pro Ser Lys Arg Ser Lys Asp Gly Arg Ile Gly Ile Lys
            100                 105                 110

Lys Phe Ile Thr Leu Val Ile Glu Asp Ala Leu Lys Gln Gly Val Leu
        115                 120                 125

Thr Asp Ile Pro Arg Asp Ile Phe Gly Cys Ala His Phe Leu Arg Ala
    130                 135                 140
```

-continued

```
Asp Phe Ser Ser Phe Lys Asn Ala Phe Ser Asp Met Lys Asp Ser Ile
145                 150                 155                 160

Lys Gly Leu Arg Asn Ser Val Ala Ser Leu Gly Glu Thr Tyr Gly Val
            165                 170                 175

Asp Ile Asp Ala Ile Asp Ala Lys Lys Val Ser Asn Leu Ser Thr Thr
        180                 185                 190

Tyr Trp Asp Lys Asn Arg Asn Ser His Pro Ile Gln Leu Ala Phe Tyr
        195                 200                 205

Asp Thr Met Phe Phe Ala Pro Ala Gly Lys Thr Leu Lys Asp Val Gly
    210                 215                 220

Glu Phe Val Gly Arg Glu Lys Leu Glu Ile Pro Glu Pro Tyr Ser Ile
225                 230                 235                 240

Asp Lys Met Asp Val Phe Leu Lys Glu Lys Val Leu Phe Glu Glu
                245                 250                 255

Tyr Gly Ile Arg Asp Ala Glu Ile Ser Ala Leu His Leu Leu Arg Thr
            260                 265                 270

Leu Gln Leu Cys Ala Ser Leu Gly Leu Lys Gly Leu Pro Tyr Thr Ile
        275                 280                 285

Gly Gly Ile Ala Val Lys Val Phe Met Ala Lys Leu Gly Thr Lys Ala
290                 295                 300

Arg Tyr Leu Glu Leu Phe Ala Leu Glu Glu Tyr Lys Val Glu Arg Trp
305                 310                 315                 320

Ser Lys Thr Lys Asn Thr Pro Val Thr Ser Thr Lys Asn Leu Leu Lys
                325                 330                 335

Ala Ser Ala Ser Phe Asp Glu His Leu Ala Ser Lys Cys Tyr His Gly
            340                 345                 350

Gly Arg Asn Glu Ala Phe Phe Thr Gly Pro Thr Pro Val Leu Pro Trp
        355                 360                 365

Phe Asp Val Asp Leu Lys Ser Cys Tyr Ser Ile Ala Val Ser Asn Leu
    370                 375                 380

Arg Pro Leu Asp His Glu Asn Arg Phe His Thr Lys Asp Ile Asn Asp
385                 390                 395                 400

Phe Ser Gly Asp Val Phe Gly Leu Ala Trp Val Glu Phe Glu Phe Pro
                405                 410                 415

Thr Ser Val Gln Tyr Pro Thr Leu Pro Val Arg Thr Asp Ser Asp Met
            420                 425                 430

Leu Val Phe Thr Gln Lys Gly Phe Ser Tyr Cys Thr Ala Gln Glu Ile
        435                 440                 445

Asp Val Ser Arg Arg Leu Gly Val Lys Ile Val Lys Glu Gly Leu
    450                 455                 460

Ile Ile Pro Trp Leu Asn Asp Asp Tyr Phe Cys Val Pro Phe Met His
465                 470                 475                 480

Ser Met Arg Ala Glu Arg Asn Lys Ala Glu Lys Gly Ser Phe Glu Asp
                485                 490                 495

Arg Met Phe Lys Glu Leu Ser Asn Thr Leu Tyr Gly Lys Ile Ala Gln
            500                 505                 510

Gly Val Lys Ser Lys Thr Ser Phe Glu Ile Ser Ser Gly Leu Ser Lys
        515                 520                 525

Pro Val Ser Pro Ser Val Val Thr Asn Pro Tyr Phe Ala Ala Tyr Ile
    530                 535                 540

Thr Gly Leu Ala Arg Ala Val Ile Gly Asp Met Ile Asn Ala Ile Pro
545                 550                 555                 560
```

```
Thr Pro Tyr Ser Val Leu Ser Val Thr Thr Asp Gly Phe Ile Thr Asp
            565                 570                 575

Ala Pro Leu Thr Glu Ile Pro Ile Asp Ser Pro Val Cys Asn Leu Phe
        580                 585                 590

Arg Glu Ser Tyr His Arg Met Asp Asp Thr Gly Gly Asp Ile Leu Glu
    595                 600                 605

Glu Lys His Arg Val Asn Gln Leu Leu Val Leu Lys Thr Arg Gly Gln
610                 615                 620

Leu Thr Leu Lys Pro Cys Asp Gly His Pro Ser Ile Ile Ala Lys Ala
625                 630                 635                 640

Gly Val Lys Thr Pro Asn Asn Cys Lys Asp Gln Asn Ala Tyr Met Val
                645                 650                 655

Asp Leu Tyr Leu Asn Arg Thr Pro Gln Thr Lys Thr Asp Ala Ser His
            660                 665                 670

Leu Thr Ala Thr Arg Pro Gln Phe Ile Gly Gln Gln Asp Leu Met Met
        675                 680                 685

Val Pro Lys Met Cys Arg Leu Asn Leu Glu Pro Asp Leu Lys Arg Lys
    690                 695                 700

Leu Leu Pro Pro Ile Glu Val Glu Val Asn Gly Val Lys His Val Ala
705                 710                 715                 720

Met Gly Ser Val Pro Tyr Glu Asp Leu Gln Thr Leu Glu Gln Asp Arg
                725                 730                 735

Leu Phe Phe Thr Arg Trp Arg Ala Asn Asn Met Lys Thr Leu Ala
            740                 745                 750

Asp Tyr Ala Ser Trp Asp Glu Phe Val Lys Leu Arg Arg Thr Lys Asn
        755                 760                 765

Leu Lys Gly Val Asn Leu Lys Val Asp Glu Thr Ala Asp Ala Phe Leu
    770                 775                 780

Val Arg Leu Phe Leu Arg Val Ile Ala Gln Glu Gln Phe Gly Val Thr
785                 790                 795                 800

Leu Gly Tyr Gly Val Lys Pro Asn Ala Ile Ser Ser Ala Lys Lys Ala
                805                 810                 815

Lys Val Ile Thr Gly Ala Val Pro Leu Thr Ala Asn Val Ile Lys Val
            820                 825                 830

Leu Lys Leu Ile Leu Ile Ile Phe Pro Asp Phe Asp Tyr Gln Ala Met
        835                 840                 845

Ile Ala Pro Glu Tyr His Leu Glu Leu Lys Gln Leu Met Ser Ser Ile
    850                 855                 860

<210> SEQ ID NO 10
<211> LENGTH: 902
<212> TYPE: PRT
<213> ORGANISM: Vibrio parahaemolyticus

<400> SEQUENCE: 10

Met Glu Glu Asn Met Asn Tyr Trp Ala Glu Asp Ser Gly Val Glu Ile
1               5                   10                  15

Glu Glu Ser Phe Asp Gly Ile Glu Val Asp Glu Ser Leu Val Glu Ala
            20                  25                  30

Trp Gly Asn Ala Ser Asn Asp Asp His Val Asp Glu Thr Leu Gly Ser
        35                  40                  45

Ile Ser Glu Glu Thr Lys Pro Leu Val Glu Asn Ile Asn Glu Tyr Glu
    50                  55                  60

Asn Ser Lys Lys Lys Ser Lys Arg Tyr Lys Ala Arg Thr Lys Phe Phe
65                  70                  75                  80
```

```
Asp Arg Pro Ile Ile Ser Phe Asp Thr Glu Tyr Val Leu Ser Lys Cys
                85                  90                  95

Gly Lys Tyr Asn Arg Val Leu Ser Tyr Gln Phe Val Thr Leu His Asn
            100                 105                 110

Gly Lys Val Ser Lys Leu Val Leu Tyr Pro Asp Ser Ala Lys Lys Ser
            115                 120                 125

Gly Arg Leu Ser Met Asp Tyr Cys Phe Ala Arg Val Ile Glu Lys Ala
            130                 135                 140

Ile Glu Asp Asp Val Leu Glu Arg Trp Pro Thr Asp Ile Ile Val Thr
145                 150                 155                 160

Ala His Phe Met Lys Ala Asp Leu Phe Asn Phe Asn Gln Ala Phe Glu
                165                 170                 175

Gln Ile Lys Thr His Ile Lys Gly Ile Arg Lys Thr Val Ala Ser Leu
                180                 185                 190

Gly Gly Ala Tyr Glu Leu Asp Leu Ser Lys Val Met Thr Arg Arg Ile
            195                 200                 205

Asp Lys Glu Pro Val Gln Ile Lys Asp Lys Asn Arg Asn Tyr His Thr
            210                 215                 220

Leu His Met Ser Phe Phe Asp Thr Met Leu Leu Ala Pro Ala Ser Ala
225                 230                 235                 240

Gln Ser Leu Ser Ala Val Gly Asn Ile Val Gly Val Pro Lys Leu Glu
                245                 250                 255

Ile Pro Glu Pro Tyr Ser Ile Glu Arg Met Asp Glu Tyr Leu Ala Gly
                260                 265                 270

Asn Lys Thr Gly Phe Glu Ala Tyr Gly Leu Thr Asp Ser Leu Ile Ser
            275                 280                 285

Ala Leu His Phe Lys Ala Thr Ala Asp Leu Cys Lys Glu Leu Gly Leu
            290                 295                 300

Lys Ser Val Pro Tyr Thr Ile Gly Gly Met Ala Val Lys Thr Phe Ile
305                 310                 315                 320

Asn Ser Leu Asp Asp Pro Lys Ser Tyr Arg Lys Leu Phe Gly Phe Glu
                325                 330                 335

Glu Glu Lys Arg Glu Ile Trp Ser Lys Glu Thr Gly Lys Val Arg Thr
            340                 345                 350

Val Thr Ile Glu Glu Pro Thr Gln Ala Arg Lys Thr Met Glu Trp Phe
            355                 360                 365

Ala Ser Glu Cys Tyr Ser Gly Gly Arg Asn Glu Ala Phe Trp Ser Gly
            370                 375                 380

Val Thr Pro Val Asp Thr Trp Leu Asp Leu Asp Val Pro Ser Cys Tyr
385                 390                 395                 400

Ser Ala Ile Thr Asn Gly Leu Arg Glu Ile Ser Tyr Glu Asp Met Tyr
                405                 410                 415

Met Ser Asn Glu Val Glu Asp Phe Phe Gly Asp Lys Met Ala Leu Ala
                420                 425                 430

Trp Val Glu Phe Glu Phe Pro Ser Ser Thr Arg His Pro Ser Leu Val
            435                 440                 445

Val Arg Asp Lys Asp Ser Leu Ile Phe Pro Leu Arg Gly Glu Thr His
            450                 455                 460

Cys Thr Gly His Glu Leu Glu Val Ala Tyr Asn Gln Gly Ala Lys Ile
465                 470                 475                 480

Lys Ile Lys Gln Gly Phe Ile Phe Pro Trp Lys Asn Asp Val Arg Ile
                485                 490                 495
```

```
Phe Glu Lys Tyr Met Lys Trp Gly Glu Lys Arg Lys Ser Tyr Glu
            500                 505                 510
Lys Gly Ser Phe Gln Glu Lys Leu Val Lys Glu Met Leu Asn Ser Thr
        515                 520                 525
Tyr Gly Lys Phe Ser Gln Asn Val Lys Pro Lys Gln Thr Phe Ser Val
        530                 535                 540
Glu Asp Gly Tyr Ser Lys Pro Gln Pro Pro Ser Lys Leu Thr Asn Pro
545                 550                 555                 560
Phe Tyr Ala Ser Tyr Thr Cys Gly Leu Ala Arg Ala Leu Leu Gly Glu
                565                 570                 575
Met Leu Ser Gly Val Pro Ser Asn Lys Thr Val Ser Val Thr Thr
            580                 585                 590
Asp Gly Phe Leu Thr Asn Ala Asp Ile Glu Glu Ile Asp Leu Ser Gly
                595                 600                 605
Pro Ile Cys Gln Arg Phe Arg Glu Leu Phe His Arg Met Glu Pro Asn
            610                 615                 620
Gly Gly Glu Ile Leu Glu Val Lys His Lys Ala Lys Gln Leu Ile Cys
625                 630                 635                 640
Ala Lys Thr Arg Ala Gln Tyr Thr Val Thr Pro Met Glu Gly Trp Glu
                645                 650                 655
Pro Val Leu Ala Lys Gly Gly Val Gln Val Pro Lys Gln Val Thr Asp
            660                 665                 670
Gln Asn Gln Tyr Met Val Asp Leu Tyr Lys Glu Arg Thr Pro Glu His
        675                 680                 685
Met Thr Asp Ser Ser His Leu Thr Ser Leu Arg Ser Met Cys Thr Glu
690                 695                 700
Arg Lys Asp Met Leu Met Glu Arg Lys Gln Ser Arg Leu Asn Leu Glu
705                 710                 715                 720
Phe Asp Met Lys Arg Glu Pro Ile Asn Pro Arg Val Ile Glu Val Asp
                725                 730                 735
Gly Val Pro Leu Val Ser Phe Glu Thr Lys Pro Phe Lys Asn Ala Phe
            740                 745                 750
Glu Met Arg Tyr Thr Arg Ile Arg Phe Asp Ala Trp Arg Lys Ser Gly
        755                 760                 765
Arg Cys Leu Lys Thr Met Asp Asp Trp Tyr Asp Trp Gln Glu Arg Leu
770                 775                 780
Ser Met Tyr Lys Ala Asn Asp Lys Gly Glu Val Arg Leu Lys Lys Asp
785                 790                 795                 800
Glu Lys Ser Asp Glu Leu Met Ala Arg Leu Phe Val Arg Phe Tyr Gly
                805                 810                 815
His Glu Ala Ser Gly Ile Thr Lys Lys Asp Ile Thr Ala Lys Ala Leu
            820                 825                 830
Ser Glu Trp Leu Val Glu Leu Gly Tyr Asp Ile Lys Pro Ser Leu Val
        835                 840                 845
Arg Gly Ala Gly Arg Thr Lys Leu Val Glu Gly Thr Val Pro Leu Thr
850                 855                 860
Pro Ser Thr Leu Lys Leu Ala Lys Leu Leu Met Asp Lys Phe Pro Gln
865                 870                 875                 880
Phe Asp Pro Val Pro Leu Phe Asn Ala Ser Asp Glu Glu Val Met Arg
                885                 890                 895
Gln Leu Glu Asn Ile Ser
            900
```

<210> SEQ ID NO 11
<211> LENGTH: 911
<212> TYPE: PRT
<213> ORGANISM: Vibrio parahaemolyticus

<400> SEQUENCE: 11

```
Met Glu Glu Asn Met Asn Val Trp Ala Gln Ser Val Glu Leu Glu Ile
 1               5                  10                  15

Asn Glu Glu Leu Thr Phe Ser Asp Val Glu Ala Asp Phe Thr Ser Ala
             20                  25                  30

Trp Gly Ser Ser Asp Glu Leu Leu Asn Glu Tyr Ala Glu Asp Glu Lys
         35                  40                  45

Gln Ser Leu Ala Asp Ala Val Val Glu Thr Ala Ser Pro Ile Asp Ser
     50                  55                  60

Glu Ala Leu Lys Ala Trp Thr Glu Pro Lys Lys Gly Gln Arg Arg
 65                  70                  75                  80

Ile Gly Thr Lys Phe Tyr Asp Arg Pro Ile Ile Gly Phe Asp Thr Glu
                 85                  90                  95

Phe Glu Leu Ser Lys Cys Lys Lys Tyr Asn His Val Ile Ser Tyr Gln
            100                 105                 110

Leu Val Val Arg His Lys Gly Arg Thr Ser Lys Leu Val Leu Tyr Pro
        115                 120                 125

Asp Ser Asn Lys Lys Ser Gly Arg Leu Ala Met Asp Tyr Cys Leu Ala
    130                 135                 140

Arg Val Ile Glu Lys Ala Ile Glu Asp Gly Thr Leu Glu Arg Trp Pro
145                 150                 155                 160

Thr Asp Val Ile Met Thr Ala His Phe Met Lys Ala Asp Leu Phe His
                165                 170                 175

Phe Asn Lys Ala Phe Asp Gln Val Lys Thr His Ile Lys Gly Ile Arg
            180                 185                 190

Lys Thr Val Ala Ser Leu Gly Asp Ala Tyr Ala Leu Asp Leu Ser Lys
        195                 200                 205

Val Leu Ser Arg Arg Ile Asp Glu Glu Pro Val Asp Val Tyr Asp Lys
    210                 215                 220

Asn Arg Asn Lys Lys Thr Leu His Leu Ser Phe Phe Asp Thr Met Leu
225                 230                 235                 240

Leu Ala Pro Ala Gly Lys Ser Leu Ala Asp Val Gly Glu Leu Val Gly
                245                 250                 255

Leu Thr Lys Leu Lys Ile Pro Glu Pro Tyr Ser Ile Glu Arg Met Gly
            260                 265                 270

Glu Tyr Leu Thr Gly Asn Lys Gln Gly Phe Glu Ala Tyr Gly Leu Arg
        275                 280                 285

Asp Ala Glu Leu Ser Ala Leu His Phe Glu Lys Thr Ala Asn Leu Cys
    290                 295                 300

Lys Glu Leu Gly Leu Lys Ser Val Pro Tyr Thr Ile Gly Gly Met Ala
305                 310                 315                 320

Val Lys Ala Phe Ile Asn Ser Leu Asp Asp Pro Lys Asn Tyr Arg Lys
                325                 330                 335

Leu Phe Gly Phe Glu Lys Lys Thr Phe Glu Val Trp Ser Lys Asp Gln
            340                 345                 350

Ala Lys Val Lys Thr Val Thr Val Asp Glu Pro Thr Pro Ala Arg Ser
        355                 360                 365

Thr Met Glu Trp Phe Ala Ser Glu Cys Tyr Ser Gly Gly Arg Asn Glu
    370                 375                 380
```

-continued

```
Ala Phe Trp Ala Ser Ala Thr His Ile Asp Thr Trp Asn Asp Leu Asp
385                 390                 395                 400

Val Pro Ser Cys Tyr Thr Ala Ile Thr Asn Ala Leu Arg Pro Ile Ala
                405                 410                 415

Tyr Asp Arg Met Tyr Met Ser Asn Arg Val Glu Asp Phe Phe Gly Asp
            420                 425                 430

Lys Met Ala Leu Ala Trp Val Glu Phe Glu Phe Pro Pro Gln Thr Arg
        435                 440                 445

Phe Pro Ser Leu Val Val Arg Asn Lys Asp Ser Leu Ile Phe Pro Leu
    450                 455                 460

Ser Gly Glu Thr His Cys Thr Gly His Glu Leu Glu Val Ala Tyr Asn
465                 470                 475                 480

Gln Gly Ala Lys Ile Thr Ile Lys Gln Gly Phe Ile Phe Pro Trp Ala
                485                 490                 495

Ser Glu Glu Arg Ile Phe Glu Lys Tyr Met Leu Trp Gly Arg Gln Lys
            500                 505                 510

Arg Lys Ser Tyr Pro Lys Asn Ser Tyr Gln Glu Lys Leu Ile Lys Glu
        515                 520                 525

Met Leu Asn Ser Thr Tyr Gly Lys Phe Ser Gln Asn Val Lys Pro Lys
    530                 535                 540

Lys Thr Phe Ser Val Ala Asp Gly Tyr Ser Gln Pro Gln Pro Ser
545                 550                 555                 560

Lys Leu Thr Asn Pro Phe Tyr Ala Ser Phe Thr Cys Gly Met Gly Arg
                565                 570                 575

Ala Leu Leu Ser Glu Met Leu Ala Gly Val Pro Asp Asp Lys Thr Val
            580                 585                 590

Val Ser Val Thr Thr Asp Gly Phe Leu Thr Asn Ala Lys Ile Glu Glu
        595                 600                 605

Ile Asp Leu Ser Gly Pro Val Cys Gln Arg Phe Arg Glu Leu Phe His
    610                 615                 620

Arg Met Glu Pro Asn Gly Gly Glu Ile Leu Glu Ile Lys His Lys Ala
625                 630                 635                 640

Lys Gln Leu Ile Cys Ala Lys Thr Arg Ala Gln Phe Thr Val Ile Pro
                645                 650                 655

Glu Glu Gly Trp Glu Pro Val Leu Ala Lys Gly Gly Val Arg Pro Pro
            660                 665                 670

Glu Gly Glu Val Asp His Asn Arg Tyr Met Val Asn Leu Tyr Lys Glu
        675                 680                 685

Arg Thr Pro Glu His Thr Val Asp Thr Ser His Leu Thr Ser Leu Arg
    690                 695                 700

Val Met Cys Thr Glu Gly Gln Asp Met Lys Met Glu Arg Lys Glu Ser
705                 710                 715                 720

Arg Leu Asn Leu Glu Phe Asp Met Lys Arg Glu Leu Ile Lys Pro Ile
                725                 730                 735

Met Val Asp Ile Glu Gly Gln Pro Asn Val Ser Phe Ser Lys Pro
            740                 745                 750

Phe Lys Asn Ala Phe Glu Met Arg Tyr Thr Arg Ile Arg Phe Asp Ala
        755                 760                 765

Trp Arg Lys Ser Gly His Cys Leu Lys Thr Leu Glu Asp Trp Tyr Asp
    770                 775                 780

Trp Gln Glu Arg Leu Arg Met Tyr Lys Ala Lys Asp Lys Ala Met Ser
785                 790                 795                 800

Asn Asp Asn Cys Lys Val Arg Phe Lys Lys Asp Glu Lys Ala Asp Glu
```

-continued

```
                        805                 810                 815
Leu Met Ala Arg Leu Phe Val Arg Phe Tyr Gly His Glu Ala Ser Gly
            820                 825                 830

Ile Ser Lys Lys Asp Ile Thr Ala Lys Ala Leu Ser Glu Phe Leu Val
            835                 840                 845

Gly Leu Gly Tyr Glu Ile Lys Pro Ser Leu Val Arg Gly Ala Gly Arg
            850                 855                 860

Thr Glu Leu Val Glu Gly Val Pro Leu Met His Ser Thr Met Gln
865                 870                 875                 880

Leu Ala Lys Gln Leu Val Glu Arg Phe Pro Gln Phe Asp Pro Thr Pro
                885                 890                 895

Leu Phe Asp Val Asp Asp Ala Glu Glu Leu Lys His Ser Leu Lys
                900                 905                 910

<210> SEQ ID NO 12
<211> LENGTH: 892
<212> TYPE: PRT
<213> ORGANISM: Moritella sp. PE36

<400> SEQUENCE: 12

Met Ile Asn Glu Leu Met Val Trp Glu Gln Asp Glu Ser Thr Val Ser
1               5                   10                  15

Glu Leu Ser Asn Glu Asp Thr Gly Leu Ser Ser Thr Trp Asp Glu Asp
            20                  25                  30

Asn Leu Ser Asp Asn Glu Ala Met Leu Ser Val Ala Glu Tyr Glu Val
        35                  40                  45

Ser His Ser Ile Thr Lys Gly Lys Gly Lys Asp Lys Ala Lys Lys Gly
    50                  55                  60

Lys Arg Arg Val Gly Thr Lys Phe Phe Glu Arg Pro Thr Val Ser Leu
65                  70                  75                  80

Asp Thr Glu Tyr Thr Glu Ser Pro Cys Gly Thr Tyr Asn Arg Ile Leu
                85                  90                  95

Ser Tyr Gln Phe Val Val Arg His Glu Gly Lys Ser Ser Gly Ile Ile
            100                 105                 110

Leu Tyr Pro Glu Ser Thr Lys Lys Ser Gly Arg Leu Ala Leu Asp Lys
        115                 120                 125

Cys Leu Val Leu Ala Leu Glu Lys Ala Met Ala Glu Asp Val Leu Thr
    130                 135                 140

Cys Trp Pro Thr Asp Ile Ile Leu Val Ala His Phe Leu Lys Ala Asp
145                 150                 155                 160

Leu Phe Asn Phe Ser Asn Ala Phe Asp Gln Leu Lys Thr His Val Lys
                165                 170                 175

Gly Leu Arg Lys Thr Val Ala Ser Leu Asp Glu Pro Tyr Gly Leu Asp
            180                 185                 190

Leu Asp Glu Val Leu Ser Arg Arg Ile Asp Lys Glu Pro Leu Glu Val
        195                 200                 205

Tyr Asp Lys Thr Arg Asn Tyr His Thr Leu Tyr Ile Thr Phe Tyr Asp
    210                 215                 220

Ser Met Leu Leu Ser Pro Asn Gly Lys Ser Leu Ala Asp Val Gly Arg
225                 230                 235                 240

Leu Val Gly Leu Pro Lys Leu Asp Ile Pro Ala Pro Tyr Ser Ile Ser
                245                 250                 255

Arg Met Asp Glu Tyr Arg Asp Ala Asp Pro Glu Gly Tyr Ala Ala Tyr
            260                 265                 270
```

```
Ala Met Asn Asp Gly Phe Val Thr Ser Leu His Phe Glu Arg Ile Ser
            275                 280                 285

Lys Phe Cys Lys Asp Ile Gly Leu Lys Ser Val Pro Phe Thr Ile Gly
    290                 295                 300

Gly Ile Ala Val Lys Ala Phe Val Asn Gly Leu Ala Asp Ser Lys Gly
305                 310                 315                 320

Tyr Arg Gln Leu Phe Gly Phe Met Lys Val Thr Lys Glu Val Trp Pro
                325                 330                 335

Glu Asp Arg Asn Lys Pro Leu Thr Leu Thr Arg Asp Val Pro Val Thr
            340                 345                 350

Ala Arg Met Thr Leu Glu Asn Phe Ala Thr Gln Ala Tyr Ser Gly Gly
        355                 360                 365

Arg Asn Glu Ser Phe Ile Ala Gly Ser Val Pro Ile Asp Thr Trp Asn
370                 375                 380

Asp Phe Asp Ala Pro Ser Cys Tyr Thr Ala Ile Cys Leu Gly Leu Arg
385                 390                 395                 400

Lys Leu Ala Tyr Asp Arg Met Phe Met Thr Lys Lys Leu Glu Asp Leu
                405                 410                 415

Phe Gly Asp Lys Cys Ala Leu Ala Trp Val Arg Phe Glu Phe Pro Ala
            420                 425                 430

Ser Thr Arg Phe Pro Ser Leu Ala Val Arg Ser Asp Lys Gly Leu Ile
        435                 440                 445

Phe Pro Leu Thr Gly Glu Thr His Cys Thr Gly His Glu Leu Glu Val
450                 455                 460

Ala Ser Asn Gln Gly Ala Ile Ile Thr Ile Lys Gln Ala Phe Val Ile
465                 470                 475                 480

Pro Trp Ala Asp Asp Val Arg Ile Phe Glu Asn Phe Met Gly Trp Val
                485                 490                 495

Arg Glu Asn Arg Gln Ala Asn Val Lys Gly Phe Glu Glu Arg Leu
            500                 505                 510

Phe Lys Glu Ile Gly Asn Thr Leu Tyr Gly Lys Phe Ser Gln Ser Leu
        515                 520                 525

Arg Pro Lys Thr Ala Phe Asp Ile Gln Ala Gly Tyr Ser Lys Gln Leu
530                 535                 540

Pro Pro Ser Thr Leu Thr Asn Pro Phe Phe Ala Ala Tyr Thr Thr Gly
545                 550                 555                 560

Leu Ala Arg Ala Leu Met Gly Glu Met Val Ala Ser Ile Pro Asp His
                565                 570                 575

Arg Thr Val Val Ser Leu Thr Asp Gly Met Ala Thr Asn Ala Thr
            580                 585                 590

Leu Glu Glu Phe Asp Leu Asn Gly Pro Ile Cys Gln Arg Phe Arg Glu
        595                 600                 605

His Phe His Arg Ile Asp Pro Asn Gly Gly Glu Ile Leu Glu Leu Lys
610                 615                 620

His Gln Ala Lys Gln Leu Ile Gly Ala Lys Thr Arg Ala Gln Tyr Thr
625                 630                 635                 640

Val Leu Glu Ser Glu Gly Phe Ala Pro Ile Leu Ala Lys Gly Gly Val
                645                 650                 655

Met Val Ala Arg Ser Val Asn Gln Ser Ala Tyr Met Val Asp Leu
            660                 665                 670

Tyr Leu Asn Arg His Val Gly Gln Leu Thr Asp Gly Ser His Leu Thr
        675                 680                 685

Ser Thr Arg Glu Met Phe Ile Gly Arg Lys Asp Met Met Asn Glu Gln
```

```
                        690                 695                 700
Arg Glu Ile Leu Leu Asn Met Glu Tyr Asp His Lys Arg Glu Leu Ile
705                 710                 715                 720

Asp Pro Val Met Ile Asp Val Lys Gly Gln Arg His Ile Ser Leu Gln
                        725                 730                 735

Ser Lys Pro His His Ser Leu Asp Asp Met Leu Phe Thr Arg Leu Arg
                740                 745                 750

Phe Asp Arg Trp Arg Lys Asn Asn Cys Leu Lys Thr Met Asp Asp Trp
            755                 760                 765

Ile Thr Trp His Asp Arg Leu Ala Met Ala Lys Ala Ser Lys Asn Lys
        770                 775                 780

Ser Val Asn Leu Lys Lys Asp Glu Thr Ser Gly Glu Tyr Met Ala Arg
785                 790                 795                 800

Leu Phe Leu Arg Phe Tyr Gly Tyr Glu His Ala Gly Ile Arg Lys Ser
                        805                 810                 815

Asp Ile Asn Ala Thr Gln Leu Ala Leu Trp Leu Thr Glu Gln Gly Tyr
                820                 825                 830

Pro Thr Lys Ala Ala Ala Val Arg Gly Ala Gly Arg Ser Asp Leu Val
            835                 840                 845

Glu Gly Ala Val Pro Leu Thr Glu Leu Thr Ile Lys Phe Ala Lys Leu
        850                 855                 860

Leu Val Ala Lys Phe Pro Asn Phe Asn Pro Glu Arg Leu Phe Glu Ala
865                 870                 875                 880

Ser Ser Arg Pro Gln Leu Arg Glu Ala Leu Lys Gln
                        885                 890

<210> SEQ ID NO 13
<211> LENGTH: 904
<212> TYPE: PRT
<213> ORGANISM: Vibrio cyclitrophicus

<400> SEQUENCE: 13

Met Ser Glu Thr Tyr Asp Trp Leu Glu Gln Asp Thr Ser Ile Thr Ile
1               5                   10                  15

Gly Asn Leu Thr Glu Thr Gly Trp Glu Glu Cys Asp Val Glu Ser Glu
            20                  25                  30

Asp Ser Trp Glu Ala Gln Glu Ser Val Asp Val Lys Asp Val Pro Phe
        35                  40                  45

Lys Thr Val Lys Pro Lys Val Lys Pro Tyr Ile Gly Lys Lys Pro Pro
    50                  55                  60

Lys Lys Val Lys Val Lys Arg Lys Lys Arg Lys Ala Thr Pro Phe Phe
65                  70                  75                  80

Glu Arg Pro Val Ile Ala Ile Asp Thr Glu Tyr Thr Glu Ser Asp Cys
                85                  90                  95

Gly Glu Tyr Asn Ser Ile Leu Ser Tyr Gln Leu Ala Ile Leu His Lys
            100                 105                 110

Gly Leu Leu Ser Thr Leu Ile Leu Tyr Pro Glu Ser Thr Lys Lys Ser
        115                 120                 125

Gly Arg Leu Ala Leu Asp Arg Cys Leu Val Gln Ala Ile Glu Lys Ala
    130                 135                 140

Met Asp Glu Gly Val Leu Asp Thr Phe Pro Thr Asp Val Ile Leu Cys
145                 150                 155                 160

Ala His Trp Leu Ser Ala Asp Leu Phe Asn Phe Ser Lys Ala Phe Asp
                165                 170                 175
```

```
Gln Leu Lys Thr His Val Asn Gly Leu Arg Lys Thr Val Ala Ser Leu
            180                 185                 190

Asp Asp Val Tyr Gly Leu Glu Leu Asp Lys Val Met Ser Arg Arg Ile
            195                 200                 205

Asp Lys Glu Pro Leu Gln Val Asn Thr Lys Ser Arg Asn Lys Lys Thr
            210                 215                 220

Leu Tyr Ile Thr Phe Phe Asp Thr Met Leu Leu Ser Pro Asn Gly Ser
225                 230                 235                 240

Ser Leu Ser Ser Val Gly Asp Leu Leu Glu Ile Pro Lys Val Glu Ile
            245                 250                 255

Pro Glu Pro Tyr Ser Ile Ser Arg Met Asp Glu Phe Leu Glu Ala Glu
            260                 265                 270

Pro Glu Lys Phe Ala Glu Tyr Ala Leu Thr Asp Ala Ile Ile Ser Ala
            275                 280                 285

Arg His Phe Glu Arg Val Ser Leu Phe Cys Gln His Thr Leu Gly Leu
            290                 295                 300

Lys Ser Val Pro Phe Thr Ile Gly Gly Ile Ala Val Lys Ala Phe Val
305                 310                 315                 320

Asn Ser Leu Glu Asp Lys Arg Gly Tyr Arg Gly Leu Phe Gly Phe Glu
            325                 330                 335

Lys Val Thr Lys Glu Ile Trp Pro Ser Asp Arg Asn Lys Pro Leu Thr
            340                 345                 350

Ile Thr Arg Asp Val Pro Val Thr Ala Arg Met Thr Leu Glu Asn Phe
            355                 360                 365

Ala Thr Gln Cys Tyr His Gly Gly Arg Asn Glu Ser Phe Ile Ala Gly
            370                 375                 380

Pro Thr Gln Val Asp Thr Trp Arg Asp Tyr Asp Ile Pro Ser Cys Tyr
385                 390                 395                 400

Ser Ala Ile Thr Leu Gly Leu Arg Glu Leu Ala Tyr Glu Lys Met Tyr
            405                 410                 415

Met Thr Glu Asp Leu His Asp Leu Phe Gly Asp Lys Cys Ala Met Ala
            420                 425                 430

Trp Val Glu Phe Lys Phe Pro Glu Asn Thr Arg Phe Pro Ser Leu Ala
            435                 440                 445

Val Arg Ser Asp Tyr Gly Leu Leu Phe Pro Ile Thr Gly Glu Thr Tyr
450                 455                 460

Val Thr Gly His Glu Leu Glu Val Ala Tyr Asn Gln Gly Ala Glu Ile
465                 470                 475                 480

Thr Ile Lys Gln Ala Phe Val Ile Pro Trp Lys Asn Asp Val Arg Ile
            485                 490                 495

Phe Glu Asp Phe Met Lys Trp Gly Arg Glu Arg Lys Ser Phe Val
            500                 505                 510

Lys Gly Ser Phe Asp Glu Arg Leu Thr Lys Glu Met Leu Asn Ser Cys
            515                 520                 525

Tyr Gly Lys Met Ala Gln Ser Leu Arg Pro Lys Ser Ala Phe Asp Ile
            530                 535                 540

Gln Ala Gly Tyr Ser Lys Gln Leu Pro Pro Ser Thr Leu Thr Asn Pro
545                 550                 555                 560

Phe Phe Ala Ala Tyr Ile Thr Gly Leu Ala Arg Ala Tyr Leu Ser Phe
            565                 570                 575

Leu Ile His Ser Val Pro Ala Asn Lys Thr Val Ile Ser Ser Thr Thr
            580                 585                 590

Asp Gly Phe Leu Thr Asn Ala Ser Leu Asp Glu Ile Asp Leu Thr Ser
```

```
                    595                 600                 605
Pro Ile Cys Gln Arg Phe Arg Asp Leu Tyr His Arg Ile Asp Pro Ser
610                 615                 620

Gly Gly Glu Ile Leu Glu Leu Lys His Gln Ala Lys Gln Leu Ile Gly
625                 630                 635                 640

Ala Lys Thr Arg Ala Gln Tyr Thr Val Ile Glu Ser Asp Gly Phe Glu
                645                 650                 655

Pro Val Leu Ala Lys Gly Gly Ile Lys Val Asp Pro Thr Ile Val Asp
                660                 665                 670

Gln Ser Ala His Met Val Asp Lys Tyr Ile Asp Arg Ser Phe Asp Asp
                675                 680                 685

Lys Val Asp Gly Ser Tyr Leu Thr Pro Asn Arg Met Arg Phe Leu Glu
690                 695                 700

His Lys Asp Leu Met Leu Glu Lys Arg Ser Ile Phe Leu Asn Met Glu
705                 710                 715                 720

Tyr Asp Gln Lys Arg Glu Leu Met Asn Pro Lys Met Leu Asp Val Lys
                725                 730                 735

Asp Arg Gln His Ile Ala Leu Glu Thr Lys Pro His Tyr Ser Leu Gly
                740                 745                 750

Asp Met Leu Phe Thr Arg Leu Arg Phe Asp His Trp Arg Lys Gln His
                755                 760                 765

Cys Leu Lys Thr Leu Glu Asp Trp Tyr Asn Trp Gln Asp Arg Leu Ala
770                 775                 780

Met Ala Lys Ala Ser Asn Asn Lys Ser Leu Arg Leu Lys Ser Asp Glu
785                 790                 795                 800

Thr Ser Asp Ser Leu Met Ala Arg Leu Phe Leu Arg Phe Tyr Ala His
                805                 810                 815

Glu Gln Gly Gly Ile Ser Lys Ser Asp Ile Asn Ala Asn Gln Leu Ala
                820                 825                 830

Ser Trp Leu Thr Glu Gln Gly Tyr Pro Thr Lys Ser Thr Leu Val Arg
                835                 840                 845

Ser Ala Gly Lys Ser Lys Leu Ile Glu Ala Ala Val Pro Leu Thr Glu
850                 855                 860

Leu Thr Ile Lys Leu Ala Ile Leu Ile Lys Ser Lys Phe Pro Ser Phe
865                 870                 875                 880

Glu Ile Glu Lys Leu Phe Glu Pro Ile Ala Arg Glu Ser Leu Arg Ala
                885                 890                 895

Ala Leu Ser Ser Gln Leu Ser Ser
                900

<210> SEQ ID NO 14
<211> LENGTH: 903
<212> TYPE: PRT
<213> ORGANISM: Vibrio jasicida

<400> SEQUENCE: 14

Met Glu Glu Ser Met Asn Asn Trp Gly Glu Asp Ala Gly Val Glu Ile
1               5                   10                  15

Asp Glu Ser Phe Asp Gly Ile Glu Val Asp Glu Asn Leu Val Glu Ala
                20                  25                  30

Trp Gly Asn Ala Ser Asn Asp Glu Leu Leu Asp Glu Ser Val Gly Ser
            35                  40                  45

Ile Val Phe Glu Arg Met Gln Pro Val Glu Lys Val Ser Glu Tyr Val
50              55                  60
```

```
Lys Ser Lys Lys Glu Lys Lys Lys Glu Lys Arg Lys Ala Thr Pro
 65              70                  75                  80

Phe Phe Glu Arg Pro Val Ile Ala Met Asp Thr Glu Tyr Val Glu Ser
             85                  90                  95

Glu Cys Gly Thr Tyr Asn Arg Ile Leu Ser Tyr Gln Phe Ala Val Leu
            100                 105             110

Tyr Lys Gly Lys Leu Ser Thr Thr Ile Leu Phe Pro Glu Ser Thr Lys
        115                 120             125

Lys Leu Gly Arg Leu Ala Leu Asp Lys Cys Leu Val Gln Ala Ile Glu
        130                 135             140

Lys Ala Met Asp Asp Glu Val Leu Asp Arg Trp Pro Thr Asp Ile Ile
145             150                 155                 160

Leu Cys Ala His Trp Leu Ser Ala Asp Leu Phe Asn Phe Ser Gln Ala
                165                 170             175

Phe Glu Gln Leu Lys Thr His Val Lys Gly Leu Arg Lys Thr Val Ala
            180                 185             190

Ser Leu Asp Asp Val Tyr Gly Leu Asp Leu Glu Asn Val Met Ser Arg
            195                 200             205

Arg Ile Asp Lys Glu Pro Leu Gln Thr Tyr Ser Lys Ser Gly Asn Lys
        210                 215             220

Lys Thr Leu Tyr Ile Thr Phe Tyr Asp Thr Met Leu Leu Ala Pro Asn
225             230                 235                 240

Gly Gln Ser Leu Ala Ser Val Gly Lys Ile Leu Lys Val Pro Lys Val
                245                 250             255

Glu Ile Pro Glu Pro Phe Ser Ile Ser Arg Met Asp Glu Phe Leu Ala
            260                 265             270

Ala Glu Pro Glu Gln Phe Ala Glu Tyr Ala Ile Thr Asp Ala Ile Ile
        275                 280             285

Ser Ala Arg His Phe Glu Arg Val Ser Ser Phe Cys Gln Gln Thr Leu
        290                 295             300

Gly Leu Lys Ser Val Pro Phe Thr Ile Gly Ile Ala Val Lys Ala
305             310                 315                 320

Phe Val Asn Ser Leu Glu Asp Lys Arg Ser Tyr Arg Gly Leu Phe Gly
            325                 330             335

Phe Glu Lys Val Thr Lys Glu Val Trp Pro Ser Asp Arg Thr Lys Pro
            340                 345             350

Leu Thr Leu Thr Arg Asp Val Pro Val Thr Ala Arg Met Thr Leu Glu
        355                 360             365

Asn Phe Ala Thr Gln Cys Tyr His Gly Gly Arg Asn Glu Ser Phe Ile
370             375                 380

Ala Gly Pro Thr Val Ile Asp Thr Trp Arg Asp Tyr Asp Val Pro Ser
385             390                 395             400

Cys Tyr Ser Ala Ile Thr Leu Gly Leu Arg Glu Leu Ala Tyr Glu Gln
            405                 410             415

Met Tyr Met Thr Lys Asp Leu Asn Asp Leu Phe Gly Asp Lys Cys Ala
            420                 425             430

Met Ala Trp Val Glu Phe Lys Phe Pro Glu Arg Thr Arg Phe Pro Ser
        435                 440             445

Leu Ala Val Arg Ser Asp Tyr Gly Leu Val Phe Pro Leu Thr Gly Val
        450                 455             460

Thr His Cys Thr Gly His Glu Leu Glu Val Ala Lys Asn Gln Gly Ala
465             470                 475             480

Glu Ile Thr Val Lys Gln Ala Phe Val Ile Pro Trp Ala Asn Asp Glu
```

-continued

```
                485                 490                 495
Arg Ile Phe Glu Pro Phe Met Lys Trp Gly Arg Glu Arg Lys Ser
                500                 505                 510
Phe Asp Lys Gly Ser Phe Asp Glu Lys Leu Thr Lys Glu Met Leu Asn
                515                 520                 525
Ser Cys Tyr Gly Lys Leu Ala Gln Ser Leu Arg Pro Lys Thr Ala Phe
                530                 535                 540
Asp Ile Gln Ala Gly Tyr Ser Lys Gln Leu Pro Ser Ser Thr Leu Thr
545                 550                 555                 560
Asn Pro Phe Phe Ala Ala Tyr Thr Thr Gly Leu Ala Arg Ala Leu Leu
                565                 570                 575
Gly Glu Met Leu His Ser Ile Pro Asp Asp Lys Val Val Ser Val
                580                 585                 590
Thr Thr Asp Gly Phe Leu Thr Asn Ala Thr Leu Asp Glu Ile Lys Leu
                595                 600                 605
Asp Gly Val Ile Cys Gln Arg Phe Arg Asp Leu Tyr His Arg Ile Asp
                610                 615                 620
Pro Ser Lys Gly Lys Val Leu Glu Leu Lys His Gln Ala Thr Gln Leu
625                 630                 635                 640
Ile Gly Ala Lys Thr Arg Ala Gln Tyr Thr Val Ile Lys Ser Glu Gly
                645                 650                 655
Tyr Glu Pro Ile Leu Ala Lys Gly Gly Val Lys Val Asp Pro Met Val
                660                 665                 670
Thr Asp Gln Ser Ala Tyr Met Val Asn Lys Tyr Leu Glu Arg Gln Pro
                675                 680                 685
Asp Asp Lys Val Asp Gly Ser Tyr Leu Thr Pro Asn Arg Ile Arg Phe
                690                 695                 700
Leu Glu Gln Lys Asp Leu Met Leu Glu Lys Arg Ser Ile Phe Leu Asn
705                 710                 715                 720
Met Glu Tyr Asp Gln Lys Arg Glu Leu Val Asn Pro Lys Met Ile Asp
                725                 730                 735
Val Lys Gly Lys Gln His Ile Ala Leu Glu Thr Val Pro His Gln Ser
                740                 745                 750
Leu Asp Ser Met Ser Phe Thr Arg Ile Arg Phe Asp His Trp Arg Lys
                755                 760                 765
Asn His Cys Leu Lys Ser Met Gly Asp Trp His Asp Trp Gln Glu Arg
                770                 775                 780
Leu Ser Met Tyr Lys Ala Asn Asp Lys Arg Glu Ile Arg Leu Lys Lys
785                 790                 795                 800
Ala Glu Lys Ser Asp Glu Leu Met Ala Arg Leu Phe Val Arg Phe Tyr
                805                 810                 815
Gly His Glu Val Ser Gly Ile Thr Lys Lys Asp Ile Thr Ala Lys Ala
                820                 825                 830
Leu Ser Asp Trp Leu Val Ser Leu Gly Tyr Asp Ile Lys Pro Ser Leu
                835                 840                 845
Val Arg Gly Ala Gly Arg Thr Lys Leu Val Glu Gly Val Pro Val
                850                 855                 860
Thr His Ser Thr Leu Lys Leu Thr Lys Leu Leu Val Gly Lys Phe Pro
865                 870                 875                 880
Gln Phe Asp Pro Val Pro Leu Phe Asn Ser Ser Arg Glu Glu Ile Met
                885                 890                 895
Arg Gln Leu Glu Asn Ile Ser
                900
```

<210> SEQ ID NO 15
<211> LENGTH: 897
<212> TYPE: PRT
<213> ORGANISM: Vibrio sp. J2-4

<400> SEQUENCE: 15

```
Met Asn Glu Thr Tyr Ser Trp Leu Glu Gln Asp Ser Asn Leu Lys Met
1               5                   10                  15

Asp Thr Leu Ala Ala Ser Gly Trp Met Glu Asp Pro Val Ser Thr
            20                  25                  30

Trp Met Lys Pro Gln Ser Asp Val Ser Glu Pro Asp Leu Gly Val Lys
        35                  40                  45

Arg Lys Ala Lys Pro Ile Leu Leu Arg Lys Pro Lys Lys Lys Gln
    50                  55                  60

Thr Lys Arg Lys Lys Arg Lys Ala Thr Pro Phe Phe Glu Arg Pro Val
65                  70                  75                  80

Val Ala Ile Asp Thr Glu Tyr Arg Glu Ser Glu Asp Glu Thr Tyr Asn
                85                  90                  95

Arg Ile Ile Ser Tyr Gln Val Ala Val Leu Phe Arg Gly Lys Leu Ser
            100                 105                 110

Thr Ile Ile Leu Tyr Pro Glu Ser Thr Lys Lys Ser Gly Arg Leu Ala
        115                 120                 125

Leu Asp Lys Cys Leu Val Gln Ala Ile Glu Lys Ala Met Asp Glu Gly
    130                 135                 140

Val Leu Asp Ala Trp Pro Thr Asp Ile Ile Leu Cys Ala His Trp Leu
145                 150                 155                 160

Ser Ala Asp Leu Phe Asn Phe Ser Gln Ala Phe Asp Gln Leu Lys Thr
                165                 170                 175

His Val Lys Gly Leu Arg Lys Thr Val Ala Ser Leu Asp Asp Val Tyr
            180                 185                 190

Gly Leu Glu Leu Asp Lys Val Met Ser Arg Arg Ile Asp Lys Glu Pro
        195                 200                 205

Leu Gln Val Arg Thr Lys Thr Arg Asn Pro Lys Thr Leu Tyr Ile Thr
    210                 215                 220

Phe Tyr Asp Thr Met Leu Leu Ser Pro Asn Gly Ser Ser Leu Ala Ser
225                 230                 235                 240

Val Gly Glu Leu Leu Lys Val Pro Lys Val Glu Ile Pro Glu Pro Tyr
                245                 250                 255

Ser Ile Ser Arg Met Asp Glu Phe Leu Glu Ala Glu Pro Glu Met Phe
            260                 265                 270

Ala Glu Tyr Ala Ile Thr Asp Ala Ile Ile Ser Ala Arg His Phe Glu
        275                 280                 285

Arg Val Ser Ala Phe Cys Gln His Thr Leu Gly Leu Asn Ser Val Pro
    290                 295                 300

Phe Thr Ile Gly Gly Ile Ala Val Lys Ala Phe Val Asn Ser Leu Glu
305                 310                 315                 320

Glu Gln Gln Gly Tyr Arg Gly Leu Phe Gly Phe Glu Lys Val Thr Lys
                325                 330                 335

Glu Val Trp Pro Ser Asp Arg Thr Lys Pro Leu Thr Ile Thr Arg Asp
            340                 345                 350

Val Pro Val Thr Ala Arg Met Thr Leu Glu Asn Phe Ala Thr Gln Cys
        355                 360                 365

Tyr His Gly Gly Arg Asn Glu Ser Phe Ile Ala Gly Pro Ser Val Ile
```

```
              370                 375                 380
Asp Thr Trp Arg Asp Tyr Asp Val Pro Ser Cys Tyr Ser Ala Ile Thr
385                 390                 395                 400

Leu Gly Leu Arg Glu Leu Ala Tyr Asp Gln Met Tyr Met Thr Lys Asp
                405                 410                 415

Leu His Asp Leu Phe Gly Asp Lys Cys Ala Leu Ala Trp Val Glu Phe
            420                 425                 430

Lys Phe Pro Glu Asn Thr Arg Phe Pro Ser Leu Ala Val Arg Ser Glu
        435                 440                 445

Tyr Gly Leu Ile Phe Pro Leu Ser Gly Glu Thr His Cys Thr Gly His
    450                 455                 460

Glu Leu Glu Val Ala Tyr Asn Gln Gly Val Glu Ile Thr Ile Lys Gln
465                 470                 475                 480

Ala Phe Val Val Pro Trp Lys Asn Asp Glu Arg Ile Phe Glu Ser Phe
                485                 490                 495

Met Lys Trp Gly Arg Glu Arg Lys Ser Phe Val Lys Gly Ser Phe
            500                 505                 510

Asp Glu Lys Leu Thr Lys Glu Met Leu Asn Ser Cys Tyr Gly Lys Leu
        515                 520                 525

Ala Gln Ser Leu Arg Pro Lys Asn Ser Phe Asp Ile Gln Ala Gly Tyr
    530                 535                 540

Ser Lys Gln Leu Pro Pro Ser Thr Leu Thr Asn Pro Phe Phe Ala Ala
545                 550                 555                 560

Tyr Thr Thr Gly Leu Ala Arg Ala Leu Leu Gly Glu Gln Leu His Ser
                565                 570                 575

Ile Pro Asp Asp Lys Val Val Ser Val Thr Thr Asp Gly Phe Leu
            580                 585                 590

Thr Asn Ala Glu Leu Asp Glu Ile Asp Leu Ser Gly Ser Ile Cys Gln
        595                 600                 605

Arg Phe Arg Glu Leu Tyr His Arg Ile Asp Pro Thr Gly Gly Glu Val
    610                 615                 620

Leu Glu Leu Lys His Gln Ala Thr Gln Leu Ile Gly Ala Lys Thr Arg
625                 630                 635                 640

Ala Gln Tyr Thr Val Ile Glu Ser Glu Gly Phe Glu Pro Val Leu Ala
                645                 650                 655

Lys Gly Gly Val Lys Val Asp Pro Thr Ile Thr Asp Gln Ser Ala Tyr
            660                 665                 670

Met Val Glu Lys Tyr Leu Ala Arg Lys Pro Gly Asp Lys Val Asp Gly
        675                 680                 685

Ser Tyr Leu Thr Pro Asn Arg Met Arg Phe Leu Glu His Lys Asp Leu
    690                 695                 700

Met Leu Glu Lys Arg Ser Ile Tyr Leu Asn Met Glu Phe Asp Gln Lys
705                 710                 715                 720

Arg Glu Met Leu Asn Pro Val Met Val Asp Val Gln Gly Arg Gln His
                725                 730                 735

Ile Ala Leu Glu Thr Lys Pro His Gln Ser Leu Asp Glu Met Leu Phe
            740                 745                 750

Thr Arg Leu Arg Phe Asp Arg Trp Arg Lys Ser His Val Leu Lys Asp
        755                 760                 765

Phe Asp Asp Trp Cys Ser Trp Gln Asp Arg Leu Val Met Ala Glu Ser
    770                 775                 780

Thr Ser His Lys Asp Val Arg Leu Lys Ala Asp Glu Thr Ser Asp Ser
785                 790                 795                 800
```

```
Leu Met Ala Arg Leu Phe Leu Arg Phe Tyr Ala His Glu Lys Asn Gly
                805                 810                 815

Met Arg Lys Lys Asp Ile Thr Ala Lys Ala Leu Ala Glu Trp Leu Thr
            820                 825                 830

Asp Leu Gly Tyr Pro Thr Lys Ala Thr Ala Val Arg Ser Ala Lys Gln
            835                 840                 845

Ser Lys Leu Ile Glu Gly Ala Val Pro Ile Thr Glu Leu Thr Thr Asn
        850                 855                 860

Leu Ala Arg Leu Ile Val Ser Lys Phe Pro Asp Phe Glu Val Glu Ile
865                 870                 875                 880

Leu Phe Asn Pro Asp Ser Arg Ser Leu Arg Glu Ala Leu Ser Val
                885                 890                 895

Asn

<210> SEQ ID NO 16
<211> LENGTH: 897
<212> TYPE: PRT
<213> ORGANISM: Vibrio parahaemolyticus NBRC 12711

<400> SEQUENCE: 16

Met Ser Lys Asn Phe Asn Trp Leu Glu Gln Ser Ser Asp Leu Ser Met
1               5                   10                  15

Asp Asn Leu Ala Thr Ser Gly Trp Thr Glu Glu Ala Val Ser Ala
            20                  25                  30

Trp Gly Glu Ala Gln Pro Ser Glu Pro Ala Ser Phe Asp Gly Val Lys
        35                  40                  45

Arg Lys Ala Lys Ser Ile Val Leu Arg Lys Pro Lys Lys Lys Gln
    50                  55                  60

Thr Lys Arg Lys Lys Arg Lys Ala Thr Pro Phe Glu Arg Pro Val
65                  70                  75                  80

Ile Ala Met Asp Thr Glu Tyr Val Val Ser Lys Cys Gly Gly Tyr Asn
                85                  90                  95

Arg Ile Leu Ser Tyr Gln Phe Ala Val Leu Phe Gln Gly Lys Leu Ser
            100                 105                 110

Thr Ile Ile Leu Phe Pro Glu Ser Thr Lys Ser Gly Arg Leu Ala
            115                 120                 125

Leu Asp Lys Cys Leu Val Gln Ala Ile Glu Lys Ala Met Glu Asp Glu
        130                 135                 140

Val Leu Asp Lys Trp Pro Thr Asp Ile Ile Leu Cys Ala His Trp Leu
145                 150                 155                 160

Ser Ala Asp Leu Phe Asn Phe Ser Gln Ala Phe Asp Gln Leu Lys Thr
                165                 170                 175

His Val Lys Gly Leu Arg Lys Thr Val Ala Ser Leu Asp Asp Val Tyr
            180                 185                 190

Gly Leu Glu Leu Asp Lys Val Met Ser Arg Arg Ile Asp Lys Glu Pro
        195                 200                 205

Leu Gln Ala Tyr Ser Lys Ser Gly Asn Lys Lys Thr Leu Phe Ile Thr
    210                 215                 220

Phe Tyr Asp Thr Met Leu Leu Ser Pro Asn Gly Ser Ser Leu Ala Ser
225                 230                 235                 240

Val Gly Glu Leu Leu Lys Ile Pro Lys Val Glu Ile Pro Glu Pro Tyr
                245                 250                 255

Ser Ile Ser Arg Met Asp Glu Phe Leu Glu Ala Glu Pro Glu Lys Phe
            260                 265                 270
```

```
Ala Glu Tyr Ala Ile Thr Asp Ser Ile Ile Ser Ala Arg His Phe Glu
            275                 280                 285

Arg Val Ser Ser Phe Cys Gln Asn Thr Leu Gly Leu Asn Ser Val Pro
290                 295                 300

Phe Thr Ile Gly Gly Ile Ala Val Lys Ala Phe Val Asn Ser Leu Glu
305                 310                 315                 320

Asp Lys Arg Gly Tyr Arg Gly Leu Phe Gly Phe Glu Lys Val Thr Lys
                325                 330                 335

Glu Val Trp Pro Ser Asp Arg Ser Lys Pro Leu Thr Ile Thr Arg Asp
                340                 345                 350

Val Pro Ala Thr Ala Arg Met Thr Leu Glu Asn Phe Ala Thr Gln Cys
            355                 360                 365

Tyr His Gly Gly Arg Asn Glu Ser Phe Ile Ala Gly Pro Thr Gly Ile
        370                 375                 380

Asp Thr Trp Arg Asp Tyr Asp Val Pro Ser Cys Tyr Ser Ala Ile Thr
385                 390                 395                 400

Leu Gly Leu Arg Glu Leu Asp Tyr Asp Gln Met Tyr Met Thr Lys Asp
                405                 410                 415

Leu Asn Asp Leu Leu Gly Asp Lys Cys Ala Leu Ala Trp Val Glu Phe
            420                 425                 430

Lys Phe Pro Glu His Thr Arg Phe Pro Ser Leu Ala Val Arg Ser Glu
        435                 440                 445

Tyr Gly Leu Ile Phe Pro Leu Ser Gly Glu Thr His Cys Thr Gly His
        450                 455                 460

Glu Leu Glu Val Ala Tyr Asn Gln Gly Ala Glu Ile Thr Ile Lys Gln
465                 470                 475                 480

Ala Phe Val Val Pro Trp Lys Asn Asp Lys Arg Ile Phe Glu Asp Phe
                485                 490                 495

Met Arg Trp Gly Arg Glu Arg Lys Ser Phe Val Lys Gly Ser Phe
                500                 505                 510

Asp Glu Lys Leu Thr Lys Glu Met Leu Asn Ser Cys Tyr Gly Lys Leu
            515                 520                 525

Ala Gln Ser Leu Arg Pro Lys Arg Ser Phe Asp Ile Gln Ala Gly Tyr
        530                 535                 540

Ser Thr Gln Leu Pro Pro Ser Thr Leu Thr Asn Pro Phe Phe Ala Ala
545                 550                 555                 560

Tyr Thr Thr Gly Leu Ala Arg Ala Leu Leu Gly Glu Met Leu His Ser
                565                 570                 575

Ile Pro Asp Asp Lys Val Val Val Ser Val Thr Thr Asp Gly Phe Leu
                580                 585                 590

Thr Asn Ala Glu Leu His Glu Ile Asp Leu Lys Gly Pro Ile Cys Gln
            595                 600                 605

Arg Phe Arg Glu Leu Tyr His Arg Ile Asp Pro Thr Gly Gly Glu Val
        610                 615                 620

Leu Glu Leu Lys His Gln Ala Lys Gln Leu Ile Gly Ala Lys Thr Arg
625                 630                 635                 640

Ala Gln Tyr Thr Val Ile Glu Ser Glu Gly Phe Glu Pro Ile Leu Ala
                645                 650                 655

Lys Gly Ser Val Lys Val Asp Pro Met Val Thr Asp Gln Ser Ala Tyr
                660                 665                 670

Met Val Asn Lys Tyr Leu Thr Arg Lys Pro Gly Asp Lys Val Asp Gly
            675                 680                 685
```

Ser Tyr Leu Thr Pro Asn Arg Met Arg Phe Leu Glu His Lys Asp Leu
690                 695                 700

Met Leu Glu Lys Arg Ser Ile Tyr Gln Asn Met Glu Phe Asp Gln Lys
705                 710                 715                 720

Arg Glu Leu Leu Asn Pro Val Met Ile Asp Val Gln Gly Ser Lys His
                725                 730                 735

Ile Ala Leu Glu Thr Lys Pro His Lys Ser Leu Asp Glu Met Leu Phe
            740                 745                 750

Thr Arg Leu Arg Phe Asp His Trp Arg Lys Ala His Cys Leu Lys Thr
        755                 760                 765

Phe Glu Asp Trp Tyr Asp Trp Gln Asp Arg Leu Val Met Ala Glu Ser
770                 775                 780

Thr Ser His Lys Asp Leu Arg Leu Lys Ala Asp Glu Thr Ser Asp Ser
785                 790                 795                 800

Leu Met Ala Arg Leu Phe Leu Arg Phe Tyr Ala Gln Glu Gln Gly Gly
                805                 810                 815

Met Ser Lys Lys Gln Ile Ser Ala Lys Ala Leu Ala Glu Trp Leu Thr
            820                 825                 830

Asp Asn Gly Tyr Ser Thr Lys Ala Asn Ser Val Ser Arg Ala Met Lys
        835                 840                 845

Ala Lys Leu Ile Glu Gly Ala Val Pro Met Thr Glu Leu Thr Val Asn
850                 855                 860

Leu Ala Arg Leu Ile Val Ser Lys Phe Pro Asp Phe Glu Val Glu Ile
865                 870                 875                 880

Leu Phe Asn Pro Asp Ser Arg Ser Ser Leu Arg Glu Ala Leu Ser Pro
                885                 890                 895

Asn

<210> SEQ ID NO 17
<211> LENGTH: 897
<212> TYPE: PRT
<213> ORGANISM: Vibrio furnissii NCTC 11218

<400> SEQUENCE: 17

Met Asn Glu Asn Phe Asp Trp Leu Glu Gln Ala Ser Asp Leu Ser Met
1               5                   10                  15

Asp Asn Leu Ala Thr Ser Gly Trp Thr Glu Glu Ala Val Ser Ala
            20                  25                  30

Trp Gly Glu Ala Gln Pro Ser Glu Pro Thr Ser Phe Asp Ser Val Lys
        35                  40                  45

Arg Lys Ala Lys Pro Leu Val Gly Arg Lys Pro Lys Lys Lys Gln
50                  55                  60

Thr Lys Arg Lys Arg Arg Glu Ala Thr Pro Phe Phe Glu Arg Pro Val
65                  70                  75                  80

Ile Ala Met Asp Thr Glu Tyr Val Glu Ser Glu Cys Gly Thr Tyr Asn
                85                  90                  95

Arg Ile Leu Ser Tyr Gln Phe Ala Val Leu Phe Glu Gly Lys Leu Ser
            100                 105                 110

Thr Ile Ile Leu Leu Pro Glu Ser Thr Lys Lys Ser Gly Arg Leu Ala
        115                 120                 125

Leu Asp Arg Cys Leu Val Gln Ala Ile Glu Lys Ala Met Asp Asp Glu
130                 135                 140

Val Leu Asp Lys Trp Pro Thr Asp Ile Ile Leu Cys Ala His Trp Leu
145                 150                 155                 160

```
Ser Ala Asp Leu Phe Asn Phe Ser Gln Ala Phe Asp Gln Leu Lys Thr
            165                 170                 175
His Val Lys Gly Leu Arg Lys Thr Val Ala Ser Leu Asp Asp Val Tyr
        180                 185                 190
Gly Leu Asp Leu Asp Lys Val Met Ser Arg Arg Ile Asp Lys Glu Pro
            195                 200                 205
Leu Asn Val His Asp Lys Ser Arg Asn Arg His Thr Leu Tyr Ile Thr
        210                 215                 220
Phe Tyr Asp Thr Met Leu Leu Ser Pro Asn Gly Ser Ser Leu Ala Ser
225                 230                 235                 240
Val Gly Glu Leu Leu Lys Ile Pro Lys Val Glu Ile Pro Glu Pro Tyr
            245                 250                 255
Ser Ile Ser Arg Met Asp Glu Phe Leu Glu Ala Gln Pro Gln Lys Phe
        260                 265                 270
Ala Glu Tyr Ser Ile Thr Asp Ser Ile Ile Ser Ala Arg His Phe Glu
            275                 280                 285
Arg Val Ser Ala Phe Cys Gln His Thr Leu Gly Leu Lys Ser Val Pro
        290                 295                 300
Phe Thr Ile Gly Gly Ile Ala Val Lys Ala Phe Val Asn Ser Leu Glu
305                 310                 315                 320
Asp Lys Arg Gly Tyr Arg Gly Leu Phe Gly Phe Glu Lys Val Thr Lys
            325                 330                 335
Glu Val Trp Pro Ser Asp Arg Ser Lys Pro Leu Thr Ile Thr Arg Asp
        340                 345                 350
Val Pro Ala Thr Ala Arg Met Thr Leu Glu Asn Phe Ala Thr Gln Cys
        355                 360                 365
Tyr His Gly Gly Arg Asn Glu Ser Phe Ile Ala Gly Pro Thr Gly Ile
        370                 375                 380
Asp Thr Trp Arg Asp Tyr Asp Val Pro Ser Cys Tyr Ser Ala Ile Thr
385                 390                 395                 400
Leu Gly Leu Arg Glu Leu Ala Tyr Asp Gln Met Tyr Met Ile Arg Asp
            405                 410                 415
Leu Asn Glu Leu Phe Gly Asp Lys Cys Ala Leu Ala Trp Val Glu Phe
        420                 425                 430
Lys Phe Pro Glu His Thr Arg Phe Pro Ser Leu Ala Val Arg Ser Glu
        435                 440                 445
Tyr Gly Leu Ile Phe Pro Leu Ser Gly Glu Thr His Cys Thr Gly His
        450                 455                 460
Glu Leu Glu Val Ala Tyr Asn Gln Gly Ala Glu Ile Thr Ile Lys Gln
465                 470                 475                 480
Ala Phe Val Val Pro Trp Lys Asn Asp Val Arg Ile Phe Glu Pro Phe
            485                 490                 495
Met Lys Trp Gly Arg Glu Arg Arg Lys Ser Phe Thr Lys Gly Ser Phe
        500                 505                 510
Asp Glu Lys Leu Thr Lys Glu Met Leu Asn Ser Cys Tyr Gly Lys Leu
        515                 520                 525
Ala Gln Ser Leu Arg Pro Lys Arg Ser Phe Asp Ile Gln Ala Gly Tyr
        530                 535                 540
Ser Thr Gln Leu Pro Pro Ser Thr Leu Thr Asn Pro Phe Phe Ala Ala
545                 550                 555                 560
Tyr Thr Thr Gly Leu Ala Arg Ala Leu Leu Gly Glu Met Leu His Asn
            565                 570                 575
Ile Pro Asp Asp Lys Val Val Val Ser Val Thr Thr Asp Gly Phe Leu
```

```
            580                 585                 590

Thr Asn Ala Glu Leu His Glu Ile Asp Leu Lys Gly Pro Ile Cys Lys
        595                 600                 605

Arg Phe Arg Glu Leu Tyr His Arg Ile Asp Pro Thr Gly Gly Glu Val
    610                 615                 620

Leu Glu Leu Lys His Gln Ala Lys Gln Leu Ile Gly Ala Lys Thr Arg
625                 630                 635                 640

Ala Gln Tyr Thr Val Ile Glu Ser Glu Gly Phe Glu Pro Ile Leu Ala
                645                 650                 655

Lys Gly Ser Val Lys Val Asp Pro Met Val Thr Asp Gln Ser Ala Tyr
            660                 665                 670

Met Val Asn Lys Tyr Leu Thr Arg Lys Pro Gly Asp Lys Val Asp Gly
        675                 680                 685

Ser Tyr Leu Thr Pro Asn Arg Met Arg Phe Leu Glu His Lys Asp Leu
    690                 695                 700

Met Leu Glu Lys Arg Ser Ile Tyr Gln Asn Met Glu Phe Asp Gln Lys
705                 710                 715                 720

Arg Gln Leu Leu Asn Pro Val Met Val Asp Val Lys Gly Arg Ser His
                725                 730                 735

Ile Ala Leu Glu Thr Lys Pro His Lys Ser Leu Asp Glu Met Leu Phe
            740                 745                 750

Thr Arg Leu Arg Phe Asp His Trp Arg Lys Ser His Val Leu Lys Asp
        755                 760                 765

Phe Asp Asp Trp Cys Ser Trp Gln Asp Arg Leu Val Met Ala Glu Ser
    770                 775                 780

Thr Ser His Lys Met Leu Arg Leu Lys Ala Asp Glu Thr Ser Asp Arg
785                 790                 795                 800

Leu Met Ala Arg Leu Phe Leu Arg Phe Tyr Ala Gln Glu Gln Gly Gly
                805                 810                 815

Met Ser Lys Lys Gln Ile Thr Ala Lys Ala Leu Ala Glu Trp Met Thr
            820                 825                 830

Asp Ile Gly Tyr Pro Thr Lys Ala Thr Ala Val Arg Ser Ala Lys Asn
        835                 840                 845

Ala Lys Leu Ile Glu Gly Ala Val Pro Ile Thr Glu Leu Thr Ile Asn
    850                 855                 860

Leu Ala Arg Leu Ile Val Ser Lys Phe Pro Asp Phe Glu Val Glu Ile
865                 870                 875                 880

Leu Phe Asn Pro Glu Ser Arg Ser Ser Leu Arg Glu Ala Leu Tyr Ala
                885                 890                 895

Arg

<210> SEQ ID NO 18
<211> LENGTH: 900
<212> TYPE: PRT
<213> ORGANISM: Vibrio fluvialis

<400> SEQUENCE: 18

Met Asn Glu Lys Tyr Asp Trp Leu Glu Gln Ala Ser Asp Leu Ser Met
1               5                   10                  15

Asp Asn Leu Ala Thr Ser Gly Trp Thr Glu Glu Glu Ala Val Ser Ala
            20                  25                  30

Trp Gly Glu Ala Gln Pro Ser Glu Pro Ala Ser Phe Asp Gly Val Lys
        35                  40                  45

Arg Lys Ala Lys Ser Ile Val Leu Arg Lys Pro Lys Lys Lys Lys Gln
```

```
                50                  55                  60
Thr Lys Arg Lys Lys Arg Lys Ala Thr Pro Phe Phe Glu Arg Pro Val
 65                  70                  75                  80

Ile Ala Met Asp Thr Glu Tyr Val Glu Ser Glu Cys Gly Thr Tyr Asn
                     85                  90                  95

Arg Ile Leu Ser Tyr Gln Phe Ala Val Leu Phe Glu Gly Lys Leu Ser
                100                 105                 110

Thr Ile Ile Leu Phe Pro Glu Ser Thr Lys Lys Ser Gly Arg Leu Ala
                115                 120                 125

Leu Asp Arg Cys Leu Val Gln Ala Ile Glu Lys Ala Met Asp Asp Lys
130                 135                 140

Val Leu Asp Lys Trp Pro Thr Asp Ile Ile Leu Cys Ala His Trp Leu
145                 150                 155                 160

Ser Ala Asp Leu Phe Asn Phe Ser Gln Ala Phe Asp Gln Leu Lys Thr
                165                 170                 175

His Val Lys Gly Leu Arg Lys Thr Val Ala Ser Leu Asp Asp Val Tyr
                180                 185                 190

Gly Leu Glu Leu Asp Lys Val Met Ser Arg Arg Ile Asp Lys Glu Pro
                195                 200                 205

Leu Gln Ala Tyr Ser Lys Ser Gly Asn Lys Lys Thr Leu Phe Ile Thr
210                 215                 220

Phe Tyr Asp Thr Met Leu Leu Ser Pro Asn Gly Ser Ser Leu Ser Ser
225                 230                 235                 240

Leu Ser Ser Val Gly Asp Leu Leu Ser Ile Pro Lys Val Glu Ile Pro
                245                 250                 255

Glu Pro Tyr Ser Ile Ser Arg Met Asp Glu Phe Leu Glu Ala Gln Pro
                260                 265                 270

Glu Lys Phe Ala Glu Tyr Ala Ile Thr Asp Ser Ile Ile Ser Ala Arg
                275                 280                 285

His Phe Glu Arg Val Ser Ser Phe Cys Gln Asn Thr Leu Gly Leu Asn
                290                 295                 300

Ser Val Pro Phe Thr Ile Gly Gly Ile Ala Val Lys Ala Phe Val Asn
305                 310                 315                 320

Ser Leu Glu Asp Lys Arg Gly Tyr Arg Gly Leu Phe Gly Phe Glu Lys
                325                 330                 335

Val Thr Lys Glu Val Trp Pro Ser Asp Arg Ser Lys Pro Leu Thr Ile
                340                 345                 350

Thr Arg Asp Val Pro Ala Thr Ala Arg Met Thr Leu Glu Asn Phe Ala
                355                 360                 365

Thr Gln Cys Tyr His Gly Gly Arg Asn Glu Ser Phe Ile Ala Gly Pro
                370                 375                 380

Thr Asp Ile Asp Thr Trp Arg Asp Tyr Asp Val Pro Ser Cys Tyr Ser
385                 390                 395                 400

Ala Ile Thr Leu Gly Leu Arg Glu Leu Asp Tyr Asp Gln Met Tyr Met
                405                 410                 415

Thr Lys Asp Leu Asn Asp Leu Leu Gly Asp Lys Cys Ala Leu Ala Trp
                420                 425                 430

Val Glu Phe Thr Phe Pro Ser Thr Cys Arg Phe Pro Ser Leu Ala Val
                435                 440                 445

Arg Ser Glu Tyr Gly Leu Ile Phe Pro Leu Ser Gly Glu Thr His Cys
450                 455                 460

Thr Gly His Glu Leu Glu Val Ala Tyr Asn Gln Gly Ala Glu Ile Thr
465                 470                 475                 480
```

```
Ile Lys Gln Ala Phe Val Val Pro Trp Lys Asn Asp Val Arg Ile Phe
            485                 490                 495

Glu Pro Phe Met Lys Trp Gly Arg Glu Arg Lys Ser Phe Val Lys
            500                 505                 510

Gly Ser Phe Asp Glu Lys Leu Thr Lys Glu Met Leu Asn Ser Cys Tyr
            515                 520                 525

Gly Lys Leu Ala Gln Ser Leu Arg Pro Lys Asn Ser Phe Asp Ile Gln
530                 535                 540

Ala Gly Tyr Ser Lys Gln Leu Pro Pro Ser Thr Leu Thr Asn Pro Phe
545                 550                 555                 560

Phe Ala Ala Tyr Thr Thr Gly Leu Ala Arg Ala Leu Leu Gly Glu Met
                565                 570                 575

Leu His Asn Ile Pro Asp Asp Lys Val Val Ser Val Thr Thr Asp
            580                 585                 590

Gly Phe Leu Thr Asn Ala Glu Leu His Glu Ile Asp Leu Lys Gly Pro
            595                 600                 605

Ile Cys Gln Arg Phe Arg Glu Leu Tyr His Arg Ile Asp Pro Thr Gly
            610                 615                 620

Gly Glu Val Leu Glu Leu Lys His Gln Ala Lys Gln Leu Ile Gly Ala
625                 630                 635                 640

Lys Thr Arg Ala Gln Tyr Thr Val Ile Glu Ser Glu Gly Phe Glu Pro
                645                 650                 655

Ile Leu Ala Lys Gly Ser Val Lys Val Asp Pro Met Val Thr Asp Gln
            660                 665                 670

Ser Ala Tyr Met Val Asn Lys Tyr Leu Thr Arg Lys Pro Gly Asp Lys
            675                 680                 685

Val Asp Gly Ser Tyr Leu Thr Pro Asn Arg Met Arg Phe Leu Glu His
            690                 695                 700

Lys Asp Leu Met Leu Glu Lys Arg Ser Ile Tyr Gln Asn Met Glu Phe
705                 710                 715                 720

Asp Gln Lys Arg Gln Leu Leu Asn Pro Val Met Val Asp Val Lys Gly
                725                 730                 735

Arg Ser His Ile Ala Leu Glu Thr Lys Pro His Lys Ser Leu Asp Glu
            740                 745                 750

Met Leu Phe Thr Arg Leu Arg Phe Asp His Trp Arg Lys Ala His Cys
            755                 760                 765

Leu Lys Thr Ser Glu Asp Trp Tyr Asp Trp Gln Asp Arg Leu Val Met
770                 775                 780

Ala Glu Thr Ala Ser Asn Gln Asn Leu Arg Leu Lys Ala Lys Glu Ala
785                 790                 795                 800

Ser Asp Ser Leu Met Ala Arg Leu Phe Leu Arg Phe Tyr Ala His Glu
                805                 810                 815

Lys Ser Gly Met Ser Lys Lys Gln Ile Thr Ala Lys Ala Leu Ala Glu
            820                 825                 830

Trp Met Thr Asp Ile Gly Tyr Pro Thr Lys Ala Thr Ala Val Arg Ser
            835                 840                 845

Ala Lys Asn Ala Lys Leu Ile Glu Gly Ala Val Pro Met Thr Glu Leu
850                 855                 860

Thr Ile Asn Leu Ala Arg Leu Ile Val Ser Lys Phe Pro Asp Phe Glu
865                 870                 875                 880

Val Glu Ile Leu Phe Asn Pro Glu Ser Arg Ser Ser Leu Arg Glu Ala
                885                 890                 895
```

```
Leu Asn Ala Arg
            900

<210> SEQ ID NO 19
<211> LENGTH: 887
<212> TYPE: PRT
<213> ORGANISM: Actinobacillus minor NM305

<400> SEQUENCE: 19

Met Leu Pro Asn Asn Val Ser Ser Leu Lys Lys Asp Ile Pro Leu Arg
1               5                   10                  15

Gly Asp Ile Ser Leu Ser Asp Asn Pro Leu Leu Asp Ile Leu Pro Asn
            20                  25                  30

Val Leu Asp His Phe Ser His Asn Val Gly Asp Glu Glu Asn Glu Asp
        35                  40                  45

Glu Gly Lys Gln Pro Phe Ile Ile Ala Leu Asp Ser Glu Tyr Gln Leu
    50                  55                  60

Ala Glu Asp Gly Lys Arg Asn Ile Ile Leu Ser Tyr Gln Tyr Val Ala
65                  70                  75                  80

Ala Thr Arg Asp Asn Gln His Ser Pro Ile Lys Gly Ile Ile Tyr Thr
                85                  90                  95

Arg Arg Arg Lys Asn Gly Glu Glu Ile Arg Leu Arg Leu Lys Ser Phe
            100                 105                 110

Leu Arg Lys Val Ile Leu Asp Ala Leu Gln Lys Asn Val Ile Thr Gln
        115                 120                 125

Phe Pro Lys Thr Val Tyr Val Val Ala His Phe Leu Arg Ala Asp Leu
    130                 135                 140

Ser Ser Phe Leu Asp Phe Phe Gln Glu Lys Thr Ile Val Gln Gly Ile
145                 150                 155                 160

Arg Lys Thr Leu Ala Ser Ile Thr Asp Thr Tyr Gly Val Asp Val Asp
                165                 170                 175

Glu Leu Leu Gly Lys Ser His His Lys Glu Leu Val Asn Leu Ser Asp
            180                 185                 190

Asn Asn Asn Asn Met Lys Gln Ile Ser Ile Arg Phe Ile Asp Thr Gln
        195                 200                 205

Leu Leu Thr Pro Ala Gln Gln Gly Leu Ala Thr Leu Gly Glu Ile Val
    210                 215                 220

Gly Leu Glu Lys Leu Ser Ile Pro Glu Pro Tyr Ser Ile Glu Arg Met
225                 230                 235                 240

Glu Glu Tyr Leu Lys Glu Asp Lys Gln Gly Phe Glu Ala Tyr Ala Leu
                245                 250                 255

Arg Asp Ala Glu Ile Val Phe Leu Tyr Ala Met Lys Leu Leu Asp Phe
            260                 265                 270

Thr Glu Ser Glu Phe Asn Arg Ala Tyr Leu Pro Val Thr Leu Ala Ser
        275                 280                 285

Ile Gly Val Ser Gln Phe Leu Asp Glu Leu Lys Ile Gln Gly Ile Lys
    290                 295                 300

Ser Ser Ser Phe Leu Gly Met Ser Glu Glu Ser Lys Leu Thr Phe Asn
305                 310                 315                 320

Thr Asn Thr Gly Lys Tyr Lys Arg Met Lys Ile Lys Ser Leu Ser Gly
                325                 330                 335

Gly Ala Leu Thr Leu Glu Arg Phe Ala Ile Glu Cys Tyr His Gly Gly
            340                 345                 350

Arg Asn Glu Ala Phe Cys Cys Gly Tyr Thr Pro Ile Glu Thr Trp Tyr
        355                 360                 365
```

```
Asp Tyr Asp Leu Pro Ser Ala Tyr Thr Thr Ala Leu Ile Asn Ile His
        370                 375                 380

Pro Leu Asn Tyr Asp Gly Tyr Phe Gln Thr Thr Asn Val Asn Asp Phe
385                 390                 395                 400

Lys Gly His Thr Leu Gly Leu Ala Arg Val Glu Phe Arg Phe Pro Glu
                405                 410                 415

Asp Thr Arg Tyr Pro Cys Leu Pro Val Lys Thr Glu Asn Gly Leu Ile
            420                 425                 430

Tyr Pro Leu Ser Gly Ile Ser Tyr Cys Thr Ala Pro Glu Ile Glu Val
        435                 440                 445

Ala Leu Gly Leu Gly Cys Glu Ile Val Ile Leu Glu Gly Phe Val Ile
450                 455                 460

Pro Trp Glu Thr Thr Asp Lys Thr Pro Phe Ser Ser Phe Val Lys Phe
465                 470                 475                 480

Ile Arg Lys Lys Arg Glu Met Cys Ile Ser Lys Glu Ser Pro Asn Asn
                485                 490                 495

Met Ile Ala Glu Ile Ser Glu Lys Leu Trp Lys Glu Ile Gly Asn Ser
            500                 505                 510

Leu Tyr Gly Lys Leu Ala Gln Gly Leu Lys Gly Lys Lys Thr Phe Asp
        515                 520                 525

Val Ala Lys Gly Leu Asn Lys Leu Val Pro Arg Ser Lys Ile Thr Asn
530                 535                 540

Ala Phe Tyr Ala Ser Tyr Val Thr Gly Phe Val Arg Ala Val Val Ser
545                 550                 555                 560

Gln Leu Leu Ser Ala Ile Pro Pro Asp Lys Val Ala Val Ser Val Thr
                565                 570                 575

Thr Asp Gly Phe Ile Thr Asn Ala His Leu Ser Glu Phe Asp Leu Ser
            580                 585                 590

Ser Leu Ser Val Val Gln Arg Phe Ser Ser Leu Val Lys Glu Leu Thr
        595                 600                 605

Ser Asp Glu Asn Arg Pro Val Leu Glu Leu Lys His Gln Val Lys Gln
610                 615                 620

Leu Cys Cys Met Lys Asn Arg Gly Gln Phe Thr Val Glu Ala Asp Gly
625                 630                 635                 640

Glu Tyr Pro Leu Ile Leu Ala Lys Ala Ser Val Gln Val Pro Asp Ser
                645                 650                 655

Leu Arg Gln Phe Gly Gln Ser Ser Ala Glu Arg Gln Val Glu Asn
            660                 665                 670

Ser Tyr Ile Ala Glu Leu Tyr Phe Asn Arg Glu Ala Asn Gln Lys Val
        675                 680                 685

Ser Arg Ser Thr Met Ile Ser Thr Arg Glu Ser Phe Ile Ser Gln Arg
690                 695                 700

Asp Leu Ile Lys Ile Arg Ser Asp Ile Lys Leu Asn Leu Glu Phe Asp
705                 710                 715                 720

Met Lys Arg His Phe Ser Val Ala Asn Ser Leu Ile Ile Asn Asn Asp
                725                 730                 735

Glu Arg Leu Phe Ile Gln Thr Lys Pro Trp Lys Asp Val Gln Ser Phe
            740                 745                 750

Tyr His Tyr Arg Ala Ile Phe Asp Glu Trp Lys Ile His His Thr Leu
        755                 760                 765

Lys Lys Ile Cys Asp Phe His His Trp Ile Glu Phe Ser Ser Ala Lys
770                 775                 780
```

```
Val Ser Ala Lys Gly Lys Arg Val Asn Val Ser Lys Thr Phe Gly Ala
785                 790                 795                 800

Asp Lys Val Leu Leu Arg Gln Phe Leu Arg Cys Phe Ala Lys Gly Val
            805                 810                 815

His Gly Gly Arg Val Asp Met Thr Tyr Lys Arg Leu Ser Lys Phe Leu
            820                 825                 830

Thr Glu Lys Gly Tyr Thr Val Ser Glu Val Asp Ile Lys Asn Ala Ala
            835                 840                 845

Arg Ala Ser Ala Lys Ile Gln Glu Lys Ser Val Ala Arg Thr Pro Asn
850                 855                 860

Thr Glu Lys Leu Leu Ser Val Leu Leu Glu Ile Ala Pro Asn Phe Glu
865                 870                 875                 880

Ala Gln Arg Phe Phe Val Thr
                885

<210> SEQ ID NO 20
<211> LENGTH: 866
<212> TYPE: PRT
<213> ORGANISM: Enterobacter hormaechei

<400> SEQUENCE: 20

Met Ser His Asn Leu Gln Asp Ile Leu Ala Ala Ser Gly Tyr Gln
1               5                   10                  15

Ser Val Thr Ser Glu Pro Ala Leu Asn Leu Lys Arg Pro Lys Thr Leu
            20                  25                  30

Asp Asp Tyr Pro Val Ile Pro Pro Ala Ser Glu Lys Val Ser Val Ile
            35                  40                  45

Ser Ser Asp Leu Thr Leu His Ile Gly Phe Asp Thr Glu Tyr Val Phe
50                  55                  60

Asn Pro Glu Thr Gln Gln Asn Asp Ile Leu Ser Tyr Gln Ser Tyr Val
65                  70                  75                  80

Val Leu Pro Glu Asn Thr Gly Ile Ser Asn Ile Ile Tyr Pro Pro Asp
            85                  90                  95

Ser Gln Lys Lys Ser Arg Leu Ser Phe Lys Glu Phe Leu Cys Gln Thr
            100                 105                 110

Ile Thr Pro Leu Leu Glu Thr Gly Val Ile Thr Lys Trp Pro Gly Ile
            115                 120                 125

Ile Asn Ile Tyr Ala His Phe Ile Arg Ala Asp Ile Ala Ser Phe Ala
            130                 135                 140

Asn Phe Trp Ser Asp Tyr Lys Ile Leu Leu Lys Gly Ile Arg Gly Thr
145                 150                 155                 160

Val Ser Ser Phe Lys Asn Arg Tyr Gly Ile Asp Phe Asp Glu Gln Gln
            165                 170                 175

Glu Arg Arg Val Lys Thr Glu Gln Ile Met Phe Asp Lys Arg Thr Ser
            180                 185                 190

Pro Pro Arg Cys Ser Asn Val Ala Phe Ile Asp Thr Leu Leu Ile Thr
            195                 200                 205

Pro Gly Asp Met Gly Leu Ala Glu Cys Gly Glu Leu Leu Gly Leu Pro
            210                 215                 220

Lys Leu Thr Ile Pro Ala Pro Tyr Ser Ile Thr Asn Met Arg Glu Tyr
225                 230                 235                 240

Leu Leu Gly Asp Arg Ala Gly Phe Glu Ala Tyr Ala Leu Arg Asp Ala
            245                 250                 255

Glu Ile Ala Val Arg Tyr Ala Leu Gln Val Arg Asn Phe Cys Ala Arg
            260                 265                 270
```

```
Glu Leu Met Ile Asp Arg Val Pro Ala Thr Ile Gly Ala Met Ala Val
        275                 280                 285

Ser Arg Phe Thr Lys Thr Leu Lys Glu Asn Asn Ile Ser Pro Glu Val
        290                 295                 300

Cys Leu Gly Thr His Ile Lys Thr Arg Glu Leu Trp Leu Thr Glu Lys
305                 310                 315                 320

Gln Ala Phe Arg Thr Ile Lys Asn Pro Ala Ser Val Pro Ser Arg Glu
                325                 330                 335

Leu Phe Glu Thr Phe Pro Ile Asn Cys Tyr His Gly Arg Asn Glu
        340                 345                 350

Cys Phe Met Met Gly Val Thr Pro Ser Asp His Trp Tyr Asp Tyr Asp
        355                 360                 365

Leu Ala Gly Ala Tyr Thr Thr Gly Leu Leu Asp Ile Leu Thr Pro Asp
        370                 375                 380

Tyr Gly Asn Ile Arg Leu Ser Lys Asn Pro Asp Asp Tyr Cys Gly His
385                 390                 395                 400

Val Met Gly Phe Ala Leu Val Thr Phe Arg Phe Pro Glu Ser Val Pro
                405                 410                 415

Tyr Pro Ser Leu Pro Val Arg Thr Asp Gln Tyr Gly Leu Phe Phe Pro
                420                 425                 430

Leu Ser Gly Glu Ser Trp Ala Thr Ala Pro Glu Ile Glu Leu Ala Leu
        435                 440                 445

Ser Leu Gly Ala Glu Met Thr Ile His Asn Gly Ile Ile Val Pro Trp
        450                 455                 460

Ile Cys Asp Thr Ser Pro His Asn Ser Glu Ser Thr Ser Val Phe Leu
465                 470                 475                 480

Pro Phe Val Gln Gln Val Arg Glu Asn Arg Asn Arg His Ile Lys Gly
                485                 490                 495

Ser Leu Glu Glu Lys Phe Trp Lys Glu Ile Gly Asn Ser Leu Tyr Gly
                500                 505                 510

Lys Leu Ala Gln Gly Leu Arg Ala Lys Thr Ala Phe Asp Thr Ala Arg
        515                 520                 525

Gly Leu Asn Arg Ser Leu Pro Pro Ser Ser Val Thr Gln Pro Phe Phe
        530                 535                 540

Ala Ala His Val Thr Gly Phe Ile Arg Ala Val Val Gly Glu Leu Met
545                 550                 555                 560

Asn Ala Leu Pro Ser Asp Ser Ser Val Val Ser Val Thr Thr Asp Gly
                565                 570                 575

Phe Leu Thr Asn Cys Pro Leu Asn Lys Ile Asn Met Ser Gly Pro Leu
                580                 585                 590

Ser Ser Arg Phe Gln Ser Leu Cys Asp Ile Val Asp Pro Gly Ser Ser
        595                 600                 605

Met Leu Thr Cys Lys His Glu Val Ser Gln Leu Ile Ala Met Lys Thr
        610                 615                 620

Arg Gly Gln Leu Thr Tyr Arg Ala Ile Gln Gly Lys Pro Val Val His
625                 630                 635                 640

Ala Arg Ala Gly Val Lys Pro Pro Ala Asp Ile Pro Arg Ser Asp Tyr
                645                 650                 655

Asn Asp Tyr Met Val Asp Leu Tyr Leu Asn Arg Leu Pro Gly Gln Thr
                660                 665                 670

Leu Ser Arg Ser Thr Leu Ile Ser Thr Arg Glu Met Trp Leu Ser Glu
        675                 680                 685
```

```
Ser Asp Leu Val Ser Arg Glu Gln Asp Ile Arg Leu Asn Leu Glu Phe
    690             695                 700

Asp Phe Lys Arg Gln Pro Val Gln Pro Ala Met Asn Glu Gly His Leu
705             710                 715                 720

Leu Met Phe Ser Arg Pro Trp Asp Asn Met Glu Glu Ala Met Gln Gln
            725                 730                 735

Arg Ser Leu Phe Asp Asp Trp Arg Gln Thr His Thr Leu Lys Thr Leu
        740                 745                 750

Ala Asp Trp Asp Asp Trp Cys Asp Phe Leu Tyr Cys Arg Thr Val Phe
            755                 760                 765

Ser Asp Met Lys Leu Lys Val Gly Ser Lys Arg Ser Asp Asp Ile Leu
770             775                 780

Val Arg Leu Phe Leu Arg Ala Leu Thr Gln Cys Gln Trp Gly Leu Met
785             790                 795                 800

Leu Lys Asp Lys Lys Ser Tyr Ser Cys Lys Glu Val Ala Glu Trp Leu
                805                 810                 815

Thr Ser Glu Gly Tyr Ser Val Thr Val Thr Asp Val Lys Asn Ala Val
            820                 825                 830

Arg Ala Lys Ile Pro Gln Met Lys Phe Ser Ser Val Thr Pro Arg Met
        835                 840                 845

Lys Ser Leu Met Asp Ile Ile Ala Arg Lys Tyr Pro Thr Phe Cys Leu
850             855                 860

Pro Val
865

<210> SEQ ID NO 21
<211> LENGTH: 866
<212> TYPE: PRT
<213> ORGANISM: Escherichia coli ETEC H10407

<400> SEQUENCE: 21

Met Ser Asn Asn Leu Gln Asp Ile Leu Ala Ala Ser Gly Tyr Gln
1               5                   10                  15

Ser Val Thr Ser Glu Pro Ala Leu Asn Arg Lys Arg Pro Lys Thr Leu
            20                  25                  30

Asp Asp Tyr Pro Val Ile Pro Pro Ala Ser Lys Lys Val Ser Val Ile
        35                  40                  45

Ser Ser Asp Leu Thr Leu His Ile Gly Phe Asp Thr Glu Tyr Val Phe
    50                  55                  60

Asn Pro Glu Thr Gln Gln Asn Asp Ile Leu Ser Tyr Gln Ser Tyr Val
65              70                  75                  80

Val Leu Pro Asp Asn Thr Gly Ile Ser Asn Ile Ile Tyr Pro Pro Asp
            85                  90                  95

Ser Gln Lys Lys Ser Arg Leu Ser Phe Lys Asp Phe Leu Cys Gln Thr
        100                 105                 110

Ile Thr Pro Leu Leu Glu Thr Gly Val Ile Thr Lys Trp Pro Gly Ile
    115                 120                 125

Ile Asn Ile Tyr Ala His Phe Ile Arg Ala Asp Ile Ala Ser Phe Ala
    130                 135                 140

Asn Phe Trp Ser Asp Tyr Lys Ile Leu Leu Lys Gly Ile Arg Gly Thr
145             150                 155                 160

Val Ser Ser Phe Lys Asn Arg Tyr Gly Ile Asp Phe Asp Glu Gln Gln
            165                 170                 175

Glu Arg Arg Val Lys Thr Glu Gln Ile Met Phe Asp Lys Arg Thr Ser
        180                 185                 190
```

```
Pro Pro Arg Cys Ser Asn Val Ala Phe Ile Asp Thr Leu Leu Ile Thr
    195                 200                 205

Pro Gly Gly Met Gly Leu Ala Glu Cys Gly Glu Leu Leu Gly Leu Pro
    210                 215                 220

Lys Leu Thr Ile Pro Ala Pro Tyr Ser Ile Thr Asn Met Arg Glu Tyr
225                 230                 235                 240

Leu Leu Gly Asp Arg Ala Gly Phe Glu Ala Tyr Ala Leu Arg Asp Ala
                245                 250                 255

Glu Ile Ala Val Arg Tyr Ala Leu Gln Val Arg Asn Phe Cys Ala Arg
                260                 265                 270

Glu Leu Met Ile Asp Arg Val Pro Ala Thr Ile Gly Ala Met Ala Val
            275                 280                 285

Ser Arg Phe Thr Lys Thr Leu Lys Glu Asn Asn Met Ser Pro Glu Val
    290                 295                 300

Cys Leu Gly Thr His Ile Lys Thr Arg Glu Leu Trp Leu Thr Glu Lys
305                 310                 315                 320

Gln Ala Phe Arg Thr Ile Lys Asn Pro Ala Ser Val Pro Ser Arg Glu
                325                 330                 335

Leu Phe Glu Thr Phe Pro Ile Asn Cys Tyr His Gly Gly Arg Asn Glu
            340                 345                 350

Cys Phe Met Met Gly Ile Thr Pro Ser Asp His Trp Tyr Asp Tyr Asp
            355                 360                 365

Leu Ala Gly Ala Tyr Thr Thr Gly Leu Leu Asp Ile Leu Thr Pro Asp
    370                 375                 380

Tyr Gly Asn Ile Arg Leu Ser Lys Asn Pro Asp Tyr Cys Gly His
385                 390                 395                 400

Val Met Gly Phe Ala Leu Val Thr Phe Arg Phe Pro Glu Ser Val Pro
                405                 410                 415

Tyr Pro Ser Leu Pro Val Arg Thr Asp Gln Tyr Gly Leu Phe Phe Pro
            420                 425                 430

Leu Ser Gly Glu Ser Trp Ala Thr Ala Pro Glu Ile Glu Leu Ala Leu
    435                 440                 445

Ser Leu Gly Ala Glu Met Thr Ile His Asn Gly Ile Ile Val Pro Trp
    450                 455                 460

Ile Cys Asp Thr Ser Pro His Asn Ser Glu Ser Thr Ser Val Phe Leu
465                 470                 475                 480

Pro Phe Val Gln Gln Val Arg Glu Asn Arg Asn Arg His Ile Lys Gly
                485                 490                 495

Ser Leu Glu Glu Lys Phe Trp Lys Glu Ile Gly Asn Ser Leu Tyr Gly
            500                 505                 510

Lys Leu Ala Gln Gly Leu Arg Ala Lys Thr Ala Phe Asp Thr Ala Arg
            515                 520                 525

Gly Leu Asn Arg Ser Leu Pro Pro Ser Val Thr Gln Pro Phe Phe
530                 535                 540

Ala Ala His Val Thr Gly Phe Ile Arg Ala Val Val Gly Glu Leu Met
545                 550                 555                 560

Asn Ala Leu Pro Ser Asp Ser Ser Val Val Ser Val Thr Thr Asp Gly
                565                 570                 575

Phe Leu Thr Asn Cys Ser Leu Asn Lys Ile Asn Met Ser Gly Pro Leu
            580                 585                 590

Ser Ser Arg Phe Gln Ser Leu Cys Asp Ile Val Asp Pro Gly Ser Ser
        595                 600                 605
```

```
Met Leu Thr Cys Lys His Glu Val Ser Gln Leu Ile Ala Met Lys Thr
            610                 615                 620

Arg Gly Gln Leu Thr Tyr Arg Ala Ile Gln Gly Lys Pro Val Val His
625                 630                 635                 640

Ala Arg Ala Gly Val Lys Pro Pro Ala Asp Ile Pro Arg Ser Asp Tyr
                645                 650                 655

Asn Asp Tyr Met Val Asp Leu Tyr Leu Asn Arg Leu Pro Gly Gln Thr
                660                 665                 670

Leu Ser Arg Ser Thr Leu Ile Ser Thr Arg Glu Met Trp Leu Ser Glu
            675                 680                 685

Ser Asp Leu Val Ser Arg Glu Gln Asp Ile Arg Leu Asn Leu Glu Phe
690                 695                 700

Asp Phe Lys Arg Gln Pro Val Arg Pro Ala Met Asn Glu Gly His Leu
705                 710                 715                 720

Leu Met Phe Ser Arg Pro Trp Asp Asn Met Glu Ala Leu Gln Gln
                725                 730                 735

Arg Ser Leu Phe Asp Asp Trp Arg Gln Thr His Thr Leu Lys Thr Leu
                740                 745                 750

Ala Asp Trp Asp Asp Trp Cys Asp Phe Leu Tyr Cys Arg Thr Val Phe
            755                 760                 765

Ser Asp Met Lys Leu Lys Val Gly Ser Lys Arg Ser Asp Ile Leu
770                 775                 780

Val Arg Leu Phe Leu Arg Ala Leu Thr Gln Cys Gln Trp Gly Leu Met
785                 790                 795                 800

Leu Lys Asp Lys Lys Ser Tyr Ser Cys Lys Glu Val Ala Glu Trp Leu
                805                 810                 815

Thr Ser Glu Gly Tyr Ser Val Thr Val Thr Asp Val Lys Asn Ala Val
                820                 825                 830

Arg Ala Lys Ile Pro Gln Met Lys Phe Ser Ser Val Thr Pro Arg Met
            835                 840                 845

Lys Ser Leu Met Asp Ile Ile Ala Arg Lys Tyr Pro Thr Phe Cys Leu
850                 855                 860

Pro Ala
865

<210> SEQ ID NO 22
<211> LENGTH: 887
<212> TYPE: PRT
<213> ORGANISM: Escherichia coli E1520

<400> SEQUENCE: 22

Met Leu Leu Asn Leu Asp Ser Leu Cys Arg Asp Thr Ala Pro Gly Ile
1               5                   10                  15

Phe Ser Glu Leu Thr Met Ser Asn Asn Leu Gln Asp Ile Leu Ala Ala
                20                  25                  30

Ala Ser Gly Tyr Gln Ser Val Thr Ser Glu Pro Ala Leu Asn Arg Lys
            35                  40                  45

Arg Pro Lys Thr Leu Asp Asp Tyr Pro Val Ile Pro Pro Ala Ser Lys
50                  55                  60

Lys Val Ser Val Ile Ser Ser Asp Leu Thr Leu His Ile Gly Phe Asp
65                  70                  75                  80

Thr Glu Tyr Val Phe Asn Pro Glu Thr Arg Gln Asn Asp Ile Leu Ser
                85                  90                  95

Tyr Gln Ser Tyr Val Val Leu Pro Asp Asn Thr Gly Ile Ser Asn Ile
            100                 105                 110
```

```
Ile Tyr Pro Pro Asp Ser Gln Lys Lys Ser Arg Leu Ser Phe Lys Glu
            115                 120                 125

Phe Leu Cys Gln Thr Ile Thr Pro Leu Leu Glu Thr Gly Val Ile Thr
130                 135                 140

Lys Trp Pro Gly Ile Ile Asn Ile Tyr Ala His Phe Ile Arg Ala Asp
145                 150                 155                 160

Ile Ala Ser Phe Ala Asn Phe Trp Ser Asp Tyr Lys Ile Leu Leu Lys
                165                 170                 175

Gly Ile Arg Gly Thr Val Ser Ser Phe Lys Asn Arg Tyr Gly Ile Asp
            180                 185                 190

Phe Asp Glu Gln Gln Glu Arg Val Lys Thr Glu Gln Ile Met Phe
        195                 200                 205

Asp Lys Arg Thr Ser Pro Pro Arg Cys Ser Asn Val Ala Phe Ile Asp
    210                 215                 220

Thr Leu Leu Ile Thr Pro Gly Met Gly Leu Ala Glu Cys Gly Glu
225                 230                 235                 240

Leu Leu Gly Leu Pro Lys Leu Thr Ile Pro Ala Pro Tyr Ser Ile Thr
                245                 250                 255

Asn Met Arg Glu Tyr Leu Leu Gly Asp Arg Ala Gly Phe Glu Ala Tyr
            260                 265                 270

Ala Leu Arg Asp Ala Glu Ile Ala Val Arg Tyr Ala Leu Gln Val Arg
        275                 280                 285

Asn Phe Cys Ala Arg Glu Leu Met Ile Asp Arg Val Pro Ala Thr Ile
    290                 295                 300

Gly Ala Met Ala Val Ser Arg Phe Thr Lys Thr Leu Lys Glu Asn Asn
305                 310                 315                 320

Met Ser Pro Glu Val Cys Leu Gly Thr His Ile Lys Thr Arg Glu Leu
                325                 330                 335

Trp Leu Thr Glu Lys Gln Ala Phe Arg Thr Ile Lys Asn Pro Ala Ser
            340                 345                 350

Val Pro Ser Arg Glu Leu Phe Glu Thr Phe Pro Ile Asn Cys Tyr His
        355                 360                 365

Gly Gly Arg Asn Glu Cys Phe Met Met Gly Val Thr Pro Ser Asp His
    370                 375                 380

Trp Tyr Asp Tyr Asp Leu Ala Gly Ala Tyr Thr Thr Gly Leu Leu Asp
385                 390                 395                 400

Ile Leu Thr Pro Asp Tyr Gly Asn Ile Arg Leu Ser Lys Asn Pro Asp
                405                 410                 415

Asp Tyr Cys Gly His Val Met Gly Phe Ala Leu Val Thr Phe Arg Phe
            420                 425                 430

Pro Glu Ser Val Pro Tyr Pro Ser Leu Pro Val Arg Thr Asp Gln Tyr
        435                 440                 445

Gly Leu Phe Phe Pro Leu Ser Gly Glu Ser Trp Ala Thr Ala Pro Glu
    450                 455                 460

Ile Glu Leu Ala Leu Ser Leu Gly Ala Glu Met Thr Ile His Asn Gly
465                 470                 475                 480

Ile Ile Val Pro Trp Ile Cys Asp Thr Ser Pro His Asn Ser Glu Ser
                485                 490                 495

Thr Ser Val Phe Leu Pro Phe Val Gln Gln Val Arg Glu Asn Arg Asn
            500                 505                 510

Arg His Ile Lys Gly Ser Leu Glu Glu Lys Phe Trp Lys Glu Ile Gly
        515                 520                 525
```

Asn Ser Leu Tyr Gly Lys Leu Ala Gln Gly Leu Arg Ala Lys Thr Ala
    530                 535                 540

Phe Asp Thr Ala Arg Gly Val Asn Arg Ser Leu Pro Pro Ser Ser Val
545                 550                 555                 560

Thr Gln Pro Phe Phe Ala Ala His Val Thr Gly Phe Ile Arg Ala Val
                565                 570                 575

Val Gly Glu Leu Met Asn Ala Leu Pro Ser Asp Ser Thr Val Val Ser
            580                 585                 590

Val Thr Thr Asp Gly Phe Leu Thr Asn Cys Pro Leu Asp Lys Ile Asn
        595                 600                 605

Met Ser Gly Pro Leu Ser Ser Arg Phe Gln Ser Leu Cys Asp Ile Val
    610                 615                 620

Asp Pro Gly Ser Ser Met Leu Thr Cys Lys His Glu Val Ser Gln Leu
625                 630                 635                 640

Ile Ala Met Lys Thr Arg Gly Gln Leu Thr Tyr Arg Ala Ile Gln Gly
                645                 650                 655

Lys Pro Val Val His Ala Arg Ala Gly Val Lys Pro Pro Ala Asp Ile
            660                 665                 670

Pro Arg Ser Asp Tyr Asn Asp Tyr Met Val Asp Leu Tyr Leu Asn Arg
        675                 680                 685

Leu Pro Gly Gln Thr Leu Ser Arg Ser Thr Leu Ile Ser Thr Arg Glu
    690                 695                 700

Met Trp Leu Ser Glu Ser Asp Leu Val Ser Arg Glu Gln Asp Ile Arg
705                 710                 715                 720

Leu Asn Leu Glu Phe Asp Phe Lys Arg Gln Pro Val Gln Pro Ala Met
                725                 730                 735

Asn Glu Gly His Leu Leu Met Phe Ser Arg Pro Trp Asp Asn Met Glu
            740                 745                 750

Glu Ala Leu Gln Gln Arg Ser Leu Phe Asp Asp Trp Arg Gln Thr His
        755                 760                 765

Thr Leu Lys Thr Leu Ala Asp Trp Asp Asp Trp Cys Asp Phe Leu Tyr
    770                 775                 780

Cys Arg Thr Val Phe Ser Asp Met Lys Leu Lys Val Gly Ser Lys Arg
785                 790                 795                 800

Ser Asp Asp Ile Leu Val Arg Leu Phe Leu Arg Ala Leu Thr Gln Cys
                805                 810                 815

Gln Trp Gly Leu Met Leu Lys Asp Lys Lys Ser Tyr Ser Cys Lys Glu
            820                 825                 830

Val Ala Glu Trp Leu Thr Ser Glu Gly Tyr Ser Val Thr Val Thr Asp
        835                 840                 845

Val Lys Asn Ala Val Arg Ala Lys Ile Pro Gln Met Lys Phe Ser Ser
    850                 855                 860

Val Thr Pro Arg Met Lys Ser Leu Met Asp Ile Ile Ala Arg Lys Tyr
865                 870                 875                 880

Pro Thr Phe Cys Leu Pro Val
                885

<210> SEQ ID NO 23
<211> LENGTH: 887
<212> TYPE: PRT
<213> ORGANISM: Cronobacter sakazakii 696

<400> SEQUENCE: 23

Met Leu Leu Asn Leu Asp Ser Leu Cys Arg Asp Thr Ala Pro Gly Ile
1               5                   10                  15

```
Phe Ser Glu Leu Thr Met Ser His Asn Leu Gln Asp Ile Leu Ala Ala
            20                  25                  30

Ala Ser Gly Tyr Gln Ser Val Thr Ser Glu Pro Ala Leu Asn Arg Lys
            35                  40                  45

Arg Pro Lys Thr Leu Asp Asp Tyr Pro Val Met Pro Pro Ala Ser Lys
 50                  55                  60

Asn Val Ser Val Ile Ser Asn Asp Leu Thr Leu His Ile Gly Phe Asp
 65                  70                  75                  80

Thr Glu Tyr Val Phe Asn Pro Glu Thr Arg Gln Asn Asp Ile Leu Ser
                     85                  90                  95

Tyr Gln Ser Tyr Val Val Leu Pro Asp Asn Thr Gly Ile Ser Asn Ile
            100                 105                 110

Ile Tyr Pro Pro Asp Ser Gln Lys Lys Ser Arg Leu Ser Phe Lys Glu
            115                 120                 125

Phe Leu Cys Gln Thr Ile Thr Pro Leu Leu Glu Thr Gly Val Ile Thr
    130                 135                 140

Lys Trp Pro Cys Ile Ile Asn Ile Tyr Ala His Phe Ile Arg Ala Asp
145                 150                 155                 160

Ile Ala Ser Phe Ala Asn Phe Trp Ser Asp Tyr Lys Ile Leu Leu Lys
                165                 170                 175

Gly Ile Arg Gly Thr Val Ser Ser Phe Lys Asn Arg Tyr Gly Ile Asp
            180                 185                 190

Phe Asp Glu Gln Gln Glu Arg Arg Val Lys Thr Glu Gln Ile Met Phe
            195                 200                 205

Asp Lys Arg Thr Ser Pro Pro Arg Cys Ser Asn Val Ala Phe Ile Asp
    210                 215                 220

Thr Leu Leu Ile Thr Pro Gly Met Gly Leu Ala Glu Cys Gly Glu
225                 230                 235                 240

Leu Leu Gly Leu Pro Lys Leu Thr Ile Pro Ala Pro Tyr Ser Ile Thr
                245                 250                 255

Asn Met Arg Glu Tyr Leu Leu Gly Asp Arg Ala Gly Phe Glu Ala Tyr
            260                 265                 270

Ala Leu Arg Asp Ala Glu Ile Ala Val Arg Tyr Ala Leu Gln Val Arg
            275                 280                 285

Asn Phe Cys Ala Arg Glu Leu Met Ile Asp Arg Val Pro Ala Thr Ile
    290                 295                 300

Gly Ala Met Ala Val Ser Arg Phe Thr Lys Thr Leu Lys Glu Asn Asn
305                 310                 315                 320

Met Ser Pro Glu Val Cys Leu Gly Thr His Ile Lys Thr Arg Glu Leu
                325                 330                 335

Trp Leu Thr Glu Lys Gln Ala Phe Arg Thr Ile Lys Asn Pro Ala Ser
            340                 345                 350

Val Pro Ser Arg Glu Leu Phe Glu Thr Phe Pro Ile Asn Cys Tyr His
            355                 360                 365

Gly Gly Arg Asn Glu Cys Phe Met Met Gly Val Thr Pro Ser Asp His
    370                 375                 380

Trp Tyr Asp Tyr Asp Leu Ala Gly Ala Tyr Thr Thr Gly Leu Leu Asp
385                 390                 395                 400

Ile Leu Thr Pro Asp Tyr Gly Asn Ile Arg Leu Ser Lys Asn Pro Asp
                405                 410                 415

Asp Tyr Cys Gly His Val Met Gly Phe Ala Leu Val Thr Phe Arg Phe
            420                 425                 430
```

-continued

```
Pro Glu Ser Val Pro Tyr Pro Ser Leu Pro Val Arg Thr Asp Gln Tyr
            435                 440                 445

Gly Leu Phe Phe Pro Leu Ser Gly Glu Ser Trp Ala Thr Ala Pro Glu
    450                 455                 460

Ile Glu Leu Ala Leu Ser Leu Gly Ala Glu Met Thr Ile His Asn Gly
465                 470                 475                 480

Ile Ile Val Pro Trp Ile Cys Asp Thr Ser Pro His Asn Ser Glu Ser
                485                 490                 495

Thr Ser Val Phe Leu Pro Phe Val Gln Val Arg Glu Asn Arg Asn
                500                 505                 510

Arg His Ile Lys Gly Ser Leu Glu Glu Lys Phe Trp Lys Glu Ile Gly
            515                 520                 525

Asn Ser Leu Tyr Gly Lys Leu Ala Gln Gly Leu Arg Ala Lys Thr Ala
530                 535                 540

Phe Asp Thr Ala Arg Gly Leu Asn Arg Ser Leu Pro Pro Ser Ser Val
545                 550                 555                 560

Thr Gln Pro Phe Phe Ala Ala His Val Thr Gly Phe Ile Arg Ala Val
                565                 570                 575

Val Gly Glu Leu Met Asn Ala Leu Pro Ser Asp Ser Ser Val Val Ser
            580                 585                 590

Val Thr Thr Asp Gly Phe Leu Thr Asn Cys Pro Leu Asp Lys Ile Asn
            595                 600                 605

Met Ser Gly Pro Leu Ser Ser Arg Phe Gln Ser Leu Cys Asp Ile Val
            610                 615                 620

Asp Pro Gly Ser Ser Met Leu Thr Cys Lys His Glu Val Ser Gln Leu
625                 630                 635                 640

Ile Ala Met Lys Thr Arg Gly Gln Leu Thr Tyr Lys Ala Ile Gln Gly
                645                 650                 655

Lys Pro Val Val His Ala Arg Ala Gly Val Lys Pro Pro Ala Asp Ile
            660                 665                 670

Pro Arg Ser Asp Tyr Asn Asp Tyr Met Val Asp Leu Tyr Leu Asn Arg
            675                 680                 685

Leu Pro Gly Gln Thr Leu Ser Arg Ser Thr Leu Ile Ser Thr Arg Glu
690                 695                 700

Met Trp Leu Ser Glu Ser Asp Leu Val Ser Arg Glu Gln Asp Ile Arg
705                 710                 715                 720

Leu Asn Leu Glu Phe Asp Phe Lys Arg Gln Pro Val Arg Pro Ala Met
                725                 730                 735

Asn Glu Gly His Leu Leu Met Phe Ser Arg Pro Trp Asp Asn Met Glu
            740                 745                 750

Glu Ala Leu Gln Gln Arg Ser Leu Phe Asp Asp Trp Arg Gln Thr His
            755                 760                 765

Thr Leu Lys Thr Leu Ala Asp Trp Asp Asp Trp Cys Asp Phe Leu Tyr
770                 775                 780

Cys Arg Thr Val Phe Ser Asp Met Lys Leu Lys Val Gly Ser Lys Arg
785                 790                 795                 800

Ser Asp Asp Ile Leu Val Arg Leu Phe Leu Arg Ala Leu Thr Gln Cys
                805                 810                 815

Gln Trp Gly Leu Met Leu Lys Asp Lys Lys Ser Tyr Ser Cys Lys Glu
            820                 825                 830

Val Ala Glu Trp Leu Thr Ser Glu Gly Tyr Ser Val Thr Val Thr Asp
            835                 840                 845

Val Lys Asn Ala Val Arg Ala Lys Ile Pro Gln Met Lys Phe Ser Ser
```

```
                    850                 855                 860
Val Thr Pro Arg Met Lys Ser Leu Met Asp Ile Ile Ala Arg Lys Tyr
865                 870                 875                 880

Pro Thr Phe Cys Leu Pro Ala
                885
```

<210> SEQ ID NO 24
<211> LENGTH: 866
<212> TYPE: PRT
<213> ORGANISM: Escherichia coli

<400> SEQUENCE: 24

```
Met Ser His Asn Leu Gln Asp Ile Leu Ala Ala Ser Gly Tyr Gln
1               5                   10                  15

Ser Val Thr Ser Glu Pro Ala Leu Asn Arg Lys Arg Pro Lys Thr Leu
                20                  25                  30

Asp Asp Tyr Pro Val Ile Pro Pro Ala Ser Lys Lys Val Ser Val Ile
                35                  40                  45

Ser Ser Asp Leu Thr Leu His Ile Gly Phe Asp Thr Glu Tyr Val Phe
            50                  55                  60

Asn Pro Glu Thr Arg Gln Asn Asp Ile Leu Ser Tyr Gln Ser Tyr Val
65                  70                  75                  80

Val Leu Pro Asp Asn Thr Gly Ile Ser Asn Ile Ile Tyr Pro Pro Asp
                85                  90                  95

Ser Gln Lys Lys Ser Arg Leu Ser Phe Lys Asp Phe Leu Cys Gln Thr
            100                 105                 110

Ile Thr Pro Leu Leu Glu Thr Gly Val Ile Thr Lys Trp Pro Gly Ile
            115                 120                 125

Ile Asn Ile Tyr Ala His Phe Ile Arg Ala Asp Ile Ala Ser Phe Ala
130                 135                 140

Asn Phe Trp Ser Asp Tyr Lys Ile Leu Leu Lys Gly Ile Arg Gly Thr
145                 150                 155                 160

Val Ser Ser Phe Lys Asn Arg Tyr Gly Ile Asp Phe Asp Glu Gln Gln
                165                 170                 175

Glu Arg Arg Val Lys Thr Glu Gln Ile Met Phe Asp Lys Arg Thr Ser
            180                 185                 190

Pro Pro Arg Cys Ser Asn Val Ala Phe Ile Asp Thr Leu Leu Ile Thr
            195                 200                 205

Pro Gly Gly Met Gly Leu Ala Glu Cys Gly Glu Leu Leu Gly Leu Pro
            210                 215                 220

Lys Leu Thr Ile Pro Ala Pro Tyr Ser Ile Thr Asn Met Arg Glu Tyr
225                 230                 235                 240

Leu Leu Gly Asp Arg Ala Gly Phe Glu Ala Tyr Ala Leu Arg Asp Ala
                245                 250                 255

Glu Ile Ala Val Arg Tyr Ala Leu Gln Val Arg Asn Phe Cys Ala Arg
            260                 265                 270

Glu Leu Met Ile Asp Arg Val Pro Ala Thr Ile Gly Ala Met Ala Val
            275                 280                 285

Ser Arg Phe Thr Lys Thr Leu Lys Glu Asn Asn Met Ser Pro Glu Val
            290                 295                 300

Cys Leu Gly Thr His Ile Lys Thr Arg Glu Leu Trp Leu Thr Glu Lys
305                 310                 315                 320

Gln Ala Phe Arg Thr Ile Lys Asn Pro Ala Ser Val Pro Ser Arg Glu
                325                 330                 335
```

-continued

```
Leu Phe Glu Thr Phe Pro Ile Asn Cys Tyr His Gly Gly Arg Asn Glu
            340                 345                 350
Cys Phe Met Met Gly Val Thr Pro Ser Asp His Trp Tyr Asp Tyr Asp
        355                 360                 365
Leu Ala Gly Ala Tyr Thr Thr Gly Leu Leu Asp Ile Leu Thr Pro Asp
        370                 375                 380
Tyr Gly Asn Ile Arg Leu Ser Lys Asn Pro Asp Asp Tyr Cys Gly His
385                 390                 395                 400
Val Met Gly Phe Ala Leu Val Thr Phe Arg Phe Pro Glu Ser Val Pro
                405                 410                 415
Tyr Pro Ser Leu Pro Val Arg Thr Asp Gln Tyr Gly Leu Phe Phe Pro
                420                 425                 430
Leu Ser Gly Glu Ser Trp Ala Thr Ala Pro Glu Ile Glu Leu Ala Leu
            435                 440                 445
Ser Leu Gly Ala Glu Met Thr Ile His Asn Gly Ile Ile Val Pro Trp
        450                 455                 460
Ile Cys Asp Thr Ser Pro His Asn Ser Glu Ser Thr Ser Val Phe Leu
465                 470                 475                 480
Pro Phe Val Gln Gln Val Arg Glu Asn Arg Asn Arg His Ile Lys Gly
                485                 490                 495
Ser Leu Glu Glu Lys Phe Trp Lys Glu Ile Gly Asn Ser Leu Tyr Gly
            500                 505                 510
Lys Leu Ala Gln Gly Leu Arg Ala Lys Thr Ala Phe Asp Thr Ala Arg
        515                 520                 525
Gly Leu Asn Arg Ser Leu Pro Pro Ser Val Thr Gln Pro Phe Phe
530                 535                 540
Ala Ala His Val Thr Gly Phe Ile Arg Ala Val Val Gly Glu Leu Met
545                 550                 555                 560
Asn Ala Leu Pro Ser Asp Ser Val Val Ser Val Thr Thr Asp Gly
                565                 570                 575
Phe Leu Thr Asn Cys Pro Leu Asp Lys Ile Asn Met Ser Gly Pro Leu
        580                 585                 590
Ser Ser Arg Phe Gln Ser Leu Cys Asp Ile Val Asp Pro Gly Ser Ser
        595                 600                 605
Met Leu Thr Cys Lys His Glu Val Ser Gln Leu Ile Ala Met Lys Thr
        610                 615                 620
Arg Gly Gln Leu Thr Tyr Arg Ala Ile Gln Gly Lys Pro Val Val His
625                 630                 635                 640
Ala Arg Ala Gly Val Lys Pro Pro Ala Asp Ile Pro Arg Ser Asp Tyr
                645                 650                 655
Asn Asp Tyr Met Val Asp Leu Tyr Leu Asn Arg Leu Pro Gly Gln Thr
                660                 665                 670
Leu Ser Arg Ser Thr Leu Ile Ser Thr Arg Glu Met Trp Leu Ser Glu
        675                 680                 685
Ser Asp Leu Val Tyr Arg Glu Gln Asp Ile Arg Leu Asn Leu Glu Phe
        690                 695                 700
Asp Phe Lys Arg Gln Pro Val Gln Pro Ala Met Asn Glu Gly His Leu
705                 710                 715                 720
Leu Met Phe Ser Arg Pro Trp Asp Asn Met Glu Glu Ala Leu Gln Gln
                725                 730                 735
Arg Ser Leu Phe Asp Asp Trp Arg Gln Thr His Thr Leu Lys Thr Leu
        740                 745                 750
Ala Asp Trp Asp Asp Trp Cys Asp Phe Leu Tyr Cys Arg Thr Val Phe
```

```
                755                 760                 765
Ser Asp Met Lys Leu Lys Val Gly Ser Lys Arg Ser Asp Ile Leu
            770                 775                 780
Val Arg Leu Phe Leu Arg Ala Leu Thr Gln Cys Gln Trp Gly Leu Met
785                 790                 795                 800
Leu Lys Asp Lys Lys Ser Tyr Ser Cys Lys Glu Val Ala Glu Trp Leu
                805                 810                 815
Thr Ser Glu Gly Tyr Ser Val Thr Val Thr Asp Val Lys Asn Ala Val
                820                 825                 830
Arg Ala Lys Ile Pro Gln Met Lys Phe Ser Ser Val Thr Pro Arg Met
                835                 840                 845
Lys Ser Leu Met Asp Ile Ile Ala Arg Lys Tyr Pro Thr Phe Cys Leu
                850                 855                 860
Pro Val
865

<210> SEQ ID NO 25
<211> LENGTH: 903
<212> TYPE: PRT
<213> ORGANISM: Enterobacter sp. MGH85

<400> SEQUENCE: 25

Met Asn Lys Lys Ser Asn Phe Leu Arg Ile Phe Ala Gln Pro Leu Ser
1               5                   10                  15
Asp Phe Pro Ser Ile Ser Gly Val Asp Asn Asp Thr Ala His Leu Asn
                20                  25                  30
Lys Lys Lys Ile Leu Met Phe Asp Met Asn Ala Leu Leu Ala Asn Ala
                35                  40                  45
Ala Gly Val Thr Gln Ser Asp Ser Arg Pro Thr Lys Thr Arg Asp Asn
            50                  55                  60
Phe Pro Leu Ile Pro Gln Lys Ser Lys Lys Arg Leu Asp Val Ser Ser
65                  70                  75                  80
Gln Leu His Leu Asp Ile Gly Phe Asp Thr Glu Tyr Val Tyr Asn Pro
                85                  90                  95
Gln Thr Lys Gln Asn Asp Ile Leu Ser Tyr Gln Ser Tyr Val Val Leu
                100                 105                 110
Pro Asp Gly Thr Gly Val Pro Gly Ile Leu Tyr Pro Ala Ser Ala His
            115                 120                 125
Lys Lys Asp Arg Leu Ser Leu Lys Asn Phe Leu Ala Lys Thr Leu Thr
            130                 135                 140
Pro Leu Leu Lys Asn Glu Gln Ile Thr Glu Trp Pro Gly Ser Ile Thr
145                 150                 155                 160
Leu Tyr Ala His Phe Leu Arg Ala Asp Val Ala Ser Phe Ser Asp Phe
                165                 170                 175
Trp Ser Asp His Lys Ile Leu Lys Gly Ile Arg Ser Thr Val Ser
                180                 185                 190
Ser Phe Lys Asn Arg Tyr Gly Ile Asp Phe Asp Glu Val Glu Asn Arg
            195                 200                 205
Arg Glu Lys Asn Ser Leu Ile Thr Phe Asp Lys Arg Thr Ser Pro Pro
        210                 215                 220
Arg Cys Ser Asn Val Met Phe Thr Asp Thr Leu Leu Ile Thr Pro Gly
225                 230                 235                 240
Gly Met Gly Leu Ala Glu Cys Gly Gln Leu Leu Gly Leu Pro Lys Leu
                245                 250                 255
```

-continued

```
Thr Ile Pro Ala Pro Tyr Ser Ile Ser Asp Met Arg Gln Tyr Leu Lys
            260                 265                 270

Gly Asp Arg Arg Gly Phe Glu Ala Tyr Ala Val Arg Asp Ala Glu Ile
        275                 280                 285

Ala Val Arg Tyr Ala Leu Gln Val Lys Ser Phe Cys Thr Glu Ser Leu
    290                 295                 300

Met Ile Glu Arg Ile Pro Thr Thr Ile Gly Ala Met Ala Val Ser Arg
305                 310                 315                 320

Phe Leu Lys Thr Ile Lys Glu Ser Gly Gln Ser Pro Glu Val Cys Met
                325                 330                 335

Gly Thr Trp Thr Asp Ser Arg Gln Arg Trp Asn Pro Asp Thr Gln Gly
            340                 345                 350

Phe Arg Thr Leu Lys Ser Thr Gln Ser Ile Pro Ala Arg Glu Leu Tyr
        355                 360                 365

Glu Thr Phe Ala Ile Asn Cys Tyr His Gly Gly Arg Asn Glu Cys Phe
    370                 375                 380

Met Met Gly Ile Thr Pro Glu Ser Gln Trp Tyr Asp Tyr Asp Leu Ala
385                 390                 395                 400

Gly Ala Tyr Thr Thr Gly Leu Leu Asp Ile Leu Gln Pro Asp Tyr Asp
                405                 410                 415

Asn Ile Tyr Gln Ser Gln Asn Pro Glu Glu Phe Cys Gly His Thr Met
            420                 425                 430

Gly Phe Ala Leu Val Ser Phe Arg Phe Pro Asp Thr Val Arg Tyr Pro
        435                 440                 445

Cys Leu Pro Val Arg Thr Asp Gln Tyr Gly Leu Phe Phe Pro Leu Thr
    450                 455                 460

Gly Glu Ser Trp Ala Thr Ala Pro Glu Met Ala Leu Ala Leu Ser Leu
465                 470                 475                 480

Gly Ala Glu Met Thr Ile Gln His Gly Ile Ile Pro Trp Arg Gln
                485                 490                 495

Tyr Lys Ser Asn Asp Ser Ser Ser Pro Ala Glu Pro Val Cys Ser Val
            500                 505                 510

Phe Leu Pro Phe Val Gln Gln Val Arg Glu Asn Arg Asn Arg His Asp
        515                 520                 525

Lys Gly Ser Leu Glu Glu Lys Phe Trp Lys Glu Ile Gly Asn Ser Leu
    530                 535                 540

Tyr Gly Lys Leu Ala Gln Gly Leu His Ala Lys Thr Ala Phe Asp Thr
545                 550                 555                 560

Ala Arg Gly Leu Asn Ser Pro Leu Pro Ser Ser Val Thr Gln Pro
                565                 570                 575

Phe Phe Ala Ala His Val Thr Gly Phe Val Arg Ala Val Val Gly Glu
            580                 585                 590

Leu Met Asn Ala Leu Pro Pro Asn Ala Thr Val Val Ser Val Thr Thr
        595                 600                 605

Asp Gly Phe Leu Thr Asp Ser Ala Ile Glu Asn Ile Asp Met Ser Gly
    610                 615                 620

Pro Leu Ser Ser Arg Phe Gln Ala Leu Cys Gly Ile Ala Asp Pro Gly
625                 630                 635                 640

Ser Ser Met Leu Thr Cys Lys His Gln Val Arg Gln Leu Val Ala Met
                645                 650                 655

Lys Thr Arg Gly Gln Leu Thr Tyr Lys Glu Leu Ala Gly Tyr Pro Ile
            660                 665                 670

Val His Ala Arg Ala Gly Val Lys Pro Pro Ala Asp Ile Pro Arg Asp
```

```
              675                 680                 685
Asp Tyr Asn Arg Tyr Met Val Asp Leu Tyr Leu Asn Arg Ala Pro Gly
    690                 695                 700

Gln Lys Leu Arg Arg Gly Ser Leu Ile Ser Thr Arg Asp Met Trp Leu
705                 710                 715                 720

Asn Glu Ser Asp Leu Val Ala Val Glu Ser Asp Ile Arg Leu Asn Leu
                725                 730                 735

Glu Phe Asp Phe Lys Arg Gln Leu Ile Ala Pro Thr Met Asn Asp Gly
            740                 745                 750

His Leu Leu Met Tyr Ser Arg Pro Trp Asn Asp Ile Ala Gln Ala Leu
        755                 760                 765

Lys Gln Arg Gln Leu Phe Asp Asp Trp Arg Gln Thr His Ser Leu Lys
    770                 775                 780

Asp Glu Ala Asp Trp Glu Asp Trp Cys Asp Phe Leu Tyr Cys Arg Asn
785                 790                 795                 800

Ile Phe Thr Pro Leu Lys Leu Lys Val Gly Gln Asn Arg Ser Asp Asp
                805                 810                 815

Val Leu Val Arg Leu Phe Leu Arg Ala Leu Ala Gln Tyr Gln Trp Gly
            820                 825                 830

Leu Thr Pro Asp Asp Arg Lys Arg Gln Thr Ser Val Glu Ile Ala Ala
        835                 840                 845

Trp Leu Val Glu Ala Gly Tyr Ser Val Thr Pro Ser Asp Val Lys Asn
    850                 855                 860

Ala Gly Arg Ala Lys Leu Pro Pro Ile Ile Phe Asp Ser Leu Thr Ala
865                 870                 875                 880

Arg Met Asn Arg Leu Met Asp Leu Ile Lys Leu Val Tyr Pro Gly Phe
                885                 890                 895

Ala Leu Pro Ser Ala Val Leu
            900

<210> SEQ ID NO 26
<211> LENGTH: 866
<212> TYPE: PRT
<213> ORGANISM: Enterobacter cloacae

<400> SEQUENCE: 26

Met Phe Asp Met Asn Ala Leu Leu Ala Asp Ala Gly Val Thr Gln
1               5                   10                  15

Pro Val Ala Arg Ser Ala Lys Thr Leu Asp Asn Phe Pro Leu Ile Pro
            20                  25                  30

Gln Lys Ser Lys Asn Arg Leu Asp Val Ser Ser Glu Leu His Leu Asp
        35                  40                  45

Ile Gly Phe Asp Thr Glu Tyr Val Tyr Asn Pro His Thr Lys Gln Asn
    50                  55                  60

Asp Ile Leu Ser Tyr Gln Ser Tyr Val Val Leu Pro Asp Gly Lys Gly
65                  70                  75                  80

Val Pro Gly Ile Leu Tyr Pro Ala Ser Ala His Lys Lys Asp Arg Leu
                85                  90                  95

Ser Leu Lys Asn Phe Leu Ala Lys Thr Leu Thr Pro Leu Leu Lys Asn
            100                 105                 110

Glu Gln Ile Asn Glu Trp Pro Gly Ser Ile Thr Leu Tyr Ala His Phe
        115                 120                 125

Leu Arg Ala Asp Val Ala Ser Phe Ser Asp Phe Trp Ser Asp His Lys
    130                 135                 140
```

```
Ile Leu Leu Lys Gly Ile Arg Ser Thr Val Ser Ser Phe Lys Asn Arg
145                 150                 155                 160

Tyr Gly Ile Asp Phe Asp Glu Val Glu Asn Arg Arg Glu Lys Asn Ser
            165                 170                 175

Leu Ile Thr Phe Asp Lys Arg Thr Ser Pro Pro Arg Cys Ser Asn Val
        180                 185                 190

Thr Phe Thr Asp Thr Leu Leu Ile Thr Pro Gly Gly Met Gly Leu Ala
    195                 200                 205

Glu Cys Gly Gln Leu Leu Gly Leu Pro Lys Leu Thr Ile Pro Ala Pro
210                 215                 220

Tyr Ser Ile Ser Asp Met Arg Gln Tyr Leu Lys Gly Asp Arg Arg Gly
225                 230                 235                 240

Phe Glu Ala Tyr Ala Val Arg Asp Ala Glu Ile Ala Val Arg Tyr Ala
            245                 250                 255

Leu Gln Val Lys Ser Phe Cys Thr Glu Ser Leu Met Ile Glu Arg Val
            260                 265                 270

Pro Thr Thr Ile Gly Ala Met Ala Val Ser Arg Phe Leu Lys Thr Ile
        275                 280                 285

Lys Glu Ser Gly Gln Ser Pro Glu Val Cys Met Gly Thr Arg Thr Ile
290                 295                 300

Ser Gln Gln Cys Trp Asn Pro Asp Thr His Gly Phe Arg Thr Leu Lys
305                 310                 315                 320

Ser Thr Gln Ser Ile Pro Ala Arg Glu Leu Tyr Glu Thr Phe Ala Ile
                325                 330                 335

Asn Cys Tyr His Gly Gly Arg Asn Glu Cys Phe Met Met Gly Ile Thr
            340                 345                 350

Pro Glu Ser Gln Trp Tyr Asp Tyr Asp Leu Ala Gly Ala Tyr Thr Thr
            355                 360                 365

Gly Leu Leu Asp Val Leu Gln Pro Asp Tyr Asp Asn Leu Tyr Thr Ser
        370                 375                 380

Gln Asn Pro Glu Glu Phe Cys Gly His Thr Met Gly Phe Ala Leu Val
385                 390                 395                 400

Ser Phe Arg Phe Pro Asp Thr Val Arg Tyr Pro Cys Leu Pro Val Arg
            405                 410                 415

Thr Asp Gln Tyr Gly Leu Phe Phe Pro Leu Thr Gly Glu Ser Trp Ala
        420                 425                 430

Thr Ala Pro Glu Ile Ala Leu Ala Leu Ser Leu Gly Ala Glu Ile Ala
        435                 440                 445

Ile Gln His Gly Ile Ile Pro Trp Arg Gln Tyr Lys Ser Asp Asn
450                 455                 460

Ala Ser Ser Pro Thr Lys Pro Ala Ser Ser Val Phe Leu Pro Phe Val
465                 470                 475                 480

Gln Gln Val Arg Glu Asn Arg Asn Arg His Asp Lys Gly Ser Leu Glu
            485                 490                 495

Glu Lys Phe Trp Lys Glu Ile Gly Asn Ser Leu Tyr Gly Lys Leu Ala
            500                 505                 510

Gln Gly Leu His Ala Lys Thr Ala Phe Asp Thr Ala Arg Gly Leu Asn
        515                 520                 525

Ser Pro Leu Pro Pro Ser Ser Val Thr Gln Pro Phe Phe Ala Ala His
        530                 535                 540

Val Thr Gly Phe Val Arg Ala Val Val Gly Glu Leu Met Asn Ala Leu
545                 550                 555                 560

Pro Pro Asn Ala Thr Val Val Ser Val Thr Thr Asp Gly Phe Leu Thr
```

```
                    565                 570                 575
Asp Val Ser Leu Glu Asn Ile Asp Met Ser Gly Pro Leu Ser Ser Arg
            580                 585                 590

Phe Gln Ala Leu Cys Asp Ile Ala Asp Pro Gly Ser Ser Met Leu Thr
            595                 600                 605

Cys Lys His Gln Val Arg Gln Leu Val Ala Met Lys Thr Arg Gly Gln
610                 615                 620

Leu Thr Tyr Lys Glu Ser Glu Gly Phe Pro Ile Val His Ala Arg Ala
625                 630                 635                 640

Gly Val Lys Pro Pro Ala Asp Ile Pro Arg Asp Tyr Asn Arg Tyr
            645                 650                 655

Met Val Val Leu Tyr Met Asn Arg Ala Pro Gly Gln Lys Leu Arg Arg
            660                 665                 670

Gly Ser Leu Ile Ser Thr Arg Asp Met Trp Leu Asn Glu Ser Asp Leu
            675                 680                 685

Val Ala Val Glu Ser Glu Ile Arg Leu Asn Leu Glu Phe Asp Phe Lys
            690                 695                 700

Arg Gln Leu Ile Thr Pro Thr Met Asn Glu Gly His Leu Leu Met His
705                 710                 715                 720

Ser Arg Pro Trp Asp Met Ser Gln Ala Leu Lys Gln Arg Gln Leu
            725                 730                 735

Phe Asp Asp Trp Arg Gln Thr His Ala Leu Lys Asp Glu Ala Asp Trp
            740                 745                 750

Glu Asp Trp Cys Asp Phe Leu Tyr Cys Arg Asn Val Phe Thr Pro Leu
            755                 760                 765

Lys Leu Lys Val Gly Gln Asn Arg Ser Asp Asp Val Leu Val Arg Leu
770                 775                 780

Phe Leu Arg Ala Leu Ala Gln His Gln Trp Gly Leu Thr Pro Asp Asp
785                 790                 795                 800

Arg Lys Arg Gln Thr Ser Val Glu Ile Ala Ala Trp Leu Val Glu Ala
            805                 810                 815

Gly Tyr Ser Val Thr Pro Ser Asp Val Lys Asn Ala Gly Arg Ala Lys
            820                 825                 830

Leu Pro Pro Ile Ile Phe Asp Ser Leu Thr Ala Arg Met Asn Arg Leu
            835                 840                 845

Met Asp Leu Ile Lys Leu Val Tyr Pro Gly Phe Ala Leu Pro Ser Ala
            850                 855                 860

Val Leu
865

<210> SEQ ID NO 27
<211> LENGTH: 962
<212> TYPE: PRT
<213> ORGANISM: Aeromonas eucrenophila

<400> SEQUENCE: 27

Met Lys Arg Gln Glu Lys Pro Thr Asp Asn Ala Gly Gly Thr Ala Val
1               5                   10                  15

Ser Phe Pro Tyr Ala Asp Ala Asn Leu Gln Pro Asp Leu Asn Asn Arg
            20                  25                  30

Pro Pro His Gly Gly Tyr Asp Met Phe Asn Asp Ala Gln His Gln Ser
            35                  40                  45

Ala Leu Ala Leu Ala Ile Glu Ser Ala Leu Asp Pro Cys Gln Tyr Met
50                  55                  60
```

```
Asn Ser Pro Ser His Asp Pro Gly Trp Val Met Asn Gly Leu Ser Thr
 65                  70                  75                  80

Asp Val Ile Ala Gly Asp Pro Asp Ile Pro Asp Tyr Leu Leu Pro Val
                 85                  90                  95

Gln Glu Asn Ser Thr Asp Lys Ala Leu Arg Leu Arg Thr Gln His Tyr
            100                 105                 110

Leu Lys Pro Gly Glu Thr Val Val Pro Ala Lys Gly Ser Val Leu His
        115                 120                 125

Ile Gly Ile Asp Ser Glu Tyr Val Tyr Asn Pro Lys Thr Lys His Asn
    130                 135                 140

Asp Ile Leu Ser Tyr Gln Phe Phe Val Ile Thr Glu Lys Gly Glu His
145                 150                 155                 160

Ala Glu Val Ile Tyr Pro Ala Ser Ser Lys Lys Ser Asp Arg Leu Ser
                165                 170                 175

Phe Glu Arg Ser Ile Ser His Ile Val Val Cys Lys Glu Lys Gly
            180                 185                 190

Leu Ile Thr Glu Trp Pro Lys His Val Phe Val Tyr Ala His Phe Leu
        195                 200                 205

Arg Ala Asp Leu Ala Ser Phe Gly Asp Phe Trp Leu Phe Lys Thr Gln
210                 215                 220

Met Asp Gly Ile Arg Lys Thr Val Ala Ser Ile Asn Ser Ala Tyr Gly
225                 230                 235                 240

Ile Asp Leu Asp Asn Ile Leu Arg Arg Ala Lys Pro Thr Pro Leu
                245                 250                 255

Ile Leu Arg Asp Lys Gln Arg Lys Ala Gln Arg Thr Leu Leu Thr Phe
            260                 265                 270

Val Asp Thr Met Leu His Thr Pro Gly Gly Ala Gly Leu Ala Ala Val
        275                 280                 285

Gly Glu Leu Ile Asp Leu Pro Lys Leu Ser Leu Pro Ala Gly His Ser
    290                 295                 300

Ile Glu Arg Met Asp Glu Leu Leu Ala Gly Asp Lys Ala Ala Phe Glu
305                 310                 315                 320

Ala Tyr Ala Leu Arg Asp Ala Glu Ile Ala Val Lys Tyr Gly Leu Arg
                325                 330                 335

Leu His Glu Phe Ala Lys Thr Leu Gly Leu Ser Ser Leu Pro Lys Thr
            340                 345                 350

Ile Gly Gly Cys Ala Thr Ser Val Phe Leu Lys His Leu Arg Glu Thr
        355                 360                 365

Ala Gln Asp Arg Asp Gln Leu Phe Gly Thr His Glu Val Glu Gln Thr
    370                 375                 380

Gly Trp Ser Lys Asn Ser Ser Arg Pro Val Thr Lys Lys Val Arg Glu
385                 390                 395                 400

Met Thr Pro Ala Ala Lys Leu Phe Glu Asn Leu Ala Ile Asp Cys Tyr
                405                 410                 415

His Gly Gly Arg Asn Glu Cys Phe Trp Cys Gly Pro Thr Pro Leu Ser
            420                 425                 430

Leu Phe Asn Asp Phe Asp Leu Ser Gly Ala Tyr Thr Thr Gly Leu Val
        435                 440                 445

Asp Leu Phe Pro Leu Asp Tyr Glu Arg Ala Arg Met Thr Thr Asn Thr
    450                 455                 460

Ala Glu Phe Cys Gly His Val Phe Gly Leu Ala Arg Val Lys Tyr Arg
465                 470                 475                 480

Phe Pro Tyr Gly Thr Arg Tyr Pro Ser Leu Pro Val Arg Thr Glu Ile
```

```
                485                 490                 495
Gly Leu Leu Phe Pro Leu Thr Gly Glu Ser Leu Cys Thr Ala Pro Glu
                500                 505                 510

Ile Glu Val Ala Leu Arg Met Gly Cys Gln Ile Glu Ile His Gln Gly
                515                 520                 525

Val Ile Ile Pro Trp Thr Asp Thr Thr Gln Arg Leu Phe Glu Pro Phe
                530                 535                 540

Val Ser Gln Val Arg Glu Lys Arg Gln Ser Tyr Val Lys Lys Ser Phe
545                 550                 555                 560

Glu Glu Leu Leu Trp Lys Glu Ile Gly Asn Ser Leu Tyr Gly Lys Leu
                565                 570                 575

Ala Gln Gly Leu Arg Gly Lys Ser Ala Phe Asp Thr Ser Ser Gly Leu
                580                 585                 590

Ser Lys Pro Ile Glu Arg Ser Ala Ile Thr Asn Ala Phe Phe Ala Ala
                595                 600                 605

His Thr Thr Gly Leu Ile Arg Ala Val Leu Gly Glu Val Leu Ala Ser
                610                 615                 620

Ile Pro Ala His Arg Thr Val Val Ser Val Thr Thr Asp Gly Phe Leu
625                 630                 635                 640

Thr Asp Ala Thr Tyr Asp Glu Leu Val Leu Asn Gly Pro Ile Cys Arg
                645                 650                 655

Arg Phe Gln Glu Leu Gly Glu Arg Leu Asp Gly Pro Gly Phe Arg Met
                660                 665                 670

Leu Glu Gln Lys His Gln Val Lys Gln Val Ile Ala Met Lys Thr Arg
                675                 680                 685

Gly Gln Leu Thr Pro Glu Gly Val Glu Gly Gln Pro Gln Ile Leu Ala
                690                 695                 700

Lys Ala Gly Val Lys Pro Pro Cys Ser Lys Glu Leu His Gln Ala Tyr
705                 710                 715                 720

Met Leu Asp Leu Tyr Leu Asn Arg Thr Pro Gly Gln Lys Val Glu Ser
                725                 730                 735

Asp His Leu Ile Ser Thr Ala Glu Met Trp Ile Asn Glu His Asp Leu
                740                 745                 750

Val Ser Val Ser Arg Ser Lys Thr Leu Asn Leu Glu Phe Asp Phe Lys
                755                 760                 765

Arg Gln Pro Met Leu Pro Ser Met Gln Ser Val Leu Gly Thr Glu His
                770                 775                 780

Ile Cys Phe Asp Thr Arg Pro Trp Pro Thr Val Ala Ala Ala Met Glu
785                 790                 795                 800

Gln Arg Val Val Phe Asp Asn Trp Arg Arg Thr Asn Cys Leu Lys Thr
                805                 810                 815

Leu Asn Asp Trp Glu Ser Trp Glu Asp Tyr Phe Val Cys Lys Thr Ser
                820                 825                 830

Ile Lys Gly Leu Pro Met Arg Val Thr Asp Glu Gly Ser Leu Gly Ile
                835                 840                 845

Leu Lys Arg Val Phe Leu Arg Ala Tyr Thr Gln Ser Ala Phe Gly Met
                850                 855                 860

Thr Lys Thr Met Gly Tyr Asp Glu Leu Ala Glu Trp Leu Thr Ile Asn
865                 870                 875                 880

Gly Cys Pro Thr Ser Val Asp Asp Cys Lys Ser Ala Lys Arg Ala Lys
                885                 890                 895

Leu Val Gly Gln Cys Val Pro Val Thr Thr Arg Thr Val Arg Leu Val
                900                 905                 910
```

```
Arg Val Ile Leu Gln Glu Cys Pro Gly Leu Glu Leu Gly Ala Leu Phe
        915                 920                 925

Lys Pro Glu Asp Met Pro Gln Leu Gln Ser Arg Leu Asn Asn Pro Lys
        930                 935                 940

Thr Glu Ile Ala Gln Ile Thr Gln Asp Ala Pro Ser His Glu Val Ile
945                 950                 955                 960

Thr Asp

<210> SEQ ID NO 28
<211> LENGTH: 947
<212> TYPE: PRT
<213> ORGANISM: Aeromonas hydrophila YL17

<400> SEQUENCE: 28

Met Ser Ile His Asn Gln Pro Pro Leu Gln Ser Gly Thr Ala Val Ala
1               5                   10                  15

Met Asp Cys Pro Ile Asn Asp Ser Leu Phe Ala Phe Pro Glu Pro Asp
            20                  25                  30

Ala Met Thr Val Asn Glu Asp Tyr Ala Gln Pro Asp Ile Ser Tyr Glu
        35                  40                  45

Gln Leu Glu Leu Ala Arg Ser Ile Gln Leu Ala Leu Asp Pro Ser Thr
    50                  55                  60

Tyr Ile Leu Asp Ser Arg Asn Ala Val Asp Pro Ile Met Arg Gly Gln
65                  70                  75                  80

Ser Ala Ser Ala Glu Glu Asp Leu Leu Leu Lys Lys Ala Leu Thr Arg
                85                  90                  95

Leu Arg Ala Gly Glu Thr Val Thr Leu Ala Lys Gly Glu Pro Ile His
            100                 105                 110

Ile Gly Ile Asp Ser Glu Tyr Val Tyr Asp Pro Lys Thr Lys Arg Asn
        115                 120                 125

Val Ile Leu Ser Tyr Gln Phe His Val Ile Thr Glu Leu Gly Ser His
    130                 135                 140

Ser Gly Ile Ile Tyr Pro Lys Ser Gly Lys Val Ser Asp Arg Leu Glu
145                 150                 155                 160

Phe Asp Pro Phe Ile Ala Arg Ile Val Ile Met Cys Lys Glu Lys Gly
                165                 170                 175

Ile Ile Thr Lys Trp Pro Lys Lys Ile Tyr Val Tyr Ala His Phe Leu
            180                 185                 190

Arg Ala Asp Leu Ala Ser Phe Ser Asp Phe Phe Arg Lys Lys Thr Lys
        195                 200                 205

Val Ser Gly Ile Arg Lys Thr Val Thr Thr Met Thr Glu Thr Tyr Gly
    210                 215                 220

Val Asp Ile Lys Ala Leu Leu Ala Arg Arg Ala Gln Pro Glu Pro Met
225                 230                 235                 240

Ile Leu Lys Asp Ser Gln Arg Lys Lys His Met Thr Leu Ile Ala Phe
                245                 250                 255

Val Asp Thr Met Leu His Thr Pro Gly Gly Thr Gly Leu Ala Thr Val
            260                 265                 270

Gly Glu Met Ile Gly Ile Pro Lys Leu Ser Ile Pro Asp Gly Tyr Ser
        275                 280                 285

Ile Glu Arg Met Asp Glu Leu Leu Ala Gly Asp Lys Ser Ala Phe Glu
    290                 295                 300

Ala Tyr Ala Leu Arg Asp Ala Glu Ile Ala Val Lys Tyr Gly Leu Arg
305                 310                 315                 320
```

```
Leu His Glu Phe Ile Lys Gln His Gly Leu Thr Arg Leu Pro Ala Ser
            325                 330                 335
Leu Gly Ser Leu Ser Cys Ser Met Phe Leu Lys Phe Leu Arg Asp Gln
            340                 345                 350
Glu Tyr Asp Gln His Gln Leu Leu Gly Thr Glu Val Val Glu Arg Ser
            355                 360                 365
Arg Trp Asn Asp Lys Glu Ser Arg Leu Thr Ser Gln Lys Leu Arg Gln
    370                 375                 380
Met Thr Ser Leu Ala Arg Thr Phe Glu Pro Leu Ala Ile Asp Cys Tyr
385                 390                 395                 400
His Gly Gly Arg Asn Glu Ser Tyr Trp Asn Gly Pro Thr Pro Val Ser
                405                 410                 415
Ser Phe Tyr Asp Phe Asp Leu Ser Gly Ala Tyr Thr Thr Ala Leu Val
                420                 425                 430
Asp Leu Phe Pro Leu Asp Tyr Gly Asn Ala Arg Leu Thr Ser Asn Pro
            435                 440                 445
Glu Asp Tyr Arg Gly His Val Leu Gly Leu Ala Arg Val Arg Phe Ser
            450                 455                 460
Phe Pro Thr Gly Leu Arg Phe Pro Cys Leu Pro Val Phe Asp Glu Lys
465                 470                 475                 480
Tyr Gly Leu Leu Tyr Pro Leu Ser Gly Glu Ser Asn Cys Thr Ala Pro
                485                 490                 495
Glu Ile Glu Val Ala Leu Asn Met Gly Cys Gln Ile Asp Ile Ile Gln
                500                 505                 510
Gly Ile Ile Pro Trp Cys Asp Val Glu Val Ser Pro Phe Glu Ser
            515                 520                 525
Phe Val Ser Phe Val Arg Lys Met Arg Lys Ser Tyr Thr Lys Lys Ser
            530                 535                 540
Cys Asp Glu Leu Leu Trp Lys Glu Ile Gly Asn Ser Val Tyr Gly Lys
545                 550                 555                 560
Leu Ala Gln Gly Leu Gln Gly Lys Thr Ala Phe Asp Thr Thr Thr Gly
                565                 570                 575
Leu Ser Lys Lys Ile Asp Arg Ser Ala Ile Thr Asn Ala Tyr Phe Ala
            580                 585                 590
Ala His Thr Thr Gly Ile Val Arg Ala Val Leu Ser Glu Ile Leu Ala
            595                 600                 605
Ala Ile Pro Ala Asn Lys Thr Val Ile Ser Ala Thr Thr Asp Gly Leu
            610                 615                 620
Leu Thr Asp Ala Thr Tyr Glu Glu Leu Asp Leu Ser Gly Pro Leu Cys
625                 630                 635                 640
Arg Arg Phe Gln Ala Leu Gly Glu Arg Leu Asp Gly Asp Ser Phe Arg
                645                 650                 655
Met Leu Glu Leu Lys His Gly Ala Asn Gln Leu Ile Ala Met Lys Thr
                660                 665                 670
Arg Gly Gln Leu Thr Ala Ile Pro Met Glu Gly Gln Pro Asp Ile Leu
            675                 680                 685
Ala Lys Ala Gly Val Lys Pro Pro Cys Ser Lys Asp Gln His Gln Asn
            690                 695                 700
Tyr Met Leu Asp Leu Tyr Leu Asn Arg Thr Pro Gly Gln Lys Val Asp
705                 710                 715                 720
Ser Glu Gln Leu Val Ser Ile Ser Glu Met Trp Ile Asn Glu Cys Asp
                725                 730                 735
```

```
Leu Val Ser Met Thr Lys Thr Lys Thr Leu Asn Leu Glu Phe Asp Phe
            740                 745                 750

Lys Arg Lys Pro Met Gln Pro Ser Met Gln Ser Val Leu Gly Ile Glu
            755                 760                 765

His Ile Cys Phe Glu Thr Gln Pro Trp Pro Thr Ala Gln Ala Ala Ile
            770                 775                 780

Glu Glu Arg Ile Ile Phe Asp Ser Trp Arg Lys Asn His Cys Leu Lys
785                 790                 795                 800

Thr Leu Glu Asp Trp Glu Asn Trp Glu Asp Tyr Leu Thr Cys Lys Gly
            805                 810                 815

Ser Met Lys Ser Asn Val Met Arg Met Thr Asp Glu Gly Ser Leu Gly
            820                 825                 830

Ile Leu Lys Arg Val Phe Leu Arg Ala Tyr Thr Gln Ser Ala Phe Gly
            835                 840                 845

Met Thr Lys Thr Met Gly Tyr Ser Glu Leu Ala Glu Trp Leu Thr Val
            850                 855                 860

Asn Gly Cys Pro Thr Ser Val Asp Asp Cys Lys Ser Ala Lys Arg Ala
865                 870                 875                 880

Lys Leu Val Glu Gln Cys Val Pro Val Thr Thr Arg Thr Val Arg Leu
            885                 890                 895

Val Arg Val Ile Met Gln Glu Cys Pro Gly Leu Asp Leu Gly Ala Leu
            900                 905                 910

Phe Lys Pro Glu Asp Met Gln Leu Gln Gly Arg Leu Asn Asn Pro
            915                 920                 925

Lys Thr Glu Met Ala Gln Ile Thr Gln Asp Ala Pro Ser His Glu Val
            930                 935                 940

Ile Thr Asp
945

<210> SEQ ID NO 29
<211> LENGTH: 627
<212> TYPE: PRT
<213> ORGANISM: Photobacterium kishitanii

<400> SEQUENCE: 29

Met Ser Glu Val Lys Phe Phe Asn Asn Met Val Ala Ile Asp Gly Glu
1               5                   10                  15

Ala Asp Leu Ser Ala Phe Met His Asp Met Ala Ser Pro Pro Ile Ile
            20                  25                  30

Pro Asp Thr Gln Met Ser Asn Asp Ile Pro Val Asp Ile Lys Ser Gly
            35                  40                  45

Leu Met Ala Leu Glu Asn Asp Ile Pro Ser Glu Pro Phe Pro Ile Gly
50                  55                  60

Leu Pro Ala Tyr Gln Leu Met Thr Leu Glu Trp Ala Ser Gly Glu Thr
65                  70                  75                  80

Leu Tyr Ala Gly Phe Asp Thr Glu Tyr Gln His Asn Ala Ile Thr Gly
            85                  90                  95

Gln Asn Glu Ile Ile Ser Tyr Gln Val Val Gly Gln Thr Gln Arg Gly
            100                 105                 110

Gln Cys Ser Val Ile Val Tyr Pro Lys Ser Gly Ala Lys His His Arg
            115                 120                 125

Trp Thr Phe Glu Ala Leu Val Gly His Val Leu Glu Gln Met Phe Glu
            130                 135                 140

Gln Glu Leu Leu Asp Glu Val Pro Lys Gln Val Val Phe Gly His
145                 150                 155                 160
```

```
Phe Leu Arg Ala Asp Leu Thr Thr Phe Ser Asp Phe Trp Lys Lys Gln
                165                 170                 175

Lys Thr Thr Leu Arg Gly Val Ser Arg Thr Val Thr Ser Ala Met Gln
            180                 185                 190

Asp Tyr Gly Val Asp Val His Ala Leu Cys Lys Arg Lys Ala Gly Lys
        195                 200                 205

Asp Pro His Val Val Glu Ala Pro Ser Gly Glu Lys Tyr Arg Thr Lys
    210                 215                 220

Val Arg Phe Val Asp Thr Leu Ala Leu Ser Pro Asn Gly Ser Gly Leu
225                 230                 235                 240

Ala Val Ile Gly Arg Leu Ile Gly Leu Pro Lys Leu Glu Leu Pro Asp
                245                 250                 255

Gly Tyr Ala Lys Asp Glu Met Arg Arg Phe Lys Asp Glu Lys Pro Asp
            260                 265                 270

Leu Phe Tyr Ser Tyr Ala Met Arg Asp Ala Glu Ile Ala Leu Ala Tyr
        275                 280                 285

Gly Leu Arg Met Phe Lys Phe Ala Thr Val Glu Leu Gly Leu Ser Lys
    290                 295                 300

Cys Pro Ile Thr Leu Gly Ala Met Gly Val Ala Val Phe Gln Lys Met
305                 310                 315                 320

Leu Lys Glu Thr Gly Val Asp Lys Arg Asp Val Phe Gly Glu Arg Glu
                325                 330                 335

Ile Thr Thr Gln His Trp Asn Ala Lys Leu Gly Arg Pro His Thr Lys
            340                 345                 350

Lys Glu Leu Val Pro Thr Asp Ala Arg Glu Leu Phe Glu His Leu Ala
        355                 360                 365

Ile Arg Cys Tyr Met Gly Gly Arg Asn Glu Ser Phe Thr Cys Gly Pro
    370                 375                 380

Ser Asp Ile Gly Thr Phe Tyr Asp Phe Asp Leu Val Gly Ala Tyr Leu
385                 390                 395                 400

Gly Gly Met Val Asp Ile Tyr Pro Leu Asp Tyr Asp Arg Ala Tyr Met
                405                 410                 415

Ser Ile Asp Val Asn Ala Phe Cys Gly His Val Cys Gly Phe Ala Arg
            420                 425                 430

Val Arg Phe Ser Phe Pro Asp Gly Thr Arg Phe Pro Cys Ile Ala Val
        435                 440                 445

His His Asp Leu Tyr Gly Leu Tyr Phe Pro Met Thr Gly Glu Thr Tyr
    450                 455                 460

Thr Thr Ala Pro Glu Ile Glu Ala Ala Arg Asn Met Gly Ala Thr Ile
465                 470                 475                 480

Glu Ile Leu Gln Gly Val Val Thr Pro Trp Gln His Asp Ser Glu Leu
                485                 490                 495

Leu Phe Leu Ser Phe Val Gln Leu Ile Arg Glu Lys Arg Thr Ser Tyr
            500                 505                 510

Pro Lys Lys Ser Tyr Glu Glu Ser Met Trp Lys Glu Ile Gly Asn Ser
        515                 520                 525

Leu Tyr Gly Lys Thr Ala Gln Gly Leu Arg Thr Lys Thr Ala Phe Glu
    530                 535                 540

Leu Val Ser Gly Leu Asn Lys Asp Ile Pro Arg Ser Ala Val Thr Asn
545                 550                 555                 560

Pro Tyr Phe Ala Ala His Thr Thr Gly Phe Ile Arg Ala Val Ile Gly
                565                 570                 575
```

-continued

```
Glu Leu Leu Ala Ser Val Pro Thr Asn Arg Gln Val Ile Ser Val Thr
                580                 585                 590

Thr Asp Gly Phe Leu Thr Asp Ala Pro Met Asn Glu Leu Asp Leu Thr
            595                 600                 605

Gly Pro Leu Cys Ala Arg Phe Asn Ala His Asn Glu Leu Val Thr Asn
        610                 615                 620

Tyr Leu Asn
625

<210> SEQ ID NO 30
<211> LENGTH: 623
<212> TYPE: PRT
<213> ORGANISM: Vibrio ponticus

<400> SEQUENCE: 30

Met Ser Glu Asn Pro Gln Phe Phe Asn Asn Leu Val Ala Ile Asp Glu
1               5                   10                  15

Pro Asp Val Ser Leu Phe Leu Gly Asn Asp Leu Gly Leu Pro Asp Leu
            20                  25                  30

Ser Gly Met Ser Phe Ser Asn Asp Val Pro Asp Val Lys Pro Glu
        35                  40                  45

Leu Met Thr Leu Ala Asn Asp Ile Pro Thr Glu Val Met Gly Tyr Glu
50                  55                  60

Pro Met Ser Leu Glu Trp Ala Ser Gly Glu Thr Leu Tyr Val Gly Phe
65                  70                  75                  80

Asp Thr Glu Tyr Gln His Asn Ala Ile Thr Gly Gln Asn Glu Ile Ile
            85                  90                  95

Ser Tyr Gln Val Val Gly Gln Thr Gln Arg Gly Gln Cys Ser Val Ile
        100                 105                 110

Val Tyr Pro Lys Ser Gly Ala Lys His His Arg Trp Thr Phe Glu Ala
            115                 120                 125

Leu Val Gly His Leu Ile Ala Ala Met Phe Glu Gln Glu Gln Leu Asp
        130                 135                 140

Glu Val Pro Lys Gln Val Val Phe Gly His Phe Leu Arg Ala Asp
145                 150                 155                 160

Leu Thr Thr Phe Ser Asp Phe Trp Lys Asn Gln Lys Thr Thr Leu Arg
                165                 170                 175

Gly Ile Arg Arg Thr Val Thr Ser Ala Met Gln Asp Tyr Gly Val Asp
            180                 185                 190

Val His Ala Leu Gly Lys Arg Lys Ala Gly Lys Asp Pro His Val Val
        195                 200                 205

Glu Ala Pro Ser Gly Glu Lys Tyr Arg Thr Gln Val Arg Phe Val Asp
    210                 215                 220

Thr Leu Ala Leu Ser Pro Gly Gly Ser Gly Leu Ala Val Ile Gly Glu
225                 230                 235                 240

Leu Ile Gly Leu Pro Lys Leu Asp Leu Pro Asp Gly Tyr Ala Lys Asp
                245                 250                 255

Glu Met Arg Arg Phe Lys Asp Glu Gln Pro Asp Ala Phe Glu Ala Tyr
            260                 265                 270

Ala Met Arg Asp Ala Glu Ile Ala Leu Ala Tyr Gly Leu Arg Met Phe
        275                 280                 285

Lys Phe Ser Thr Val Glu Leu Gly Leu Ser Lys Cys Pro Thr Thr Leu
    290                 295                 300

Gly Ala Ile Gly Val Ser Val Phe Gln Lys Thr Leu Asn Glu Ser Gly
305                 310                 315                 320
```

Val Asp Lys Arg Asp Ala Phe Gly Glu Arg Glu Ile Thr Thr Gln His
              325                 330                 335

Trp Asn Ala Lys Leu Gly Arg Pro His Thr Lys Lys Glu Phe Ile Pro
              340                 345                 350

Thr Glu Ala Arg Glu Leu Phe Glu Arg Leu Ala Ile Lys Ser Tyr Phe
              355                 360                 365

Gly Gly Arg Asn Glu Cys Phe Thr Cys Gly Val Thr Glu Val Gly Thr
              370                 375                 380

Tyr Tyr Asp Phe Asp Leu Ser Gly Ala Tyr Thr Thr Gly Met Val Asp
385                 390                 395                 400

Leu Arg Pro Leu Asp Tyr Glu Asn Ala Phe Met Ser Arg Ser Met Asn
              405                 410                 415

Asp Phe Cys Gly His Val Cys Gly Phe Ala Arg Val Arg Phe Ser Phe
              420                 425                 430

Pro Asn Gly Thr Arg Phe Pro Cys Leu Pro Val His His Glu Leu Tyr
              435                 440                 445

Gly Leu Tyr Phe Pro Leu Thr Gly Glu Thr Tyr Ala Thr Ala Pro Glu
              450                 455                 460

Leu Glu Val Ala Arg Asn Met Gly Ala His Val Glu Ile Leu Gln Gly
465                 470                 475                 480

Val Val Ile Pro Trp Met Val Glu Ser Glu Pro Leu Phe Leu Pro Phe
              485                 490                 495

Val Arg Leu Ile Arg Glu Lys Arg Thr Ser Tyr Pro Lys Lys Ser Phe
              500                 505                 510

Glu Glu Ala Thr Trp Lys Glu Ile Gly Asn Ser Leu Tyr Gly Lys Thr
              515                 520                 525

Ala Gln Gly Leu Arg Asp Lys Thr Ala Phe Glu Leu Ala Asn Gly Leu
              530                 535                 540

Thr Lys Asp Ile Pro Arg Ser Ala Val Thr Asn Pro Tyr Phe Ala Ala
545                 550                 555                 560

His Thr Thr Gly Phe Val Arg Ala Val Ile Gly Leu Leu Ala Ser
              565                 570                 575

Ile Pro Glu His Arg Gln Val Ile Ser Val Thr Thr Asp Gly Phe Leu
              580                 585                 590

Thr Asp Ala Thr Lys Glu Glu Leu Asn Leu Ser Gly Ala Met Cys Leu
              595                 600                 605

Arg Phe Asn Glu His Asp Gln Met Ile Met Thr Asn Phe Lys
              610                 615                 620

<210> SEQ ID NO 31
<211> LENGTH: 593
<212> TYPE: PRT
<213> ORGANISM: Aeromonas media

<400> SEQUENCE: 31

Met Phe Glu Phe Lys Lys Ala Glu Ile Gly Val Ile Glu Glu Asp Gln
1               5                   10                  15

Pro Glu Pro Pro His Leu Lys Phe Ala Ile Lys Lys Val Ser Phe Asp
              20                  25                  30

Pro Lys Gln Pro Pro Ile Ser Phe Ala Asp Gly Glu Asp Leu Trp Ile
              35                  40                  45

Gly Val Asp Ala Glu Trp Val Thr Arg Asp Gly Gln Asn Ile Val Leu
              50                  55                  60

Ser Tyr Gln Val Tyr Cys Val Asn Ser Arg Asp Glu Thr Leu Gly Lys

```
             65                  70                  75                  80
Val Ile Tyr Pro Glu Leu Gly Lys Arg Leu Ala Phe Glu Thr Leu Ile
                     85                  90                  95

Ser Met Ala Val Glu Asp Cys Arg Ala Ala Gly Leu Ile Lys Lys Trp
                    100                 105                 110

Pro Arg Lys Ile Val Val Ala His Phe Leu Arg Ala Asp Leu Ser
                115                 120                 125

Thr Phe Lys Asp Phe Trp Ser Met Lys Thr Arg Leu Asp Gly Gln Gly
            130                 135                 140

Gly Ser Val Val Gly Gln Ile Ile Thr Asp Ser Gly Tyr Gly Val Asp
145                 150                 155                 160

Glu Thr Ala Glu Arg Lys Arg Arg Ala Pro Leu Lys Pro Ile Thr Leu
                165                 170                 175

Arg Asp Arg Asn Arg Lys Leu Arg Lys Ser Ile Ile Gln Phe Val Asp
                180                 185                 190

Thr Leu Phe Leu Ser Pro Asn Lys Ser Pro Leu Ser Ala Leu Gly Ser
            195                 200                 205

Met Leu Gly Leu Pro Lys Val Glu Ile Pro Glu Gly Tyr Ser Ile Glu
210                 215                 220

Arg Met Asp Glu Leu Leu Val Gly Asp Lys Glu Ala Phe Glu Arg Tyr
225                 230                 235                 240

Ala Leu Arg Asp Ala Glu Ile Ala Val Lys Tyr Ala Leu Lys Val Arg
                245                 250                 255

Asp Phe Leu Gly Gly Gln Phe Gly Leu Gln Lys Leu Pro Arg Ser Leu
                260                 265                 270

Gly Ala Val Gly Val Ala Val Phe Arg Gln Leu Leu Lys Ala Ala Asp
            275                 280                 285

Val Asp Tyr Met Ala Ala Phe Gly Leu Val Ile Lys Lys Glu Glu Arg
            290                 295                 300

Trp Asn Ser Gly Lys Gly Lys Val Ala Thr Lys Ala Val Lys Arg Pro
305                 310                 315                 320

Ser Pro Asp Arg Trp Arg Cys Glu Ala Leu Ala Ile Cys Cys Tyr Tyr
                325                 330                 335

Gly Gly Arg Asn Glu Ser Phe Met Ile Gly Pro Thr Pro Ile Gly Asp
                340                 345                 350

Trp Tyr Asp Trp Asp Leu Lys Gly Ala Tyr Thr Thr Gly Leu Cys Asp
            355                 360                 365

Leu Leu Glu Pro Asp Tyr Ala Asn Met Tyr Thr Ser Ser Asp Pro Gln
            370                 375                 380

Asp Phe Ile Gly His Val Met Gly Phe Ala Tyr Val Glu Phe Ala Phe
385                 390                 395                 400

Pro Ala Gly Thr Arg Phe Pro Cys Leu Pro Val Arg Ser Glu Gln Tyr
                405                 410                 415

Gly Leu Arg Phe Pro Leu Ser Gly Leu Ala Tyr Val Thr Ala Pro Glu
                420                 425                 430

Ile Glu Leu Ala Leu Ser Met Gly Ala Thr Ile Ala Ile Lys His Gly
            435                 440                 445

Val Ile Val Pro Trp Val Ala Gly Ser Gln Pro Leu Phe Glu Asp Phe
450                 455                 460

Thr Arg Met Ile Gln Arg Leu Arg Arg Glu Tyr Pro Lys Lys Ser Leu
465                 470                 475                 480

Glu Glu Val Met Val Lys Glu Ile Gly Asn Ser Leu Tyr Gly Lys Leu
                485                 490                 495
```

-continued

```
Ala Gln Gly Leu Ser Asp Lys Thr Ala Phe Asp Thr Ala Thr Gly Leu
            500                 505                 510

Ser Lys Lys Ile Gly Pro Ser Ala Val Thr Asn Pro Tyr Met Ala Ala
        515                 520                 525

His Thr Thr Gly Leu Ile Arg Ala Val Cys Gly Glu Leu Leu His Arg
    530                 535                 540

Ile Pro Ser His Arg Thr Val Val Ser Val Thr Thr Asp Gly Phe Leu
545                 550                 555                 560

Thr Asp Ala Pro Leu Glu Glu Leu Asp Gln Thr Gly Pro Leu Cys Arg
                565                 570                 575

Arg Tyr Gln Ala Leu Cys Gln Arg Leu His Gly Asp Glu Glu Val Gly
            580                 585                 590

Gln

<210> SEQ ID NO 32
<211> LENGTH: 896
<212> TYPE: PRT
<213> ORGANISM: Aeromonas allosaccharophila

<400> SEQUENCE: 32

Met Trp Leu Val Pro Ala Leu Tyr Tyr Gly Arg Leu Glu Ile Met Gly
1               5                   10                  15

Asp His Val Val Leu Val Trp Arg Asn Leu Met Phe Glu Phe Lys Lys
            20                  25                  30

Ala Glu Ile Gly Ile Ile Glu Glu Asp Gln Pro Ala Pro Ser His Leu
        35                  40                  45

Pro Phe Ala Ile Lys Lys Ala Thr Phe Asp Pro Lys Gln Pro Pro Ile
    50                  55                  60

Ser Leu Ala Asp Gly Glu Asp Leu Trp Val Gly Ile Asp Ala Glu Trp
65                  70                  75                  80

Val Thr Arg Asp Gly Gln Asn Ile Val Leu Ser Tyr Gln Gly Tyr Cys
                85                  90                  95

Val Asn Ser Arg Asp Glu Thr Leu Gly Lys Val Ile Tyr Pro Glu Pro
            100                 105                 110

Gly Lys Arg Leu Ala Phe Glu Thr Leu Ile Ser Met Ala Val Glu Asp
        115                 120                 125

Cys Arg Ala Ala Gly Leu Ile Lys Lys Trp Pro Lys Lys Ile Val Val
    130                 135                 140

Val Ala His Phe Leu Arg Ala Asp Leu Ser Thr Phe Lys Asp Phe Trp
145                 150                 155                 160

His Met Lys Ala Ser Leu Asp Gly Gln Gly Gly Ser Val Val Gly Gln
                165                 170                 175

Ile Ile Thr Asp Ser Asp Tyr Gly Val Asp Glu Thr Ala Glu Arg Lys
            180                 185                 190

Arg Arg Ala Pro Leu Lys Pro Ile Thr Leu Arg Asp Arg Asn Arg Lys
        195                 200                 205

Pro Gln Lys Ser Ile Ile Gln Phe Val Asp Thr Leu Phe Leu Ser Pro
    210                 215                 220

Asn Lys Ser Pro Leu Ser Ala Leu Gly Ser Met Leu Gly Leu Pro Lys
225                 230                 235                 240

Val Glu Ile Pro Glu Gly Tyr Ser Ile Glu Arg Met Asp Glu Leu Leu
                245                 250                 255

Val Gly Asp Lys Glu Ala Phe Glu Arg Tyr Ala Leu Arg Asp Ala Glu
            260                 265                 270
```

```
Ile Ala Val Gln Tyr Ala Leu Lys Val Arg Gly Phe Leu Gly Ser Gln
            275                 280                 285

Phe Gly Leu Gln Lys Leu Pro Arg Ser Leu Gly Ala Val Gly Val Ser
        290                 295                 300

Val Phe Arg Arg Leu Leu Lys Asp Ala Asp Ile Asp Tyr Met Val Ala
305                 310                 315                 320

Phe Gly Leu Glu Leu Ala Lys Ile Glu Arg Trp Asn Thr Gly Lys Gly
                325                 330                 335

Lys Val Thr Thr Lys Ala Val Thr Arg Pro Ser Pro Ala Arg Gly Leu
            340                 345                 350

Tyr Glu Asp Leu Ala Ile Arg Ser Tyr His Gly Gly Arg Asn Glu Ser
        355                 360                 365

Phe Met Ile Gly Pro Thr Glu Ile Gly Asp Trp Tyr Asp Trp Asp Leu
370                 375                 380

Lys Gly Ala Tyr Thr Thr Gly Leu Cys Asp Leu Leu Val Pro Asp Tyr
385                 390                 395                 400

Ala Asn Met His Thr Ser Ser Asp Pro Gln Asp Phe Val Gly His Val
                405                 410                 415

Met Gly Phe Ala Tyr Ile Glu Phe Thr Phe Pro Ala Gly Thr Ser Phe
            420                 425                 430

Pro Cys Phe Pro Val Arg Ser Glu Gln Tyr Gly Leu Arg Phe Pro Leu
        435                 440                 445

Ser Gly Leu Ala Tyr Val Thr Ala Pro Glu Ile Glu Leu Ala Leu Ser
450                 455                 460

Met Gly Ala Ser Ile His Ile Lys His Gly Val Ile Val Pro Trp Leu
465                 470                 475                 480

Ser Gly Ser Gly Pro Leu Phe Glu Glu Phe Thr Arg Met Ile Gln Arg
                485                 490                 495

Leu Arg Gln Glu Tyr Pro Lys Lys Ser Leu Glu Glu Val Met Val Lys
            500                 505                 510

Glu Ile Gly Asn Ser Leu Tyr Gly Lys Leu Ala Gln Gly Leu Arg Asp
        515                 520                 525

Lys Thr Ala Phe Asp Thr Ala Thr Gly Lys Asn Asn Lys Ile Gly Pro
530                 535                 540

Ser Ala Val Thr Asn Pro Tyr Met Ala Ala His Thr Thr Gly Leu Ile
545                 550                 555                 560

Arg Ala Val Cys Gly Glu Leu Leu His Arg Ile Pro Leu His Arg Thr
                565                 570                 575

Val Val Ser Val Thr Thr Asp Gly Phe Leu Thr Asp Ala Pro Leu Glu
            580                 585                 590

Glu Leu Asp Gln Thr Gly Pro Leu Cys Arg Arg Tyr Gln Ala Leu Cys
        595                 600                 605

Gln Gln Leu His Gly Asp Glu Ser Gly Asp Pro Val Pro Met Leu Glu
610                 615                 620

Leu Lys His His Ala Arg Gln Ile Val Ser Ile Lys Thr Arg Gly Gln
625                 630                 635                 640

Cys Thr Ala Ile Gln Gly Asp Thr Pro Pro Val Leu Ala Lys Ala Gly
                645                 650                 655

Val Lys Cys Ala Gly Thr Thr Glu Glu Gln Asn Glu Trp Ile Met Arg
            660                 665                 670

Leu Tyr Leu Asp Arg Glu Pro Gly Gln Lys Ile Asp Ala Ser His Leu
        675                 680                 685
```

```
Ile Ser Leu Arg Glu Gln Trp Leu Thr Glu Ser Asp Leu Ile Glu Ile
690                 695                 700

Lys Lys Gln Ser Arg Leu Ser Tyr Glu Phe Asp Gln Lys Arg Gln Leu
705                 710                 715                 720

Val Asn Pro Gln Ile Val Glu Val Ala Gly Gly Ser His Ile Ala Cys
                725                 730                 735

Asp Thr Val Pro Trp Gly Asp Ala Gly Met Ala Asp His Cys Arg Ala
                740                 745                 750

Arg Phe Glu Gly Trp Arg Glu Asp Asn Cys Leu Lys Thr Leu Glu Asp
            755                 760                 765

Trp Ala Ser Trp Glu Asp Tyr Tyr Glu Ser Ala Leu Ala Leu Gln Gly
770                 775                 780

Ser Lys Met Arg Val Arg Glu Asp Gly Ser Leu Gly Ile Leu Thr Arg
785                 790                 795                 800

Ile Leu Thr Arg Ser Leu Val Gln Lys Ala Trp Phe Asp His Thr Met
                805                 810                 815

Thr Tyr Gly Glu Ile Ser Ala Leu Leu Thr Ser Val Gly Leu Pro Val
                820                 825                 830

Thr Val Asp Thr Cys Lys Asn Ser Lys Arg Ala Ala Leu Pro Glu Asn
                835                 840                 845

Val Val Pro Val Thr Gly Glu Val Leu Arg Val Leu Ala Leu Leu Leu
850                 855                 860

Arg Gln Val Pro Glu Tyr Pro Leu Glu Pro Leu Phe Lys Pro Glu Arg
865                 870                 875                 880

Leu Asp Glu Val Lys Ser Arg Leu Asn Ser Met Glu Ile Ser His Ala
                885                 890                 895

<210> SEQ ID NO 33
<211> LENGTH: 912
<212> TYPE: PRT
<213> ORGANISM: Aeromonas allosaccharophila

<400> SEQUENCE: 33

Met Lys Ser Glu His Lys Met Pro Leu Glu Arg Val Pro Leu Pro Tyr
1               5                   10                  15

Thr Pro Ser Phe Leu Ala Glu Ser Ile Thr Gln Leu Phe Met Leu Asp
                20                  25                  30

Pro Pro Asp Leu Arg Glu Leu Met Thr Pro Pro Ser Gly Asp Ala
                35                  40                  45

Ala Pro Asp Leu Thr Asp Leu Phe Thr Pro Asn Pro Phe Ala Leu
50                  55                  60

Met Lys Thr Pro Gly Ser Ala Thr Arg Pro Leu Asp Leu Ala Pro Val
65                  70                  75                  80

Thr Leu Ala Asp Gly Ala Asp Leu Tyr Val Gly Leu Asp Ala Glu Trp
                85                  90                  95

Val Ala Asp Gly Asn Arg Asn Gln Val Leu Ser Tyr Gln Thr Tyr Cys
                100                 105                 110

Ile Asn Glu Asp Gly Thr Glu Leu Gly Lys Ile Tyr Tyr Pro Asp Ala
                115                 120                 125

Gly Lys Arg Phe Gly Phe Glu Asp Leu Ile Ser Met Met Val Glu Asp
130                 135                 140

Cys Arg Ala Ala Gly Val Ile Lys Glu Trp Pro Arg Lys Ile Ile Val
145                 150                 155                 160

Val Ala His Phe Leu Arg Ala Asp Leu Ser Thr Phe Gln Ser Phe Trp
                165                 170                 175
```

-continued

Lys Met Lys Thr Arg Val Asn Gly Gln Gly Gly Ser Val Val Gly Arg
            180                 185                 190

Val Leu Thr Asp Ser Gly Tyr Gly Val Asp Glu Thr Thr Val Arg Ser
            195                 200                 205

Arg Lys Ala Ser Pro Ala Pro Ile Leu Leu Lys Asp Lys His Arg Lys
        210                 215                 220

Pro Gln Lys Ser Ile Ile Gln Phe Val Asp Thr Leu Phe Leu Ala Pro
225                 230                 235                 240

Asn Lys Ser Pro Leu Ser Ala Leu Gly Asp Met Leu Gly Leu Pro Lys
                245                 250                 255

Val Glu Ile Pro Ala Gly Tyr Ser Ile Glu Arg Met Asn Glu Leu Leu
            260                 265                 270

Ala Gly Asp Lys Val Ala Tyr Glu Arg Tyr Ala Leu Arg Asp Ala Glu
        275                 280                 285

Leu Ala Val Lys Tyr Ala Leu Lys Val Gln Asp Tyr Leu Ala His Glu
            290                 295                 300

Phe Lys Leu Thr Ala Leu Pro Arg Ser Leu Gly Ala Val Gly Val Asn
305                 310                 315                 320

Val Phe Arg Arg Leu Leu Ala Glu His Gly Ile Asp Asp Met Ala Ser
                325                 330                 335

Phe Gly Met Arg Ser Val Ser His Val Glu Trp Asn Ala Arg Asn Gly
            340                 345                 350

Lys Val Thr Thr Lys Arg Asn Lys Arg Ser Asn Pro Ser Arg Cys Leu
        355                 360                 365

Phe Glu Thr Leu Ala Ile Asp Cys Tyr Met Gly Gly Arg Asn Glu Ser
            370                 375                 380

Phe Met Val Gly Pro Thr Ile Glu Gly His Trp Tyr Asp Trp Asp Leu
385                 390                 395                 400

Lys Gly Ala Tyr Thr Thr Gly Leu Cys Asp Leu Leu Val Pro Asp Tyr
                405                 410                 415

Ala Lys Ala Tyr Met Thr Asp Asn Pro Asn Ala Phe Val Gly His Val
            420                 425                 430

Met Gly Phe Ala Tyr Val Thr Phe Lys Phe Pro Ala Val Thr Arg Tyr
        435                 440                 445

Pro Cys Ile Pro Val Arg Ser Glu Gln Tyr Gly Leu Arg Phe Pro Leu
450                 455                 460

Glu Gly Asp Ala Tyr Val Thr Ala Pro Glu Ile Glu Leu Ala Leu Ala
465                 470                 475                 480

Met Gly Ala Thr Ile Glu Ile Lys His Gly Val Ile Val Pro Trp Val
                485                 490                 495

Val Asn Ser Pro Arg Leu Phe Glu Ser Phe Thr Ser Met Ile Gln Lys
            500                 505                 510

Arg Arg Lys Ala Leu Pro Lys Lys Ser Leu Glu Glu Val Met Ile Lys
        515                 520                 525

Glu Ile Gly Asn Ser Leu Tyr Gly Lys Leu Ala Gln Gly Leu Ser Asp
            530                 535                 540

Lys Thr Ala Phe Asp Thr Ala Thr Gly Leu Ser Lys Lys Ile Gly Ser
545                 550                 555                 560

Ser Ala Val Thr Asn Pro Tyr Met Ala Ala His Thr Thr Gly Leu Ile
                565                 570                 575

Arg Ala Val Cys Gly Glu Leu Leu His Arg Ile Pro Leu His Arg Thr
            580                 585                 590

```
Val Val Ser Val Thr Thr Asp Gly Phe Leu Thr Asp Ala Pro Leu Glu
            595                 600                 605

Glu Leu Asp Gln Thr Gly Pro Leu Cys Arg Arg Tyr Gln Ala Leu Cys
610                 615                 620

Gln Gln Leu His Gly Asp Glu Ser Gly Asp Pro Val Pro Met Leu Glu
625                 630                 635                 640

Leu Lys His His Ala Arg Gln Ile Val Ser Ile Lys Thr Arg Gly Gln
                645                 650                 655

Cys Thr Ala Ile Gln Gly Asp Thr Pro Pro Val Leu Ala Lys Ala Gly
            660                 665                 670

Val Lys Cys Ala Gly Thr Thr Glu Glu Gln Asn Glu Trp Ile Met Arg
        675                 680                 685

Leu Tyr Leu Asp Arg Glu Pro Gly Gln Lys Ile Asp Ala Ser His Leu
    690                 695                 700

Ile Ser Leu Arg Glu Gln Trp Leu Thr Glu Ser Asp Leu Ile Glu Ile
705                 710                 715                 720

Gln Lys Lys Ile Arg Leu Ser Tyr Glu Phe Asp Gln Lys Arg Gln Leu
                725                 730                 735

Val Asn Pro Arg Met Val Glu Val Ala Gly Glu Thr His Ile Ala Cys
            740                 745                 750

Asp Thr Val Pro Trp Asp Asp Ala Gly Met Ala Asp His Cys Arg Ala
        755                 760                 765

Arg Phe Asp Gly Trp Arg Glu Asp Asn Cys Leu Lys Thr Leu Glu Asp
    770                 775                 780

Trp Ala Ser Trp Glu Asp Tyr Tyr Glu Ser Ala Leu Ala Leu Gln Gly
785                 790                 795                 800

Ser Thr Met Arg Ile Arg Glu Asp Gly Ser Leu Gly Ile Leu Thr Arg
                805                 810                 815

Ile Leu Thr Arg Ser Leu Val Gln Lys Ser Trp Tyr Asp His Thr Met
            820                 825                 830

Thr Tyr Gly Glu Ile Ser Ala Leu Leu Thr Ser Val Gly Leu Pro Val
        835                 840                 845

Thr Val Asp Thr Cys Lys Asn Ser Lys Arg Ala Ala Leu Pro Glu Asn
    850                 855                 860

Val Val Pro Val Thr Gly Glu Val Leu Arg Val Leu Ala Leu Leu Leu
865                 870                 875                 880

Arg Gln Val Pro Glu Tyr Pro Leu Glu Pro Leu Phe Lys Pro Glu Arg
                885                 890                 895

Leu Asp Glu Val Lys Ser Arg Leu Asn Ser Met Glu Ile Ser His Ala
            900                 905                 910

<210> SEQ ID NO 34
<211> LENGTH: 905
<212> TYPE: PRT
<213> ORGANISM: Ferrimonas senticii

<400> SEQUENCE: 34

Asp Arg Gln Ile Lys Ile Phe Phe Asp Gly Val Arg Ser Ala Pro Trp
1               5                   10                  15

Ala Ala Leu Arg Gly Lys Gly Lys Ala Val His Ile Ala Ile Asp Ser
                20                  25                  30

Glu Trp Val Phe Asn Pro Glu Thr Gly Lys Asn Asp Ile Leu Cys Tyr
            35                  40                  45

Ser Tyr Cys Val Arg Ala Gly Asp Lys Thr Phe Lys Gly Val Lys Ser
        50                  55                  60
```

```
Thr Glu Met Ala Lys Leu Ile Lys Gln Cys Arg Asp Gln Gly Leu Thr
 65                  70                  75                  80

Lys Asp Glu Glu Met Leu Lys Arg Lys Gln Leu Ala Asn Ser Thr Lys
                 85                  90                  95

Gly Tyr Lys Ala Asn Phe Asp Gln Phe Ile Gln Glu Leu Leu Leu Lys
            100                 105                 110

Ala Lys Ala Arg Gly Phe Ile Asp Glu Trp Pro Glu His Thr Phe Ile
        115                 120                 125

Tyr Ala His Phe Leu Arg Ala Asp Ile Ala Ser Phe Asp Glu Phe Trp
    130                 135                 140

Asn Ile Gly Thr Lys Gly Lys Asn Lys Ala Asn Cys Phe Thr Ala Val
145                 150                 155                 160

Gln Gly Ser Ile Thr Ser Gly Arg Gly Ala Tyr Gly Ile Asp Leu Ala
                165                 170                 175

Ser Ile Gly Arg Ser Lys Tyr Lys Thr Glu Asn Thr Lys Phe Tyr Cys
            180                 185                 190

Gly Gly Asn Asn Val Ile Glu Thr Lys Val Arg Phe Ile Asp Thr Met
        195                 200                 205

Leu Leu Ser Ser Lys Ala Ser Leu Asp Asp Ile Gly Glu Leu Val Gly
    210                 215                 220

Ile Pro Lys Met Asn Leu Ala Asp Gly Met Ile Ala Arg Met Asp Asp
225                 230                 235                 240

Leu Tyr Cys Glu Asp Arg Gly Leu Phe Glu Arg Tyr Ala Val Arg Asp
                245                 250                 255

Ala Gln Ile Ala Leu Glu Tyr Gly Leu Lys Met Gln Gln Phe Ala Leu
            260                 265                 270

Val Asp Met Arg Glu Asp Thr Gly Leu Glu Leu Lys Gln Leu Pro Ser
        275                 280                 285

Thr Leu Gly Asn Phe Ala Val Ser Leu Phe Lys His Thr Gly Gly Gly
    290                 295                 300

Val Asp Gln Met His Glu Phe Leu Gly Tyr Glu Lys Arg Lys Ser Glu
305                 310                 315                 320

Tyr Phe His Ala Lys Ser Asn Gly Ile Arg Lys Ser Val Thr Ile Ala
                325                 330                 335

Lys Thr Val Ser Arg Glu Tyr Thr Asp Ala Leu Ala Val His Cys Phe
            340                 345                 350

Tyr Gly Gly Ala Asn Phe Gly Ala Tyr Phe Gly Val Thr Glu Gln Gly
        355                 360                 365

Asp Tyr Asn Asp Tyr Asp Leu Ser Gly Ala Tyr Thr Thr Ala Leu Val
    370                 375                 380

Asp Ile Leu Glu Ala Asp Tyr Leu Asn Ser Phe Glu Ser Lys Asn Leu
385                 390                 395                 400

Glu Asp Tyr Leu Gly His Thr Met Gly Phe Ala Tyr Val Arg Phe Lys
                405                 410                 415

His Pro Glu Gly Thr Lys Trp Gly Leu Leu Pro Cys Arg Thr Asp Leu
            420                 425                 430

Arg Gly Ile Tyr Tyr Pro Leu Glu Gly Glu Thr Tyr Val Thr Ala Pro
        435                 440                 445

Glu Leu Gln Leu Ala His Asp Ala Gly Val Glu Ile Glu Ile Leu His
    450                 455                 460

Gly Gln Val Ile Pro Trp Lys Ser Gly Ser Val Ser Gln Phe Lys Ala
465                 470                 475                 480
```

-continued

```
Phe Thr Lys Ile Ile Arg Glu Gln Arg Ser Lys Tyr Lys Arg Glu Gly
                485                 490                 495

Asn Glu Leu Tyr Asp Gln Leu Trp Lys Leu Ile Gly Asn Thr Leu Tyr
            500                 505                 510

Gly Lys Val Gly Gln Gly Leu Arg Glu Lys Ser Gly Phe Asp Val Ser
        515                 520                 525

Ser Gly Leu Ser Ser Lys Ile Pro Tyr Ser Pro Val Thr Asn Ala His
    530                 535                 540

Tyr Ala Ala His Ala Thr Gly Phe Val Arg Ala Thr Met Met Glu Ile
545                 550                 555                 560

Ile Arg Lys Leu Thr Met Asp Glu Gln Val Gln Ile Val Ser Ala Thr
                565                 570                 575

Thr Asp Gly Phe Leu Thr Asn Ala Thr Gln Glu Gln Leu Asp Lys Cys
            580                 585                 590

Leu Asp Gly Pro Leu Ala Lys Arg Phe Gln His Ile Cys Asn Glu Val
        595                 600                 605

Ser Gly Glu Asp Met Met Gln Leu Lys His His Ala Lys Gln Ile Val
    610                 615                 620

Ser Met Lys Thr Arg Gly Gln Leu Thr Thr Glu Leu Gly Asp Thr Lys
625                 630                 635                 640

Pro Val Cys Ala Lys Ala Gly Val Lys Pro Pro Lys Gly Val Asp Glu
                645                 650                 655

Asn Ala Trp Met Val Glu Leu Phe Leu Asp Arg Tyr Pro Lys Gln Lys
            660                 665                 670

Ile Glu Arg Ser His Leu Ala Ser Ala Arg Glu Met Trp Leu Lys Glu
        675                 680                 685

Leu Asp Leu Ile Ser Ile His Thr Glu Gln Thr Leu Asn Leu Glu Trp
    690                 695                 700

Asp Phe Lys Arg Arg Pro Val Thr Pro Arg Met Val Thr Val Arg His
705                 710                 715                 720

Pro Val Ser Gly Glu Ile Val Glu His Leu Ser Phe Asp Thr Val Pro
                725                 730                 735

Trp Ser Thr Val Asp Glu Ala Leu Asp Ala Arg Thr Tyr Phe Asp Glu
            740                 745                 750

Trp Arg Ala Ser His Cys Leu Lys Thr Met Glu Asp Trp Glu Ser Trp
        755                 760                 765

Met Asp Phe Tyr Lys Val Arg Arg Tyr Leu Lys Gly Thr Gly Val Lys
    770                 775                 780

Tyr Leu Glu Asp Gly Ser Glu Gly Ile Phe Lys Val Gln Met Leu Arg
785                 790                 795                 800

Ala Ile Val Gln Gly Gly Trp Gly Leu Pro Glu Ala Pro Gln Arg Ala
                805                 810                 815

Pro Arg Gly His Tyr Asp Lys Leu Val Ala Met Phe Asp Val Asp Gly
            820                 825                 830

Ile Gly Gly Ile Thr Lys Gln Asp Leu Ala Asn Ala Lys Ser Arg Lys
        835                 840                 845

Leu Leu Thr Ala Arg Leu Pro Ile Thr Ser Arg Met Leu Pro Leu Leu
    850                 855                 860

Ser Trp Phe Ala Arg Gln Tyr Pro Thr Val Asp Leu Thr Leu Val Phe
865                 870                 875                 880

His Pro Asp Glu Val Asp Ala Val Leu Met Leu Glu Thr Tyr Asn
                885                 890                 895

Ala Asp Ala Ala Glu Lys Leu Ala Ala
```

<210> SEQ ID NO 35
<211> LENGTH: 964
<212> TYPE: PRT
<213> ORGANISM: Vibrio vulnificus

<400> SEQUENCE: 35

| | | | | | | | | | | | | | | |
|---|---|---|---|---|---|---|---|---|---|---|---|---|---|---|
| Met | Asn | Ile | Phe | Glu | Gln | Glu | Ala | Lys | Ala | Asn | Tyr | Gln | Leu | Met | Arg |
| 1 | | | | 5 | | | | | 10 | | | | | 15 | |
| Gln | Thr | Asp | Arg | Glu | Val | Gly | Asp | Phe | Leu | Val | Asn | Thr | Phe | Ser | Asn |
| | | | 20 | | | | | 25 | | | | | 30 | | |
| Asn | Arg | Ser | Tyr | Ile | Leu | Asp | Asp | Gln | Val | Ala | Lys | Phe | Gln | Gln | Glu |
| | | 35 | | | | | 40 | | | | | 45 | | | |
| Leu | Arg | Thr | Arg | Glu | Glu | Val | Lys | Lys | Thr | Val | Asp | Glu | Gln | Val | Lys |
| | 50 | | | | | 55 | | | | | 60 | | | | |
| Arg | Tyr | Phe | Glu | Gly | Leu | Arg | Ser | Ala | Pro | Trp | Ala | Ala | Ile | Arg | Gly |
| 65 | | | | | 70 | | | | | 75 | | | | | 80 |
| Lys | Gly | Lys | Ala | Val | His | Ile | Ala | Ile | Asp | Ser | Glu | Trp | Val | Phe | Asn |
| | | | | 85 | | | | | 90 | | | | | 95 | |
| Pro | Glu | Thr | Gly | Lys | Asn | Asp | Ile | Leu | Cys | Tyr | Ser | Tyr | Tyr | Val | Gln |
| | | | 100 | | | | | 105 | | | | | 110 | | |
| Val | Gly | Asp | Lys | Phe | Phe | Lys | Gly | Val | Lys | His | Thr | Glu | Met | Ala | Lys |
| | | 115 | | | | | 120 | | | | | 125 | | | |
| Leu | Ile | Lys | Glu | Cys | Arg | Asp | Gln | Gly | Leu | Ser | Lys | Glu | Glu | Glu | Met |
| | 130 | | | | | 135 | | | | | 140 | | | | |
| Leu | Lys | Arg | Lys | Gln | Leu | Ala | Asn | Ser | Thr | Lys | Gly | Tyr | Lys | Val | Asn |
| 145 | | | | | 150 | | | | | 155 | | | | | 160 |
| Phe | Asp | Lys | Phe | Ile | Gln | Glu | Leu | Leu | Ile | Lys | Ala | Lys | Ser | Arg | Gly |
| | | | | 165 | | | | | 170 | | | | | 175 | |
| Phe | Ile | Asp | Glu | Trp | Pro | Glu | His | Thr | Phe | Ile | Tyr | Ala | His | Phe | Leu |
| | | | 180 | | | | | 185 | | | | | 190 | | |
| Arg | Ala | Asp | Ile | Ala | Ser | Phe | Glu | Glu | Phe | Trp | Asn | Ile | Gly | Ala | Lys |
| | | 195 | | | | | 200 | | | | | 205 | | | |
| Ser | Lys | Asn | His | Lys | Asn | Ser | Phe | Thr | Ala | Val | Gln | Gly | Ser | Ile | Thr |
| | 210 | | | | | 215 | | | | | 220 | | | | |
| Ser | Gly | Arg | Gly | Ser | Tyr | Gly | Ile | Asp | Leu | Ala | Ser | Ile | Gly | Arg | Ser |
| 225 | | | | | 230 | | | | | 235 | | | | | 240 |
| Lys | Tyr | Lys | Thr | Glu | Asn | Thr | Lys | Phe | Tyr | Thr | Gly | Ser | Asn | Asn | Thr |
| | | | | 245 | | | | | 250 | | | | | 255 | |
| Phe | Glu | Thr | Lys | Val | Arg | Phe | Ile | Asp | Thr | Leu | Leu | Leu | Ser | Ser | Lys |
| | | | 260 | | | | | 265 | | | | | 270 | | |
| Ala | Ser | Leu | Asp | Asp | Ile | Gly | Glu | Leu | Val | Gly | Ile | Pro | Lys | Met | Thr |
| | | 275 | | | | | 280 | | | | | 285 | | | |
| Leu | Ala | Asp | Gly | Met | Ile | Ser | Arg | Met | Asp | Asp | Leu | Tyr | Cys | Glu | Asp |
| | 290 | | | | | 295 | | | | | 300 | | | | |
| Gln | Ser | Leu | Phe | Asp | Arg | Tyr | Ala | Val | Arg | Asp | Ala | Glu | Ile | Ala | Leu |
| 305 | | | | | 310 | | | | | 315 | | | | | 320 |
| Lys | Tyr | Gly | Leu | Gln | Met | Gln | Arg | Phe | Ala | Leu | Val | Asp | Met | Arg | Glu |
| | | | | 325 | | | | | 330 | | | | | 335 | |
| Asp | Thr | Gly | Leu | Glu | Leu | Lys | Gln | Leu | Pro | Ser | Thr | Leu | Gly | Asn | Phe |
| | | | 340 | | | | | 345 | | | | | 350 | | |
| Ala | Val | Ser | Leu | Phe | Lys | His | Thr | Cys | Gly | Gly | Val | Asn | Glu | Met | His |
| | | 355 | | | | | 360 | | | | | 365 | | | |

-continued

```
Glu Phe Leu Gly Tyr Glu Lys Arg Lys Gly Glu Tyr His Ala Lys
370                 375                 380

Ser Asn Gly Thr Arg Lys Ser Val Thr Ile Ala Lys Thr Val Ser Arg
385                 390                 395                 400

Glu Tyr Thr Asp Ala Leu Ala Val Ser Ala Phe Tyr Gly Gly Ala Asn
                405                 410                 415

Phe Gly Ala Tyr Phe Gly Val Thr Glu Gln Gly Asp Tyr Asn Asp Tyr
                420                 425                 430

Asp Leu Ser Gly Ala Tyr Thr Thr Ala Leu Val Asp Ile Leu Glu Ala
                435                 440                 445

Asp Tyr Leu Asn Ser Phe Glu Ser Lys Asn Ile Glu Asp Tyr Leu Gly
                450                 455                 460

His Thr Met Gly Phe Ala Tyr Val Arg Phe Lys His Pro Glu Gly Thr
465                 470                 475                 480

Gln Trp Gly Leu Leu Pro Cys Arg Thr Asp Leu Arg Gly Ile Tyr Tyr
                485                 490                 495

Pro Leu Glu Gly Ala Thr Tyr Val Thr Ala Pro Glu Leu Gln Leu Ala
                500                 505                 510

His Asp Ala Gly Val Glu Ile Glu Ile Leu His Gly Gln Val Ile Pro
                515                 520                 525

Trp Lys Gln Gly Ser Val Ser Gln Phe Lys Ala Phe Thr Lys Ile Ile
530                 535                 540

Arg Lys Gln Arg Ser Lys Tyr Lys Lys Glu Gly Asn Glu Leu Tyr Asp
545                 550                 555                 560

Gln Leu Trp Lys Leu Ile Gly Asn Thr Leu Tyr Gly Lys Val Gly Gln
                565                 570                 575

Gly Leu Arg Glu Lys Ser Gly Phe Asp Val Ser Ser Gly Leu Ser Ser
                580                 585                 590

Lys Ile Pro Tyr Ser Pro Val Thr Asn Ala His Tyr Ala Ala His Ala
                595                 600                 605

Thr Gly Phe Val Arg Ala Thr Met Met Glu Ile Ile Arg Lys Leu Thr
610                 615                 620

Met Asp Asn Asp Val Gln Ile Val Ser Ala Thr Thr Asp Gly Phe Leu
625                 630                 635                 640

Thr Asn Ala Thr Pro Glu Gln Leu Glu Ser Cys Leu Asp Gly Pro Leu
                645                 650                 655

Ala Lys Arg Phe Gln Arg Ile Cys Lys Glu Val Ser Gly Glu Asp Met
                660                 665                 670

Met Gln Leu Lys His His Ala Lys Gln Ile Ile Ser Met Lys Thr Arg
                675                 680                 685

Gly Gln Leu Thr Thr Glu Leu Gly Ser Thr Lys Pro Val Cys Ala Lys
                690                 695                 700

Ala Gly Val Lys Pro Pro Lys Gly Val Asn Glu Asn Ala Trp Met Val
705                 710                 715                 720

Glu Leu Phe Leu Asp Arg Tyr Pro Lys Gln Lys Ile Glu Arg Ser His
                725                 730                 735

Leu Ala Ser Ala Arg Asp Met Trp Leu Lys Glu Met Asp Leu Val Ser
                740                 745                 750

Ile His Thr Glu Gln Thr Leu Asn Leu Glu Trp Asp Phe Lys Arg Cys
                755                 760                 765

Pro Ile Asn Pro Arg Met Val Lys Ala Arg His Val Ser Gly Glu
770                 775                 780

Met Val Glu His Leu Ser Phe Asp Thr Val Pro Trp Asn Thr Val Asp
```

-continued

```
                785                 790                 795                 800
Glu Gly Leu Asp Ala Arg Thr Tyr Phe Asp Glu Trp Arg Val Asn Asn
                    805                 810                 815
Cys Leu Lys Thr Met Glu Asp Trp Asn Trp Met Asp Phe Tyr Lys
                820                 825                 830
Val Arg Arg Tyr Leu Lys Gly Thr Gly Val Lys Tyr Leu Glu Asp Gly
                    835                 840                 845
Ser Glu Gly Val Phe Lys Val Gln Met Leu Arg Ala Ile Thr Gln Gly
            850                 855                 860
Gly Trp Gly Leu Pro Ala Val Pro Gln Arg Ala Pro Arg Gly His Tyr
865                 870                 875                 880
Asp Lys Leu Val Ala Met Phe Asp Ala Asp Gly Ile Glu Gly Ile Thr
                    885                 890                 895
Lys Gln Asp Leu Ala Asn Ser Lys Gly Arg Lys Leu Leu Glu Ser Ala
                900                 905                 910
Leu Pro Ile Thr Thr Arg Met Leu Pro Leu Leu Ser Trp Phe Ala Arg
            915                 920                 925
Lys Tyr Pro Thr Val Asp Leu Thr Leu Val Phe His Pro Asp Glu Val
        930                 935                 940
Asp Glu Ala Val Leu Met Leu Glu Glu Tyr Asn Leu Lys Cys Thr Glu
945                 950                 955                 960
Lys Leu Val Ala

<210> SEQ ID NO 36
<211> LENGTH: 965
<212> TYPE: PRT
<213> ORGANISM: Vibrio tasmaniensis

<400> SEQUENCE: 36

Met Lys Thr Leu Glu Thr Thr Pro Lys Thr Thr Tyr Gln Leu Met Arg
1               5                   10                  15
Glu Thr Glu His Glu Leu Glu Asp Phe Leu Gln Ser Thr Phe Phe Asp
                20                  25                  30
Thr Lys Ser Leu Leu Leu Asp Asp Gln Val Ser Lys Phe Glu Ala Glu
            35                  40                  45
Leu Arg Gly Arg Glu Glu Ala Lys Lys Glu Ile Asp Lys Arg Ile Asn
        50                  55                  60
Arg Tyr Leu Glu Gly Ile Lys Ser Ala Pro Trp Ala Ala Met Arg Gly
65                  70                  75                  80
Lys Gly Lys Ala Ile His Ile Ser Ile Asp Ser Glu Trp Val Phe Asn
                85                  90                  95
His Glu Thr Gly Lys Asn Asp Ile Leu Cys Tyr Ser Tyr Ser Val Arg
                100                 105                 110
Ile Gly Asp Lys Ser Phe Ser Gly Val Lys His Thr Asp Met Ala Lys
            115                 120                 125
Leu Ile Lys Gln Cys Arg Asp Gln Gly Leu Ser Lys Glu Asp Glu Met
        130                 135                 140
Asp Lys Arg Lys Gln Leu Thr Lys Lys Gly Tyr Lys Ile Gly Phe Asp
145                 150                 155                 160
Lys Phe Ile Gln Glu Leu Leu Ile Lys Ala Lys Ala Arg Gly Phe Ile
                165                 170                 175
Glu Glu Trp Pro Glu Gln Thr Phe Ile Tyr Ala His Phe Leu Arg Ala
                180                 185                 190
Asp Ile Ala Ser Phe Glu Glu Phe Trp Asn Ile Gly Lys Asn Asn Lys
```

-continued

```
            195                 200                 205
Asn His Lys Asn Ser Leu Thr Val Val Gln Gly Thr Val Ser Gly
210                 215                 220

Arg Gly Ala Tyr Gly Ile Ala Leu Asp Ser Ile Gly Arg Ser Lys Tyr
225                 230                 235                 240

Lys Ile Glu Asn Thr Lys Phe Asn Ser Ser Asn Ala Phe Glu
                245                 250                 255

Thr Lys Leu Arg Phe Ile Asp Thr Thr Leu Leu Ser Ser Lys Ala Ser
                260                 265                 270

Leu Glu Glu Leu Gly Leu Gln Cys Gly Phe Pro Lys Met Thr Leu Pro
            275                 280                 285

Asp Asn Met Ile Glu Arg Met Asp Asp Leu Tyr Cys Lys Asp Thr Ser
            290                 295                 300

Leu Phe Asn Arg Tyr Ala Val Arg Asp Ala Asp Ile Ala Leu Glu Tyr
305                 310                 315                 320

Gly Leu Arg Met Gln Lys Phe Ala Leu Val Asp Leu Arg Glu Asp Ile
                325                 330                 335

Gly Leu Glu Leu Asn Ser Leu Pro Ser Thr Leu Gly Asn Leu Gly Val
            340                 345                 350

Ser Leu Phe Arg His Thr Cys Gly Ser Thr Ala Ala Met His Asp Phe
            355                 360                 365

Leu Gly Tyr Glu Thr Arg Lys Lys Gln Tyr Tyr His Ala Lys Ser Asn
370                 375                 380

Ala Ile Arg Asn Thr Tyr Asp Ile Ser Lys Thr Val Ser Arg Glu Tyr
385                 390                 395                 400

Thr Asp Asn Leu Ala Val Ser Ala Leu Phe Gly Gly Cys Asn Phe Gly
                405                 410                 415

Ala Tyr Phe Gly Val Ser Glu Lys Gly Asp Tyr Phe Tyr Asp Leu
                420                 425                 430

Ser Gly Ala Tyr Thr Thr Ser Leu Val Asn Ser Lys Lys Ala Asp Tyr
            435                 440                 445

Pro Asn Thr Phe Glu Ser Lys Asn Ile Glu Asp Tyr Leu Gly Asp Thr
450                 455                 460

Met Gly Phe Ala Tyr Val Arg Phe Lys His Pro Asp Gly Ile Leu Phe
465                 470                 475                 480

Pro Val Met Pro Cys Arg Thr Asp Leu Arg Gly Ile Tyr Tyr Pro Met
                485                 490                 495

Glu Gly Glu Thr Tyr Val Thr Ser Pro Glu Leu Gln Leu Ala His Asp
                500                 505                 510

Ile Gly Cys Glu Ile Glu Ile Leu His Gly Met Val Ile Pro Trp Val
            515                 520                 525

Glu Gly Ser Thr Ser Met Tyr Lys Asp Phe Thr Thr Ile Ile Arg Lys
            530                 535                 540

Gln Arg Ser Lys Tyr Lys Lys Glu Gly Asn Glu Leu Tyr Ser Gly Leu
545                 550                 555                 560

Trp Lys Leu Val Gly Asn Ser Leu Tyr Gly Lys Thr Leu Gln Gly Thr
                565                 570                 575

Ser Ser His Thr Lys Gly Phe Asp Leu Ala Thr Gly Leu Ser Lys Asn
            580                 585                 590

Ile Pro Tyr Ser Pro Val Thr Asn Ala His Tyr Gly Ala Tyr Cys Thr
                595                 600                 605

Ser Tyr Val Arg Ala Thr Met Leu Glu Val Ile Gly Lys Leu Cys Glu
610                 615                 620
```

```
Arg Tyr Gly Asp Asp Ile Lys Ile Ile Ser Ala Thr Thr Asp Gly Trp
625                 630                 635                 640

Leu Cys Asn Ala Thr Gln Glu Gln Leu Glu Gln Cys Leu Asp Gly Pro
            645                 650                 655

Leu Ala Arg Arg Phe Gln Gln Ile Cys Thr Glu Val Ser Gly Glu Asp
        660                 665                 670

Met Met Gln Leu Lys His His Ala Lys Gln Ile Ile Ser Met Lys Thr
            675                 680                 685

Arg Gly Gln Leu Thr Ala Glu Leu Gly Asp Thr Lys Pro Val Cys Ala
690                 695                 700

Lys Ala Gly Val Lys Ala Pro Lys Gly Val Asp Glu Asn Glu Trp Met
705                 710                 715                 720

Val Glu Leu Phe Leu Asp Arg Tyr Pro Gly Gln Lys Val Ala Arg Lys
                725                 730                 735

His Leu Val Ser Ala Arg Asp Gln Trp Leu Lys Glu Leu Asp Leu Ile
            740                 745                 750

Ser Ile His Thr Glu Gln Thr Leu Asn Leu Glu Tyr Asp Phe Lys Arg
        755                 760                 765

Arg Pro Val Asn Pro Arg Met Val Glu Val Arg His Pro Lys Ser Gly
770                 775                 780

Glu Met Ile Glu His Leu Ser Phe Asp Thr Val Pro Trp Asn Thr Val
785                 790                 795                 800

Asp Glu Gly Leu Asp Ala Arg Thr Tyr Phe Asp Glu Trp Arg Val Asn
                805                 810                 815

Asn Cys Leu Lys Thr Met Glu Asp Trp Asp Asn Trp Met Asp Phe Tyr
            820                 825                 830

Lys Val Arg Ser Tyr Leu Lys Gly Thr Gly Val Lys Tyr Leu Glu Asp
        835                 840                 845

Gly Ser Glu Gly Ile Phe Lys Val Gln Met Leu Arg Ser Ile Thr Gln
850                 855                 860

Gly Lys Trp Gly Leu Pro Glu Asp Pro Lys Arg Ala Pro Arg Gly His
865                 870                 875                 880

Tyr Asp Lys Met Val Ala Thr Phe Glu Ala Asp Gly Ile Glu Gly Ile
                885                 890                 895

Thr Lys Gln Asp Leu Ala Asn Ser Lys Gly Arg Lys Leu Leu Glu Ser
            900                 905                 910

Lys Leu Pro Val Thr Pro Arg Met Leu Pro Leu Ser Trp Leu Val
        915                 920                 925

Arg Lys Tyr Pro Met Ala Asp Met Thr Leu Ile Phe His Pro Ile Glu
930                 935                 940

Val Glu Glu Ala Val Ser Met Leu Glu Glu Tyr Asn Arg Glu His Thr
945                 950                 955                 960

Glu Lys Leu Ala Ala
            965

<210> SEQ ID NO 37
<211> LENGTH: 960
<212> TYPE: PRT
<213> ORGANISM: Vibrio campbellii

<400> SEQUENCE: 37

Met Asn Ile Phe Glu Gln Glu Ala Lys Thr Asn Tyr Gln Leu Met Arg
1               5                   10                  15

Gln Thr Asp Arg Glu Val Glu Asp Phe Leu Val Asn Thr Phe Ser Asn
```

-continued

```
                    20                  25                  30
Asn Arg Ser Tyr Ile Leu Asp Asp Gln Val Ala Lys Phe Gln Glu Glu
                35                  40                  45
Leu Cys Ser Arg Glu Gly Ala Lys Lys Thr Val Asp Glu Gln Val Lys
 50                  55                  60
Arg Tyr Leu Glu Gly Leu Arg Ser Ala Pro Trp Ala Ala Met Arg Gly
 65                  70                  75                  80
Lys Gly Lys Ala Val His Ile Ala Ile Asp Ser Glu Trp Val Phe Asn
                85                  90                  95
Pro Glu Thr Gly Lys Asn Asp Ile Leu Cys Tyr Ser Tyr Cys Val Gln
               100                 105                 110
Val Gly Asp Lys Ser Phe Ser Gly Val Lys His Thr Asp Met Ala Lys
               115                 120                 125
Leu Ile Lys Gln Cys Arg Asp Gln Gly Leu Ser Lys Asp Glu Glu Met
               130                 135                 140
Asp Lys Arg Lys Gln Leu Thr Lys Lys Gly Tyr Lys Ile Ser Phe Asp
145                 150                 155                 160
Lys Phe Ile Gln Glu Leu Leu Ile Lys Ala Lys Ser Arg Gly Phe Ile
                165                 170                 175
Asp Glu Trp Pro Glu Tyr Thr Tyr Ile Tyr Ala His Phe Leu Arg Ala
                180                 185                 190
Asp Ile Ala Ser Phe Glu Glu Phe Trp Asn Ile Gly Ile Asn Asn Lys
                195                 200                 205
Asn Arg Lys Asn Ala Leu Thr Thr Val Gln Gly Thr Val Thr Ser Gly
                210                 215                 220
Arg Gly Ala Tyr Gly Ile Asp Leu Asp Ser Ile Gly Arg Ser Lys Tyr
225                 230                 235                 240
Lys Ile Glu Asn Thr Lys Phe Tyr Ser Ser Asn Asn Ala Phe Glu
                245                 250                 255
Thr Lys Val Arg Phe Ile Asp Thr Met Leu Leu Ser Ser Lys Ala Ser
                260                 265                 270
Leu Glu Glu Leu Gly Leu Gln Cys Gly Phe Pro Lys Met Lys Leu Pro
                275                 280                 285
Asp Asn Met Ile Glu Arg Met Asp Asp Leu Tyr Cys Asn Asp Ile Ser
                290                 295                 300
Leu Phe Asn Arg Tyr Ala Ile Arg Asp Ala Ala Ile Ala Leu Glu Tyr
305                 310                 315                 320
Gly Leu Arg Met Gln Lys Phe Ala Leu Val Asp Leu Arg Glu Asp Ile
                325                 330                 335
Gly Leu Glu Leu Asn Ser Leu Pro Ser Thr Leu Gly Asn Leu Gly Val
                340                 345                 350
Ser Leu Phe Arg His Thr Cys Gly Ser Thr Ala Ala Met His Asp Phe
                355                 360                 365
Leu Gly Tyr Glu Thr Arg Lys Lys Gln Tyr Tyr His Ala Lys Ser Asn
                370                 375                 380
Ser Ile Arg Asn Ser Tyr Asp Ile Ala Lys Thr Val Ser Arg Glu Tyr
385                 390                 395                 400
Thr Asp Asn Leu Ala Val Ser Ala Leu Tyr Gly Gly Cys Asn Phe Gly
                405                 410                 415
Ala Tyr Phe Gly Val Ser Glu Lys Gly Asp Ser Phe Asp Phe Asp Leu
                420                 425                 430
Ser Gly Ala Tyr Thr Thr Ser Leu Val Ser Cys Leu Lys Cys Asp Tyr
                435                 440                 445
```

```
Ala Asn Thr Phe Glu Ser Lys Asn Ile Glu Asp Tyr Leu Gly His Thr
    450                 455                 460

Met Gly Phe Ala Tyr Val Arg Phe Lys His Pro Glu Gly Ile Arg Phe
465                 470                 475                 480

Pro Val Met Pro Cys Arg Thr Asp Leu Arg Gly Ile Tyr Tyr Pro Met
                485                 490                 495

Glu Gly Glu Thr Tyr Val Thr Ser Pro Glu Leu Gln Leu Ala Tyr Asp
            500                 505                 510

Ile Gly Cys Glu Ile Glu Ile Leu His Gly Met Val Ile Pro Trp Val
        515                 520                 525

Glu Gly Ser Thr Ser Met Tyr Lys Asp Phe Thr Thr Ile Ile Arg Lys
    530                 535                 540

Gln Arg Ala Lys Tyr Lys Lys Glu Gly Asn Glu Met Asn Ser His Leu
545                 550                 555                 560

Trp Lys Leu Ile Gly Asn Thr Leu Tyr Gly Lys Thr Leu Gln Gly Cys
                565                 570                 575

Asn Asn Ser Lys Gly Phe Asp Leu Ala Thr Gly Leu Ser Lys Asn Ile
            580                 585                 590

Pro Tyr Ser Pro Val Thr Asn Ala His Tyr Gly Ala Tyr Cys Thr Ser
        595                 600                 605

Phe Val Arg Ala Thr Met Leu Glu Val Ile Leu Arg Leu Pro Ser Glu
    610                 615                 620

Val Gln Leu Ile Ser Ala Thr Thr Asp Gly Phe Leu Thr Asp Ala Thr
625                 630                 635                 640

Pro Glu Gln Leu Glu Gln Cys Leu Asp Gly Pro Leu Ala Gln Arg Phe
                645                 650                 655

Gln Gln Ile Cys Asn Glu Val Ser Gly Glu Asp Met Met Gln Leu Lys
            660                 665                 670

His His Ala Lys Gln Ile Ile Ser Met Lys Thr Arg Gly Gln Leu Thr
        675                 680                 685

Ala Glu Leu Gly Asp Thr Lys Pro Ile Cys Ala Lys Ala Gly Ile Lys
    690                 695                 700

Ala Pro Lys Gly Val Asp Glu Asn Glu Trp Met Val Glu Leu Phe Leu
705                 710                 715                 720

Asp Arg Tyr Pro Gly Gln Lys Val Glu Arg Lys His Leu Ala Ser Ala
                725                 730                 735

Arg Asp Gln Trp Leu Lys Glu Leu Asp Leu Ile Ser Ile His Thr Glu
            740                 745                 750

Gln Thr Leu Asn Leu Glu Tyr Asp Phe Lys Arg Cys Pro Ile Asn Pro
        755                 760                 765

Arg Met Val Lys Val Arg His Pro Val Ser Cys Glu Met Val Glu His
    770                 775                 780

Leu Ser Phe Asp Thr Ile Pro Trp Asn Thr Val Asp Glu Gly Leu Asp
785                 790                 795                 800

Ala Arg Thr Tyr Phe Asp Glu Trp Arg Val Asn Asn Cys Leu Lys Thr
                805                 810                 815

Met Glu Asp Trp Asp Asn Trp Met Asp Phe Tyr Lys Val Arg Arg Tyr
            820                 825                 830

Leu Lys Gly Thr Gly Val Lys Tyr Leu Glu Asp Gly Ser Glu Gly Ile
        835                 840                 845

Phe Lys Val Gln Met Leu Arg Ala Ile Thr Gln Gly Gly Trp Gly Leu
    850                 855                 860
```

```
Ala Ala Val Pro Gln Arg Ala Pro Arg Gly His Tyr Asp Lys Leu Val
865                 870                 875                 880

Ala Met Phe Asp Thr Asp Gly Ile Glu Gly Ile Thr Lys Gln Asp Leu
            885                 890                 895

Ala Asn Ser Lys Gly Arg Arg Leu Leu Glu Ser Ala Leu Pro Met Thr
        900                 905                 910

Thr Arg Met Leu Pro Leu Leu Ser Trp Phe Val Arg Lys Tyr Pro Ile
    915                 920                 925

Val Asp Leu Thr Leu Val Phe His Pro Asp Glu Val Asp Glu Ala Val
930                 935                 940

Met Met Leu Glu Glu Tyr Asn Leu Lys Cys Thr Glu Lys Leu Val Ala
945                 950                 955                 960
```

<210> SEQ ID NO 38
<211> LENGTH: 964
<212> TYPE: PRT
<213> ORGANISM: Vibrio parahaemolyticus

<400> SEQUENCE: 38

```
Met Lys Thr Leu Glu Thr Ala Pro Lys Thr Ala Tyr Gln Leu Met Arg
1               5                   10                  15

Glu Thr Glu Arg Glu Leu Glu Asp Phe Phe Gln Ser Thr Phe Phe Asp
                20                  25                  30

Thr Lys Ser Leu Leu Leu Asp Asp Gln Val Ser Lys Phe Glu Ala Glu
            35                  40                  45

Met Arg Gly Cys Glu Glu Ala Lys Lys Glu Ile Asp Glu Arg Ile Asn
        50                  55                  60

Gln Tyr Leu Glu Gly Ile Lys Ser Ala Pro Trp Glu Ala Ile Arg Gly
65                  70                  75                  80

Glu Gly Lys Ala Ile His Ile Ser Ile Asp Ser Glu Trp Val Phe Asn
                85                  90                  95

Gln Glu Thr Glu Lys Asn Asp Ile Leu Cys Tyr Ser Tyr Ser Val Arg
                100                 105                 110

Ile Gly Asp Lys Ser Phe Ser Gly Val Lys His Thr Asp Met Ala Lys
            115                 120                 125

Leu Ile Lys Gln Cys Arg Asp Gln Gly Leu Ser Lys Asp Glu Glu Met
        130                 135                 140

Asp Lys Arg Lys Glu Leu Thr Lys Lys Gly Tyr Lys Lys Ser Phe Asp
145                 150                 155                 160

Lys Phe Ile Gln Glu Leu Leu Ile Lys Ala Lys Ala Arg Gly Phe Ile
                165                 170                 175

Asp Glu Trp Pro Glu His Thr Phe Ile Tyr Ala His Phe Leu Arg Ala
            180                 185                 190

Asp Ile Ala Ser Phe Glu Glu Phe Trp Lys Ile Gly Thr Ser Asn Lys
        195                 200                 205

Asn His Lys Asn Ser Leu Thr Val Val Gln Gly Thr Val Thr Ser Gly
    210                 215                 220

Arg Gly Ala Tyr Gly Ile Asp Leu Asp Ser Ile Gly Arg Ser Lys Tyr
225                 230                 235                 240

Lys Met Glu Asn Thr Lys Phe Tyr Ser Ser Asn Asn Ala Phe Glu
                245                 250                 255

Thr Lys Leu Arg Phe Ile Asp Thr Thr Leu Leu Ser Ser Lys Ala Ser
            260                 265                 270

Leu Glu Glu Leu Gly Leu Gln Cys Gly Phe Pro Lys Met Thr Leu Pro
        275                 280                 285
```

```
Asp Asn Met Ile Glu Arg Met Asp Asp Met Tyr Cys Lys Asp Thr Ser
    290                 295                 300

Leu Phe Asn Arg Tyr Ala Ile Arg Asp Ala Asp Ile Ala Leu Glu Tyr
305                 310                 315                 320

Gly Leu Arg Met Gln Lys Phe Ala Leu Val Asp Leu Arg Lys Asp Ile
                325                 330                 335

Gly Leu Glu Leu Asn Ser Leu Pro Ser Thr Leu Gly Asn Leu Gly Val
                340                 345                 350

Ser Leu Phe Arg Asp Ser Cys Gly Ala Ala Glu Met His Gln Phe
                355                 360                 365

Leu Gly Tyr Glu Lys Arg Lys Asn Gln Tyr Tyr His Ala Lys Ser Asn
    370                 375                 380

Ser Ile Arg Asn Ser Val Glu Leu Ala Lys Thr Val Ser Arg Glu Tyr
385                 390                 395                 400

Thr Asp Ala Leu Ala Val Ser Ala Phe Tyr Gly Gly Ala Asn Phe Gly
                405                 410                 415

Ala Tyr Phe Gly Pro Thr Glu Val Gly Asp Tyr Asn Asp Phe Asp Leu
                420                 425                 430

Ser Gly Ala Tyr Thr Thr Ala Leu Val Asp Ile Leu Glu Ala Asp Tyr
                435                 440                 445

Leu Asn Ser Phe Glu Ser Lys Asp Ile Glu Asp Tyr Leu Gly His Lys
    450                 455                 460

Met Gly Phe Ala Tyr Val Arg Phe Lys His Asp Asp Lys Glu Asn Phe
465                 470                 475                 480

Gly Leu Leu Pro Cys Arg Thr Ser Leu Arg Gly Ile Tyr Tyr Pro Leu
                485                 490                 495

Glu Gly Glu Thr Tyr Val Thr Ala Pro Glu Leu Gln Leu Ala His Asp
                500                 505                 510

Ala Gly Val Glu Ile Glu Ile Leu His Gly Gln Val Ile Pro Trp Lys
                515                 520                 525

Asn Gly Ser Thr Ser Lys Phe Lys Glu Phe Thr Lys Thr Ile Arg Lys
    530                 535                 540

Gln Arg Ala Lys Tyr Lys Glu Lys Gly Asn Glu Leu Tyr Glu Lys Leu
545                 550                 555                 560

Trp Lys Leu Ile Gly Asn Thr Leu Tyr Gly Lys Val Gly Gln Gly Leu
                565                 570                 575

Arg Asp Lys Ser Gly Phe Asp Leu Ala Ser Gly Leu Ser Ser Lys Ile
                580                 585                 590

Pro Tyr Ser Pro Val Thr Asn Ala His Tyr Ala Ala His Ala Thr Gly
    595                 600                 605

Phe Val Arg Gly Thr Met Leu Glu Val Met Arg Lys Leu Asn Glu Arg
    610                 615                 620

Tyr Gly Asp Asp Ile Lys Ile Ile Ser Ala Thr Thr Asp Gly Trp Leu
625                 630                 635                 640

Cys Asn Ala Thr Gln Glu Gln Leu Glu Gln Cys Leu Asp Gly Pro Leu
                645                 650                 655

Ala Arg Arg Phe Gln Gln Ile Cys Thr Glu Val Ser Gly Glu Asp Met
                660                 665                 670

Met Gln Leu Lys His His Ala Lys Gln Ile Ile Ser Met Lys Thr Arg
            675                 680                 685

Gly Gln Leu Thr Ala Glu Leu Gly Asp Thr Lys Pro Val Cys Ala Lys
    690                 695                 700
```

```
Ala Gly Ile Lys Ala Pro Lys Gly Val Asp Glu Asn Glu Trp Met Val
705                 710                 715                 720

Glu Leu Phe Leu Asp Arg Tyr Pro Gly Gln Lys Val Ala Arg Lys His
            725                 730                 735

Leu Ala Ser Ala Arg Asp Gln Trp Leu Lys Glu Leu Asp Leu Ile Ser
        740                 745                 750

Ile His Thr Glu Gln Thr Leu Asn Leu Glu Tyr Asp Phe Lys Arg Arg
    755                 760                 765

Pro Val Asn Pro Arg Met Val Glu Val Arg His Pro Lys Ser Gly Glu
770                 775                 780

Met Val Glu His Leu Ser Phe Asp Thr Val Pro Trp Asn Thr Val Asp
785                 790                 795                 800

Glu Gly Leu Asp Ala Arg Thr Tyr Phe Asp Glu Trp Arg Val Asn Asn
                805                 810                 815

Cys Leu Lys Thr Met Glu Asp Trp Asp Asn Trp Met Asp Phe Tyr Lys
            820                 825                 830

Val Arg Ser Tyr Leu Lys Gly Thr Gly Val Lys Tyr Leu Glu Asp Gly
        835                 840                 845

Ser Glu Gly Ile Phe Lys Val Gln Met Leu Arg Ala Ile Thr Gln Gly
    850                 855                 860

Lys Trp Gly Leu Pro Glu Ala Pro Lys Arg Ala Pro Arg Gly His Tyr
865                 870                 875                 880

Asp Lys Met Val Ala Met Phe Glu Gly Asp Gly Ile Glu Gly Ile Thr
                885                 890                 895

Lys Gln Asp Leu Ala Asn Ala Lys Gly Arg Lys Leu Leu Glu Ser Ala
            900                 905                 910

Leu Pro Ile Thr Ser Arg Met Leu Pro Leu Leu Ser Trp Phe Val Arg
        915                 920                 925

Glu Tyr Pro Met Val Asp Met Ser Leu Ile Phe His Pro Asp Glu Val
    930                 935                 940

Asp Glu Ala Val Leu Met Leu Glu Glu Tyr Asn Leu Asp His Thr Glu
945                 950                 955                 960

Lys Leu Ala Ala

<210> SEQ ID NO 39
<211> LENGTH: 951
<212> TYPE: PRT
<213> ORGANISM: Vibrio vulnificus 93U204

<400> SEQUENCE: 39

Met Lys Asn Asp Ala Ser Lys Asp Gln Gln Lys Ala Leu Glu Gln Glu
1               5                   10                  15

Val Glu Val Phe Leu Gln Gln Glu Ser Ser Asp His Ser Thr Thr Glu
            20                  25                  30

Thr Glu Glu Gly Leu Thr Asp Phe Leu Glu Met Glu Ser Gln Ser His
        35                  40                  45

Tyr Ser Ser Lys Ala Val Glu Glu Leu Asp Ile Phe Phe Glu Asn
    50                  55                  60

Glu Asn Gln Pro Pro Trp Lys Ala Leu Lys Gly Asp Asp Glu Ser Val
65                  70                  75                  80

His Ile Gly Ile Asp Ser Glu Tyr Val Tyr Asn Glu Glu Asn Arg
                85                  90                  95

Asn Asp Ile Leu Ser Tyr Gln Tyr Tyr Leu Ile Ala Gly Lys Asn Glu
            100                 105                 110
```

```
Ile Ser Asp Val Ile Leu Thr Pro Val Ala Glu Val Ile Lys Lys Ser
        115                 120                 125

Arg Ala Ala Asn Lys Ser Arg Glu Asp Glu Leu Lys Ala Ile Asn Lys
    130                 135                 140

Val Lys Lys Pro Arg Lys Lys Phe Glu Glu Phe Leu Val Glu Ile Leu
145                 150                 155                 160

Gln Glu Ala Lys Asn Arg Gly Phe Ile Lys Gly Trp Pro Arg Thr Ile
                165                 170                 175

Tyr Ile Tyr Ala His Phe Ile Arg Ala Asp Leu Val Ser Phe Asp Ala
            180                 185                 190

Phe Trp Asp Thr Ser Gln Lys Ala Lys Leu Glu Val Ile Arg Gly Thr
        195                 200                 205

Ile Ala Ser Thr Arg Gly Ser Tyr Gly Ile Asp Leu Asn Ala Val Gly
    210                 215                 220

Arg Thr Lys Gln Ala Thr Glu Pro Val His Phe Thr Asp Lys His Gly
225                 230                 235                 240

Lys Lys Arg Glu Ser Arg Val Arg Phe Val Asp Thr Met Leu Leu Ser
                245                 250                 255

Pro Gly Gln Ser Gly Leu Asp Ser Ala Gly Glu Leu Ile Gly Ile Lys
            260                 265                 270

Lys Glu Val Ile Pro Thr Pro Tyr Arg Lys Asp Arg Met Asp Glu Leu
        275                 280                 285

Leu Val Ala Asp Glu Val Arg Phe Leu Arg Tyr Ala Leu Arg Asp Ala
    290                 295                 300

Glu Ile Thr Val Lys Tyr Gly Leu Glu Met Gln Arg Phe Ala Leu Glu
305                 310                 315                 320

Asp Ile Arg Lys Ala Leu Lys Thr Lys Leu Pro Lys Ala Gln Leu Asp
                325                 330                 335

Lys Leu Gln Phe Lys His Leu Pro Ser Thr Leu Gly Asn Phe Ser Val
            340                 345                 350

Ser Val Phe Lys Ala Leu Thr Gly Asp Lys Glu Ala Leu Asn Glu Ala
        355                 360                 365

Leu Gly Met Glu Thr Lys Glu Thr His Tyr Trp Asn His Leu Gln Lys
370                 375                 380

Arg Val Ser Thr Arg Lys Asp Thr Val Ile Thr Ala Gly Arg Arg Ile
385                 390                 395                 400

Phe Glu Gln Leu Ala Ile Asp Ser Phe His Gly Gly Arg Asn Glu Cys
                405                 410                 415

Tyr Val Phe Gly Gly Val Val Gly Asp Tyr Asn Asp Phe Asp Leu
            420                 425                 430

Ala Thr Ala Tyr Val Asn Ala Leu Met Asp Ile Asn Pro Val Glu Phe
        435                 440                 445

Glu Lys Ser Phe Thr Ser Thr Asn Val Lys Asp Tyr Leu Gly His Lys
    450                 455                 460

Met Gly Phe Ala Tyr Val Lys Thr Phe Pro Ser Glu Thr Arg Phe
465                 470                 475                 480

Pro Cys Leu Pro Val Arg Thr Asp Ile Tyr Gly Leu Tyr Tyr Pro Leu
                485                 490                 495

Glu Gly Tyr Ser Tyr Cys Thr Ala Pro Glu Ile Glu Val Ala Lys Asn
            500                 505                 510

Met Gly Cys Lys Leu Glu Ile Gln Phe Gly Val Val Pro Trp Lys
        515                 520                 525

Glu Glu Glu Glu Ser Leu Phe Lys Gly Phe Thr Glu Leu Ile Arg Glu
```

-continued

```
            530                 535                 540
Gln Arg Gln Lys Tyr Thr Glu Asn Asn Asp Lys Phe Arg Glu Lys Leu
545                 550                 555                 560

Trp Lys Glu Ile Gly Asn Thr Leu Tyr Gly Lys Leu Gly Gln Gly Leu
                565                 570                 575

Arg Gly Asn Arg Gly Phe Asn Ala Ser Thr Gly Leu Ser Lys Asp Ile
                580                 585                 590

Pro His Ser Pro Val Thr Asn Pro Tyr Phe Ala Ala His Ala Thr Gly
                595                 600                 605

Phe Val Arg Ala Val Leu Ser Glu Gln Ile Ala Gly Leu Pro Asp Thr
            610                 615                 620

Ile Asp Val Ile Ser Ala Thr Thr Asp Gly Tyr Leu Thr Asn Ala Thr
625                 630                 635                 640

Glu Ala Gln Leu Tyr Thr Ser Gly Ser Val Ser Gln Arg Phe Ala Ala
                645                 650                 655

Ile Cys Gln Gln Thr Gly Asp Gly Lys Met Ile Lys His Lys His His
                660                 665                 670

Val Arg Gln Val Ile Ala Met Lys Thr Arg Gly Gln Leu Thr Gly Glu
            675                 680                 685

His Gly Lys Ser Glu Pro Val Ile Ala Lys Ala Gly Val Lys Pro Pro
            690                 695                 700

Glu Ser Thr Leu Ser Ser Lys Lys Asp Glu Asn Ala Tyr Met Val Lys
705                 710                 715                 720

Leu Phe Leu Asp Arg Tyr Pro Gly Gln Lys Ile Pro Asn Asn Ser Leu
                725                 730                 735

Ile Ser Pro Arg Asp Met Tyr Leu Lys Asp Met Asp Leu Ile Glu Ile
                740                 745                 750

Gln Arg Glu Lys Val Leu Asn Leu Glu Phe Asp Phe Lys Arg Lys Pro
            755                 760                 765

Val Asn Pro Arg Met Thr Gln Ile Arg His Pro Asp Gly His Ile Val
            770                 775                 780

Glu His Leu Tyr Phe Asp Thr Val Pro Trp Lys Asn Ala Leu Glu Gly
785                 790                 795                 800

Gln Arg Val Arg Ala Met Phe Asp Gly Trp Arg Lys Ser Asn Cys Leu
                805                 810                 815

Lys Thr Met Glu Asp Trp Glu Asn Trp Ile Asp Tyr Ala Lys Thr Lys
                820                 825                 830

Pro Leu Leu Lys Gly Ser His Ile Lys Tyr Asp Glu Ser Gly Ser Tyr
            835                 840                 845

Gly Val Leu Leu Lys Leu Ala Val Arg Ala Leu Ser Lys Glu Ser Tyr
            850                 855                 860

Gly Leu Thr Lys Thr Ile Asn Gly Lys Lys Leu Thr Leu Lys Gln Leu
865                 870                 875                 880

Thr Asp Leu Phe Asn Asn Ala Gly Phe Glu Ile Ala Glu Asn Ala Ile
                885                 890                 895

Gly Asn Ser Arg Asp Thr Val Phe Arg Pro Asn Val Leu Ala Ala Thr
                900                 905                 910

Pro Arg Leu Met Pro Leu Leu Ser Trp Leu Val Thr Val Phe Pro Glu
            915                 920                 925

Met Glu Leu Glu Ala Phe Phe His Glu Asp Glu Leu Asp Glu Ala Lys
            930                 935                 940

Lys Met Leu Lys Ala Phe Arg
945                 950
```

```
<210> SEQ ID NO 40
<211> LENGTH: 1004
<212> TYPE: PRT
<213> ORGANISM: Vibrio splendidus 12B01

<400> SEQUENCE: 40
```

| | | | | | | | | | | | | | | |
|---|---|---|---|---|---|---|---|---|---|---|---|---|---|---|
| Met | Thr | Lys | Ser | Leu | Ser | Ser | Asp | Asn | Ala | Glu | Lys | Glu | Tyr | Val |
| 1 | | | | 5 | | | | | 10 | | | | | 15 |
| Ser | Thr | Thr | Ser | Phe | Ser | Pro | Ile | Leu | Gly | Ala | Gln | Ala | Thr | Glu | Arg |
| | | | 20 | | | | | 25 | | | | | 30 | | |
| Ala | Thr | Thr | Ser | Ala | Gln | Leu | Gln | Asp | Phe | Ile | Asp | Thr | Trp | Arg | Tyr |
| | | 35 | | | | | 40 | | | | | 45 | | | |
| Arg | Phe | Glu | Pro | Glu | Tyr | Gln | Arg | Asp | Ser | Thr | Leu | Glu | Leu | Gly | Glu |
| | 50 | | | | | 55 | | | | | 60 | | | | |
| Tyr | Leu | Lys | Ser | Arg | Lys | Gln | Pro | Ile | Lys | Glu | Gly | Val | Val | Ala |
| 65 | | | | | 70 | | | | | 75 | | | | | 80 |
| Lys | Glu | Leu | Thr | Ala | His | Leu | Ser | Ala | Arg | Lys | Ser | Arg | Phe | Lys | Tyr |
| | | | | 85 | | | | | 90 | | | | | 95 | |
| Leu | Gln | Ala | Gln | Gly | Gly | Asn | Val | His | Ile | Gly | Ile | Asp | Thr | Glu | Phe |
| | | | 100 | | | | | 105 | | | | | 110 | | |
| Glu | Tyr | Asp | Glu | Glu | Asn | Glu | Cys | Asn | Leu | Ile | Leu | Ser | Tyr | Gln | Tyr |
| | | 115 | | | | | 120 | | | | | 125 | | | |
| Cys | Leu | Leu | Thr | Ala | Asp | Gly | Arg | Glu | Phe | Lys | Gly | Val | Asp | Tyr | Pro |
| | 130 | | | | | 135 | | | | | 140 | | | | |
| Lys | Ser | Thr | Lys | Lys | Glu | Asp | Arg | Phe | Asp | Phe | Asn | Asp | Tyr | Ile | Phe |
| 145 | | | | | 150 | | | | | 155 | | | | | 160 |
| Lys | Ile | Ile | Asn | Arg | Ala | Lys | Lys | His | Gly | Trp | Ile | Ser | Glu | Tyr | Pro |
| | | | | 165 | | | | | 170 | | | | | 175 | |
| Glu | Lys | Thr | Phe | Ile | Tyr | Ala | His | Phe | Met | Arg | Ala | Asp | Leu | Ala | Ser |
| | | | 180 | | | | | 185 | | | | | 190 | | |
| Phe | His | Ala | Tyr | Trp | Asn | Ile | Lys | Ser | Asn | Lys | Leu | Asp | Ala | Ala | Lys |
| | | 195 | | | | | 200 | | | | | 205 | | | |
| Asp | Ala | Val | Asn | Ser | Ala | Arg | Gly | Asp | Tyr | Gly | Leu | Asp | Leu | Arg | Ala |
| | 210 | | | | | 215 | | | | | 220 | | | | |
| Ile | Gly | Ala | Ser | Gln | Tyr | Lys | Pro | Arg | Phe | Val | Ser | Tyr | Lys | Asp | Asn |
| 225 | | | | | 230 | | | | | 235 | | | | | 240 |
| Ser | Lys | Arg | Thr | Val | Lys | Thr | Thr | Leu | His | Leu | Lys | Asp | Thr | Leu | Phe |
| | | | | 245 | | | | | 250 | | | | | 255 | |
| Leu | Ser | Pro | Gly | Arg | Cys | Ser | Leu | Asp | Val | Ile | Gly | Asp | Ala | Ile | Gly |
| | | | 260 | | | | | 265 | | | | | 270 | | |
| Ile | Pro | Lys | Ile | Lys | Ile | Pro | Asp | Gly | Tyr | Ser | Ile | Glu | Lys | Met | Ser |
| | | 275 | | | | | 280 | | | | | 285 | | | |
| Lys | Leu | Leu | Lys | Glu | Asp | Lys | Gly | Ala | Phe | Glu | Gln | Tyr | Ala | Ile | Arg |
| | 290 | | | | | 295 | | | | | 300 | | | | |
| Asp | Ala | Glu | Ile | Ala | Val | Lys | Tyr | Gly | Arg | Tyr | Val | Glu | Asp | Phe | Ala |
| 305 | | | | | 310 | | | | | 315 | | | | | 320 |
| Leu | Thr | Glu | Leu | Asn | Asp | Val | Phe | Glu | Asp | Glu | Gly | Ser | Asp | Gln |
| | | | | 325 | | | | | 330 | | | | | 335 |
| Arg | Pro | Ala | Ser | Asn | Arg | Ile | Lys | Tyr | Leu | Pro | Asn | Thr | Leu | Gly | Asn |
| | | | 340 | | | | | 345 | | | | | 350 | | |
| Leu | Ser | Val | Ser | Leu | Phe | Lys | Asn | Val | Phe | Ala | Asp | Asp | Tyr | Ala | Lys |
| | | 355 | | | | | 360 | | | | | 365 | | | |
| Lys | Val | Gln | Val | Asn | Asp | Asp | Ser | Val | Leu | Pro | Ala | Ser | Ala | Ser | Leu |

-continued

```
             370                 375                 380
Asn Asn Ile Phe Gly Met Glu Glu Val Ile Ser Tyr Lys Trp Asp Glu
385                 390                 395                 400

Arg Asn His Arg Ser Ile Pro Asn Lys Leu Leu Val Leu Ser Gly Glu
                405                 410                 415

Arg Asp Arg Asn Glu Ala Thr Ala Arg Arg Cys Phe Phe Gly Gly Arg
            420                 425                 430

Asn Glu Asp Tyr Tyr Phe Gly Pro Ser Pro Val Gly Lys Val Ser Asp
        435                 440                 445

Trp Asp Leu Ala Gly Ala Tyr Thr Thr Gly Leu Val Asp Ile Leu Pro
    450                 455                 460

Val Asn Tyr Arg Ala Ala Phe Ser Ser Thr Lys Ile Glu Asp Tyr Leu
465                 470                 475                 480

Gly His Val Met Gly Phe Ala Tyr Val Lys Phe Lys Phe Lys Ala Gly
                485                 490                 495

Thr Arg Phe Pro Ser Leu Pro Val Arg Thr Glu Val Tyr Gly Leu Tyr
            500                 505                 510

Tyr Pro Leu Glu Gly Glu Thr Tyr Cys Thr Ala Pro Glu Ile Ala Val
        515                 520                 525

Ala Tyr Asn Met Gly Cys Glu Ile Glu Ile Leu Tyr Gly Asp Ile Ile
    530                 535                 540

Pro Trp Ala Asp Ala Glu Pro Val Phe Glu Pro Phe Thr Lys Val
545                 550                 555                 560

Ile Arg Lys Leu Arg Lys Arg His Lys Gly Thr Phe Glu Glu Lys Ile
                565                 570                 575

Val Lys Asp Val Gly Asn Thr Leu Tyr Gly Lys Ile Ala Ser Gly Val
            580                 585                 590

Gly Phe Gln Arg Asn Lys Phe Asp Thr Lys Thr Gly Leu Ser Lys Ala
        595                 600                 605

Ser Gly Thr Ser Pro Val Thr Asn Ser Tyr Phe Ser Ser His Val Thr
    610                 615                 620

Gly Phe Ile Arg Gly Val Leu Ser Glu Leu Leu Ala Asn Val Asp Glu
625                 630                 635                 640

Gly Val Thr Val Tyr Ser Ala Thr Thr Asp Gly Leu Leu Thr Asp Leu
                645                 650                 655

Asp Asn Ala Asp Ser Met Leu Val Asp Glu Tyr His Leu Lys Gly Lys
            660                 665                 670

Thr Tyr Gln Ser Thr Thr Ala Arg Phe Lys Ala Leu Cys Ala Lys Phe
        675                 680                 685

Gly Asp Asp Glu Ala Leu Val Leu Lys His Gln Val Lys Gln Ile Ile
    690                 695                 700

Ala Met Lys Thr Arg Gly Gln Leu Thr Ala Glu Met Met Val Asp Asp
705                 710                 715                 720

Gly Thr Asn Pro Asp Met Ser Gly Leu Tyr Lys Lys Pro Val Thr Ala
                725                 730                 735

Lys Ala Gly Ile Lys Pro Pro Arg Asp Cys Pro Asn Glu Asn Asp Trp
            740                 745                 750

Met Val Asn Leu Phe Leu Asn Arg Gln Pro Ser Glu Lys Ile Ala Asn
        755                 760                 765

Asn Cys Ile Val Ser Glu Arg Asp Met Tyr Leu His Glu Leu Asp Leu
    770                 775                 780

Ile Glu Ile Lys His Asp Lys Tyr Leu Asn Leu Asp Phe Asp Phe Lys
785                 790                 795                 800
```

```
Arg Arg Pro Val Asn Pro Ser Met Val Val Val Arg Asn Pro Val Thr
                805                 810                 815

Gly Glu Val Val Ser His Leu Thr Phe Asp Thr Val Pro Trp Gln Thr
            820                 825                 830

His Ile Glu Gly Glu Lys Ala Arg Ser Ala Phe Asp Gly Trp Arg Lys
        835                 840                 845

Gly Gln Leu Val Gly Lys Lys Pro Asn Gln Glu Arg Val Gly Gly Asn
    850                 855                 860

Cys Leu Lys Thr Met Asp Asp Trp Arg Asn Trp Met Asp Phe Tyr Lys
865                 870                 875                 880

Ile Lys Ala Val Met Glu Val Lys Gly Gln Lys Tyr Glu Asp Asp Ser
                885                 890                 895

Ser Asp Gly Ile Phe Lys Arg Tyr Val Met Thr Ala Ile Thr Asn Asp
            900                 905                 910

Leu Trp Gly Met Thr Lys Glu Thr Val Glu Gly Val Lys Arg Thr Tyr
        915                 920                 925

Pro Asp Leu Ala Gly Leu Phe Thr Arg Ala Gly Tyr Ser Thr Ile Gly
    930                 935                 940

Lys Asp Phe Ser Asn Ala Lys Gly Arg Gln Val Val Ala Asn Met Met
945                 950                 955                 960

Pro Ala Ala Pro Lys Leu Ile Pro Met Leu Ile Trp Leu Met Gly Glu
                965                 970                 975

Phe Pro Asp Met Glu Val Asp Lys Phe Phe Ile Pro Glu Glu Leu Asp
            980                 985                 990

Glu Val Met Thr Leu Val Ala Ser  Ala Arg Asp Lys
        995                 1000
```

<210> SEQ ID NO 41
<211> LENGTH: 1051
<212> TYPE: PRT
<213> ORGANISM: Moritella viscosa

<400> SEQUENCE: 41

```
Met Thr Thr Thr Leu Ser Pro Glu Gln Thr Lys Asp Glu Gln Asp Glu
1               5                   10                  15

Lys Thr Val Val Ser Thr Pro Val Lys Lys Ser Asp Lys Tyr Val Ser
            20                  25                  30

Thr Ile Ser Tyr Ser Thr Ile Arg Gly Gly Glu Ala Thr Glu Arg Ala
        35                  40                  45

Thr Gln Asp Ala Gln Leu Gln Asn Leu Met Asp Gly Ile Arg Arg Arg
    50                  55                  60

Phe Gly Pro Glu Tyr Gln Lys Asp Ser Thr Thr Glu Leu Arg Lys Tyr
65                  70                  75                  80

Leu Ala Asn Arg Val Lys Pro Ile Lys Glu Asn Lys Asp Val Glu Lys
                85                  90                  95

Glu Leu Ile His Tyr His Ile Asp Arg Lys Ser Arg Phe Lys Tyr Leu
            100                 105                 110

Lys Ala Gln Gly Ser Asn Ile His Ile Gly Ile Asp Thr Glu Phe Glu
        115                 120                 125

Tyr Asp Glu Glu Asn Glu Cys Asn Lys Ile Leu Ser Tyr Gln Tyr Cys
    130                 135                 140

Leu Leu Thr Ala Asp Gly Arg Glu Phe Lys Gly Val Asp Tyr Pro Ala
145                 150                 155                 160

Ser Thr Asp Lys Lys Asp Arg Phe Asp Phe Asn Asn Tyr Ile Phe Gln
```

```
                    165                 170                 175
Ile Ile Asn Tyr Ala Lys Arg His Gly Trp Leu Ser Glu Tyr Pro Glu
                180                 185                 190

Lys Thr Phe Ile Tyr Ala His Phe Met Arg Ala Asp Ile Ala Ser Phe
            195                 200                 205

Asp Ala Tyr Trp Asn Ile Lys Ser Asn Lys Leu Asp Ala Val Lys Ala
        210                 215                 220

Val Ala Ser Asn Ala Arg Gly Asp Tyr Gly Leu Asp Leu Arg Ala Ile
225                 230                 235                 240

Gly Ala Ser Gln Tyr Lys Pro Lys Tyr Val Thr Tyr Lys Asn Asn Gly
                245                 250                 255

Lys Arg Leu Glu Arg Thr Thr Leu His Leu Lys Asp Thr Leu Phe Leu
            260                 265                 270

Ser Pro Gly Arg Cys Ser Leu Asp Val Ile Gly Glu Ala Ile Gly Ile
        275                 280                 285

Pro Lys Ile Lys Leu Pro Ala Gly Tyr Ser Ile Glu Lys Met Ser Lys
    290                 295                 300

Leu Leu Glu Glu Asn Lys Gly Ala Phe Glu Lys Tyr Ala Val Arg Asp
305                 310                 315                 320

Ala Glu Ile Ala Val Lys Tyr Gly Arg Tyr Val Glu Phe Ala Leu
                325                 330                 335

Thr Glu Leu Asn Asp Val Phe Asp Asn Asp Ser Gly Ala Asn Asp
            340                 345                 350

Ala Gly Ala Val Ser Glu Gly Ala Lys Thr Lys Asn Ser Ser Ser
        355                 360                 365

Asn Arg Ile Lys Tyr Leu Pro Asn Thr Leu Gly Asn Leu Ser Val Ala
        370                 375                 380

Leu Phe Lys Asn Val Phe Ala Asp Lys Tyr Glu Lys Arg Ala Ala Glu
385                 390                 395                 400

Ala Glu Ser Tyr Thr Ala Pro Leu Ile Pro Asn Met Ala Phe Asn Glu
                405                 410                 415

Val Phe Gly Met Glu Glu Val Ile Ser Tyr Lys Trp Asp Glu Arg Arg
            420                 425                 430

His Arg Ser Ile Pro Asn Lys Leu Thr Val Leu Ser Gly Glu Arg Asp
        435                 440                 445

Arg Asn Glu Ser Thr Ala Arg Arg Cys Phe Phe Gly Gly Arg Asn Glu
    450                 455                 460

Asp Tyr Val Phe Gly Pro Ser Ala Lys Asp Ala Val Ser Asp Trp Asp
465                 470                 475                 480

Leu Ala Gly Ala Tyr Thr Thr Gly Leu Val Asp Ile Leu Pro Val Asn
                485                 490                 495

Tyr Arg Ala Ala Phe Ser Ser Thr Asp Ile Glu Asp Tyr Leu Gly His
            500                 505                 510

Val Met Gly Phe Ala Tyr Val Lys Phe Lys Phe Asp Glu Gly Thr Arg
        515                 520                 525

Phe Pro Ser Leu Pro Val Arg Thr Glu Leu Tyr Gly Leu Tyr Tyr Pro
    530                 535                 540

Leu Glu Gly Glu Thr Tyr Cys Thr Ala Pro Glu Ile Val Ala Tyr
545                 550                 555                 560

Asn Met Gly Cys Lys Ile Glu Ile Leu Tyr Gly Asp Ile Ile Pro Trp
                565                 570                 575

Val Asn Asp Ala Glu Pro Ile Phe Glu Pro Phe Thr Lys Val Ile Arg
            580                 585                 590
```

-continued

```
Lys Leu Arg Lys Lys His Lys Gly Thr Phe Glu Glu Lys Ile Val Lys
        595                 600                 605
Asp Val Gly Asn Thr Ala Tyr Gly Lys Ile Gly Gln Gly Val Gly Phe
        610                 615                 620
Gln Arg Asn Lys Phe Asp Thr Lys Thr Gly Leu Ser Lys Pro Asn Gly
625                 630                 635                 640
Asn Ser Pro Leu Thr Asn Ser Tyr Phe Ala Ser His Val Thr Gly Phe
                645                 650                 655
Ile Arg Ala Val Leu Ser Glu Leu Leu Asp Asn Val Asp Asp Asp Ile
                660                 665                 670
Thr Val Tyr Ser Ala Thr Thr Asp Gly Leu Leu Thr Asp Leu Gly Asn
        675                 680                 685
Ala Asp Ala Met Ile Ile Asp Glu Tyr Asp Leu Asp Gly Lys Ile Tyr
        690                 695                 700
Gln Ser Thr Thr Ala Arg Phe Lys Ala Leu Cys Ala Arg Phe Gly Asp
705                 710                 715                 720
Asp Asp Ala Leu Val Leu Lys His Gln Val Lys Gln Ile Ile Ala Met
                725                 730                 735
Lys Thr Arg Gly Gln Leu Thr Ala Glu Met Met Glu Asp Asp Gly Thr
        740                 745                 750
Asn Pro Glu Met Ser Ala Leu Tyr Lys Lys Pro Val Thr Ala Lys Ala
        755                 760                 765
Gly Ile Lys Pro Pro Arg Asp Cys Pro Asn Glu Asn Asp Trp Met Val
        770                 775                 780
Asp Leu Phe Leu Asn Arg Gln Pro Ser Glu Lys Val Ala Asn Asn Cys
785                 790                 795                 800
Ile Val Ser Glu Arg Asp Met Tyr Leu His Glu Leu Asp Leu Ile Glu
                805                 810                 815
Ile Lys His Asp Lys Tyr Leu Asn Leu Asp Phe Asp Phe Lys Arg Arg
                820                 825                 830
Pro Val Asn Pro Ser Met Val Asp Val Arg Asn Pro Leu Thr Gly Lys
        835                 840                 845
Thr Val Ser His Leu Thr Phe Asp Thr Val Pro Trp Lys Asn His Lys
        850                 855                 860
Glu Gly Glu Leu Ala Arg Ser Ala Phe Asp Gly Trp Arg Lys Gly Lys
865                 870                 875                 880
Leu Thr Pro Val Glu Pro Ser Glu Pro Ser Asp Glu Thr Asp Lys
                885                 890                 895
Lys Ser Ser Lys Lys Pro Glu Lys Pro Lys Lys Val Arg Val Gly
        900                 905                 910
Gly Asn Cys Leu Lys Thr Leu Asp Asp Trp Asp Asn Trp Met Asp Phe
        915                 920                 925
Tyr Lys Ile Lys Ala Val Met Thr Val Lys Gly Gln Lys Tyr Glu Asn
        930                 935                 940
Asp Ser Ser Glu Gly Ile Phe Lys Arg Leu Val Leu Thr Ala Leu Thr
945                 950                 955                 960
Asn Asp Ser Trp Gly Leu Ser Lys Asp Thr Pro Asp Gly Thr Asn Arg
                965                 970                 975
Thr Tyr Pro Glu Leu Ile Lys Leu Phe Thr Asn Ala Gly Tyr Pro Val
                980                 985                 990
Lys Lys Ser Asp Phe Thr Asn Ala  Lys Asn Arg Lys Ile  Glu Glu His
        995                 1000                1005
```

```
Met Met Pro Ala Ala Pro Lys Ser Ile Pro Leu Leu Lys Trp Val
    1010                1015                1020

Met Ser Gln Tyr Pro Asp Met Glu Val Asp Lys Phe Phe Met Lys
    1025                1030                1035

Glu Glu Phe Asp Glu Val Met Gly Leu Val Asn Lys Ser
    1040                1045                1050

<210> SEQ ID NO 42
<211> LENGTH: 998
<212> TYPE: PRT
<213> ORGANISM: Vibrio parahaemolyticus

<400> SEQUENCE: 42

Met Thr Thr Glu Thr Ala Glu Ala Thr Glu Ile Ile Glu Asn Thr Lys
1               5                   10                  15

Pro Ala Glu Thr Thr Asp Thr Leu Ser Phe Ser Pro Ile Leu Gly Val
            20                  25                  30

Gln Ala Thr Lys Arg Ala Thr Asp Thr Ala Gln Leu His Asn Leu Ile
        35                  40                  45

Glu Ser Trp Gln Lys Arg Phe Asp Leu Gly Glu Gln Gln Asp Lys Ser
    50                  55                  60

Leu Glu Leu Gln Thr Tyr Leu Glu Asn Arg Lys Leu Pro Pro Lys Ser
65                  70                  75                  80

Phe Gln Ala Leu Lys Ser Glu Leu Ala Gln Tyr Leu Lys Asp Arg Lys
                85                  90                  95

Ser Arg Phe Lys Phe Leu Lys Ala Lys Gly Gly Asn Ile His Ile Gly
            100                 105                 110

Ile Asp Thr Glu Phe Glu Tyr Asp Glu Glu Ala Glu Cys Asn Lys Ile
        115                 120                 125

Leu Ser Tyr Gln Tyr Cys Leu Leu Thr Pro Asp Gly Lys Glu Tyr Lys
    130                 135                 140

Gly Ile Asp Tyr Pro Ala Ser Ala Lys Lys Glu Asp Arg Phe Glu Phe
145                 150                 155                 160

Asn Asp Tyr Leu Phe Lys Ile Ile Val Arg Ala Arg Lys Met Gly Trp
                165                 170                 175

Ile Thr Glu Tyr Pro Glu Asn Thr Phe Val Tyr Cys His Phe Met Arg
            180                 185                 190

Ala Asp Leu Ala Ser Phe His Ala Tyr Trp Asn Ile Lys Gly Ser Lys
        195                 200                 205

Lys Tyr Asp Ala Ala Met Ala Thr Val Asn Asn Ala Arg Gly Asp Tyr
    210                 215                 220

Gly Leu Asp Leu Arg Ala Ile Gly Ala Ser Gln Tyr Lys Pro Arg Ala
225                 230                 235                 240

Ile Thr Tyr Thr Asn His Asn Lys Arg Pro Glu Ile Thr Ser Ile His
                245                 250                 255

Leu Lys Asp Thr Leu Phe Leu Ser Pro Gly Arg Cys Ala Leu Ser Val
            260                 265                 270

Ile Gly Asp Ala Ile Gly Ile Glu Lys Val Glu Leu Pro Asp Gly Tyr
        275                 280                 285

Ser Ile Glu Arg Met Ser Gln Leu Leu Glu Glu Asp Lys Gly Ser Phe
    290                 295                 300

Glu Lys Tyr Ala Ile Thr Asp Ala Lys Ile Thr Val Lys Phe Gly Arg
305                 310                 315                 320

Phe Met Glu Asp Val Val Leu Glu Glu Leu Asn Ser Ile Thr Gly Ile
                325                 330                 335
```

```
Ala Ser Ser Gly Asp Gly Lys Arg Ala Thr Asn Gln Ile Lys Tyr Leu
            340                 345                 350

Pro Asn Thr Leu Gly Asn Leu Ser Val Ala Leu Phe Lys Asn Val Ser
            355                 360                 365

Ser Asp Val Tyr Glu Gln Arg Lys Glu Ser Lys Gln Thr Pro Asn Leu
    370                 375                 380

Thr Leu Asn Glu Val Phe Gly Leu Glu Val Thr Ala Tyr Lys Trp
385                 390                 395                 400

Asp Glu Ser Ser Asn Arg Ser Ile Pro Tyr Lys Leu Val Val Leu Ser
                405                 410                 415

Gly Glu Arg Asp Arg Asn Glu Ala Thr Ala Arg Arg Cys Phe Gly
            420                 425                 430

Gly Arg Asn Glu Asp Tyr Tyr Phe Gly Pro Ser Pro Lys Gly Glu Ile
            435                 440                 445

Ser Asp Trp Asp Leu Val Gly Ala Tyr Thr Thr Gly Leu Cys Asp Ile
    450                 455                 460

Lys Pro Val Asp Tyr Arg Lys Ala Tyr Ser Ser Thr Asn Ile Glu Asp
465                 470                 475                 480

Tyr Leu Gly His Val Met Gly Phe Ala Tyr Val Arg Phe Arg Phe Lys
                485                 490                 495

Glu Gly Thr Arg Phe Pro Ser Leu Pro Val Arg Thr Glu Leu Tyr Gly
            500                 505                 510

Leu Tyr Tyr Pro Leu Glu Gly Glu Thr Tyr Cys Thr Ala Pro Glu Ile
            515                 520                 525

Ala Val Ala Tyr Asn Met Gly Cys Glu Leu Glu Ile Leu Tyr Gly Asp
            530                 535                 540

Ile Ile Pro Trp Ile Asp Asp Ala Glu Pro Val Phe Glu Pro Phe Thr
545                 550                 555                 560

Lys Val Ile Arg Glu Leu Arg Lys Lys His Lys Gly Thr Phe Leu Glu
                565                 570                 575

Ala Val Tyr Lys Asp Val Gly Asn Thr Leu Tyr Gly Lys Val Gly Gln
            580                 585                 590

Asn Val Gly Phe Gln Arg Asn Lys Phe Asp Thr Lys Ser Gly Leu Ser
            595                 600                 605

Arg Pro Ala Thr Asn Ser Pro Val Thr Asn Ser Tyr Phe Ser Ser His
            610                 615                 620

Val Thr Gly Phe Ile Arg Gly Val Leu Ser Glu Leu Leu Ala Asn Val
625                 630                 635                 640

Gly Asp Asp Lys Arg Val Tyr Ser Ala Thr Thr Asp Gly Leu Leu Thr
                645                 650                 655

Asp Leu Ser Asp Gly Glu Ala Met Leu Ile Asp Glu Tyr His Leu Asn
            660                 665                 670

Gly Gln Ser Tyr Gln Ser Val Thr Ala Arg Phe Lys Ala Leu Cys Glu
            675                 680                 685

Lys Phe Gly Asp Glu Ser Met Leu Ala Leu Lys His Gln Val Gly Gln
            690                 695                 700

Ile Ile Gly Met Lys Thr Arg Gly Gln Leu Thr Ala Glu Ile Leu Asp
705                 710                 715                 720

Ala Asp Ile Asn Thr Pro Glu Leu Asn Lys Ile Arg Lys Lys Val Ile
                725                 730                 735

Thr Ala Lys Ala Gly Val Lys Pro Pro Arg Asp Cys Gly Asp Glu Asn
            740                 745                 750
```

```
Ala Trp Met Val Asp Leu Phe Leu Asn Arg Lys Pro Ser Gln Arg Ile
            755                 760                 765

Ser Asn Asn Cys Leu Val Pro Glu Arg Asp Met Tyr Leu His Glu Leu
        770                 775                 780

Asp Leu Tyr Glu Ile Lys Arg Asp Arg Phe Met Asn Leu Glu Phe Asp
785                 790                 795                 800

Phe Lys Arg Arg Pro Val Asn Pro Thr Met Val Asp Val Arg Asp Pro
                805                 810                 815

Lys Thr Gly Cys Ile Val Ser His Leu Ala Phe Asp Thr Val Pro Trp
                820                 825                 830

Lys Asn Arg Glu Glu Gly Glu Met Ala Arg Ala Thr Phe Asp Gly Trp
            835                 840                 845

Arg Lys Gly Lys Lys Ser Gly Asp Ser Arg Val Gly Ala Asn Cys Leu
        850                 855                 860

Lys Thr Met Glu Asp Trp Tyr Asn Trp Ile Asp Phe Tyr Lys Ile Lys
865                 870                 875                 880

Ala Val Met Lys Val Lys Gly Gln Asn Tyr Glu Asn Asn Ser Ser Glu
                885                 890                 895

Gly Ile Phe Lys Arg Tyr Ile Leu Thr Ala Ile Thr Asn Glu Phe Gly
            900                 905                 910

Gly Leu Ser Arg Val Asn Arg Gln Gly Lys Arg Thr Asn Ala Glu
        915                 920                 925

Leu Ala Glu Leu Phe Thr Ser Ala Gly Tyr Pro Thr Asn Glu Lys Asp
        930                 935                 940

Val Ser Asn Ala Lys Gly Arg Lys Leu His Ser Gln Met Leu Pro Ala
945                 950                 955                 960

Ala Pro Lys Phe Met Pro Met Leu Arg Trp Ala Met Thr Gln Phe Pro
                965                 970                 975

Asp Leu Glu Leu Lys Met Phe Phe Met Pro Glu Glu Leu Gly Glu Val
            980                 985                 990

Leu Ala Leu Leu Asp Gln
        995

<210> SEQ ID NO 43
<211> LENGTH: 853
<212> TYPE: PRT
<213> ORGANISM: Enterobacter cloacae

<400> SEQUENCE: 43

Met Thr Gln Pro Val Ala Arg Ser Ala Lys Thr Arg Asp Asn Phe Pro
1               5                   10                  15

Leu Ile Pro Gln Lys Ser Lys Lys Arg Leu Asp Val Ser Ser Gln Leu
            20                  25                  30

His Leu Asp Ile Gly Phe Asp Thr Glu Tyr Val Tyr Asn Pro Ala Thr
        35                  40                  45

Lys Gln Asn Asp Ile Leu Ser Tyr Gln Ser Tyr Val Val Leu Pro Asp
    50                  55                  60

Gly Thr Gly Val Pro Gly Ile Leu Tyr Pro Ala Ser Ala His Lys Lys
65                  70                  75                  80

Asp Arg Leu Ser Leu Lys Asn Phe Leu Ala Lys Thr Leu Thr Pro Leu
                85                  90                  95

Leu Lys Asn Glu Gln Ile Asn Glu Trp Pro Gly Ser Ile Thr Leu Tyr
            100                 105                 110

Ala His Phe Leu Arg Ala Asp Val Ala Ser Phe Ser Asp Phe Trp Ser
        115                 120                 125
```

```
Asp His Lys Ile Leu Lys Gly Ile Arg Ser Thr Val Ser Ser Phe
    130                 135                 140

Lys Asn Arg Tyr Gly Ile Asp Phe Asp Glu Val Glu Thr Arg Arg Glu
145                 150                 155                 160

Lys Asn Ser Leu Ile Thr Phe Asp Lys Arg Thr Ser Pro Pro Arg Cys
                165                 170                 175

Ser Asn Val Thr Phe Thr Asp Thr Leu Leu Ile Thr Pro Gly Gly Met
                180                 185                 190

Gly Leu Ala Glu Cys Gly Gln Leu Leu Gly Leu Pro Lys Leu Asn Ile
                195                 200                 205

Pro Ala Pro Tyr Ser Ile Ser Asp Met Arg Gln Tyr Leu Lys Gly Asp
    210                 215                 220

Arg Arg Gly Phe Glu Ala Tyr Ala Val Arg Asp Ala Glu Ile Ala Val
225                 230                 235                 240

Arg Tyr Ala Leu Gln Val Lys Ser Phe Cys Thr Glu Ser Leu Met Ile
                245                 250                 255

Glu Arg Val Pro Thr Thr Ile Gly Ala Met Ala Val Ser Arg Phe Leu
                260                 265                 270

Lys Thr Ile Lys Glu Ser Gly Gln Ser Pro Glu Val Cys Met Gly Thr
                275                 280                 285

Arg Thr Ile Ser Gln Gln Cys Trp Asn Pro Asp Thr His Gly Phe Arg
    290                 295                 300

Thr Leu Lys Ser Thr Gln Ser Ile Pro Ala Arg Glu Leu Tyr Glu Thr
305                 310                 315                 320

Phe Ala Ile Asn Cys Tyr His Gly Gly Arg Asn Glu Cys Phe Met Met
                325                 330                 335

Gly Ile Thr Pro Glu Ser Gln Trp Tyr Asp Tyr Asp Leu Ala Gly Ala
                340                 345                 350

Tyr Thr Thr Gly Leu Leu Asp Val Leu Gln Pro Asp Tyr Asp Asn Leu
                355                 360                 365

Tyr Thr Ser Gln Asn Pro Glu Glu Phe Cys Gly His Thr Met Gly Phe
    370                 375                 380

Ala Leu Val Ser Phe Arg Phe Pro Asp Thr Val Arg Tyr Pro Cys Leu
385                 390                 395                 400

Pro Val Arg Thr Asp Gln Tyr Gly Leu Phe Phe Pro Leu Thr Gly Glu
                405                 410                 415

Ser Trp Ala Thr Ala Pro Glu Ile Ala Leu Ala Leu Ser Leu Gly Ala
                420                 425                 430

Glu Ile Ala Ile Gln His Gly Ile Ile Pro Trp Leu Gln Tyr Lys
                435                 440                 445

Ser Asp Asn Ala Ser Ser Pro Thr Lys Pro Ala Ser Ser Val Phe Leu
    450                 455                 460

Pro Phe Val Gln Gln Val Arg Glu Asn Arg Asn Arg His Asp Lys Gly
465                 470                 475                 480

Ser Leu Glu Glu Lys Phe Trp Lys Glu Ile Gly Asn Ser Leu Tyr Gly
                485                 490                 495

Lys Leu Ala Gln Gly Leu His Ala Lys Thr Ala Phe Asp Thr Ala Arg
                500                 505                 510

Gly Leu Asn Ser Pro Leu Pro Pro Ser Ser Val Thr Gln Pro Phe Phe
    515                 520                 525

Ala Ala His Val Thr Gly Phe Val Arg Ala Val Val Gly Glu Leu Met
    530                 535                 540
```

```
Asn Thr Leu Pro Pro Asn Thr Thr Val Val Ser Val Thr Asp Gly
545                 550                 555                 560

Phe Leu Thr Asp Val Ser Leu Glu Asn Ile Asp Met Ser Gly Pro Leu
                565                 570                 575

Ser Ser Arg Phe Gln Ala Leu Cys Asp Ile Ala Asp Pro Gly Ser Ser
            580                 585                 590

Met Leu Thr Cys Lys His Gln Val Arg Gln Leu Val Ala Met Lys Thr
            595                 600                 605

Arg Gly Gln Leu Thr Tyr Lys Glu Leu Ala Gly Tyr Pro Ile Val His
        610                 615                 620

Ala Arg Ala Gly Val Lys Pro Pro Ala Asp Ile Pro Arg Asp Asp Tyr
625                 630                 635                 640

Asn Arg Tyr Met Val Asp Leu Tyr Leu Asn Arg Ala Pro Gly Gln Lys
                645                 650                 655

Leu Arg Arg Gly Ser Leu Ile Ser Thr Arg Asp Met Trp Leu Asn Glu
            660                 665                 670

Ser Asp Leu Val Ala Val Glu Ser Asp Ile Arg Leu Asn Leu Glu Phe
            675                 680                 685

Asp Phe Lys Arg Gln Leu Ile Ala Pro Thr Met Asn Asp Gly His Leu
690                 695                 700

Leu Met Tyr Ser Arg Pro Trp Asn Asp Ile Ala Gln Ala Leu Lys Gln
705                 710                 715                 720

Arg Gln Leu Phe Asp Asp Trp Arg Gln Thr His Thr Leu Lys Asp Glu
                725                 730                 735

Ser Asp Trp Glu Asp Trp Cys Asp Phe Leu Tyr Cys Arg Asn Ile Phe
            740                 745                 750

Thr Pro Leu Lys Leu Lys Val Gly Gln Asn Arg Ser Asp Asp Val Leu
            755                 760                 765

Val Arg Leu Phe Leu Arg Ala Leu Ala Gln Tyr Gln Trp Gly Leu Thr
        770                 775                 780

Pro Asp Asp Arg Lys Arg Gln Thr Ser Val Glu Ile Ala Ala Trp Leu
785                 790                 795                 800

Val Glu Ala Gly Tyr Ser Val Thr Pro Ser Asp Val Lys Asn Ala Gly
                805                 810                 815

Arg Ala Lys Leu Pro Pro Ile Ile Phe Asp Ser Leu Thr Ala Arg Met
            820                 825                 830

Asn Arg Leu Met Asp Leu Ile Lys Leu Val Tyr Pro Gly Phe Ala Leu
            835                 840                 845

Pro Ser Ala Val Leu
    850

<210> SEQ ID NO 44
<211> LENGTH: 866
<212> TYPE: PRT
<213> ORGANISM: Enterobacter cloacae

<400> SEQUENCE: 44

Met Phe Asp Met Asn Ala Leu Leu Ala Asp Ala Ala Gly Val Thr Gln
1               5                   10                  15

Pro Val Ala Arg Ser Ala Lys Thr Leu Asp Asn Phe Pro Leu Ile Pro
                20                  25                  30

Gln Lys Ser Lys Asn Arg Leu Asp Val Ser Ser Glu Leu His Leu Asp
            35                  40                  45

Ile Gly Phe Asp Thr Glu Tyr Val Tyr Asn Pro His Thr Lys Gln Asn
        50                  55                  60
```

```
Asp Ile Leu Ser Tyr Gln Ser Tyr Val Val Leu Pro Asp Gly Lys Gly
 65                  70                  75                  80

Val Pro Gly Ile Leu Tyr Pro Ala Ser Ala His Lys Lys Asp Arg Leu
                 85                  90                  95

Ser Leu Lys Asn Phe Leu Ala Lys Thr Leu Thr Pro Leu Leu Lys Asn
            100                 105                 110

Glu Gln Ile Asn Glu Trp Pro Gly Ser Ile Thr Leu Tyr Ala His Phe
            115                 120                 125

Leu Arg Ala Asp Val Ala Ser Phe Ser Asp Phe Trp Ser Asp His Lys
    130                 135                 140

Ile Leu Leu Lys Gly Ile Arg Ser Thr Val Ser Ser Phe Lys Asn Arg
145                 150                 155                 160

Tyr Gly Ile Asp Phe Asp Glu Val Glu Asn Arg Arg Glu Lys Asn Ser
                165                 170                 175

Leu Ile Thr Phe Asp Lys Arg Thr Ser Pro Pro Arg Cys Ser Asn Val
            180                 185                 190

Thr Phe Thr Asp Thr Leu Leu Ile Thr Pro Gly Gly Met Gly Leu Ala
        195                 200                 205

Glu Cys Gly Gln Leu Leu Gly Leu Pro Lys Leu Thr Ile Pro Ala Pro
    210                 215                 220

Tyr Ser Ile Ser Asp Met Arg Gln Tyr Leu Lys Gly Asp Arg Arg Gly
225                 230                 235                 240

Phe Glu Ala Tyr Ala Val Arg Asp Ala Glu Ile Ala Val Arg Tyr Ala
                245                 250                 255

Leu Gln Val Lys Ser Phe Cys Thr Glu Ser Leu Met Ile Glu Arg Val
            260                 265                 270

Pro Thr Thr Ile Gly Ala Met Ala Val Ser Arg Phe Leu Lys Thr Ile
        275                 280                 285

Lys Glu Ser Gly Gln Ser Pro Glu Val Cys Met Gly Thr Arg Thr Ile
    290                 295                 300

Ser Gln Gln Cys Trp Asn Pro Asp Thr His Gly Phe Arg Thr Leu Lys
305                 310                 315                 320

Ser Thr Gln Ser Ile Pro Ala Arg Glu Leu Tyr Glu Thr Phe Ala Ile
                325                 330                 335

Asn Cys Tyr His Gly Gly Arg Asn Glu Cys Phe Met Met Gly Ile Thr
            340                 345                 350

Pro Glu Ser Gln Trp Tyr Asp Tyr Asp Leu Ala Gly Ala Tyr Thr Thr
        355                 360                 365

Gly Leu Leu Asp Val Leu Gln Pro Asp Tyr Asp Asn Leu Tyr Thr Ser
    370                 375                 380

Gln Asn Pro Glu Glu Phe Cys Gly His Thr Met Gly Phe Ala Leu Val
385                 390                 395                 400

Ser Phe Arg Phe Pro Asp Thr Val Arg Tyr Pro Cys Leu Pro Val Arg
                405                 410                 415

Thr Asp Gln Tyr Gly Leu Phe Phe Pro Leu Thr Gly Glu Ser Trp Ala
            420                 425                 430

Thr Ala Pro Glu Ile Ala Leu Ala Leu Ser Leu Gly Ala Glu Ile Ala
        435                 440                 445

Ile Gln His Gly Ile Ile Ile Pro Trp Arg Gln Tyr Lys Ser Asp Asn
    450                 455                 460

Ala Ser Ser Pro Thr Lys Pro Ala Ser Ser Val Phe Leu Pro Phe Val
465                 470                 475                 480
```

```
Gln Gln Val Arg Glu Asn Arg Asn Arg His Asp Lys Gly Ser Leu Glu
                485                 490                 495

Glu Lys Phe Trp Lys Glu Ile Gly Asn Ser Leu Tyr Gly Lys Leu Ala
            500                 505                 510

Gln Gly Leu His Ala Lys Thr Ala Phe Asp Thr Ala Arg Gly Leu Asn
        515                 520                 525

Ser Pro Leu Pro Pro Ser Ser Val Thr Gln Pro Phe Phe Ala Ala His
    530                 535                 540

Val Thr Gly Phe Val Arg Ala Val Val Gly Glu Leu Met Asn Ala Leu
545                 550                 555                 560

Pro Pro Asn Ala Thr Val Val Ser Val Thr Thr Asp Gly Phe Leu Thr
                565                 570                 575

Asp Val Ser Leu Glu Asn Ile Asp Met Ser Gly Pro Leu Ser Ser Arg
            580                 585                 590

Phe Gln Ala Leu Cys Asp Ile Ala Asp Pro Gly Ser Ser Met Leu Thr
        595                 600                 605

Cys Lys His Gln Val Arg Gln Leu Val Ala Met Lys Thr Arg Gly Gln
    610                 615                 620

Leu Thr Tyr Lys Glu Ser Glu Gly Phe Pro Ile Val His Ala Arg Ala
625                 630                 635                 640

Gly Val Lys Pro Pro Ala Asp Ile Pro Arg Asp Asp Tyr Asn Arg Tyr
                645                 650                 655

Met Val Val Leu Tyr Met Asn Arg Ala Pro Gly Gln Lys Leu Arg Arg
            660                 665                 670

Gly Ser Leu Ile Ser Thr Arg Asp Met Trp Leu Asn Glu Ser Asp Leu
        675                 680                 685

Val Ala Val Glu Ser Glu Ile Arg Leu Asn Leu Glu Phe Asp Phe Lys
    690                 695                 700

Arg Gln Leu Ile Thr Pro Thr Met Asn Glu Gly His Leu Leu Met His
705                 710                 715                 720

Ser Arg Pro Trp Asp Asp Met Ser Gln Ala Leu Lys Gln Arg Gln Leu
                725                 730                 735

Phe Asp Asp Trp Arg Gln Thr His Ala Leu Lys Asp Glu Ala Asp Trp
            740                 745                 750

Glu Asp Trp Cys Asp Phe Leu Tyr Cys Arg Asn Val Phe Thr Pro Leu
        755                 760                 765

Lys Leu Lys Val Gly Gln Asn Arg Ser Asp Val Leu Val Arg Leu
    770                 775                 780

Phe Leu Arg Ala Leu Ala Gln His Gln Trp Gly Leu Thr Pro Asp Asp
785                 790                 795                 800

Arg Lys Arg Gln Thr Ser Val Glu Ile Ala Ala Trp Leu Val Glu Ala
                805                 810                 815

Gly Tyr Ser Val Thr Pro Ser Asp Val Lys Asn Ala Gly Arg Ala Lys
            820                 825                 830

Leu Pro Pro Ile Ile Phe Asp Ser Leu Thr Ala Arg Met Asn Arg Leu
        835                 840                 845

Met Asp Leu Ile Lys Leu Val Tyr Pro Gly Phe Ala Leu Pro Ser Ala
    850                 855                 860

Val Leu
865

<210> SEQ ID NO 45
<211> LENGTH: 2610
<212> TYPE: DNA
```

<213> ORGANISM: Artificial Sequence
<220> FEATURE:
<223> OTHER INFORMATION: Codon-optimized sequence encoding SEQ ID NO: 2

<400> SEQUENCE: 45

| | | | | | |
|---|---|---|---|---|---|
| catatgagca | ataacctgca | agacatcctg | gctgccgctt | ctggctacca | aagtgtcacc | 60 |
| tcggaaccgg | ccctgaatcg | caaacgcccg | aaaaccctgg | atgactatcc | ggttattccg | 120 |
| ccggcgagca | agaaagtgag | cgtgattagc | tctgatctga | ccctgcatat | cggttttgac | 180 |
| acggaatacg | tgttcaaccc | ggaaacccgc | cagaatgaca | tcctgtcgta | tcaaagctac | 240 |
| gtggttctgc | cggataacac | gggcatttcc | aatattatct | atccgccgga | ctcacagaaa | 300 |
| aaatctcgtc | tgagttttca | agatttcctg | tgccaaacca | ttacgccgct | gctggaaacc | 360 |
| ggtgttatca | cgaaatggcc | gggcattatc | aacatttacg | cccactttat | tcgcgcggac | 420 |
| atcgcctcgt | ttgcaaactt | ctggagcgat | tacaaaatcc | tgctgaaagg | catccgtggt | 480 |
| accgttagtt | cctttaaaaa | ccgctacggt | atcgatttcg | acgaacagca | agaacgtcgc | 540 |
| gtcaaaaccg | aacagattat | gtttgataaa | cgtacgtctc | cgccgcgctg | cagtaatgtg | 600 |
| gccttcattg | ataccctgct | gatcacgccg | ggcggtatgg | gtctggcaga | atgtggcgaa | 660 |
| ctgctgggtc | tgccgaaact | gaccattccg | gctccgtata | gcatcacgaa | catgcgcgaa | 720 |
| tacctgctgg | gtgaccgtgc | aggttttgaa | gcgtatgcgc | tgcgtgatgc | tgaaatcgcg | 780 |
| gttcgctacg | ctctgcaggt | ccgtaatttc | tgcgcgcgcg | aactgatgat | tgatcgtgtg | 840 |
| ccggcaacca | ttggtgccat | ggccgtttct | cgtttcacca | aaacgctgaa | agaaaacaac | 900 |
| atgagtccga | agtgtgcct | gggcacccat | atcaaaacgc | gtgaactgtg | gctgaccgaa | 960 |
| aaacaggcct | ttcgcacgat | taaaaacccg | gcatccgttc | cgtcacgtga | actgtttgaa | 1020 |
| accttcccga | ttaactgcta | tcatggcggt | cgcaatgaat | gtttcatgat | gggtgtgacc | 1080 |
| ccgtcagatc | actggtatga | ttacgacctg | gcaggcgctt | ataccacggg | tctgctggat | 1140 |
| attctgaccc | cggactacgg | caacatccgt | ctgagcaaaa | atccggatga | ctattgcggc | 1200 |
| catgtgatgg | ttttgcgct | ggttaccttt | cgcttcccgg | aatccgtccc | gtatccgtca | 1260 |
| ctgccggtgc | gtacggatca | gtacggtctg | tttttcccgc | tgagcggtga | aagctgggcc | 1320 |
| accgccccgg | aaattgaact | ggccctgtcc | ctgggtgcag | aaatgacgat | ccataacggc | 1380 |
| attatcgtgc | cgtggatttg | tgataccagc | ccgcacaata | tgaatccac | gtcagttttt | 1440 |
| ctgccgtttg | tgcagcaagt | tcgcgaaaac | cgtaatcgcc | atatcaaagg | ttccctggaa | 1500 |
| gaaaaattct | ggaaagaaat | cggcaactca | ctgtatggta | aactggctca | gggcctgcgt | 1560 |
| gccaaaaccg | cattcgatac | cgcgcgtggc | ctgaatcgca | gcctgccgcc | gtcatcggtc | 1620 |
| acccaaccgt | ttttcgcggc | ccacgtgacg | ggttttattc | gcgctgtcgt | gggcgaactg | 1680 |
| atgaatgcgc | tgccgtctga | tagctctgtt | gtcagtgtga | ccacggacgg | ctttctgacc | 1740 |
| aactgtccgc | tggataaaat | caatatgtcg | ggtccgctga | gttcccgctt | ccagagcctg | 1800 |
| tgcgatattg | ttgacccggg | ttcatcgatg | ctgacctgta | acatgaagt | ctctcaactg | 1860 |
| atcgccatga | aaacccgtgg | tcagctgacg | tataaagcaa | ttcaaggcaa | accggtggtt | 1920 |
| catgcacgcg | ctggtgtcaa | accgccggcc | gacattccgc | gtagtgatta | taacgactac | 1980 |
| atggtggatc | tgtacctgaa | tcgtctgccg | ggtcagaccc | tgtcgcgtag | caccctgatc | 2040 |
| tcgacgcgcg | aaatgtggct | gtctgaaagt | gatctggtta | gccgtgaaca | ggacattcgc | 2100 |
| ctgaacctgg | aatttgattt | caacgtcaa | ccggtgcgcc | cggcgatgaa | cgaaggccat | 2160 |
| ctgctgatgt | tttctcgtcc | gtgggataat | atggaagaag | ccctgcagca | acgtagtctg | 2220 |

```
ttcgatgact ggcgccagac ccacacgctg aaaaccctgg ccgattggga tgactggtgc    2280
gactttctgt attgtcgcac ggttttctct gatatgaaac tgaaagtcgg ctctaaacgt    2340
agtgatgaca tcctggttcg tctgtttctg cgcgcactga cccagtgcca atggggtctg    2400
atgctgaaag ataaaaaatc ctactcatgt aaagaagtgg cggaatggct gacctcggaa    2460
ggctatagcg ttaccgtcac ggatgtcaaa atgctgtgc gtgcgaaaat ccgcagatg     2520 aaatttagct ctgtgacccc gcgtatgaaa tccctgatgg acattatcgc ccgtaaatat    2580 ccgaccttt gcctgccggt ttaactcgag                                     2610
```

<210> SEQ ID NO 46
<211> LENGTH: 4
<212> TYPE: PRT
<213> ORGANISM: Escherichia coli

<400> SEQUENCE: 46

Lys Thr Arg Gly
1

<210> SEQ ID NO 47
<211> LENGTH: 50
<212> TYPE: DNA
<213> ORGANISM: Artificial Sequence
<220> FEATURE:
<223> OTHER INFORMATION: Oligonucleotide used for site-directed
      mutagenesis of the D368A variant

<400> SEQUENCE: 47

```
ccccgtcaga tcactggtat gattacgccc tggcaggcgc ttataccacg              50
```

<210> SEQ ID NO 48
<211> LENGTH: 50
<212> TYPE: DNA
<213> ORGANISM: Artificial Sequence
<220> FEATURE:
<223> OTHER INFORMATION: Oligonucleotide used for site-directed
      mutagenesis of the D368A variant

<400> SEQUENCE: 48

```
gctggtataa gcgcctgcca gggcgtaatc ataccagtga tctgacgggg              50
```

<210> SEQ ID NO 49
<211> LENGTH: 48
<212> TYPE: DNA
<213> ORGANISM: Artificial Sequence
<220> FEATURE:
<223> OTHER INFORMATION: Oligonucleotide used for site-directed
      mutagenesis of the D59A/E61A variant

<400> SEQUENCE: 49

```
ccctgcatat cggttttgcc acggcatacg tgttcaaccc ggaaaccc                48
```

<210> SEQ ID NO 50
<211> LENGTH: 48
<212> TYPE: DNA
<213> ORGANISM: Artificial Sequence
<220> FEATURE:
<223> OTHER INFORMATION: Oligonucleotide used for site-directed
      mutagenesis of the D59A/E61A variant

<400> SEQUENCE: 50

```
gggtttccgg gttgaacacg tatgccgtgg caaaaccgat atgcaggg                48
```

<210> SEQ ID NO 51
<211> LENGTH: 44
<212> TYPE: DNA
<213> ORGANISM: Artificial Sequence
<220> FEATURE:
<223> OTHER INFORMATION: Oligonucleotide used for site-directed mutagenesis of the WTHis variant

<400> SEQUENCE: 51 cctttttgcct gccggtttta ctcgagcacc accaccacca ccac        44

<210> SEQ ID NO 52
<211> LENGTH: 44
<212> TYPE: DNA
<213> ORGANISM: Artificial Sequence
<220> FEATURE:
<223> OTHER INFORMATION: Oligonucleotide used for site-directed mutagenesis of the WTHis variant

<400> SEQUENCE: 52
gtggtggtgg tggtggtgct cgagtaaaac cggcaggcaa aagg        44

<210> SEQ ID NO 53
<211> LENGTH: 48
<212> TYPE: DNA
<213> ORGANISM: Artificial Sequence
<220> FEATURE:
<223> OTHER INFORMATION: Oligonucleotide used for site-directed mutagenesis of the K613A variant

<400> SEQUENCE: 53
gggttcatcg atgctgacct gtgcacatga agtctctcaa ctgatcgc        48

<210> SEQ ID NO 54
<211> LENGTH: 48
<212> TYPE: DNA
<213> ORGANISM: Artificial Sequence
<220> FEATURE:
<223> OTHER INFORMATION: Oligonucleotide used for site-directed mutagenesis of the K613A variant

<400> SEQUENCE: 54
gcgatcagtt gagagacttc atgtgcacag gtcagcatcg atgaaccc     48

<210> SEQ ID NO 55
<211> LENGTH: 48
<212> TYPE: DNA
<213> ORGANISM: Artificial Sequence
<220> FEATURE:
<223> OTHER INFORMATION: Oligonucleotide used for site-directed mutagenesis of the H614A variant

<400> SEQUENCE: 55
gggttcatcg atgctgacct gtaaagctga agtctctcaa ctgatcgc    48

<210> SEQ ID NO 56
<211> LENGTH: 48
<212> TYPE: DNA
<213> ORGANISM: Artificial Sequence
<220> FEATURE:
<223> OTHER INFORMATION: Oligonucleotide used for site-directed mutagenesis of the H614A variant

<400> SEQUENCE: 56
gcgatcagtt gagagacttc agctttacag gtcagcatcg atgaaccc    48

<210> SEQ ID NO 57

```
<211> LENGTH: 42
<212> TYPE: DNA
<213> ORGANISM: Artificial Sequence
<220> FEATURE:
<223> OTHER INFORMATION: Oligonucleotide used for site-directed
      mutagenesis of the K623A variant

<400> SEQUENCE: 57
gtctctcaac tgatcgccat ggcaacccgt ggtcagctga cg                      42

<210> SEQ ID NO 58
<211> LENGTH: 42
<212> TYPE: DNA
<213> ORGANISM: Artificial Sequence
<220> FEATURE:
<223> OTHER INFORMATION: Oligonucleotide used for site-directed
      mutagenesis of the K623A variant

<400> SEQUENCE: 58
cgtcagctga ccacgggttg ccatggcgat cagttgagag ac                      42

<210> SEQ ID NO 59
<211> LENGTH: 50
<212> TYPE: DNA
<213> ORGANISM: Artificial Sequence
<220> FEATURE:
<223> OTHER INFORMATION: Oligonucleotide used for site-directed
      mutagenesis of the R625A variant

<400> SEQUENCE: 59
gtctctcaac tgatcgccat gaaaaccgct ggtcagctga cgtataaagc              50

<210> SEQ ID NO 60
<211> LENGTH: 50
<212> TYPE: DNA
<213> ORGANISM: Artificial Sequence
<220> FEATURE:
<223> OTHER INFORMATION: Oligonucleotide used for site-directed
      mutagenesis of the R625A variant

<400> SEQUENCE: 60
gctttatacg tcagctgacc agcggttttc atggcgatca gttgagagac              50

<210> SEQ ID NO 61
<211> LENGTH: 4
<212> TYPE: DNA
<213> ORGANISM: Artificial Sequence
<220> FEATURE:
<223> OTHER INFORMATION: Oligonucleotide P4

<400> SEQUENCE: 61 gatc                                                                 4

<210> SEQ ID NO 62
<211> LENGTH: 10
<212> TYPE: DNA
<213> ORGANISM: Artificial Sequence
<220> FEATURE:
<223> OTHER INFORMATION: Oligonucleotide P10

<400> SEQUENCE: 62
gactgcttac                                                          10

<210> SEQ ID NO 63
<211> LENGTH: 15
<212> TYPE: DNA
<213> ORGANISM: Artificial Sequence
```

```
<220> FEATURE:
<223> OTHER INFORMATION: Oligonucleotide P15

<400> SEQUENCE: 63
gatcacagtg agtac                                                           15

<210> SEQ ID NO 64
<211> LENGTH: 33
<212> TYPE: DNA
<213> ORGANISM: Artificial Sequence
<220> FEATURE:
<223> OTHER INFORMATION: Oligonucleotide T33GTA

<400> SEQUENCE: 64
actggccgtc gttctattgt actcactgtg atc                                       33

<210> SEQ ID NO 65
<211> LENGTH: 33
<212> TYPE: DNA
<213> ORGANISM: Artificial Sequence
<220> FEATURE:
<223> OTHER INFORMATION: Oligonucleotide T33GTT

<400> SEQUENCE: 65
actggccgtc gttctaatgt actcactgtg atc                                       33

<210> SEQ ID NO 66
<211> LENGTH: 33
<212> TYPE: DNA
<213> ORGANISM: Artificial Sequence
<220> FEATURE:
<223> OTHER INFORMATION: Oligonucleotide T33GFT
<220> FEATURE:
<221> NAME/KEY: misc_feature
<222> LOCATION: (18)..(18)
<223> OTHER INFORMATION: THF abasic site analog (F)

<400> SEQUENCE: 66
actggccgtc gttctatngt actcactgtg atc                                       33

<210> SEQ ID NO 67
<211> LENGTH: 14
<212> TYPE: DNA
<213> ORGANISM: Artificial Sequence
<220> FEATURE:
<223> OTHER INFORMATION: Oligonucleotide P20-33

<400> SEQUENCE: 67
gaacgacggc cagt                                                            14

<210> SEQ ID NO 68
<211> LENGTH: 33
<212> TYPE: DNA
<213> ORGANISM: Artificial Sequence
<220> FEATURE:
<223> OTHER INFORMATION: Oligonucleotide  33A

<400> SEQUENCE: 68
aaaaaaaaaa aaaaaaaaaa aaaaaaaaaa aaa                                       33

<210> SEQ ID NO 69
<211> LENGTH: 33
<212> TYPE: DNA
<213> ORGANISM: Artificial Sequence
<220> FEATURE:
<223> OTHER INFORMATION: Oligonucleotide 33T*
```

```
<400> SEQUENCE: 69
tttttttttt tttttttttt tttttttttt ttt                                33

<210> SEQ ID NO 70
<211> LENGTH: 33
<212> TYPE: DNA
<213> ORGANISM: Artificial Sequence
<220> FEATURE:
<223> OTHER INFORMATION: Oligonucleotides CC31T*

<400> SEQUENCE: 70 ccttttttt tttttttttt tttttttttt ttt                                 33

<210> SEQ ID NO 71
<211> LENGTH: 33
<212> TYPE: DNA
<213> ORGANISM: Artificial Sequence
<220> FEATURE:
<223> OTHER INFORMATION: Oligonucleotide 15TCC16T*

<400> SEQUENCE: 71
tttttttttt ttttccttttt tttttttttt ttt                               33

<210> SEQ ID NO 72
<211> LENGTH: 33
<212> TYPE: DNA
<213> ORGANISM: Artificial Sequence
<220> FEATURE:
<223> OTHER INFORMATION: Oligonucleotide 15TC17T*

<400> SEQUENCE: 72
tttttttttt ttttcttttt tttttttttt ttt                                33

<210> SEQ ID NO 73
<211> LENGTH: 33
<212> TYPE: DNA
<213> ORGANISM: Artificial Sequence
<220> FEATURE:
<223> OTHER INFORMATION: Oligonucleotide  15TA17T*

<400> SEQUENCE: 73
tttttttttt ttttatttttt tttttttttt ttt                               33

<210> SEQ ID NO 74
<211> LENGTH: 17
<212> TYPE: DNA
<213> ORGANISM: Artificial Sequence
<220> FEATURE:
<223> OTHER INFORMATION: Oligonucleotide M13 UP

<400> SEQUENCE: 74
gtaaaacgac ggccagt                                                  17

<210> SEQ ID NO 75
<211> LENGTH: 553
<212> TYPE: PRT
<213> ORGANISM: Salmonella virus

<400> SEQUENCE: 75

Met Pro Arg Arg Ser Arg Lys Lys Val Glu Tyr Lys Ile Ala Ala Phe
1               5                   10                  15

Asp Phe Glu Thr Asp Pro Phe Lys His Asp Arg Ile Pro Lys Pro Phe
            20                  25                  30

Ser Trp Gly Phe Tyr Asn Gly Glu Ile Tyr Lys Asp Tyr Trp Gly Asp
```

```
                35                  40                  45
Asp Cys Ile Glu Gln Phe Ile Tyr Trp Leu Asp Thr Ile Glu Glu Pro
 50                  55                  60
His Val Ile Tyr Ala His Asn Gly Gly Lys Phe Asp Phe Leu Phe Leu
 65                  70                  75                  80
Met Lys Tyr Phe Arg Gly Lys Leu Lys Ile Val Asn Gly Arg Ile Leu
                 85                  90                  95
Glu Val Glu His Gly Ile His Lys Phe Arg Asp Ser Tyr Ala Ile Leu
                100                 105                 110
Pro Val Pro Leu Ala Ala Ser Asp Glu Lys Ile Glu Ile Asp Tyr Gly
                115                 120                 125
Lys Met Glu Arg Glu Thr Arg Glu Gln His Lys Ala Glu Ile Leu Glu
                130                 135                 140
Tyr Leu Lys Gly Asp Cys Val Thr Leu His Lys Met Val Ser Leu Phe
145                 150                 155                 160
Ile Ala Glu Phe Gly Met Arg Leu Thr Ile Gly Gly Thr Ala Met Asn
                165                 170                 175
Glu Leu Lys Gln Phe His Pro Tyr Asp Pro Val Arg Lys Gly Phe Asp
                180                 185                 190
Glu Ala Met Arg Pro Phe Tyr Phe Gly Gly Arg Cys Gln Ala Phe Glu
                195                 200                 205
Lys Gly Ile Ile Glu Asp Asp Ile Lys Val Tyr Asp Val Asn Ser Met
                210                 215                 220
Tyr Pro His Ala Met Arg Asn Phe Arg His Pro Phe Ser Asp Glu Phe
225                 230                 235                 240
Tyr Glu Ala Asn Glu Ile Thr Glu Glu Thr Tyr Phe Ile Glu Trp Glu
                245                 250                 255
Gly Glu Asn Asn Gly Ala Val Pro Val Arg Thr Lys Thr Gly Leu Asp
                260                 265                 270
Phe Asn Gln Arg Ser Gly Ile Phe His Thr Ser Ile His Glu Trp Arg
                275                 280                 285
Ala Gly Ile Asp Thr Gly Thr Ile Lys Pro Asn Arg Ile Ile Arg Thr
                290                 295                 300
Ile Asn Phe Thr Glu Thr Thr Thr Phe Gly Ala Phe Ile Asp His Phe
305                 310                 315                 320
Phe Ser Lys Arg Asp Ala Ala Lys Lys Ala Gly Asp Leu Phe His Asn
                325                 330                 335
Ile Phe Tyr Lys Leu Ile Leu Asn Ser Ser Tyr Gly Lys Phe Ala Gln
                340                 345                 350
Asn Pro Glu Asn Tyr Lys Glu Trp Cys Ile Thr Glu Gly Gly Ile Tyr
                355                 360                 365
Leu Glu Gly Tyr Asp Gly Glu Gly Cys Glu Val Gln Glu His Leu Asp
                370                 375                 380
Tyr Ile Leu Trp Gly Arg Pro Ala Glu Met Phe Asn Tyr Phe Asn Val
385                 390                 395                 400
Ala Val Ala Ala Ser Ile Thr Gly Ala Ala Arg Ser Val Leu Leu Arg
                405                 410                 415
Ala Leu Ala Gln Ala Glu Arg Pro Leu Tyr Cys Asp Thr Asp Ser Ile
                420                 425                 430
Ile Cys Arg Asp Leu Lys Asn Val Pro Leu Asp Ala Tyr Gln Leu Gly
                435                 440                 445
Ala Trp Asp Leu Glu Ala Thr Gly Asp Lys Ile Ala Ile Ala Gly Lys
450                 455                 460
```

Lys Leu Tyr Ala Leu Tyr Ala Gly Asp Asn Cys Val Lys Ile Ala Ser
465                 470                 475                 480

Lys Gly Ala Ser Leu Val Pro Arg Asp Ile Gly Phe Leu Met Pro Pro
            485                 490                 495

Asp Met Glu Pro Lys Ala Ala Lys Lys Val Ala Gln Gln Lys Ala Lys
        500                 505                 510

Asn Ile Gly Gly Glu Lys Ile Leu Lys Val Ala Asn Gly Gly Val Tyr
            515                 520                 525

Asp Phe Val Asn Asp Ala Pro Ser Phe Lys Leu Asn Gly Asn Val Gln
        530                 535                 540

Phe Ile Lys Arg Thr Ile Lys Gly Thr
545                 550

<210> SEQ ID NO 76
<211> LENGTH: 568
<212> TYPE: PRT
<213> ORGANISM: Streptococcus phage

<400> SEQUENCE: 76

Met Thr Cys Tyr Tyr Ala Gly Asp Phe Glu Thr Thr Thr Asn Glu Glu
1               5                   10                  15

Glu Thr Glu Val Trp Leu Ser Cys Phe Ala Lys Val Ile Asp Tyr Asp
            20                  25                  30

Lys Leu Asp Thr Phe Lys Val Asn Thr Ser Leu Glu Asp Phe Leu Lys
        35                  40                  45

Ser Leu Tyr Leu Asp Leu Asp Lys Thr Tyr Thr Glu Thr Gly Glu Asp
50                  55                  60

Glu Phe Ile Ile Phe Phe His Asn Leu Lys Phe Asp Gly Ser Phe Leu
65                  70                  75                  80

Leu Ser Phe Phe Leu Asn Asn Asp Ile Glu Cys Thr Tyr Phe Ile Asn
                85                  90                  95

Asp Met Gly Val Trp Tyr Ser Ile Thr Leu Glu Phe Pro Asp Phe Thr
            100                 105                 110

Leu Thr Phe Arg Asp Ser Leu Lys Ile Leu Asn Phe Ser Ile Ala Thr
        115                 120                 125

Met Ala Gly Leu Phe Lys Met Pro Ile Ala Lys Gly Thr Thr Pro Leu
130                 135                 140

Leu Lys His Lys Pro Glu Val Ile Lys Pro Glu Trp Ile Asp Tyr Ile
145                 150                 155                 160

His Val Asp Val Ala Ile Leu Ala Arg Gly Ile Phe Ala Met Tyr Tyr
                165                 170                 175

Glu Glu Asn Phe Thr Lys Tyr Thr Ser Ala Ser Glu Ala Leu Thr Glu
            180                 185                 190

Phe Lys Arg Ile Phe Arg Lys Ser Lys Arg Lys Phe Arg Asp Phe Phe
        195                 200                 205

Pro Ile Leu Asp Glu Lys Val Asp Phe Cys Arg Lys His Ile Val
210                 215                 220

Gly Ala Gly Arg Leu Pro Thr Leu Lys His Arg Gly Arg Thr Leu Asn
225                 230                 235                 240

Gln Leu Ile Asp Ile Tyr Asp Ile Asn Ser Met Tyr Pro Ala Thr Met
                245                 250                 255

Leu Gln Asn Ala Leu Pro Ile Gly Ile Pro Lys Arg Tyr Lys Gly Lys
            260                 265                 270

Pro Lys Glu Ile Lys Glu Asp His Tyr Tyr Ile Tyr His Ile Lys Ala

```
                275                 280                 285
Asp Phe Asp Leu Lys Arg Gly Tyr Leu Pro Thr Ile Gln Ile Lys Lys
        290                 295                 300

Lys Leu Asp Ala Leu Arg Ile Gly Val Arg Thr Ser Asp Tyr Val Thr
305                 310                 315                 320

Thr Ser Lys Asn Glu Val Ile Asp Leu Tyr Leu Thr Asn Phe Asp Leu
                325                 330                 335

Asp Leu Phe Leu Lys His Tyr Asp Ala Thr Ile Met Tyr Val Glu Thr
            340                 345                 350

Leu Glu Phe Gln Thr Glu Ser Asp Leu Phe Asp Tyr Ile Thr Thr
                355                 360                 365

Tyr Arg Tyr Lys Lys Glu Asn Ala Gln Ser Pro Ala Glu Lys Gln Lys
        370                 375                 380

Ala Lys Ile Met Leu Asn Ser Leu Tyr Gly Lys Phe Gly Ala Lys Ile
385                 390                 395                 400

Ile Ser Val Lys Lys Leu Ala Tyr Leu Asp Asp Lys Gly Ile Leu Arg
                405                 410                 415

Phe Lys Asn Asp Asp Glu Glu Val Gln Pro Val Tyr Ala Pro Val
            420                 425                 430

Ala Leu Phe Val Thr Ser Ile Ala Arg His Phe Ile Ile Ser Asn Ala
                435                 440                 445

Gln Glu Asn Tyr Asp Asn Phe Leu Tyr Ala Asp Thr Asp Ser Leu His
        450                 455                 460

Leu Phe His Ser Asp Ser Leu Val Leu Asp Ile Asp Pro Ser Glu Phe
465                 470                 475                 480

Gly Lys Trp Ala His Glu Gly Arg Ala Val Lys Ala Lys Tyr Leu Arg
                485                 490                 495

Ser Lys Leu Tyr Ile Glu Glu Leu Ile Gln Glu Asp Gly Thr Thr His
            500                 505                 510

Leu Asp Val Lys Gly Ala Gly Met Thr Pro Glu Ile Lys Glu Lys Ile
        515                 520                 525

Thr Phe Glu Asn Phe Val Ile Gly Ala Thr Phe Glu Gly Lys Arg Ala
530                 535                 540

Ser Lys Gln Ile Lys Gly Gly Thr Leu Ile Tyr Glu Thr Thr Phe Lys
545                 550                 555                 560

Ile Arg Glu Thr Asp Tyr Leu Val
                565

<210> SEQ ID NO 77
<211> LENGTH: 717
<212> TYPE: PRT
<213> ORGANISM: His 1 virus

<400> SEQUENCE: 77

Met Ala Lys Cys Asp Lys Ser Leu Glu Ala Ile Asp Leu Asp Arg Ala
1               5                   10                  15

Tyr Thr Ala Pro Arg Lys Ala Lys Trp Ala Glu Asn Lys Arg Ile Asn
            20                  25                  30

Gly Leu Asp Thr Glu Thr Ser Asp Gly Asp Ile Phe Cys Ile Ser Val
        35                  40                  45

Cys Trp Glu Gly Glu Lys Pro Met Val Gln His Asn Asp Arg Glu Lys
    50                  55                  60

Leu Thr Ser Lys Gln Val Trp Gln Val Leu Thr Asp His Lys Ala Arg
65                  70                  75                  80
```

```
Ser Ser Leu Asn Met Trp Tyr Asn Leu Asp Phe Asp Ala Asn Val Val
                85                  90                  95

Leu Asn His Val Cys Ser Glu Glu Gln Leu Ala Glu Leu Val Val Ser
            100                 105                 110

Gly Thr Thr Leu Ala Asn Ser Asp Arg Thr Tyr Arg Gln Tyr Met Asp
            115                 120                 125

Thr Asp Lys Glu Leu Arg Lys Gly Glu Tyr Leu Ile Thr Tyr Ile Gln
130                 135                 140

Ser Lys Phe Leu Glu Ile Lys Asp His Asn Ser His Ile Tyr Thr His
145                 150                 155                 160

Tyr Asp Ala Ser Gln Phe Phe Tyr Thr Ser Leu Glu Asn Ala Val Thr
                165                 170                 175

Glu Trp Leu Gly Glu Ser Lys Ala Asn Asp Gly Leu Glu Ala Gly Leu
            180                 185                 190

Phe Gly Ser Gln Thr Pro Asn Gln Leu Arg Glu Thr Val Ala Glu Ser
            195                 200                 205

Asp Cys Val Thr Trp Thr Asn Leu Ser Leu Thr Tyr Asn Val Ser Lys
    210                 215                 220

Gly Asp Lys Trp Thr Ile His Asn Ala Lys Ser Tyr Ile Ser Lys Asn
225                 230                 235                 240

Trp Ser Asp Ile Leu Lys Tyr Ala Gln Ile Asp Ala Glu Leu Val Arg
                245                 250                 255

Asp Leu Trp Gln Glu Ala Val Asn Val Gly Glu Leu Asp Ile Pro
            260                 265                 270

Met Gly Arg Pro Phe Ser Thr Gly Tyr Leu Ala Glu Ser Tyr Leu Asp
            275                 280                 285

Asn Arg Leu Arg Glu Lys Pro Gly Leu Gly Pro Met Pro Met Ala Lys
    290                 295                 300

Met Ala Trp Glu Ser Tyr Ala Gly Gly Arg Phe Glu Val Leu Lys Arg
305                 310                 315                 320

Gly Asn Val Gly Arg Val Ala Gly Pro Asp Ile Asn Ser Ala Tyr Pro
                325                 330                 335

Ala Val Leu Ala Glu Leu Pro Asp Pro Lys Thr Leu Arg Trp Lys Arg
            340                 345                 350

Ala Lys His Ala Ser Ile Ser Glu Ile Glu Thr Ala Asp Tyr Gly Phe
            355                 360                 365

Met Thr Val Lys Val Ser Thr Asp Pro Thr Arg Glu Ile Gln Pro Phe
    370                 375                 380

Ala Val Lys Asp Glu Lys Gln Asp Lys Leu Val Tyr Pro Ser Pro Gln
385                 390                 395                 400

Asn Thr Glu Ile Thr Val Val Lys Asp Ile Phe Ile His Ala Tyr Asn
                405                 410                 415

Gln Gly Tyr Val Thr Asp Tyr Glu Val Ile Asp Cys Trp Leu Gly Tyr
            420                 425                 430

Lys Thr Glu Gly Thr Thr Phe Pro Phe Asp Phe Ile Pro Glu Leu Tyr
            435                 440                 445

Asp Asn Arg Lys Thr Ala Glu Ala Asn Gly Leu Glu Lys Arg Gly Leu
    450                 455                 460

Leu Leu Lys Ile Val Leu Asn Ser Met Tyr Gly Lys Thr Cys Gln Thr
465                 470                 475                 480

Thr Pro Lys Arg Arg Glu Leu Ala Glu Ser Thr Glu Leu Glu Leu His
                485                 490                 495

Glu Ser Tyr Val Pro Asp Met Ser Leu Pro Lys Met Ile Arg Glu Lys
```

```
                500             505             510
Tyr Ser Glu Gly Phe Ile Glu Ser Leu Thr Ala Gly Ala Trp Phe Asn
            515                 520             525

Pro Phe Leu Ala Ser Tyr Ile Thr Gly Leu Thr Arg Leu Glu Leu His
        530                 535             540

Lys Gln Ile Cys Lys His Asp Leu Glu Glu Asn Thr Val Met Leu Ala
545                 550                 555                 560

Thr Asp Cys Val Met Ile Glu Glu Lys Pro Phe Glu Glu Ser Asn Phe
                565                 570                 575

Val Glu Asn Leu Val Gln Asp Gly Leu Gly Tyr Trp Asp Met Glu Tyr
            580                 585                 590

Lys Gly Asp Ala Phe Val Leu Gly Ala Gly Val Tyr Gln Ile Asp Phe
        595                 600                 605

Asp Thr Cys Gln Lys Gly Cys Lys Asp Asn Cys Asn Lys Phe Ser His
    610                 615                 620

Lys His Lys Val Lys Thr Arg Gly Phe Ser Glu Ala Asp Leu Glu Lys
625                 630                 635                 640

Gly Leu Val Asn Ala Ala Glu Lys Ala Asn Gly His Ile Glu Ile Glu
                645                 650                 655

Ser Thr Arg Pro Gln Thr Ile Ser Glu Ile Ile Trp Ser Asn Glu Glu
            660                 665                 670

Leu Ser Gln Val Gly Asn Phe Leu Glu Gln Arg Lys Ile Lys Pro
        675                 680                 685

Glu Met Asp Thr Lys Arg Lys Trp Ser Glu Asn Thr Asp Phe Lys Lys
    690                 695                 700

Leu Leu Ser Thr Cys Glu Thr Ser Leu Pro Leu Lys Ile
705                 710                 715

<210> SEQ ID NO 78
<211> LENGTH: 720
<212> TYPE: PRT
<213> ORGANISM: His2 virus

<400> SEQUENCE: 78

Met Ala Lys Ser Asp Arg Asn Leu Asp Glu Val Asn Leu Tyr Pro Ala
1               5                   10                  15

Tyr Gln Asp Gln Tyr Ser Ala Thr Phe Val Asp Gly Lys Leu Ile Asn
            20                  25                  30

Ala Phe Asp Thr Glu Thr Ser Ser Gly Thr Val Phe Met Leu Thr Ser
        35                  40                  45

Ala Tyr Gly Asp Lys Thr Gln Ala Tyr Tyr Asn Arg Asp Val Ser Glu
    50                  55                  60

Leu Asp Ala Glu Thr Ile Met Asp Ala Leu Thr Asp Tyr Lys Thr Arg
65                  70                  75                  80

Ser Asn Ile Asn Ile Trp Tyr Asn Leu Asp Phe Asp Ala Asn Ala Ile
                85                  90                  95

Leu Ser Gly Ile Leu Ser Gln Lys Glu Met Ser Glu Leu Val Val Thr
            100                 105                 110

Asn Glu Thr Thr Thr Thr Val Ala Gly Ile Glu Tyr Glu Ile Phe Tyr
        115                 120                 125

Ile Lys Gly Lys Met Leu Arg Ile Val Asp Glu Asn Gly Asn Ile Ser
    130                 135                 140

Pro His Tyr Asp Ile Ala Gln Phe Phe Tyr Thr Ser Leu Asp Asn Ala
145                 150                 155                 160
```

```
Ala Glu Glu Trp Leu Gly Glu Asn Lys Lys Gly Ile Asp Thr Ser
            165                 170                 175

Lys Phe Asp Asp Lys Glu Tyr Ile Lys Asp Asn Phe Asp Glu Ile Leu
        180                 185                 190

Lys Tyr Ala Lys Lys Asp Ala Ser Leu Thr Gln Asp Leu Ala Ile Glu
        195                 200                 205

Leu Thr Asn Glu Ala Glu Asn Leu Asp Ile Pro Met Gly Arg Pro Ile
    210                 215                 220

Ser Thr Gly Tyr Leu Ser Ala Glu Tyr Leu Arg Ala Asn Thr Glu Glu
225                 230                 235                 240

Lys Pro Ser Leu Gly Asn Glu Ala Met Gln Asn Leu Phe Trp Glu Ser
            245                 250                 255

Tyr Tyr Gly Gly Arg Phe Glu Val Phe Gln Arg Gly Asn Val Gly Glu
            260                 265                 270

Val Val Ala Pro Asp Ile Asn Ser Ala Tyr Pro Ala Ile Met Lys Asp
        275                 280                 285

Leu Pro Asp Pro Thr Thr Leu Asn Trp Asn His Tyr Leu Asn Glu Val
    290                 295                 300

Ser Asp Lys Glu Pro Phe Ser His Ser Ile Asn Lys Phe Gly Tyr Glu
305                 310                 315                 320

Glu Ile Glu Asn Gly His Tyr Gly Val Val Lys Ala Arg Val Thr Thr
                325                 330                 335

Asp Ser Ser Arg Met Ile Gln Pro Phe Ala Cys Lys Ile Asp Gly Lys
            340                 345                 350

Val Lys Phe Pro Ala Met Thr Asn Lys Val Val Thr Val Ile Lys Pro
        355                 360                 365

Ile Phe Glu Phe Ala Val Asn Asn Gly Leu Val Thr Asp Phe Glu Leu
    370                 375                 380

Ile Glu Ala Trp Ile Gly Asn Ile Thr Asp Arg Thr Ser Lys Pro Phe
385                 390                 395                 400

Glu Phe Ile Gly Asp Met Tyr Ala Glu Arg Lys Val Phe Glu Gln Leu
                405                 410                 415

Lys Asn Lys Pro Lys Lys Gly Gln Leu Leu Lys Ile Val Leu Asn Ser
            420                 425                 430

Ser Tyr Gly Lys Thr Cys Gln Thr Thr Glu Lys Arg His Lys His Asp
        435                 440                 445

Leu Asp Lys Asp Gly Lys Lys Ile Met Gln Ala His Glu Thr Gln Tyr
    450                 455                 460

Pro Arg Phe Tyr Leu Ser Lys Lys Gln Arg Glu Ala Leu Gly Asp Asp
465                 470                 475                 480

Glu Ile Ile Ile Thr Glu Leu Glu Ala Gly Lys Arg Phe Asn Pro Phe
                485                 490                 495

Phe Ala Ser Tyr Ile Thr Gly Leu Thr Arg Leu Glu Leu His Lys Gln
            500                 505                 510

Val Val Glu His Asp Ile Glu Asp Ser Thr Val Met Phe Ala Thr Asp
        515                 520                 525

Cys Leu Met Val Glu Lys Glu Ala Tyr Glu Asn Ser Ser Phe Asp Glu
    530                 535                 540

Gln Ile His Val Pro Asp Asp Ser Leu Pro Glu Ser Glu Phe Arg Lys
545                 550                 555                 560

Glu Ala Thr Arg Ser Leu Gly Ala Trp Asp Phe Asp Tyr Glu Gly Ser
                565                 570                 575

Ala Phe Ile Val Gly Ser Gly Val Tyr Glu Val Asp Thr Ile Gln Gly
```

```
                        580                 585                 590
Lys Thr Lys Thr Lys Thr Arg Gly Phe Ile Glu Ser Asn Leu Gly Asp
                    595                 600                 605

Thr Leu Lys Gly Leu Ala Lys Lys His Lys Glu Ala Ile Pro Leu Asp
                610                 615                 620

Asn Glu Arg Pro Leu Thr Met Ala Glu Val Leu Ile Asn Thr Glu Arg
625                 630                 635                 640

Gly Ser Val Ser Glu Phe Val Glu Asn Ser Lys Lys Leu Lys Pro Asp
                    645                 650                 655

Phe Asp Asp Lys Arg Asn Trp Asn Arg Glu Asn Pro Asn Phe His Asp
                660                 665                 670

Leu Leu Asn Asp Lys Glu Tyr Ser Lys Pro Ile Asp Leu Gln Glu Gln
            675                 680                 685

Lys Glu Glu Met Ile Gln Glu Gln Met Asp Ile Asn Glu Lys Met Ile
        690                 695                 700

Gly Asp Ala Thr Pro Asn Gly Asn Glu Thr Val Val Lys Asp Asp
705                 710                 715                 720

<210> SEQ ID NO 79
<211> LENGTH: 33
<212> TYPE: DNA
<213> ORGANISM: Artificial Sequence
<220> FEATURE:
<223> OTHER INFORMATION: Oligonucleotide template substrate used in the
      examples

<400> SEQUENCE: 79
actggccgtc gttctattgt actcactgtg atc                                  33

<210> SEQ ID NO 80
<211> LENGTH: 33
<212> TYPE: DNA
<213> ORGANISM: Artificial Sequence
<220> FEATURE:
<223> OTHER INFORMATION: Oligonucleotide template substrate used in the
      examples

<400> SEQUENCE: 80
actggccgtc gttctaatgt actcactgtg atc                                  33

<210> SEQ ID NO 81
<211> LENGTH: 33
<212> TYPE: DNA
<213> ORGANISM: Artificial Sequence
<220> FEATURE:
<223> OTHER INFORMATION: Oligonucleotide template substrate used in the
      examples
<220> FEATURE:
<221> NAME/KEY: misc_feature
<222> LOCATION: (18)..(18)
<223> OTHER INFORMATION: THF abasic site analog (F)

<400> SEQUENCE: 81
actggccgtc gttctatngt actcactgtg atc                                  33

<210> SEQ ID NO 82
<211> LENGTH: 33
<212> TYPE: DNA
<213> ORGANISM: Artificial Sequence
<220> FEATURE:
<223> OTHER INFORMATION: Oligonucleotide template substrate used in the
      examples
<220> FEATURE:
<221> NAME/KEY: misc_feature
```

```
<222> LOCATION: (18)..(18)
<223> OTHER INFORMATION: THF abasic site analog (F)

<400> SEQUENCE: 82
actggccgtc gttctaangt actcactgtg atc                                33

<210> SEQ ID NO 83
<211> LENGTH: 33
<212> TYPE: DNA
<213> ORGANISM: Artificial Sequence
<220> FEATURE:
<223> OTHER INFORMATION: Oligonucleotide template substrate used in the
      examples
<220> FEATURE:
<221> NAME/KEY: misc_feature
<222> LOCATION: (18)..(18)
<223> OTHER INFORMATION: T, THF, Tg or T:T

<400> SEQUENCE: 83
actggccgtc gttctatngt actcactgtg atc                                33

<210> SEQ ID NO 84
<211> LENGTH: 33
<212> TYPE: DNA
<213> ORGANISM: Artificial Sequence
<220> FEATURE:
<223> OTHER INFORMATION: Oligonucleotide template substrate used in the
      examples
<220> FEATURE:
<221> NAME/KEY: misc_feature
<222> LOCATION: (18)..(18)
<223> OTHER INFORMATION: T or THF

<400> SEQUENCE: 84
actggccgtc gttctaangt actcactgtg atc                                33

<210> SEQ ID NO 85
<211> LENGTH: 14
<212> TYPE: PRT
<213> ORGANISM: Artificial Sequence
<220> FEATURE:
<223> OTHER INFORMATION: SEQ ID NO: 1 in which X2 is H and X3-10 is SEQ
      ID NO: 5

<400> SEQUENCE: 85

Lys His Glu Val Ser Gln Leu Ile Ala Met Lys Thr Arg Gly
1               5                   10
```

PRIMER-INDEPENDENT DNA POLYMERASES AND THEIR USE FOR DNA SYNTHESIS

CROSS-REFERENCE TO RELATED APPLICATIONS

The present patent application is a U.S. national phase application of International Application No. PCT/EP2018/078737, filed Oct. 19, 2018, which claims priority to Spanish Patent Application No. P201731236, filed Oct. 20, 2017, the disclosures of which are incorporated herein by reference.

INCORPORATION BY REFERENCE

The content of the ASCII text file of the sequence listing named "PCT1641_1302_Seq_List_Untitled_ST25", which is 341 kb in size, was created on and electronically submitted via EFS-Web Apr. 16, 2020, is incorporated herein by reference in its entirety.

The present invention falls within the fields of molecular biology, biotechnology and DNA amplification or replication methods. Particularly, this invention refers to a new group of DNA polymerase enzymes with DNA priming activity, which can be used for in vitro amplification of DNA templates without the presence of externally added primers.

BACKGROUND ART

DNA polymerases (DNAPs) are key enzymes essential for genome replication, recombination and repair across all cellular life forms and their viruses. DNAPs can be divided in seven families (A, B, C, D, X, Y and RTs). Family B DNAPs (PolBs) comprise enzymes involved in genome replication in eukaryotes and archaea, but also in viruses from the three domains of life. For initiation of DNA synthesis, all PolBs characterized thus far depend on the presence of an external primer, a hydroxyl group presented either by a nucleic acid (RNA or DNA) or the so-called terminal protein (TP). Thus, based on the primer requirement for initiation of genome replication as well as phylogenetic clustering, these enzymes can be broadly divided into two major groups: RNA-primed (rPolBs) and protein-primed (pPolBs) PolBs. The evolutionary relationship between the two groups is unknown and it is thus unclear whether the putative ancestral PolB would have employed a protein or an RNA oligonucleotide as a primer. The rPolB group contains mainly replicases devoted to accurate and efficient copying of large cellular and viral genomes. By contrast, pPolBs are exclusive to viruses and selfish mobile elements with moderately-sized linear genomes (<50 kb). The signature of pPolBs is the presence of specific subdomains, named TPR1 and TPR2, which were originally described in Φ29 DNA polymerase (Φ29DNAP). TPR1 is required for the DNAP interaction with the TP, whereas TPR2 endows pPolB with the processivity and strand-displacement capacities, the two properties ensuring the superiority of Φ29DNAP in various molecular biology applications, such as multiple displacement single molecule DNA amplification.

Protein-priming has been described for a number of bacterial and eukaryotic viruses as well as for linear plasmids found in yeast, filamentous fungi and plants. More recently, pPolB-encoding genes were also identified in two superfamilies of mobile genetic elements (MGE) integrated in various cellular genomes (Krupovic and Koonin, 2016, Curr Opin Microbiol, 31, 25-33). The first superfamily comprises eukaryotic virus-like transposable elements, called polintons (also known as Mavericks), which besides pPolB, encode retrovirus-like integrases and a set of proteins predicted to be involved in formation of viral particles (Krupovic, et al., 2014a, Biol Direct, 9, 6). The second supergroup of pPolB-encoding elements, denoted casposons, is present in a wide range of archaea and some bacteria (Krupovic, et al., 2014b, BMC biology, 12, 36). For integration into the cellular genome, these elements employ endonucleases homologous to the enzyme Cas1, a signature protein of the CRISPR-Cas systems responsible for the immunization process. It has been postulated that pPolBs participate in the replication of the casposon and polinton genomes (Kapitonov, V. V., and Jurka, J., 2006, Proc Natl Acad Sci USA, 103, 4540-4545); accordingly, these MGEs are referred to as self-synthesizing, or self-replicating, elements. Comparative genomics and phylogenetic analyses suggested that polintons and casposons have played key roles in the evolution of many groups of eukaryotic dsDNA viruses and CRISPR-Cas systems, respectively. However, experimental evidence for replication and, in particular, for the initiation of replication of these self-replicating integrated elements is lacking.

Regarding primases, PrimPol domain-containing DNA primases belonging to the large archaeo-eukarotic primase (AEP) superfamily have been shown to possess multiple enzymatic activities in vitro, including primer-dependent and primer-independent DNA polymerase activity, nucleotidyl-transferase, translesion synthesis and even reverse transcriptase activities (Gill, et al., 2014, Nucleic Acids Res, 42, 3707-3719; Martinez-Jimenez, et al., 2015, DNA Repair (Amst), 29, 127-138). Although in certain virus or plasmid-encoded proteins the AEP domain is fused to various helicases and can synthesize large DNA products, as in the case of the recently discovered primase-polymerase encoded by the phage NrS-1 (Zhu, et al., 2017, Proc Natl Acad Sci USA, 114, E2310-E2318), these enzymes lack the exonuclease domain, and their DNA polymerization on longer templates appears to be mainly distributive. Thus, it is generally considered that the role of AEP proteins in vivo is largely restricted to the synthesis of short primers, which are extended by the cellular replicative DNAPs (Beck, et al., 2010, Nucleic Acids Res, 38, 6707-6718).

To the date, no known DNA polymerase is able to begin a new DNA chain (de novo) but it can only add a nucleotide onto a pre-existing 3'—OH group, and therefore needs a primer at which it can add the first nucleotide. Primers are synthesized by another enzyme called primase. No PolBs have been described which show both primase and DNA polymerase activity at the same time. Thus, at least two different enzymes are required to perform DNA replication in vivo, a primase capable of providing a primer and a DNA polymerase that elongates it. For in vitro replication or amplification of a template DNA, primers must be externally added to the reaction mixture so that they can be elongated by the DNA polymerase.

For whole-genome amplification from single cells, a novel method, dubbed TruePrime, using a combination of an AEP primase, TthPrimPol, and the CD29DNAP has been recently proposed (Picher, et al., 2016, Nature communications, 7, 13296).

However, in this framework, there is a need in the art to have improved replicative DNA polymerases which do not require externally added primers for initiating and performing the DNA replication. These improved polymerases would present a primer-independent activity or primase activity allowing thus the use of simplified amplification reaction mixtures. These enzymes could be even used as single-enzyme solutions for processive and faithful amplification of whole-genomes.

DESCRIPTION OF THE INVENTION

The present invention provides new DNA polymerase enzymes with priming activity that do not require externally provided primers for DNA replication. These polymerases are able to initiate and perform a faithful and processive de novo DNA synthesis of circular and linear templates in the absence of pre-existing primers or additional protein factors. Therefore, these enzymes of the invention act both as primases and DNA polymerases. Furthermore, they show translesion synthesis capacity so that they may be useful for the amplification of damaged DNA templates.

These DNA polymerase enzymes are a new group within the family B DNA polymerases, representing thus the third major group of PolBs, besides rPolBs and pPolBs. These enzymes of the invention, which will be also called "piPolBs" from "primer-independent family B polymerases", are efficient and faithful DNA polymerases. piPolBs of the invention are capable of an intrinsic template-dependent de novo DNA synthesis, so that they do not require a presynthesized primer for DNA synthesis. Furthermore, they are full-fledged replicative DNA polymerases endowed with proofreading and strand-displacement capacities. Thus, this invention challenges a long-standing dogma in the field which states that replicative DNA polymerases are unable to synthesize DNA de novo, without a preexisting primer providing a hydroxyl moiety to anchor the incoming nucleotide.

This new major group of PolBs, piPolBs of the invention, is encoded by a novel type of self-replicating mobile genetic elements (MGE), dubbed pipolins, integrated in the genomes of bacteria from diverse phyla, including Actinobacteria, Firmicutes and Proteobacteria, and also present as circular plasmids in mitochondria. The majority of pipolins are found to be integrated in bacterial genomes, although some persist as extrachromosomal plasmids. Biochemical characterization of a representative piPolB from *Escherichia coli* (shown in SEQ ID NO: 2) showed that the protein displays an efficient and versatile DNA polymerization activity, able to replicate undamaged and damaged DNA templates, further endowed with the proofreading and strand-displacement capacities, similar to typical pPolBs, such as the one encoded by bacteriophage phi29. Remarkably, the protein is also capable of an intrinsic template-dependent de novo DNA synthesis, i.e. DNA priming activity, unexpected and previously unseen among all seven DNA polymerase families (A, B, C, D, X, Y and RTs). Thus, piPolBs alone are sufficient for replication of DNA templates, such as the circular MGE molecules, in the absence of additional replication initiation factors, thereby breaking the long-standing dogma that replicative DNA polymerases require a preexisting primer for initiation of DNA synthesis. piPolBs of the invention could be used for developing new applications for whole-genome amplification without the need of external primers that may cause amplification bias.

Moreover, enhanced survival of *E. coli* cells expressing piPolB upon replication blockage by DNA damaging agents (see examples below) suggests an additional role of these piPolBs of the invention in DNA damage tolerance.

Summarizing, the main advantages of the piPolBs described in the present invention are:

They do not require an external (presynthesized) primer to be added to the reaction mixture for DNA amplification, since they present priming activity. Thus, these enzymes can synthesize de novo DNA exclusively dependent on an intrinsic template, in the absence of pre-existing primers or additional protein factors that initiate the replication.

Furthermore, their priming capacity does not rely on a specific template sequence. Since they do not display a strong template sequence requirement for replication initiation, multiple replication origins may be selected in a random manner, a property useful for efficient primer-independent whole-genome amplification.

They are able to initiate and perform DNA replication of circular and linear templates, preferably single stranded.

These enzymes maintain the desirable properties of DNA polymerases B, such as DNA polymerase from phi29 phage. These properties are an efficient DNA primer extension and DNA polymerization activity, as well as proofreading and strand-displacement capacities.

They present an efficient intrinsic processive translesion synthesis (TLS) capacity, elongating the primer processively without introducing frameshift mutations. This means that piPolBs of the invention have high tolerance to DNA damage and repair capacity. These piPolBs may use undamaged and damaged DNA templates since, as shown in examples provided below (see for instance FIG. 2A), they are able to replicate damaged templates. This capacity can be used, for instance, for amplification of damaged or ancient DNA templates.

piPolBs of the invention could be used as single-enzyme solutions for whole-genome amplification from single cells. This represents an advantage over the prior art wherein solutions for whole-genome replication consist of a more complex combination of different enzymes, such as for instance a primase, a Prim-Pol and the phi29 DNAP.

Additionally, inventors of the present invention have identified the common conserved amino acid motif needed for the priming activity in the piPolBs described herein. Therefore, a first aspect of the present invention refers to a peptide consisting of the amino acid sequence SEQ ID NO: 1. This SEQ ID NO: 1 is the common conserved domain within the piPolBs described in this invention needed for priming activity and it consists of $KX_2-X_{3-10}$-KTRG, wherein $X_2$ is an amino acid selected from the list consisting of A, H, K, T, D, Y, G or R, preferably A or H, more preferably H; and $X_{3-10}$ is a sequence of 8 amino acids in length wherein said amino acids may be any amino acid identical o different among them. Even more preferably, $X_{3-10}$ is the amino acid sequence EVSQLIAM (SEQ ID NO: 5). In a particular embodiment, $X_2$ is H and $X_{3-10}$ is SEQ ID NO: 5. The sequence SEQ ID NO: 1 in which $X_2$ is H and $X_{3-10}$ is SEQ ID NO: 5 is SEQ ID NO: 85. This SEQ ID NO: 85 is the most preferred one.

SEQ ID NO: 1, preferably SEQ ID NO: 85, corresponds to positions 613 to 626 of SEQ ID NO: 2, wherein SEQ ID NO: 2 is one of the piPolBs of *E. coli* described and tested in this invention and the most preferred piPolB of the invention.

This motif of SEQ ID NO: 1 may be recombinantly introduced in other known DNA polymerases, preferably in PolBs, more preferably in pPolBs, in order to endow them with primase activity.

Thus, another aspect of the invention refers to a recombinant or mutant DNA polymerase enzyme (DNAP) comprising an amino acid sequence of a parental DNA polymerase of family B (DNA PolB) wherein the KxY motif has been substituted by the peptide consisting of SEQ ID NO: 1, preferably by the peptide consisting of SEQ ID NO: 85, wherein said recombinant DNA polymerase enzyme has DNA polymerase activity and primase activity. This recombinant DNA polymerase enzyme will be also referred to herein as "the recombinant DNAP of the invention".

The term "recombinant" or "mutant", as used herein, relates to a DNA polymerase enzyme that derives from a parental DNA PolB by means of one or more substitutions of one or more amino acids at the points(s) described herein within its amino acid sequence and, therefore, has a different sequence to that of the natural or wild-type parental enzyme. As used herein, the expression "recombinant DNAP" means a polypeptide having DNA polymerase activity and priming activity produced by chemical synthesis or recombinantly by an organism that expresses a nucleotide sequence that encodes the parental DNA PolB modified in the sense described herein. Said modified nucleotide sequence is obtained by means of human intervention by modifying the nucleotide sequence that encodes parental DNA PolB. The term "modification" means any chemical modification of the amino acid or nucleic acid sequence of parental DNA PolB. Therefore, the recombinant DNAP of the invention may be obtained by any genetic engineering technique known in the art for the production of recombinant polypeptides.

Amino acid substitutions described herein introduced in the parental DNA PolB can be obtained using genetic engineering or recombinant ADN techniques, such as for example by mutating the encoding sequence of parental DNA PolB by means of directed mutagenesis or they can be obtained by means of chemical synthesis of the nucleotide sequence which codes for the sequence of the recombinant DNAP of the invention that carries said amino acid substitutions.

Therefore, the recombinant DNAP of the invention can be synthesised, for example, but without limitations, in vitro. For example, by means of the synthesis of solid-phase peptides or recombinant DNA approaches. The recombinant DNAP of the invention can be produced in a recombinant manner, including its production as a mature polypeptide or as a pre-protein that includes a signal peptide.

The recombinant DNAP of the invention is not the enzyme of SEQ ID NO: 2, SEQ ID NO: 8 or SEQ ID NOs: 9 to 42 (piPolBs disclosed in the present description).

A "parental DNA polymerase of family B" is a wild type family B DNA polymerase, either rPolB or pPolB, preferably pPolB, but not piPolB, of those known in the art. pPolBs comprise, in N-terminal to C-terminal sense, an exonuclease domain, at least two palm domains separated by a TPR1 domain, fingers domains and a TPR2 domain and a thumb domain.

Motif of SEQ ID NO: 1 may be introduced in the parental PolB, preferably pPolB, in substitution of its conserved domain comprising the KxY motif. The skilled in the art knows where this KxY motif is located within the PolBs, however as a way of example, this KxY motif corresponds to positions 498 to 500, both included, of SEQ ID NO: 6, wherein SEQ ID NO: 6 is the pPolB of phage phi29. Thus, in a preferred embodiment of this aspect of the invention, positions 498 to 500 of the parental phi29 PolB (SEQ ID NO: 6) are substituted by the SEQ ID NO: 1, preferably by the SEQ ID NO: 85. On the other hand, this KxY motif corresponds to positions 535 to 537, both included, of SEQ ID NO: 7, wherein SEQ ID NO: 7 is the pPolB of phage Bam35. Thus, in another preferred embodiment of this aspect of the invention, positions 535 to 537 of the parental Bam35 PolB (SEQ ID NO: 7) are substituted by the SEQ ID NO: 1, preferably by the SEQ ID NO: 85.

Preferably, the recombinant DNAP of the invention shows priming or primase, exonuclease and DNA polymerase activities as well as proofreading and strand-displacement capacities.

"DNA polymerase activity" is the activity consisting of the synthesis of DNA molecules or sequences from deoxyribonucleotides. DNA polymerases are therefore capable of DNA replication from a DNA template by adding free nucleotides to the 3' end of the newly forming DNA strand. This results in elongation of the newly forming strand in a 5'-3' direction.

"Priming or primase activity" is the activity consisting of the synthesis of primers. Primase activity catalyzes the synthesis of short RNA or DNA segments, called primers, complementary to a ssDNA template.

DNA polymerase and primase activities may be assessed, for instance but without limitation, by placing in contact a template DNA and the DNA polymerase enzyme to be tested under conditions that enable the amplification of DNA, in the presence of at least dNTPs, a buffer and magnesium or manganese ions as cofactors and in the absence of externally added primers. After this incubation, the product of the amplification reaction may be visualized for instance in an electrophoresis gel. If amplification products are visualized in the gel, then the DNA polymerase used in the reaction presents both replicative DNA polymerase and primase activities.

In another preferred embodiment of this aspect of the invention, the parental DNA polymerase of family B is Bam35 DNA polymerase, PRD1 DNA polymerase, Cp-1 DNA polymerase, His1 DNA polymerase, His2 DNA polymerase or phi-29 DNA polymerase, or polypeptides at least 80%, more preferably at least 85%, 86%, 87%, 88%, 89%, 90%, 91%, 92%, 93%, 94%, 95%, 96%, 97%, 98% or 99%, identical to any of them having (replicative) DNA polymerase activity. In a more preferred embodiment, the parental DNA polymerase of family B is phi-29 DNA polymerase or Bam35 DNA polymerase or polypeptides at least 80% identical to any of them having (replicative) DNA polymerase activity. In an even more preferred embodiment, the parental DNA polymerase of family B is phi-29 DNA polymerase or Bam35 DNA polymerase. In a particular embodiment, the parental DNA polymerase of family B is phi-29 DNA polymerase.

The term "identity", as used herein, in the context of describing two or more polypeptide sequences, relates to a specified percentage of coincidences of amino acid residues at the positions from an alignment of two amino acid sequences. Sequence alignment methods for comparison are well known in the state of the art. Thus, the degree of identity can be determined using, for instance, the Clustal method (Higgins, 1989, CABIOS 5: 151-153), the Wilbur-Lipman method (Wilbury Lipman, 1983, *Proceedings of the National Academy of Science USA* 80: 726-730), the GAG program, including GAP (Devereux et al. 1984, *Nucleic Acids Research* 12: 287 Genetics Computer Group University of Wisconsin, Madison, 25 (WI)); sequence alignment algorithms Basic Local Alignment Search Tool (BLAST) or nucleotide BLAST (BLASTN), EMBOSS Needle and FASTA (Altschul et al. 1999, *J. Mol. Biol.* 215: 403-410). Additionally, the Smith-Waterman algorithm can also be used for the purpose of determining the degree of identity between two sequences.

Bam35 DNA polymerase is, preferably, the enzyme comprising SEQ ID NO: 7. phi-29 DNA polymerase is, preferably, the enzyme comprising SEQ ID NO: 6. PRD1 DNA polymerase is, preferably, the enzyme comprising SEQ ID NO: 75. Cp-1 DNA polymerase is, preferably, the enzyme comprising SEQ ID NO: 76. His1 DNA polymerase is, preferably, the enzyme comprising SEQ ID NO: 77. His2 DNA polymerase is, preferably, the enzyme comprising SEQ ID NO: 78.

In a particular embodiment of the recombinant DNAP of the invention, it comprises the amino acid sequence SEQ ID NO: 3 or SEQ ID NO: 4, preferably SEQ ID NO: 3. SEQ ID NO: 3 corresponds to parental DNA pPolB of phi29 (SEQ ID NO: 6) comprising its KxY motif substituted by SEQ ID NO: 1. SEQ ID NO: 4 corresponds to parental DNA pPolB of Bam35 (SEQ ID NO: 7) comprising its KxY motif substituted by SEQ ID NO: 1.

Another aspect of the present invention refers to an isolated nucleic acid sequence, hereinafter the "nucleic acid sequence of the invention", encoding the recombinant DNAP enzyme of the invention. Preferably, this nucleic acid sequence is cDNA.

Due to the degeneration of the genetic code, various nucleotide sequences can encode the same amino acid sequence. An "isolated nucleic acid molecule", "nucleotide sequence", "nucleic acid sequence" or "polynucleotide" is a nucleic acid molecule (polynucleotide) that has been eliminated from its natural medium (i.e. it has been subjected to human manipulation) and can include DNA, RNA or DNA or RNA derivatives, including cDNA. The nucleotide sequence of the present invention may or may not be chemically or biochemically modified and can be artificially obtained by means of cloning and selection methods or by means of sequencing.

The nucleic acid sequence of the invention can encode the mature polypeptide or a pre-protein consisting of a signal peptide joined to the mature enzyme that must subsequently be processed.

The nucleotide sequence of the present invention may also comprise other elements, such as introns, non-encoding sequences at ends 3' and/or 5', ribosome binding sites, etc. This nucleotide sequence can also include encoding sequences for additional amino acids that are useful for the purification or stability of the encoded polypeptide.

The nucleic acid sequence of the invention can be included in a genetic construct, preferably in an expression vector. Said genetic construct may also comprise one or more gene expression-regulating sequences, such as promoters, terminators, enhancers, etc.

Thus, another aspect of the invention refers to a genetic construct, hereinafter "the genetic construct of the invention", comprising the nucleic acid sequence of the invention. In a preferred embodiment, this genetic construct is an expression vector.

The expression "gene construct", "genetic construct" or "nucleic acid construct" relates to a functional unit required to transfer and/or express a gene of interest, herein the nucleotide sequence of the invention as described, and regulating sequences including, for example, a promoter, operably linked to the sequence that encodes the protein. It refers to a nucleic acid molecule, mono or bicatenary, which is isolated from a natural gene or that is modified in order to contain nucleic acid segments in such a manner that they would otherwise not exist in nature. The expression "nucleic acid construct" is synonymous to the expression "expression cassette" when the construct of nucleic acid contains the control sequences required for the expression of the encoding sequence.

The term "expression vector" relates to a DNA molecule, linear or circular, that comprises the nucleic acid sequence of the invention operably linked to additional segments that provide the transcription of the encoded peptide. Generally, a plasmid is used to introduce a specific gene in a target cell. Once the expression vector is in the interior of the cell, the protein encoded by the gene is produced by means of the ribosome complexes of the cellular transcription and translation machinery. The plasmid is often subject to engineering to contain regulating sequences that act as enhancing and promoter regions that lead to an efficient transcription of the gene carried on the expression vector. The objective of a well-designed expression vector is the production of large amounts of stable messenger RNA and, therefore, of proteins. Expression vectors are basic tools for biotechnology and for the production of proteins, such as enzymes. The expression vector of the invention is introduced in a host cell such that the vector remains as a chromosome constituent or as an extra-chromosome self-replicating vector.

The term "expression" relates to the process whereby a polypeptide is synthesised from a polynucleotide. The term includes the transcription of the polynucleotide in a messenger RNA (mRNA) and the translation of said mRNA into a protein or polypeptide.

Examples of expression vectors are phages, cosmids, phagemids, yeast artificial chromosomes (YAC), bacterial artificial chromosomes (BAC), human artificial chromosomes (HAC) or viral vectors, such as adenovirus, retrovirus or lentivirus.

Appropriate expression vectors for the insertion of the polynucleotide of the invention are, preferably, plasmids used for the protein expression in prokaryotes such as, by way of example: pUC18, pUC19, Bluescript and its derivatives, mp18, mp19, pBR322, pMB9, ColE1, pCR1, RP4, pET plasmids, phages and "launcher" vectors, such as pSA3 and pAT28; yeast expression vectors such as the 2-micron plasmid of *Saccharomyces cerevisiae*, integration plasmids, YEP vectors, centromere plasmids and similar; expression vectors in insect cells such as the vectors of the pAC and pVL series; expression vectors in plant cells such as piBi, pEarleyGate, PAVA, pCAMBIA, PGSA, PGWB, PMDC, PMY, pore series and similar, and other protein expression plasmids used in eukaryote cells, including baculovirus adequate for cell transfection. In a more preferred embodiment, the expression vector is a plasmid pET23a.

Another aspect of the invention refers to a host cell, hereinafter "the host cell of the invention", comprising the nucleic acid sequence or the genetic construct of the invention.

The term "host cell", as used in this description, relates to any prokaryote or eukaryote cell that may be the recipient of an expression vector, cloning vector or any other exogenous DNA molecule. Therefore, the term includes any cultivable cell that may be modified through the introduction of DNA not contained naturally therein. Preferably, a host cell is that in which the polynucleotide of the invention may be expressed, giving rise to a stable polypeptide, post-translationally modified and located in the appropriate subcellular compartment. The election of an appropriate host cell may also be influenced by the election of the detection signal. For example, the use of constructions with reporter genes (for example, lacZ, luciferase, thymidine kinase or green fluorescent protein "GFP") can provide a signal selectable through the activation or inhibition of the transcription of the gene of interest in response to a transcription-regulating protein. In order to achieve optimum selection or screening, the phenotype of the host cell must be considered.

In a preferred embodiment of the host cell of the invention, it is an *E. coli* cell.

Another aspect of the invention refers to the use of the host cell of the invention for the production (expression) of the recombinant DNAP enzyme of the invention.

The host cell of the invention may be cultivated for such purpose. A "host cell culture" relates to the process of in vitro maintaining and growing the host cells. Cell cultures need controlled conditions of temperature, pH, percentages of gases (oxygen and carbon dioxide), in addition to the presence of the adequate nutrients to permit cellular viability and division. Cell cultures can be carried out in solid substrates such as agar or in a liquid medium, which enables the cultivation of large amounts of cells in suspension. In vitro culture conditions will depend on the type of host cell selected and its requirements. Those skilled in the art will know which specific culture conditions and requirement should be applied in each case.

Once the host cell of the invention has been cultivated and the recombinant DNAP enzyme of the invention has been expressed, it can be purified. The term "purify", as used in the description, relates to the isolation of the recombinant DNAP enzyme of the invention and its concentration, from the other polypeptides present in the culture medium of the host cell of the invention. The isolation of the enzyme can be carried out using differential solubility techniques, chromatography, electrophoresis or isoelectric focusing. Chromatography techniques can be based on molecular weight, ion charge (based on the ionisation state of the amino acids under working conditions), the affinity of the protein for certain matrixes or chromatographic columns, or by means of purification tags, and can be carried out on a column, on paper or on a plate. The isolation of the protein can be carried out, for example, by means of precipitation with ammonium sulphate, fast protein liquid chromatography (FPLC) or high performance liquid chromatography (HPLC), using automated systems that significantly reduce purification time and increase purification efficiency.

Another aspect of the invention refers to a kit for amplifying or replicate a template DNA, hereinafter "the kit of the invention", comprising the following elements:
a. the recombinant DNAP of the invention,
b. at least one buffer,
c. dNTPs, and
d. magnesium or manganese ions, preferably manganese ions.

Preferably, this kit of the invention does not comprise oligonucleotides or primers.

The "buffer", indicated throughout the present description and claims, may be selected, for instance but without limitation, from the list consisting of: tris-hydrochloric (Tris-HCl), tris-acetic, HEPES, BSA, polyethylene glycol sorbitan monolaurate (TWEEN® 20), glycerol, EDTA, DTT, beta-mercaptoethanol, or any combination thereof.

The term "dNTPs" relates to deoxynucleoside triphosphates such as, for example, but not limited to, dATP, dCTP, dITP, dUTP, dGTP, dTTP or derivatives thereof. Preferably, the deoxynucleoside triphosphates used in the present invention are dATP, dTTP, dGTP and dCTP. Even more preferably, these four dNTPs are in equimolar conditions in the kit of the invention and in the methods of the invention described below.

In general, the kit of the invention comprises all the necessary reagents to carry out the methods of the invention described below. The kit can also include, without any type of limitation, other buffers, for instance for pH control, enzymes, such as, for example, but not limited to, additional polymerases, helicases, topoisomerases and the like, cofactors for obtaining an optimum activity thereof, reagents for preventing contamination, etc. Furthermore, the kit may include all the necessary supports, devices and receptacles for its implementation and optimization. The kit can also contain other molecules, genes, proteins or probes of interest, which may serve as positive and/or negative controls. Preferably, the kit also comprises the instructions for carrying out the methods of the invention described below.

Another aspect of the invention relates to the use of the recombinant DNAP enzyme of the invention or the kit of the invention for the in vitro amplification or replication of a template DNA.

The term "amplification", as used in the present description and claims, relates to the increase in the number of copies of a template DNA.

The term "replication", as used in the present description and claims, relates to the synthesis of complementary DNA from a template DNA.

In a preferred embodiment of this aspect of the invention, the amplification or replication of the template DNA is performed in the absence of externally added oligonucleotides (primers).

Another aspect of the invention refers to the use of a DNA polymerase enzyme comprising the peptide consisting of SEQ ID NO: 1, or a kit comprising said DNA polymerase enzyme and elements (b) to (d) of the kit of the invention mentioned above, for the in vitro amplification or replication of a template DNA in the absence of externally added oligonucleotides (primers).

The expressions "in the absence of externally added oligonucleotides (primers)" and "primer-independent activity", as used in the present invention, mean that the amplification or replication reaction is not externally provided with presynthesized primers.

"DNA polymerase enzymes comprising the peptide consisting of SEQ ID NO: 1" comprise said amino acid sequence at the end of the last palm domain and preferably further comprise a PolC motif which is TTD, which is a difference with the pPolBs, since pPolBs have a PolC motif which is DxD wherein "x" is any amino acid.

Examples of DNA polymerases comprising the peptide consisting of SEQ ID NO: 1 are, but without limitation, SEQ ID NO: 2, SEQ ID NO: 8 or any of the sequences shown in SEQ ID NOs: 9 to 42. DNA polymerases comprising the peptide consisting of SEQ ID NO: 1 and having at least 70%, more preferably at least 80%, 85%, 86%, 87%, 88%, 89%, 90%, 91%, 92%, 93%, 94%, 95%, 96%, 97%, 98% or 99%, sequence identity to SEQ ID NO: 2, or SEQ ID NO: 8 or any of the sequences shown in SEQ ID NOs: 9 to 42, are also comprised within this aspect of the invention. Examples of DNA polymerases comprising the peptide consisting of SEQ ID NO: 1 and having at least 70% sequence identity to these sequences are SEQ ID NO: 43 and 44.

In a preferred embodiment, the DNA polymerase enzyme comprising the peptide consisting of SEQ ID NO: 1 comprises the amino acid sequence consisting of SEQ ID NO: 2. More preferably, this SEQ ID NO: 2 is encoded by the codon-optimized nucleic acid sequence of SEQ ID NO: 45.

The term "template DNA" relates to a DNA molecule to be copied, replicated or amplified in an amplification method through the synthesis of a complementary DNA strand; i.e. it relates to a DNA molecule that will be replicated or amplified. Template DNA may be, but without limitations, plasmid DNA or genomic DNA, more preferably genomic DNA. In another preferred embodiment, the template DNA of the present invention is the whole genome comprised in a cell.

In another preferred embodiment of the present invention, the template DNA referred to throughout the description and the claims is linear or circular, wherein said linear or circular DNA may be doubled or singled stranded. More preferably, the template DNA referred to in the present invention is single stranded; even more preferably single stranded circular DNA.

The template DNA referred to throughout the present invention may be damaged or undamaged DNA. Preferably, it is damaged DNA. "Damaged DNA" is a DNA that comprises damages in its sequence, wherein said damages preferably block the DNA synthesis by replicatives DNAPs. Preferably, this damage is caused by, for instance, the presence of one or more abasic sites, oxidized basis such as thymine-glycol (Tg), or genotoxic challenges linked to DNA damaging agents such as exposure to mitomycin C (MMC) or UV light irradiation. More preferably, the damaged DNA comprises non-bulky base damages.

A large number of methods that enable DNA amplification are known in the art. Some methods require a thermocycling process such as, for example, but not limited to, polymerase chain reaction (PCR). Other methods do not require a thermocycling process, but rather are carried out at an essentially constant temperature such as, for example, but not limited to, rolling circle amplification (RCA), multiple displacement amplification (MDA), strand displacement amplification (SDA) or loop mediated amplification (LAMP), among others.

In another preferred embodiment of the present invention, the amplification of the template DNA referred to throughout the description and the claims is performed by a technique selected from the list consisting of: polymerase chain reaction (PCR), multiple displacement isothermal amplification (MDA), rolling circle amplification (RCA), strand displacement amplification (SDA), nucleic acid sequence based amplification (NASBA), ligase chain reaction (LCR), helicase dependent amplification (HDA), ramification amplification method (RAM) or loop mediated amplification (LAMP). More preferably, the amplification is performed by RCA.

Another aspect of the invention refers to an in vitro method, hereinafter "the first method of the invention", for amplifying or replicate a template DNA comprising:
a. placing a template DNA in contact with a reaction mixture that comprises:
the recombinant DNAP enzyme of the invention,
a buffer,
magnesium or manganese ions, preferably manganese ions, and
dNTPs, and
b. incubating the template DNA with the reaction mixture under conditions that enable DNA amplification.

In a preferred embodiment of this first method of the invention, the reaction mixture does not comprise oligonucleotides (primers).

The term "primer" or "oligonucleotide" relates to short DNA or RNA oligonucleotides, for instance of 18-22 bases, which are complementary to the sequence of a certain template nucleic acid, and which act as a starting point for the addition of nucleotides in the copying process of a strand complementary to the sequence of said template nucleic acid, for example, but not limited to, in a PCR. The term "primer" therefore relates to an oligonucleotide capable of acting as a starting point of DNA synthesis when it is under primer extension conditions.

Another aspect of the invention refers to an in vitro method, hereinafter "the second method of the invention", for amplifying or replicate a template DNA comprising:
a. placing a template DNA in contact with a reaction mixture that comprises:
a DNA polymerase enzyme comprising the peptide consisting of SEQ ID NO: 1 or a kit comprising said DNA polymerase enzyme,
a buffer,
magnesium or manganese ions, preferably manganese ions, and
dNTPs, and
b. incubating the template DNA with the reaction mixture under conditions that enable DNA amplification,
wherein the reaction mixture of step (a) does not comprise oligonucleotides (primers).

In a preferred embodiment of the second method of the invention, the DNA polymerase enzyme comprising the peptide consisting of SEQ ID NO: 1 comprises the amino acid sequence consisting of SEQ ID NO: 2. More preferably, this SEQ ID NO: 2 is encoded by the optimized nucleic acid sequence of SEQ ID NO: 45.

In another preferred embodiment of the first and second methods of the invention, the template DNA is linear or circular, wherein said linear or circular DNA may be doubled or singled stranded. More preferably, the template DNA is single stranded; even more preferably single stranded circular DNA.

In another preferred embodiment of the first and second methods of the invention, if the template DNA is doubled stranded, these methods further comprise an additional step before step (a) of denaturalization of the template DNA. This denaturalization may consist, for instance but without limitation, of the use of enzymes capable of unwind DNA from a double-strand structure to a single-strand structure to facilitate replication of each strand, such enzymes may be for instance helicase and/or topoisomerase II.

In another preferred embodiment of the first and second methods of the invention, the amplification of the template DNA is performed by a technique selected from the list consisting of: polymerase chain reaction (PCR), multiple displacement isothermal amplification (MDA), rolling circle amplification (RCA), strand displacement amplification (SDA), nucleic acid sequence based amplification (NASBA), ligase chain reaction (LCR), helicase dependent amplification (HDA), ramification amplification method (RAM) or loop mediated amplification (LAMP). More preferably, the amplification is performed by RCA.

To "place in contact" is understood to be that the template DNA and the reaction mixture are incubated under DNA extension conditions. The expression "DNA extension conditions" or "conditions that enable DNA amplification" makes reference to the conditions under which the template DNA-dependent synthesis can take place.

The expression "conditions that enable DNA amplification" relates to the conditions under which the incorporation of the nucleotides to a nascent DNA by means of base complementarity with a template nucleic acid can take place. In general, the conditions under which DNA amplification takes place include: (a) placing the template nucleic acid in contact with the DNA polymerase in a mixture that also comprises a divalent cation, for example magnesium or manganese, and nucleotides, and (b) subjecting said mixture to a sufficient temperature and time for the DNA polymerase to initiate the incorporation of the nucleotides to the nascent DNA by means of base complementarity with the template nucleic acid and give rise to a population of complementary DNA molecules of different sizes.

In some preferred embodiments of the replication or amplification methods of the invention, at least one dNTP is marked by means of well-known techniques in art. Detectable tags include, for example, radioactive isotopes, fluorescent tags, quimioluminescent tags, bioluminescent tags or enzymatic tags.

In another preferred embodiment of the first and second methods of the invention, the DNA polymerase enzyme is in a concentration of between 50 nM and 100 µM, more preferably 500 nM.

In another preferred embodiment of the first and second methods of the invention, the dNTPs are in a concentration of between 100 nM and 1 mM, more preferably between 100 nM and 500 µM, even more preferably between 10 µM and 100 M.

In another preferred embodiment of the first and second methods of the invention, the buffer has a pH of between 7.0 and 8.5.

In another preferred embodiment of the first and second methods of the invention, the magnesium or manganese ions are in a concentration of between 0.1 and 20 mM.

In another preferred embodiment of the first and second methods of the invention, the incubation of step (b) takes place at a constant temperature of between 20 and 40° C. and during between 5 min and 24 h.

One or more DNA polymerase enzymes selected among those known in the art may be used in combination with the piPolBs of the invention in the methods and uses referred to herein. Preferably, phi-29 DNA polymerase is used in combination with the piPolBs of the invention in the methods or uses mentioned herein.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided byway of illustration and are not intended to be limiting of the present invention.

EXAMPLES

Figure 1:
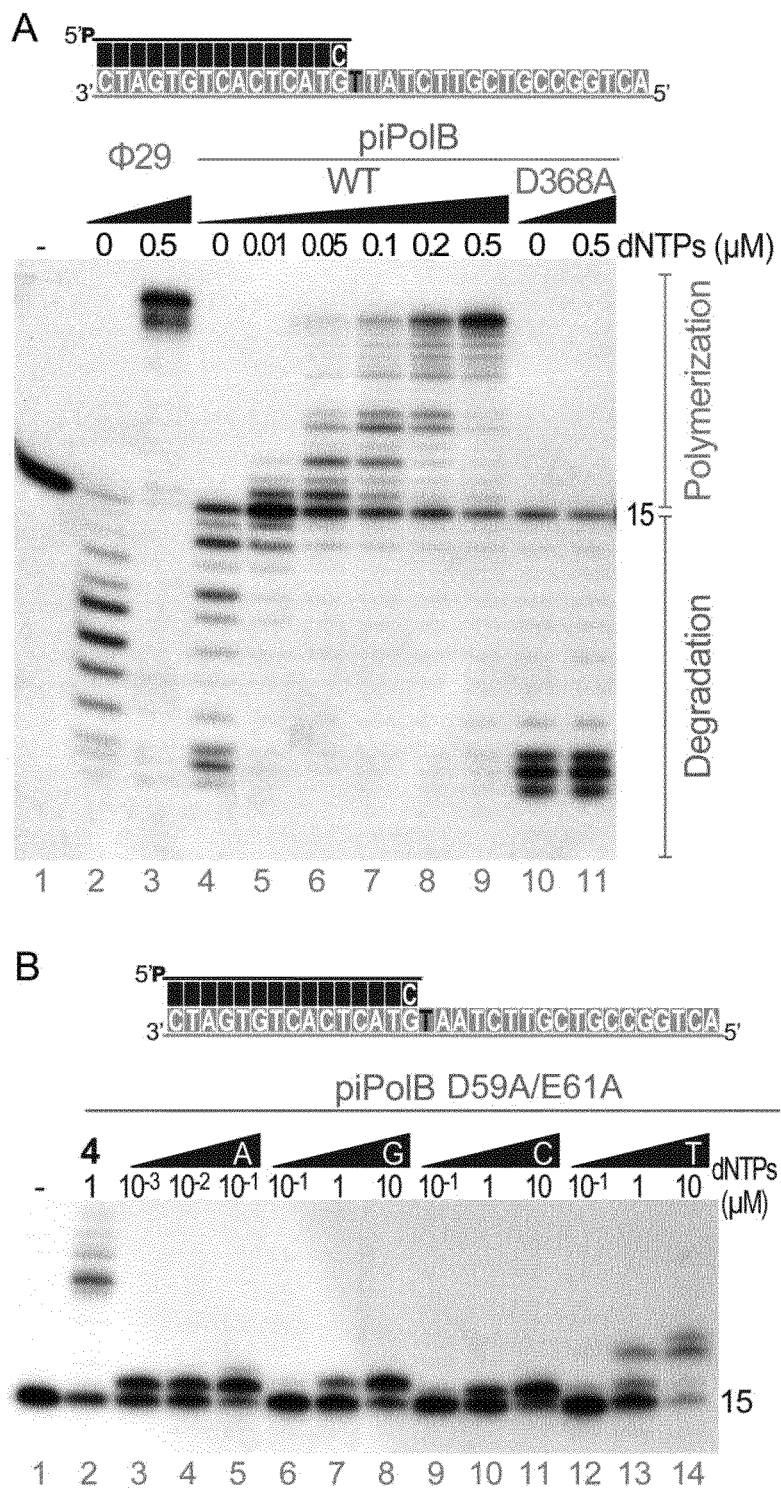
FIG. 1. Recombinant piPolB from *E. coli* 3-373-03_S1_C2 pipolin is an active and faithfull DNAP with intrinsic proofreading activity. (A) Primer extension assays with an oligonucleotide template/primer duplex substrate (1 nM) as depicted above the gel (SEQ ID NO: 79). Reactions were incubated for 10 min at 30° C. in the presence of 10 nM of either wild type or D368A polymerase deficient variant of piPolB, the indicated amount of dNTPs and triggered with 10 mM $MgCl_2$. When indicated, Φ29 DNA polymerase (Φ29) was used as a control. Positions of the 15-mer substrate and degradation and polymerization products are indicated on the right. (B) Nucleotide insertion preference by the D59A/E61A exonuclease deficient piPolB variant in the presence of increasing amounts of each dNTP as indicated. Template above the gel (SEQ ID NO: 80).

The following examples are provided to illustrate the invention, but are not intended to limit the scope of the same. Said examples are based on assays carried out by the inventors and show the efficient primer-independent replication activity of the piPolB of SEQ ID NO: 2, as well as its translesion synthesis capacity.

Example 1. A Novel Major Group of Family B DNA Polymerases

PSI-BLAST searches against the RefSeq bacterial genome database at NCBI seeded with the sequence of experimentally characterized pPolB from bacteriophage Bam35 (NP_943751) retrieved numerous hits to PolBs. These could be categorized into two groups: (i) highly significant hits (38-99% sequence identity) to pPolBs encoded within genomic contigs related to bacteriophages Bam35 (family Tectiviridae) and CD29 (subfamily Picovirinae, family Podoviridae); (ii) hits to highly divergent pPolB homologs encoded within chromosomes and several plasmids from widely diverse bacteria, such as Firmicutes, Actinobacteria and Proteobacteria. The latter proteins displayed ~16-20% sequence identity to the pPolB of Bam35. Nevertheless, analysis of multiple sequence alignments of these putative divergent DNAPs showed that all of them contain the TPR1 and TPR2 subdomains, a hallmark of pPolBs, and the active site residues of the exonuclease and DNA polymerase domains of PolBs are conserved, albeit with notable variations within the KxY and PolC motifs. The PolC motif (DTD) is almost universally conserved in PolBs and contains two catalytic aspartic acid residues required for protein activity. In the present invention, it was noticed that in all members of the novel piPolB group, the first of the two aspartates within the PolC motif is substituted for a threonine residue (TTD). Notably, some archaeal pPolBs also show variation within this motif, but none of these proteins has been experimentally characterized.

Additional searches seeded with representative sequences of the novel PolB group from proteobacteria, such as *Escherichia coli* (KDU42669) or *Rhodobacterales bacterium* Y41 (WP_008555115), yielded significant hits to several homologs encoded by pCRY1-like circular mitochondrial plasmids. Notably, the latter plasmids are distinct from the extensively studied linear mitochondrial plasmids which encode pPolBs (see below). Sequence analysis of the mitochondrial proteins confirmed their close similarity to the divergent group of bacterial PolBs.

To gain further understanding on the relationship between the newly discovered group of DNAPs and pPolBs, a maximum likelihood phylogenetic analysis of representative sequences from all known clades of pPolBs, including bacterial, archaeal and eukaryotic viruses, casposons, polintons, as well as eukaryotic cytoplasmic and mitochondrial linear plasmids, was performed. In the phylogenetic tree rooted with rPolB sequences, all previously characterized pPolBs formed a well-supported monophyletic clade, with a branching pattern consistent with previous phylogenetic analyses. The new DNAPs formed a distinct, well-supported clade, which in the present invention was denoted "piPolB" (see below), separated from all other pPolBs, suggesting that it has diverged early in the evolution of PolBs. Thus, piPolB represents the third major group of PolBs, besides rPolBs and pPolBs.

Within the piPolB clade, there are two major groups, which are roughly congruent with the bacterial taxonomy. The first one predominantly includes sequences from Actinobacteria and several orders of Firmicutes, namely Bacillales, Lactobacillales and Clostridiales. The second group contains sequences from different classes of Proteobacteria, namely Alphaproteobacteria, Betaproteobacteria, Gammaproteobacteria and Deltaproteobacteria. Notably, the latter group also includes piPolBs from circular mitochondrial plasmids which cluster with sequences from alphaproteobacteria. Although the latter clustering is not strongly supported in this analysis, this observation is most consistent with a possibility that piPolBs were imported into eukaryotes together with the alphaproteobacterial symbiont at the origin of mitochondria. Thus, piPolBs appear to have coevolved with their hosts for an extended period, several potential cases of horizontal gene transfer notwithstanding.

Example 2. piPolBs are Encoded within a Novel Group of Self-Replicating Elements Genomic context analysis provided compelling evidence that the majority of piPolBs are encoded within MGEs integrated into bacterial chromosomes. Unlike casposons and polintons which integrate into the genome using Cas1-like endonucleases and retrovirus-like family integrases, respectively, the vast majority of piPolB-carrying MGEs encode integrases of the tyrosine recombinase (Y-integrase) superfamily. Some of the elements carry additional copies of Y-integrases or integrases/invertases of the serine recombinase superfamily. Nevertheless, several bacterial and all mitochondrial piPolB homologs are encoded by extrachromosomal, rather than integrated plasmids and, accordingly, lack the integrase genes, suggesting that integration into the chromosome is optional for these elements. Hence, in the present invention, all these new bacterial and mitochondrial elements were referred to as pipolins (for piPolB-encoding mobile genetic elements).

MGE integration leaves a molecular mark on the cellular chromosome which manifests in the form of direct repeats, corresponding to the left and right attachment sites (attL and attR), which flank the integrated element. The Y-integrases typically catalyze recombination between homologous sites present on the cellular genome and the circular dsDNA molecules of MGEs. Thorough analysis of the piPolB-encompassing genomic regions, allowed to define the precise integration sites for many pipolins from diverse bacterial taxa. The vast majority of integrations occurred within tRNA genes, as is common for bacterial and archaeal MGEs employing Y-integrases. Some bacteria carry more than one pipolin. For instance, *Vibrio vulnificus* genome contains two related piPolB-encoding elements inserted into different tRNA genes.

Comparative genomic analysis of pipolins showed that they form groups which are generally consistent with the phylogeny of the piPolBs. The similarity between elements from distantly related hosts is limited to the piPolB and, to a lesser extent, Y-integrase genes. Besides piPolB and integrases, pipolins often encode excisionases, which assist in excision of integrated MGEs; components of type I and type II restriction modification systems; and various components of the plasmid mobilization machinery. In addition, the less conserved genes found in pipolins encode different DNA-binding proteins with ribbon-helix-helix, zinc-finger or helix-turn-helix motifs, but also histone-like H-NS chromatin proteins, various nucleases and toxin-antitoxin systems. None of the elements encodes virus-specific proteins. By contrast, the pangenome of pipolins consists of various genes typical of plasmids. Indeed, protein BLAST (BLASTP) analysis shows that most of the pipolin genes are conserved in various unrelated plasmids. Consistent with this assertion, four of the bacterial and five mitochondrial piPolBs are encoded by circular plasmids. Notably, the mitochondrial plasmids carry no other genes than those encoding piPolB, suggesting that following the introduction of a mitochondrial ancestor into a proto-eukaryotic host, the MGEs underwent reductive evolution, losing all genes except for the piPolB.

Although piPolB is the only DNA replication-associated protein conserved in all pipolins, some elements encode putative helicases of superfamilies 1 and 2; 3'-5' exonucleases; uracil-DNA glycosylases; ribonucleases H; and an Orc1/Cdc6-like AAA+ATPase. Unlike pPolB-encoding plasmids and viruses which, as a rule, have linear genomes, pipolins represent circular dsDNA molecules and thus the protein-priming mechanism is unlikely to be applicable. The overwhelming majority (94%) of dsDNA viruses encoding RNA-primed DNAPs also encode their own primases. By contrast, none of the pipolins possesses genes for recognizable primases, raising questions regarding the priming mechanism.

Collectively, results of the phylogenetic and comparative genomic analyses underscore the uniqueness of piPolBs and pipolins, which may be considered as the third major superfamily of self-replicating MGEs, next to polintons and casposons.

Example 3. Pipolin DNA Polymerase is a Proficient Replicase

To verify whether piPolBs were indeed active DNAPs, a representative enzyme from *E. coli* 3-373-03-S1_C2 pipolin (SEQ ID NO: 2) was chosen and its recombinant form was purified. The synthetic and degradative activities of this protein in a primer extension assay were first analyzed, in the presence of increasing concentrations of dNTPs (FIG. 1A, lanes 4-9). As expected, only degradation products could be detected in the absence of dNTPs. However, addition of dNTPs resulted in a switch from exonucleolysis to polymerization activity, indicating that both activities are coordinated. Protein variants with deficient polymerization (D368A, FIG. 1A, lanes 10-11 and FIG. 7A) or exonuclease (D59A/E61A, FIG. 7A) activities, confirmed that 5'-3' synthetic and 3'-5' degradative capacities are intrinsic to the recombinant purified piPolB. The presence of proficient DNA polymerization activity in piPolB confirms that only the second carboxylate moiety in the PolC motif is required for metal coordination, in agreement with the previous suggestions that the first conserved aspartate residue in the PolC motif in the pPolB and rPolB groups has a structural rather than catalytic role.

To further characterize the DNA polymerization activity of piPolB, the insertion preference for Watson-Crick base pairs was analyzed using the piPolB exonuclease-deficient variant D59A/E61A. As shown in FIG. 1B, insertion of the correct nucleotide could be detected at approximately 1000-fold lower dNTP concentration compared with the incorrect dNTP, indicating a very strong preference for the insertion of the complementary nucleotide. These results confirm that piPolB of pipolins is an efficient and faithful DNA polymerase, as would be expected from a replicative family B DNAP.

Figure 2:
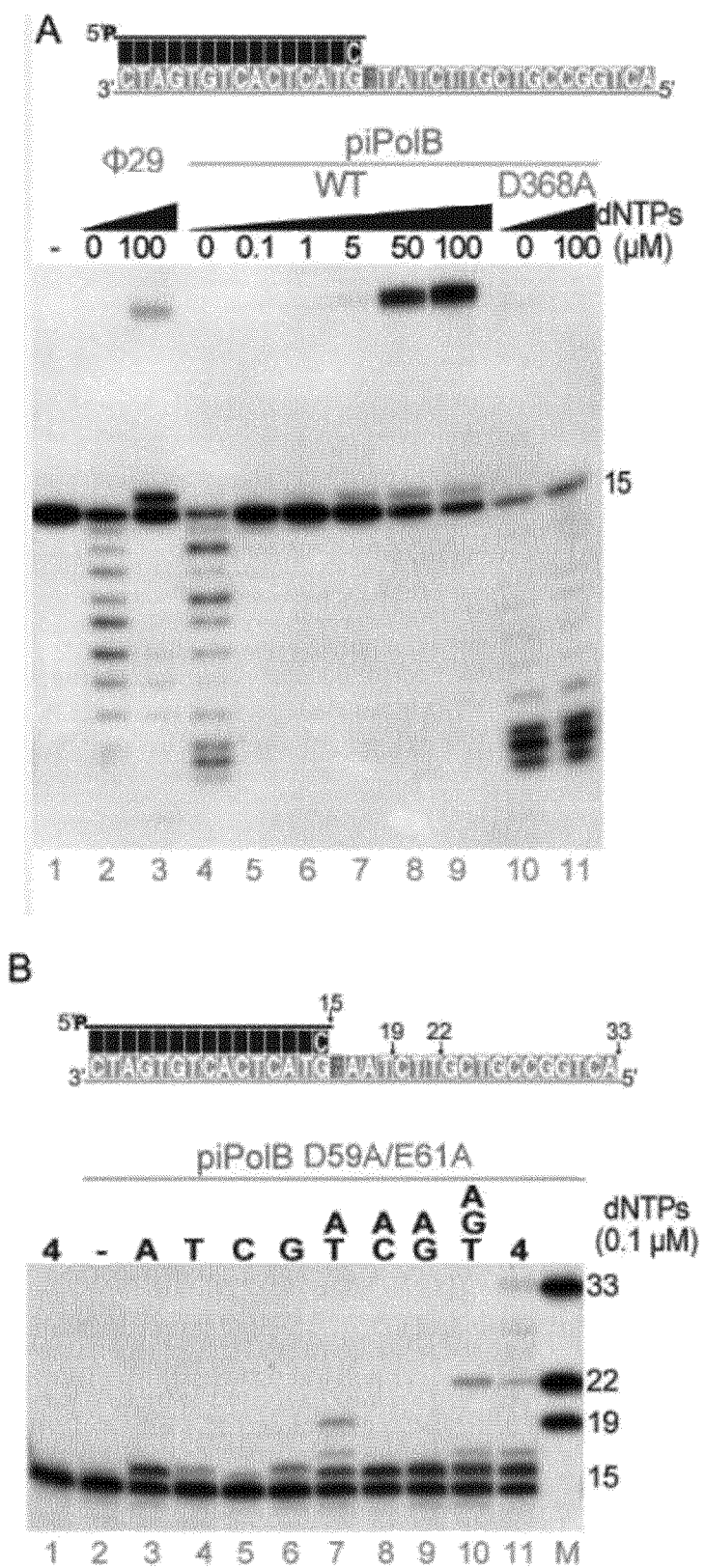
FIG. 2. Characterization of piPolB efficient TLS capacity. (A) Primer extension experiment opposite abasic site-containing template. Assay was carried out as in FIG. 1A, but with a template/primer substrate containing a THF abasic site analog (F) as depicted above the gel (SEQ ID NO: 81). (B) Step-by-step monitoring of piPolB replication of THF-containing template by sequential addition of dNTPs (0.1 µM), as indicated. Substrate is depicted above the gel (SEQ ID NO: 82) and the expected size indicated. Positions of the 15-mer substrate as well as 19, 22 and 33-mer markers (lane M) are also indicated on the right. (C) Effect of divalent metal cofactors on piPolB polymerization capacity on undamaged and damaged templates (SEQ ID NO: 83). Reactions were triggered either with 1 mM $MnCl_2$ or 10 mM $MgCl_2$, as indicated. (D) TLS capacity of piPolB on alternative DNA damaged templates, containing thymine-glycol (Tg) or ciclobutane thymine dimers (T:T) (SEQ ID NO: 83) triggered by either presence of manganese or magnesium ions.
Figure 2:
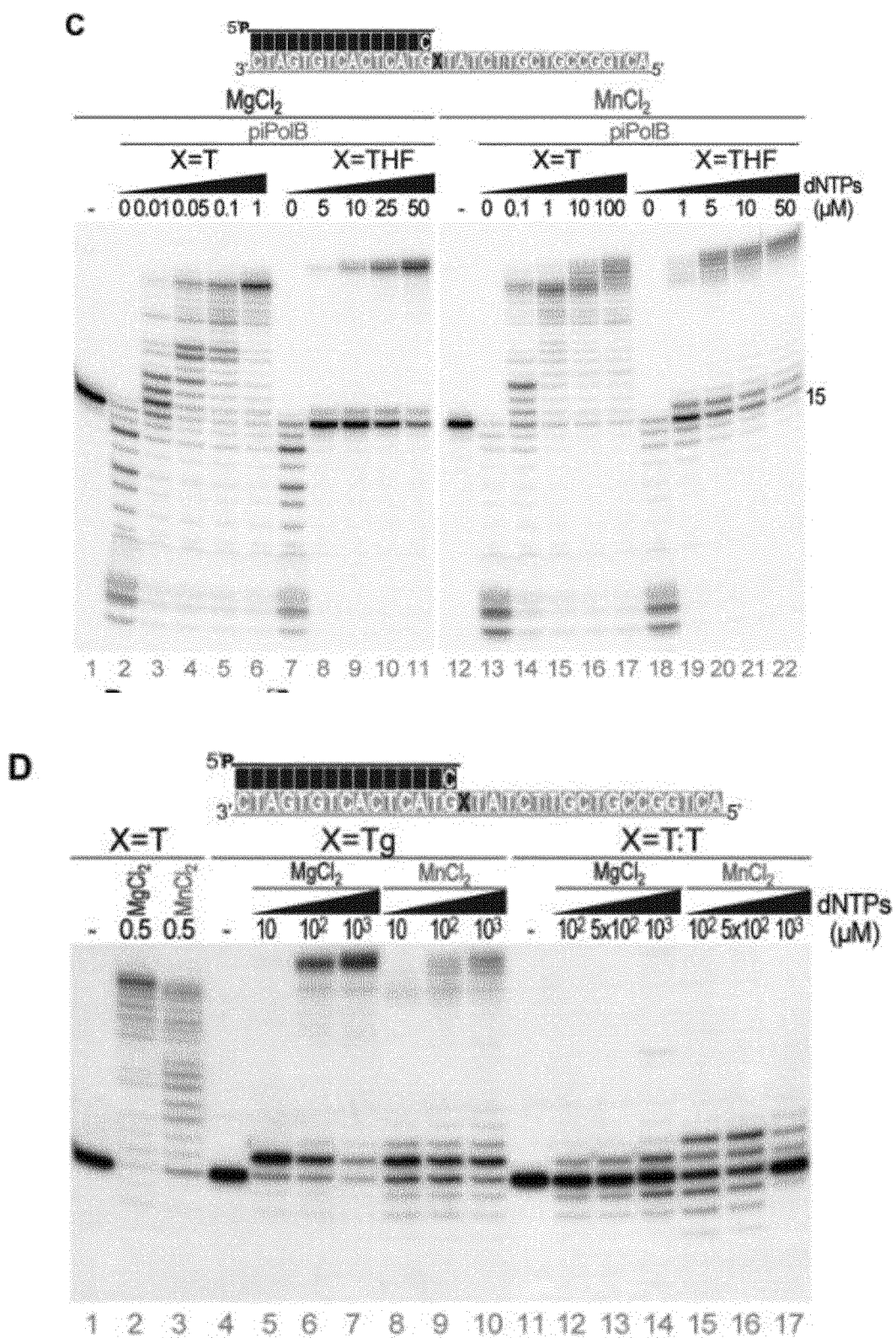
Figure 7:
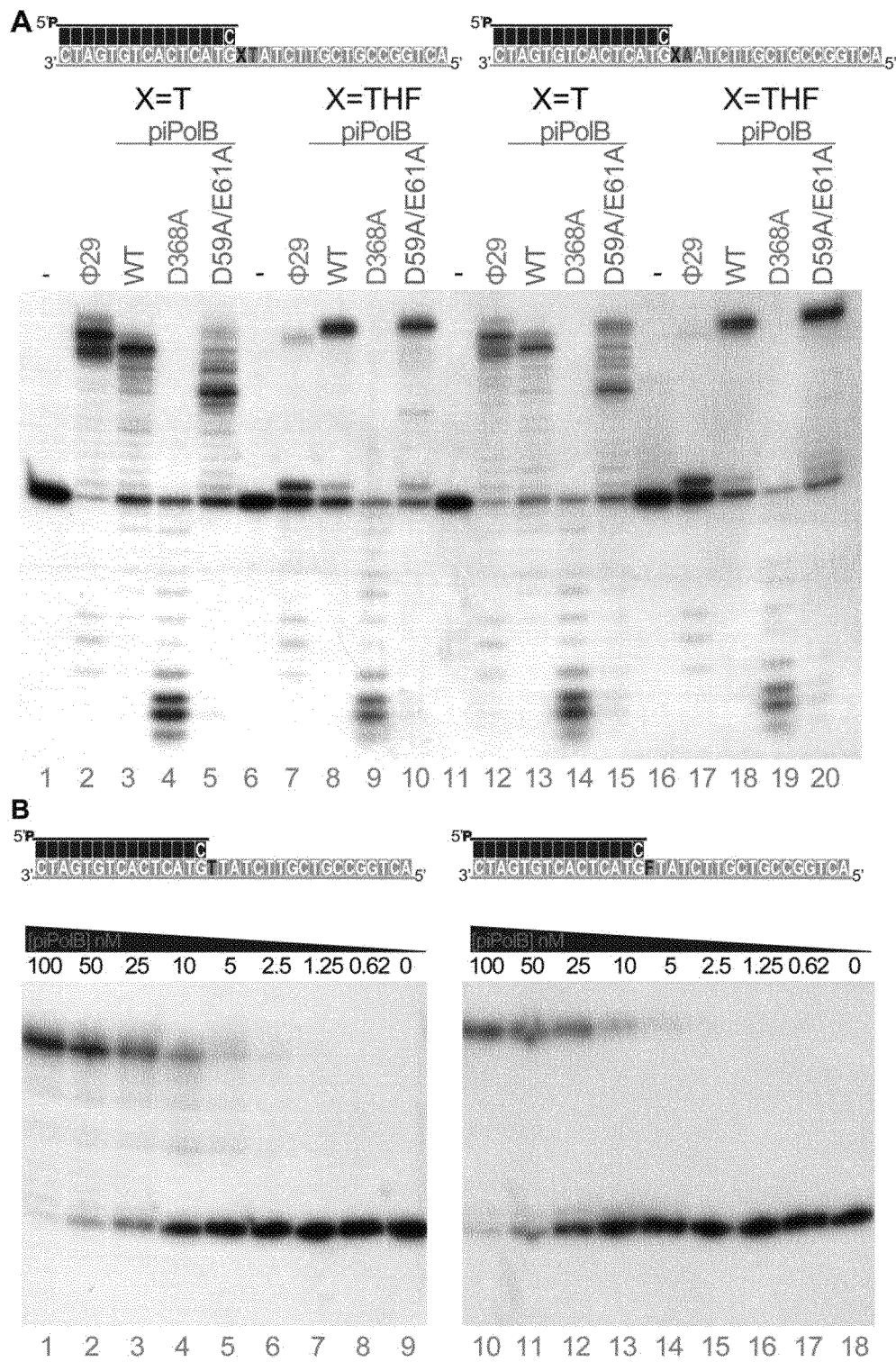
FIG. 7. Effect of sequence context and enzyme concentration on TLS capacity by piPolB. (A) Denaturing PAGE analysis of primer extension products by Φ29 DNA polymerase (Φ29) and piPolB. As indicated, wild type, D368A (polymerase deficient) and D59A/E61A (exonuclease deficient) piPolB variants were tested using two different sequence contexts (lanes 1-10, SEQ ID NO: 83, vs. 11-20, SEQ ID NO: 84), in the absence (lanes 1-5 and 11-15) or presence (lanes 6-10 and 16-20) of a THF abasic site analog. Schematic representations of each template/primer substrate are depicted above. (B) Processive replication of primer/template substrates by decreasing concentrations of wild type piPolB. Reactions were performed in the presence of either 1 μM (lanes 1-9) or 100 μM (lanes 10-18) dNTPs for undamaged (SEQ ID NO: 79) or damaged (SEQ ID NO: 81) templates, respectively.

Example 4. PiPolB is Endowed with Intrinsic Translesion Synthesis Across DNA Containing Non-Bulky Nucleotides Analogs Abasic (AP) sites constitute the most common DNA lesion that may arise from spontaneous depurination but also occur as intermediates in base excision repair. A prevailing model is that high-fidelity replicative DNAPs are unable to replicate through such lesions in the DNA, leading to stalled replication and subsequent triggering of DNA damage tolerance mechanisms, involving specialized DNAPs that can bypass the DNA damage by translesion synthesis (TLS). Additionally, recent works reported examples of TLS by cellular and viral replicases from families A, B or C during processive genome replication. Thus, to ascertain whether piPolB was able to replicate damaged templates, it was first analyzed primer extension opposite a tetrahydrofuran (THF) moiety, a stable analog of an abasic site, in the first template nucleotide position. As shown in FIG. 2A, piPolB is able to insert the first nucleotide and extend the primer beyond the THF (lines 4-9) whereas, as expected, CD29DNAP only gave rise to negligible replication (lines 2-3). The bypass capacity often depends on the sequence context and is counteracted by the proofreading activity. However, piPolB TLS capacity does not seem to be affected by the template sequence context (FIG. 7A). A minor band of partial product at the lesion site (16-mer) could be detected, suggesting that, as shown previously for the Bam35 DNAP, elongation of the primer beyond the abasic site is a limiting step in the TLS by piPolB, despite the fact that replication of both, undamaged and damaged oligonucleotide templates can be processive (FIG. 7B).

It was then analyzed the incorporation preference opposite to the THF site. Using the exonuclease deficient variant D59A/E61A, it was found that piPolB preferentially inserts purines over pyrimidines (FIG. 2B, lanes 3-6), in the preference order A>G>T>C, in agreement with the so-called "A rule" previously described for many DNAPs. The TLS by DNAPs may occur via a misalignment mechanism, resulting in a one or two nucleotide deletion and, accordingly, a shorter DNA product. FIGS. 2A and 7A show that the final product synthesized by piPolB reached the full product length using both damaged and undamaged substrates, suggesting that, instead of a misalignment mechanism, the piPolB can insert and further elongate a nucleotide opposite to the abasic site. To verify this mechanism, it was monitored step-by-step polymerization in a primer extension assay in the presence of different dNTP combinations (FIG. 2B, lanes 7-11). In particular, it was provided dATP in combination with another single dNTP (dTTP, dCTP and dGTP, lanes 7-9, respectively). Whereas insertion opposite to the THF was detected in all cases, only the combination dATP and dTTP (AT, lane 7) allowed primer extension beyond the abasic site, giving rise to a product that corresponds with the 19-mer marker (FIG. 2B, lane M), indicating accurate replication of the template up to this position (see substrate scheme above the gel). Consistently, the presence of dATP, dTTP and dGTP (ATG, lane 10) allowed the copy of the template up to the 22-mer product length, and only when the four dNTPs were provided, the full-length replication product could be detected (lane 11). Taken together, these results indicate that TLS capacity of piPolB preferably inserts an A opposite to the abasic sites and subsequently elongates the primer processively without introducing frameshift mutations.

In order to obtain a more comprehensive understanding of the piPolB-mediated DNA replication and TLS performance, it was analyzed the abasic site bypass with different metal cofactors and replication-blocking DNA damages. As shown in FIG. 2C, abasic site TLS in the presence of manganese ions was more efficient at lower dNTPs concentrations (lanes 19-22 vs. 8-11), in agreement with previous reports on other PolBs. It was noted that replication of undamaged template required higher dNTPs concentration in the presence of manganese ions (lanes 14-17) when compared with the magnesium-triggered reactions (lanes 3-6). The template specificity of piPolB TLS capacity with substrates containing thymine-glycol (Tg) oxidized base and cyclobutane thymine dimers (T:T), was next explored. Tg is the most common oxidative product of thymine and presents a strong block for DNA synthesis by most replicative DNAPs. On the other hand, T:T arises upon exposure to ultraviolet light radiation and constitutes a particularly sharp hindrance for most DNAPs because the covalent linkage of two adjacent nucleobases prevents a kink in the DNA backbone that normally delivers one template base at a time to the polymerase active site. Results indicate that piPolB was able to bypass thymine-glycol (Tg) oxidized base in the presence of magnesium ions (FIG. 2D, lanes 5-8). Interestingly, however, primer extension beyond the damage was less efficient, because the 16-mer pause is stronger than in the case of the THF-containing template (lanes 8-11 in panel C vs. lanes 5-7 in panel D). In line with the impairment in processive primer extension beyond the damage, manganese ions apparently did not stimulate the TLS. On the contrary, Tg bypass was reduced in the presence of this metal cofactor (lanes 9-10). In the case of T:T, insertion of only 1 or 2 nucleotides opposite to the damage could be detected, either with magnesium or manganese ions (lanes 12-14 and 15-17, respectively). In conclusion, piPolB has an efficient TLS capacity that allows it to bypass abasic sites and oxidative base modifications but is unable to overcome bulkier modifications such as T:T, likely because this damage induces major structural changes in the DNA helix that strongly obstructs DNA replication.

Example 5. Primer-Independent DNA Replication

Figure 3:
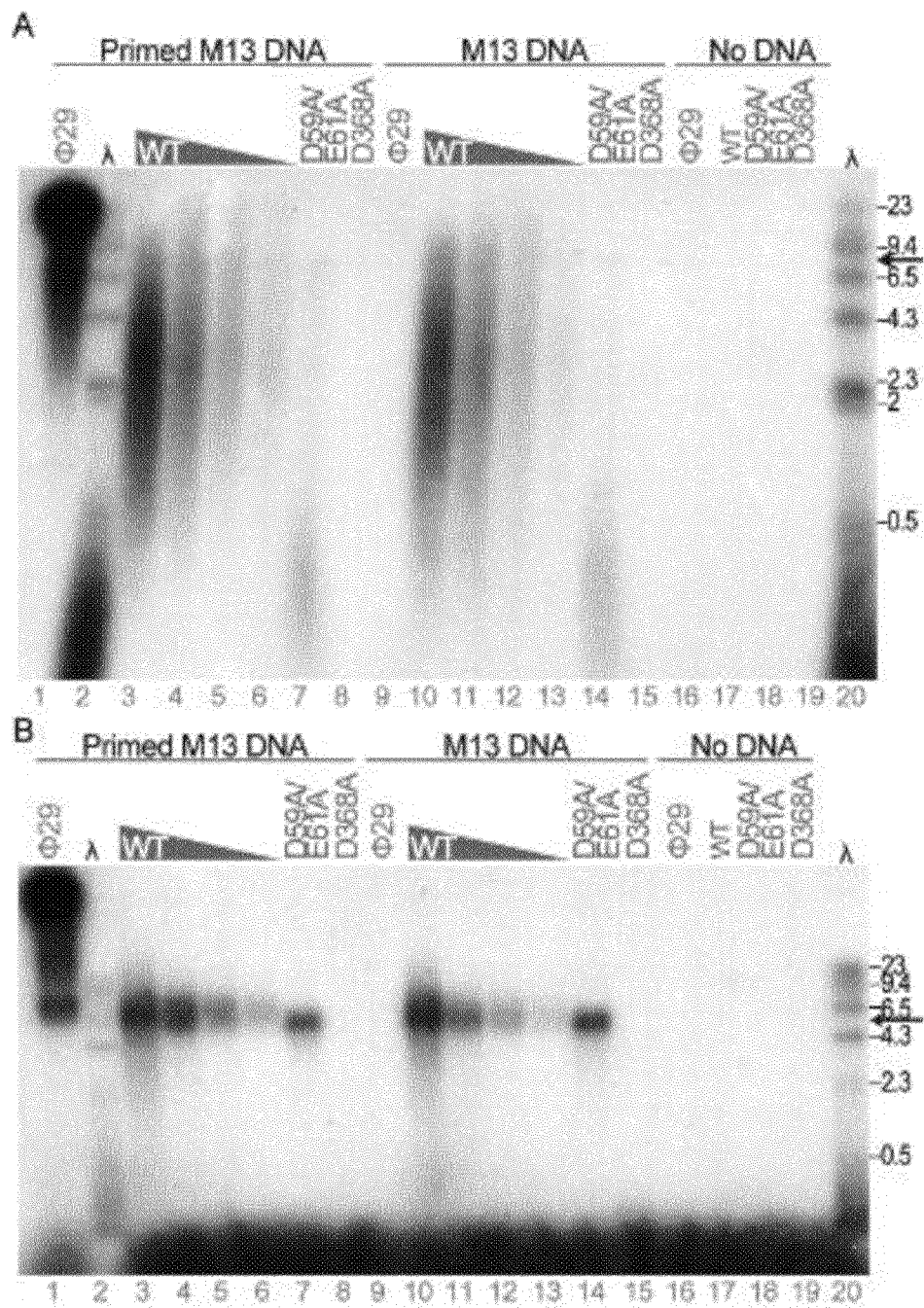
FIG. 3. Primer-independent DNA synthesis by pipolin piPolB. Alkaline (A) and non-denaturing TAE (B) agarose electrophoresis of M13 DNA replication products. Assays (20 µL) were carried out in the presence of 20 nmol of primed (lanes 1, 3-8) or not-primed (lanes 9-15) M13 ssDNA, 100 µM dNTPs and 1 µCi [$\alpha^{32}$P]dATP. Wild type, D368A and D59A/E61A variants of piPolB were assayed at 500 nM or, when indicated, decreasing concentrations of wild type piPolB (500, 250, 100 and 50 nM, lanes 3-6 and 10-13). For reference, 100 nM Φ29 DNA polymerase was used as control (lanes 1 and 9). Control assays without input DNA template were also performed as negative controls (lanes 16-19). The reactions were incubated for 20 min at 30° C. and, after the addition of stop solution (50 mM EDTA, 0.5% SDS), divided to load the same samples in both gels. See STAR Methods for details. A DNA markers (lanes 2 and 20) and the M13 ssDNA unit length (arrow) are indicated on the right. (C) Non-denaturing TAE agarose electrophoresis of M13 replication products in the presence of either 100 µM dNTPs (lanes 1-3 and 7-9) or NTPs (lanes 4-6 and 10-12), as indicated. Replication assays were carried out with wild type or D59A/E61A piPolB variants and triggered with either 10 mM $MgCl_2$ (lanes 1-6) or 1 mM $MnCl_2$ (lanes 7-12). (D) Primer synthesis and replication of homopolymeric poly-dT DNA template (1 µM) by piPolB (500 nM). Reactions were triggered with 1 mM $MnCl_2$ and resolved in high resolution 8 M urea-20% PAGE. The P4, P10, P15 and 33A primers (see Table 2) labeled with a 5'-$^{32}$P were loaded as size markers (lane M), and the size of the shorter products detected are indicated on the right.
Figure 3:
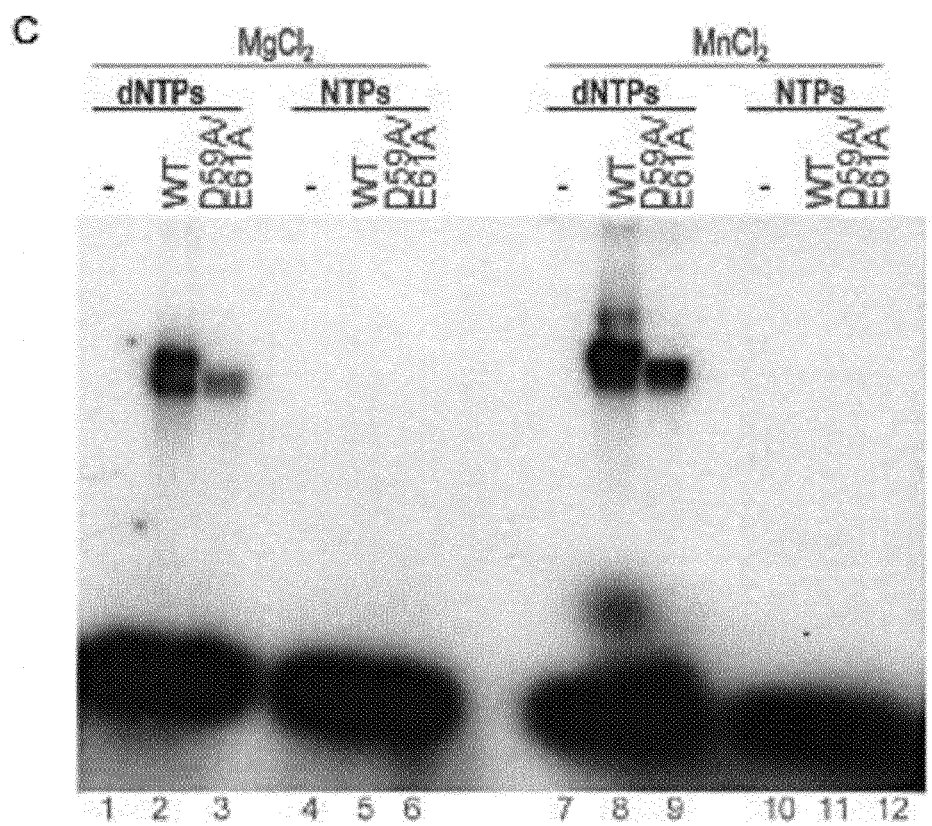
Figure 3:
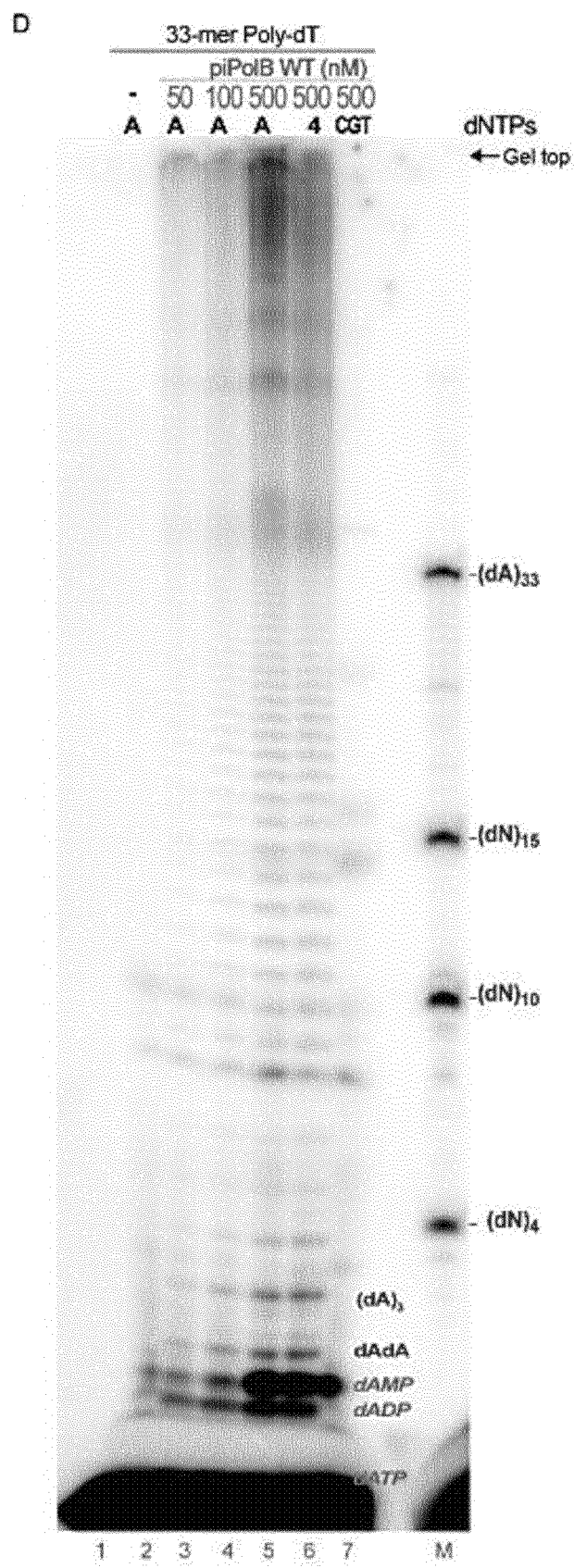
Figure 8:
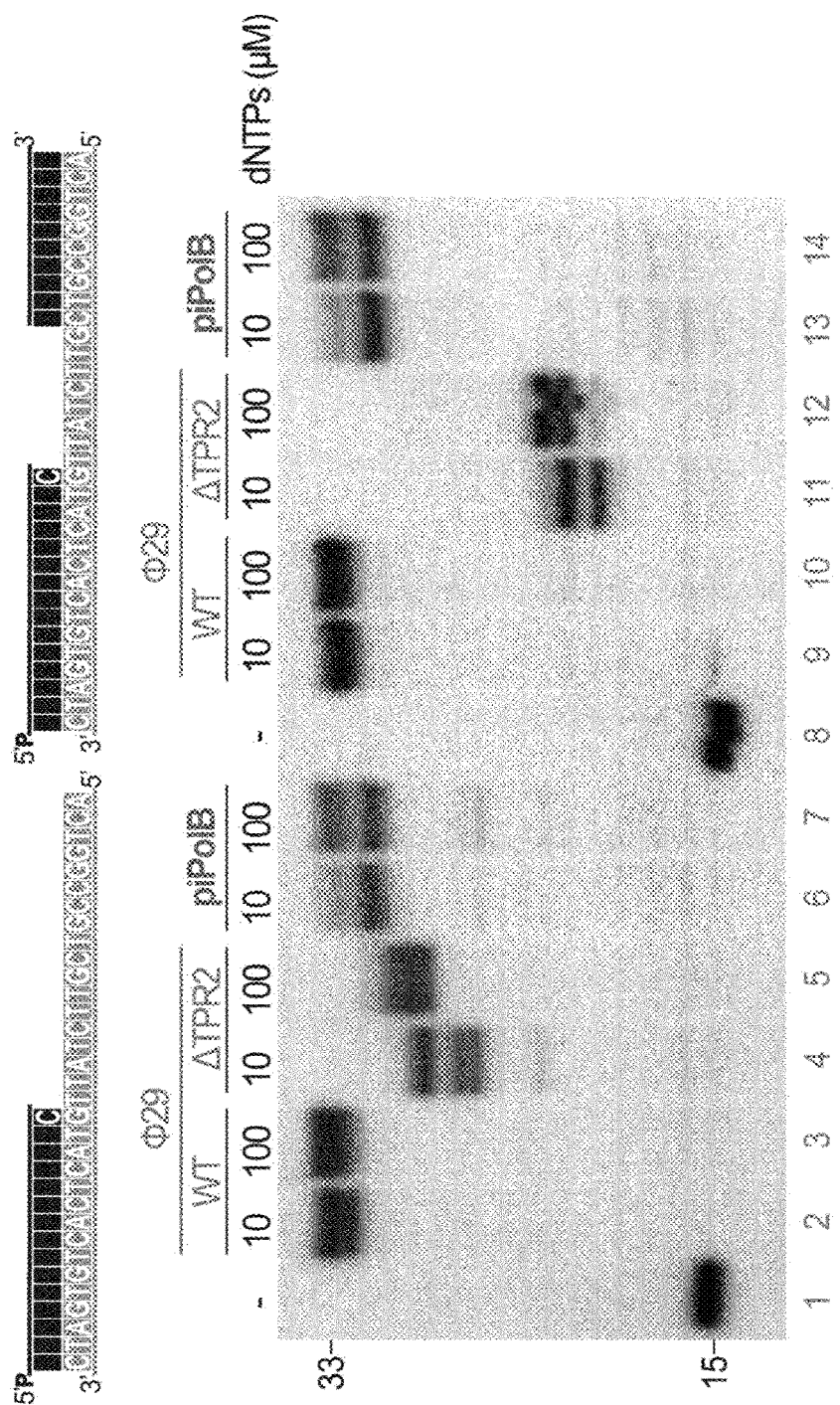
FIG. 8. Strand displacement capacity of piPolB. Denaturing PAGE analysis of replication of a recessed primer/template duplex (SEQ ID NO: 79) (lanes 1-7) or a 5 nucleotides gap (lanes 8-14) obtained with a downstream oligonucleotide (P20-33, Table 2) that must be displaced to resume replication by piPolB (lanes 6-7 and 13-14). Wild type and ΔTPR2 variants of Φ29 DNA polymerase were used as positive and negative controls, respectively.

To gain insights into the processivity of the DNA replication by piPolB, it was performed singly primed ssDNA rolling circle replication assays using M13 DNA as a template and resolved the products by alkaline denaturing electrophoresis. Due to its high processivity, coupled with strand-displacement capacity, CD29DNAP was able to synthesize very large ssDNA fragments under these conditions (FIG. 3A, lane 1). By contrast, piPolB gave rise to a smeared signal of replication products spanning 0.5 to 10 kb, with apparent peak at about 3 kb (FIG. 3A, lanes 3-6), which indicates that piPolB is not as processive as Φ29DNAP and thus generates shorter DNA fragments. However, the maximal product length obtained with piPolB remained similar even at 20-fold lower enzyme concentration, suggesting that it is a processive DNA replicase. A considerable portion of replication products was larger than the M13 DNA, suggesting that piPolB DNA replication is coupled with strand displacement. The latter activity was subsequently confirmed using an oligonucleotide template/primer substrate with a 5-nt gap (FIG. 8).

Strikingly, a very similar replication pattern was detected regardless of whether the M13 was primed or not (FIG. 3A, lanes 10-13). By contrast, as expected, Φ29DNAP was unable to synthesize any product in the absence of a primer (lane 9). When the same samples were loaded on a non-denaturing agarose gel (FIG. 3B), the replication product appeared as a single band that corresponded to the expected M13 unit length, suggesting that the single-stranded DNA products detected in alkaline denaturing electrophoresis gel are M13 replication products. Consistently, no product could be detected in the absence of input DNA template (lanes 16-19), ruling out the replication of possible contaminant DNA traces in any of the polymerase variants. Similarly, no product was obtained when the reactions were performed with the D368A variant deficient for polymerization activity (lanes 8 and 15). Notably, the fragments detected with the D59A/E61A mutant were slightly smaller (by <0.5 kb) than with the wild type enzyme (FIG. 3A lanes 7 and 14), presumably because exonuclease deficiency gives rise to the accumulation of replication mistakes that may result in the impairment of strand-displacement or processivity. These results further confirm that M13 DNA replication, with or without the added primer, is intrinsic to piPolB. De novo DNA synthesis on non-primed M13 DNA could be detected using both, magnesium or manganese ions, as cofactors (FIG. 3C, lanes 2-3 and 8-9), albeit with a somewhat higher intensity of total replication product with manganese ions. However, replication was not detected when deoxyribonucleotides were substituted with ribonucleotides (lanes 5-6 and 11-12), as expected for a family B DNAP that contains the conserved tyrosine steric gate. Smaller DNA fragments were detected with the wild type polymerase that might be products of the exonucleolytic degradation (lane 8).

Figure 9:
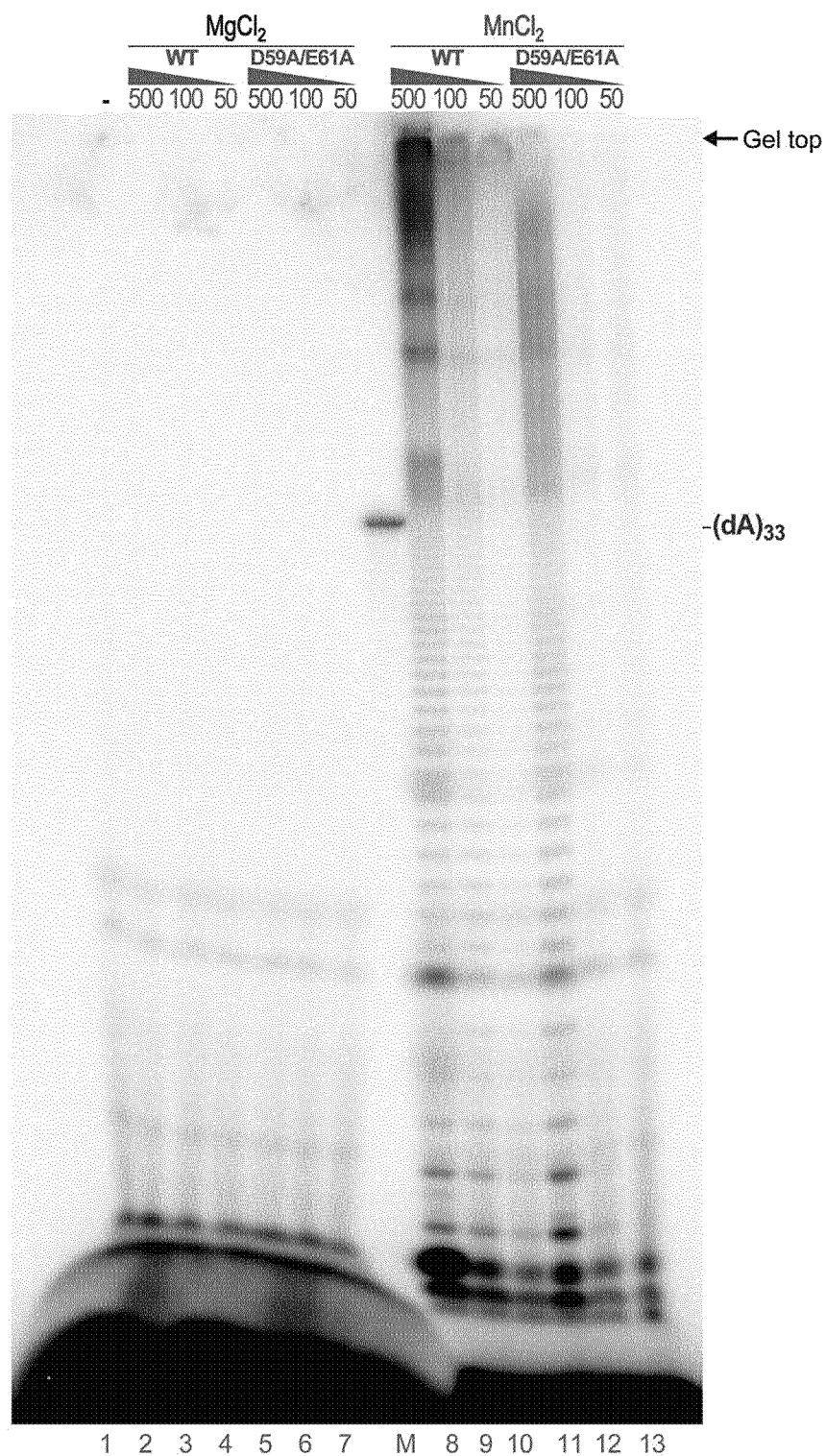
FIG. 9. Effect of divalent cations on de novo replication of homopolymeric ssDNA substrate by piPolB. Primer synthesis and replication of homopolymeric poly-dT DNA template (1 μM) by wild type (WT) or exonuclease deficient (D59A/E61A) piPolB variants (500 nM). Reactions were triggered either with 10 mM $MgCl_2$ or 1 mM $MnCl_2$ and resolved in high resolution 8 M urea-20% PAGE. The P4, P10, P15 and 33A primers (Table 2) labeled with a 5'-$^{32}$P were loaded as size markers (lane M), and the size of the shorter products detected are indicated on the left and right, respectively.

To investigate a possible sequence requirement for de novo initiation of DNA replication, assays using a single-stranded homolymeric poly-dT 33-mer as a template were performed. As shown in FIG. 3D, piPolB could replicate this template, suggesting that there might not be a requirement for a specific template sequence under the conditions used. DNA replication in the presence of the complementary dATP gave rise to large DNA products and a laddered pattern indicating that replication started de novo, with the synthesis of short primers. This laddered pattern could correspond either to a distributive replication or alternative initiation positions throughout the template. Replication products obtained using the exonuclease-deficient piPolB where overall shorter, suggesting a processivity impairment, as found in the case of M13 replication (FIG. 9, lanes 8-10 vs. 11-13). Using this short, homopolymeric substrate, DNA primer synthesis was negligible with magnesium ions (FIG. 9, lanes 2-7 vs. 8-13), underlining the higher efficiency of manganese as a cofactor for DNA priming, in agreement with the previous results with M13 DNA (FIG. 3C).

Interestingly, when all dNTPs were added, generation of large DNA products was somewhat reduced (FIG. 3D, lane 6) and, if dATP was reduced to the labeled nucleotide (16 nM compared with 100 μM of the non-labeled, lane 7), replication products were negligible, which suggests that formation of correct Watson-Crick base pairs is required for replication initiation.

Collectively, these results indicate that piPolB from *E. coli* 3-373-03_S1_C2 pipolin is able to initiate and perform DNA replication of circular and linear templates in the absence of pre-existing primers or additional protein factors. Furthermore, replication of homopolymeric DNA substrates suggests that, contrary to canonical DNA primases from the archaeo-eukarotic primase (AEP) superfamily, piPolB DNA priming capacity does not rely on a specific template sequence.

Example 6. De Novo Synthesis of DNA Primers

To further confirm that piPolB is able to synthesize DNA de novo, it was performed M13 ssDNA replication using $\gamma^{32}$P-ATP as a labeled nucleotide. Thus, only newly synthesized DNA fragments would incorporate the radioactive label. As shown in FIG. 4A, small DNA fragments (up to 4-5 nucleotides in length) were generated in a distributive manner by wild type and exonuclease deficient piPolBs, but not by the D368A variant. Again, this reaction was considerably more efficient in the presence of manganese ions than with magnesium ions (lanes 1-8 vs. 9-16). Furthermore, the products were only detected in the presence of dNTPs but not with NTPs (not shown). Instead of the large DNA fragments detected in the assays described above (FIG. 3A), only di- and trinucleotide primers were observed, which may be abortive initiation products resulting from the incorporation of a ribonucleotide (rather than dNTP) as a terminal 5' nucleotide.

Figure 10:
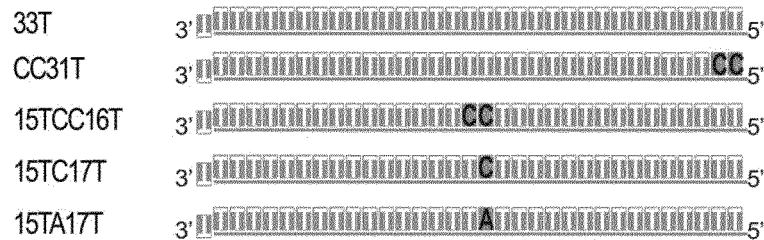
FIG. 10. Small effect of single modifications of template sequence on de novo replication of homopolymeric ssDNA substrate by piPolB. Alternative ssDNA templates are depicted above the gel (SEQ ID NO: 69 to 73).
Figure 10:
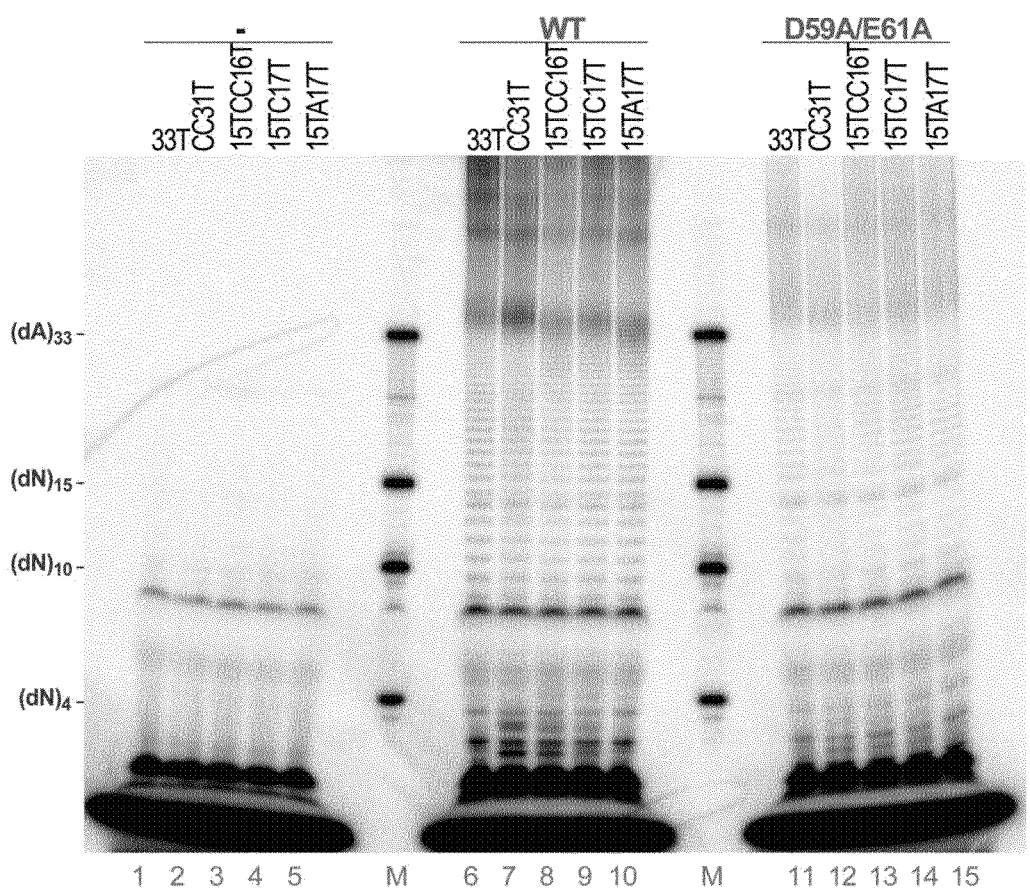

The use of high resolution PAGE allowed to identify alternative di- and trinucleotide primers with similar intensity, suggesting that DNA synthesis initiation by piPolB does not require a specific template sequence. In line with this, when each dNTP was provided separately (FIG. 4B), the reaction was clearly stimulated by dGTP, in the presence of either magnesium or manganese ions (lanes 4 and 14) and, to a lesser extent, by dCTP and dTTP, either alone or in combination with other deoxyribonucleotides. The fact that A-dG dinucleotide was the most efficiently synthetized initiation product is in agreement with the observation that pyrimidines are the preferential template substrates for the priming reaction by most DNA primases. In line with these results, single nucleotide changes in the poly-dT homopolymer substrate did not substantially change the efficiency of de novo DNA synthesis (FIG. 10), although short di- and tri-nucleotides could be detected when one or two Cs were included in the template sequence, even at the 5' end of the template molecule (lanes 7 and 12). Taken together, these results demonstrate that piPolB is able to initiate de novo DNA primer synthesis without a strong requirement for specific template sequence.

Figure 11:
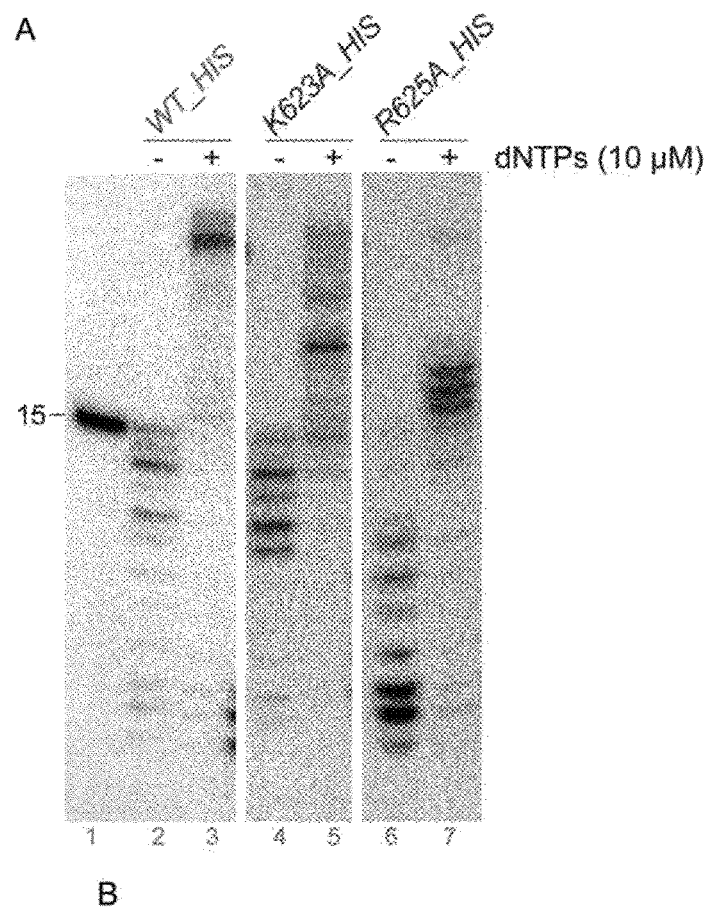
FIG. 11. Polymerase and primase capacities of piPolB variants in the analog residues of PolB KxY motif. Primer extension (A) and primer synthesis (B) capacity of wild type, K623A and R625A His-tagged piPolBs. Assays were performed as in FIG. 4. For reference, non-tagged wild type and exonuclease and polymerase deficient piPolB variants were also included in panel B.
Figure 11:
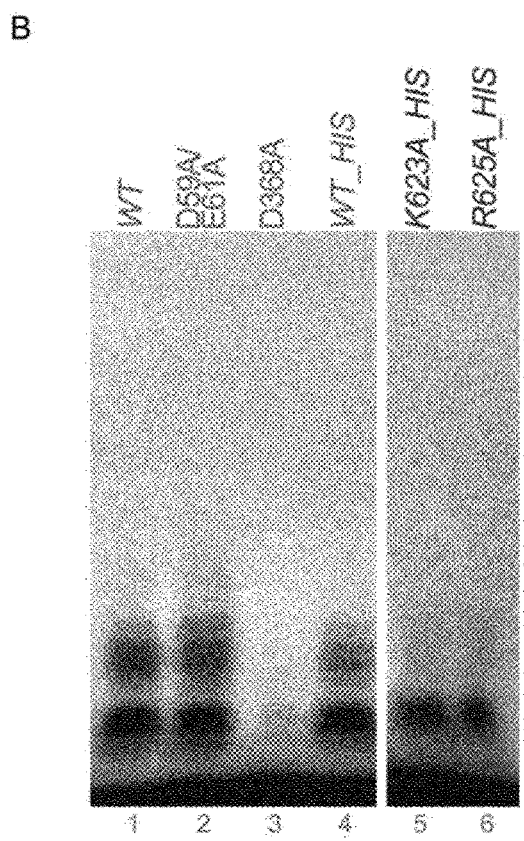

Example 7. An Invariable Lysine Plays a Role in TLS and Primer Synthesis Activities PolBs contain a conserved KxY motif within a β-strand in the palm domain involved in stabilization of the primer terminus. It was hypothesized that structural adaptations of this motif or nearby residues would be required for stable binding of a nucleoside triphosphate at the 5'-side of the nascent primer to allow dinucleotide formation. Indeed, analysis of the multiple sequence alignment showed that the piPolBs lack the canonical KxY motif and instead contain an alternative conserved sequence KTRG (SEQ ID NO: 46). An additional $KX_2$ pattern within an N-terminal extension of the same β-strand is also highly conserved in piPolB homologs, defining an extended $KX_2$-$X_{3-10}$-KTRG motif (SEQ ID NO: 1). In the representative enzyme of SEQ ID NO: 2 tested herein, $X_2$ is H and $X_{3-10}$ is SEQ ID NO: 5, i.e. SEQ ID NO: 1 is SEQ ID NO: 85, and this motif $KX_2$-$X_{3-10}$-KTRG corresponds to positions 613 to 626 of this sequence. Thus, alanine variants of these K613, H614, K623 and R625 residues were generated. In agreement with a putative role in primer terminus stabilization, K623A and R625A variants had impaired primer extension capacity (FIG. 11A) and primer synthesis beyond the dinucleotide formation (FIG. 11B). On the other hand, K613A and H614A proteins had normal primer extension capacity under the tested conditions (FIG. 5A). However, whereas H614A was able to synthetize new primers with a similar pattern as the wild type piPolB (FIG. 5B, lanes 6-7), K613A priming capacity was strongly reduced (lanes 4-5), suggesting a specific role of this residue during the de novo DNA synthesis.

It was next analyzed the TLS capacity of K613A variant by primer extension assay on the THF-containing template. FIG. 5C shows that the activity of K613A protein was strongly impaired compared to the wild type piPolB (lanes 3-4 vs. 7-8). Thus, although DNA primer synthesis and primer extension opposite to the undamaged and damaged substrates appears to rely on the same conserved catalytic residues, as shown for the D368A variant (see above), we were able to partially uncouple these activities. This result further confirms the unique intrinsic TLS and DNA primase capacities of piPolB and also unveils the role of the extended primer-stabilization motif of piPolB group that would be required for these activities.

Example 8. Biological Role of piPolB in De Novo DNA Synthesis

Figure 6:
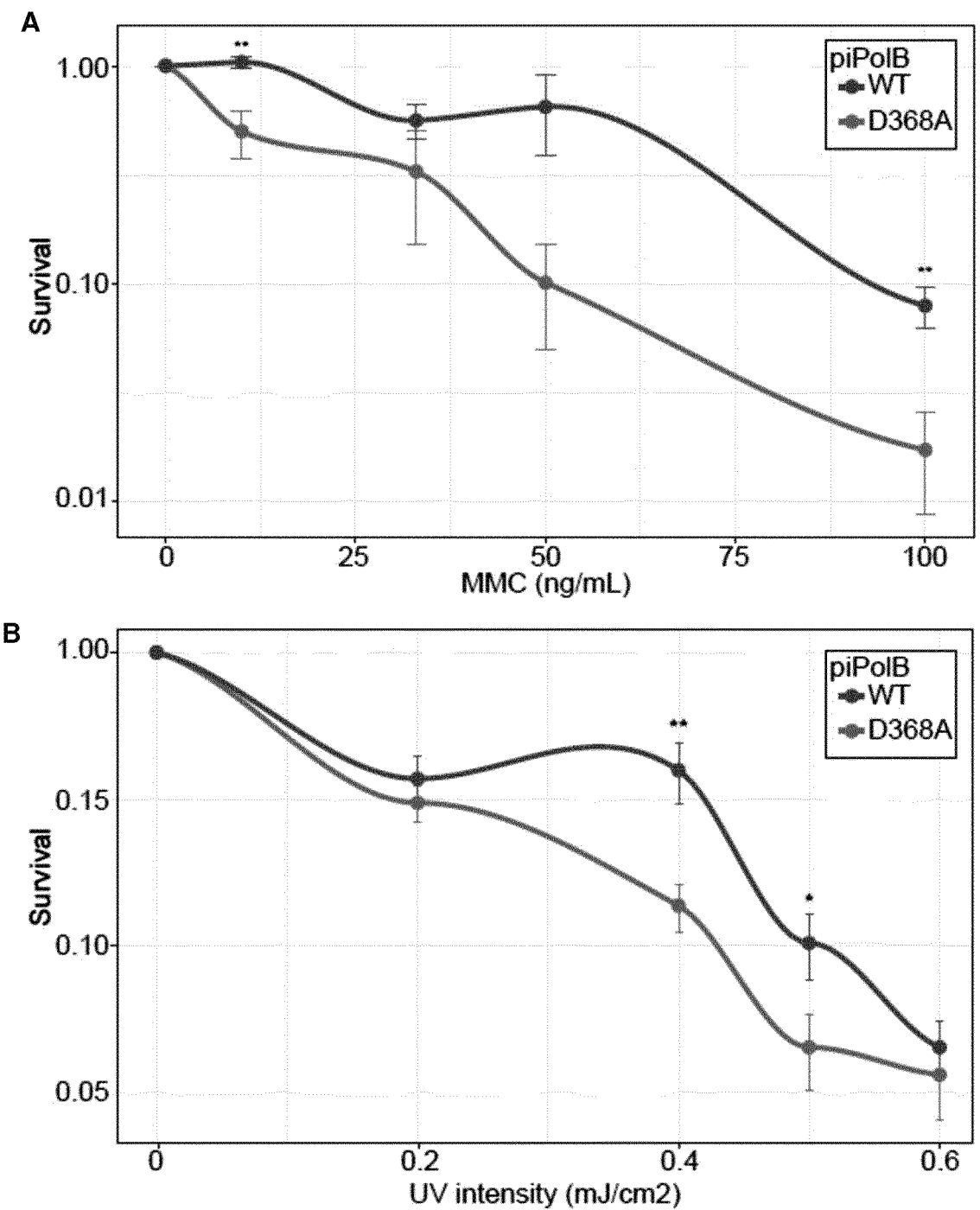
FIG. 6. Survival of *E. coli* (DE3) cells expressing wild type or inactive D368A piPolB variants upon DNA damage challenges. The graphs show relative survival (mean and standard error of four independent experiments) of cells overexpressing wild type or DNA polymerization deficient piPolB variants after genotoxic challenge with MMC (A) or UV light irradiation (B).

Considering the DNA priming capacity of piPolB, which is unprecedented in PolB family enzymes, it was decided to investigate its biological role in vivo. To this end, the piPolB-expressing bacteria were challenged with Mitomycin C (MMC) and ultraviolet-light (UV) irradiation, the two DNA damaging agents known to block DNA replication by introducing bulky base modifications and interstrand crosslinks (ICLs). Since piPolB was unable to replicate a T:T containing template (FIG. 2D), it is unlikely that its TLS capacity may allow bypass of DNA damage induced by MMC treatment or UV-irradiation. However, given that replication blockage on the leading strand can be circumvented by re-priming events downstream of the UV-generated lesions, it was hypothesized that the de novo DNA synthesis by piPolB might contribute to relieving the genotoxic stress generated by DNA damaging agents. The results suggest that this is indeed the case, because expression of the wild type piPolB in E. coli B121(DE3) cultures significantly enhanced cell survival upon both MMC treatment and UV-irradiation, as compared with bacteria expressing D368A inactive piPolB variant (FIG. 6). These results indicate a possible role of piPolB in DNA damage tolerance or repair in the context of E. coli cells.

Thus, the present invention reports the discovery and biochemical characterization of a new, previously overlooked major group of replicative PolBs, which were named herein "piPolBs" due to their unique capacity to perform primer-independent, templated DNA synthesis. Within the global PolB phylogeny, piPolB form a distinct, ancient clade on a par with the two previously described groups, rPolB and pPolB. The piPolB-encoding genes are found in MGEs, dubbed pipolins, most of which are integrated into genomes of bacteria from three different phyla (Firmicutes, Actinobacteria and Proteobacteria), but also replicating as circular plasmids in mitochondria. The distribution of pipolins is rather patchy, which is typical of integrated MGEs. To a large extent, pipolins seem to have coevolved with their hosts, because piPolB-based phylogeny is congruent with the general bacterial taxonomy (e.g., proteobacteria group together and are further divided into clades corresponding to different proteobacterial classes). Notably, phylogenetic analysis showed that piPolBs from mitochondrial plasmids cluster with proteobacterial homologs, in particular with those from alphaproteobacteria. Given that in all likihood mitochondria have evolved from an alphaproteobacterial ancestor at the onset of eukaryogenesis, it is tempting to speculate that piPolBs were introduced into eukaryotes along with the proto-mitochondrial alphaproteobacterial endosymbiont. According to conservative estimates based on the microfossil record, eukaryotes emerged ~2 billion years ago. Thus, piPolB clade should be at least as old if not older, especially if the emergence of pipolins predated the divergence of the major bacterial phyla. However, the possibility that pipolins were horizontally introduced into mitochondria from proteobacteria in a more recent past cannot be excluded.

The piPolBs share the conserved active site with other PolBs and also contain TPR1 and TPR2 subdomains, a hallmark of pPolBs. Consistently, it was showed herein that piPolB displays efficient DNA polymerization and strand displacement activities. A more detailed biochemical characterization of piPolB also showed intrinsic TLS capacity across non-bulky base damages (FIG. 2), which, although leading to mutation accumulation, will ultimately favor the maintenance of the damaged genome. Strikingly, unlike all other PolBs, piPolB does not require an externally provided primer for DNA replication. Conversely, it was found here that piPolB is able to initiate DNA synthesis de novo, a capacity so far exclusive to DNA primases. In the case of CD29DNAP, the TPR1 motif has been shown to make contacts with the template strand and to play a key role in the interaction with the TP during the early steps of protein-primed replication. Given that piPolBs in all likelihood do not interact with a TP, the function of TPR1 region may be limited to the interaction with the DNA. One additional possibility might be that this subdomain also interacts with certain cellular cofactors, which would modulate the piPolB activity in vivo. It was also noted that certain components of the cellular replication machinery (e.g., DNA ligase) might be involved in the pipolins' replication cycle.

Figure 4:
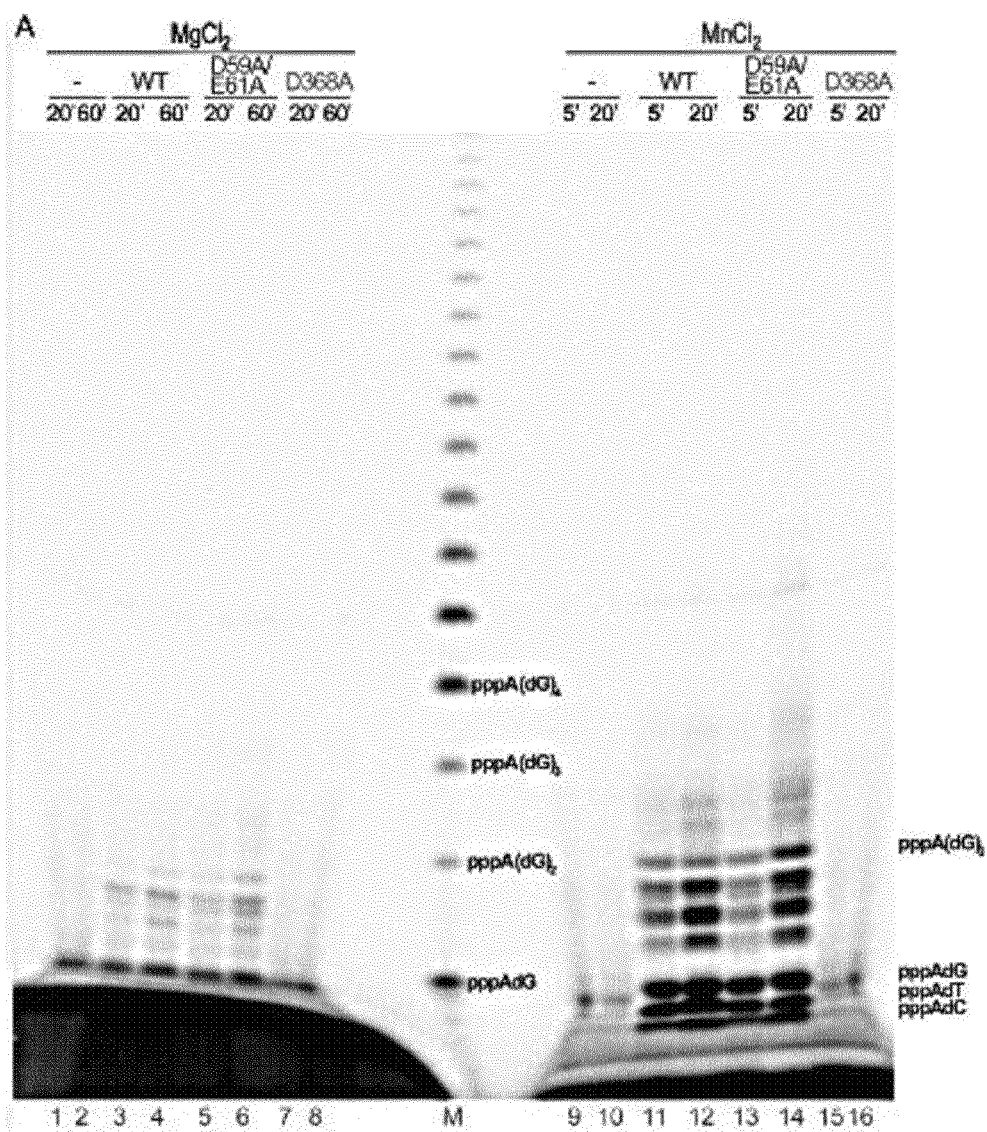
FIG. 4. De novo DNA synthesis by piPolB. (A) Primer synthesis by piPolB. M13 DNA was incubated with either dNTPs or NTPs (100 µM) and wild type (WT) piPolB or the polymerase (D368A) or exonuclease (D59A/E61A) deficient variants (500 nM). Detected products are labeled with [$\gamma^{32}$P]ATP (1 µCi) that only could be incorporated in the 5' position of the newly synthetized primers. (B) Insertion preference for the first steps of DNA primer synthesis by exonuclease deficient piPolB. The assay was performed as in panel A but with each dNTP (100 µM) provided independently or in the indicated combinations. Reactions were triggered with either 10 mM $MgCl_2$ or 1 mM $MnCl_2$ and resolved in high resolution 8 M urea-20% PAGE.
Figure 4:
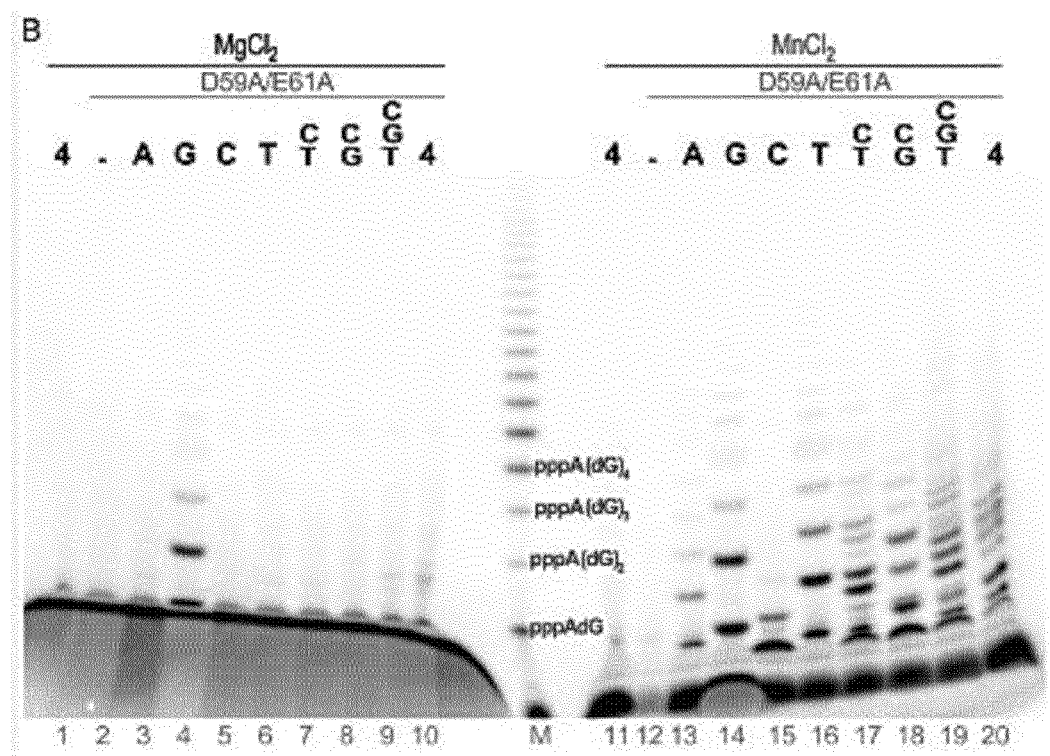

The use of manganese as divalent cofactor instead of magnesium increased TLS across abasic sites (FIG. 2C) as well as de novo DNA synthesis (FIGS. 3C, 9 and 4).

Figure 5:
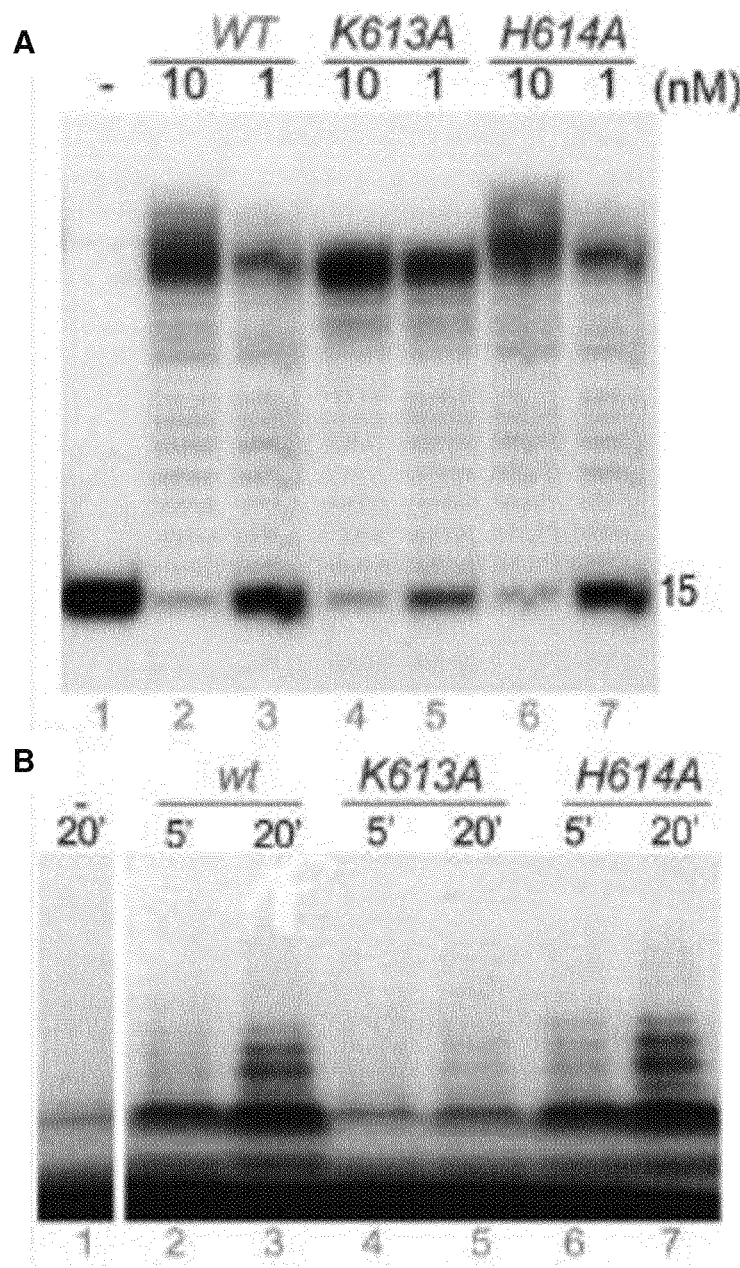
FIG. 5. The piPolBs invariant K613 residue plays a role in TLS and de novo primer synthesis. (A) Primer extension assays of wild type, K613A and H614A His-tagged piPolBs. Assays were carried out for 10 min at 30° C. in the presence of 1 nM primer/template duplex, 10 µM dNTPs and the indicated concentration of piPolB variants. (B) Primer synthesis by wild type, K613A and H614A His-tagged piPolBs. (C) Comparison of primer-extension capacity of wild type and K613A His-tagged piPolBs opposite to undamaged (X=T) or damaged (X=THF) templates (SEQ ID NO: 83). Reactions were triggered with 1 mM $MnCl_2$ and resolved in 8 M Urea-20% PAGE.
Figure 5:
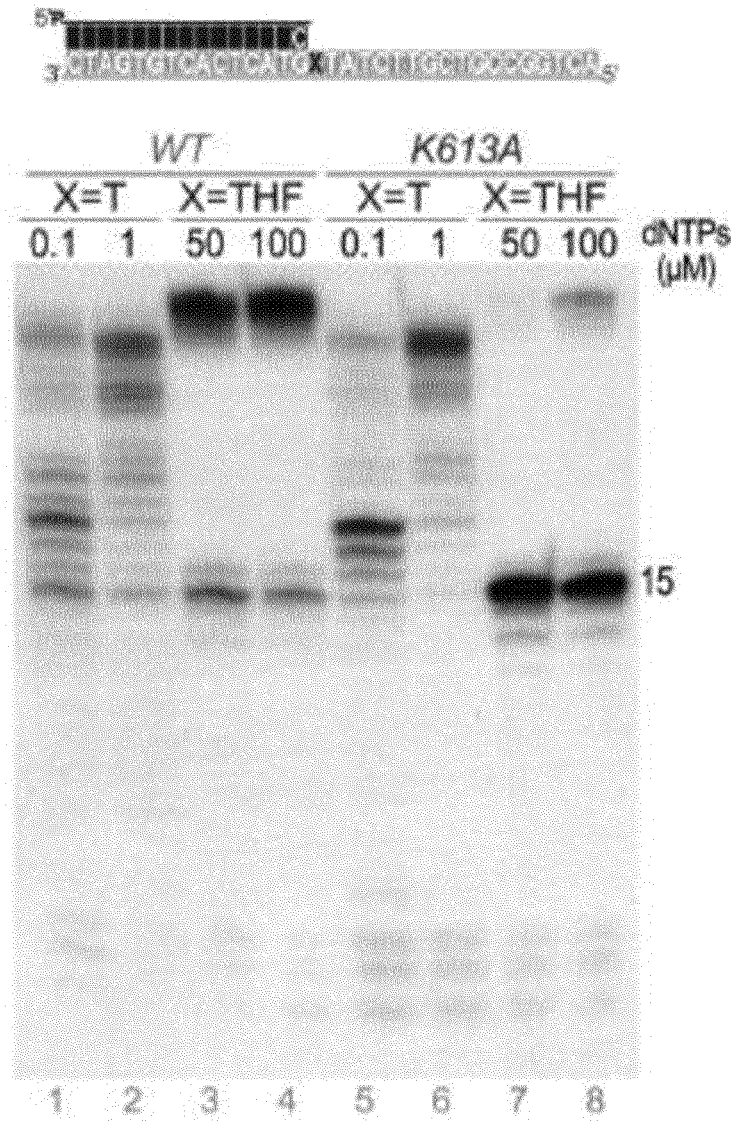

The enzyme tested in these examples acts both as a primase and a DNA polymerase. Here, it has been shown that piPolBs have a unique KTRG motif (SEQ ID NO: 46), alternative to the conserved KxY motif of PolBs, which interacts with the primer terminus. Moreover, an invariant lysine nearby the KTRG motif plays a key role both in TLS and de novo primer synthesis (FIG. 5). Given the positive charge of this and nearby residues in the piPolB group, it is likely that the extended KX$_2$-X$_{3-10}$-KTRG motif (SEQ ID NO: 1) may induce a highly stable primer terminus binding mechanism that may favor the binding of the incoming nucleotide and the subsequent stabilization of the ternary complex, which would result in enhanced polymerization capacity. These results establish a structural liaison between TLS and priming capacities of piPolB.

As mentioned above, all DNA primases lack proofreading capacity. This seems advantageous for the efficient synthesis of short-lived Okazaki fragments. Conversely, the 3'-5' exonuclease proofreading activity, which is necessary for faithful DNA replication by a DNA polymerase, could hinder the primase capacity. Thus, piPolB synthetic and degradative activities must be highly coordinated to allow efficient primer synthesis and faithful DNA replication. Furthermore, the piPolB exonuclease activity is also compatible with translesion synthesis of non-bulky base damages which, as reported previously for pPolB of bacteriophage Bam35, does not require template strand misalignment but tolerates damage-containing mismatches during processive DNA synthesis. Previous studies have shown that replication of pCRY1-like pipolins from fungal mitochondria can be initiated from multiple origins rather than from a fixed origin. However, this observation remained unexplained. These plasmids do not code for a putative TP; indeed, they only contain the piPolB gene. Thus, in the light of the results presented herein, such replication pattern is consistent with the possibility that pCRY1-like pipolins are replicated by their cognate piPolBs in a primer-independent manner. Analogously, the circular episomal form of bacterial pipolins could be replicated by piPolBs from multiple origins.

Replication across bulkier DNA lesions that could not be bypassed by piPolB might benefit from possible downstream re-priming. Accordingly, it has been shown here that expression of the wild type piPolB promotes survival of *E. coli* cells exposed to replication-blocking DNA damage agents (FIG. 6). Hence, it was hypothesized that piPolB might have evolved to maintain pipolins' DNA by providing faithful and processive de novo DNA replication as well as tolerance to DNA damage, which may also increase the fitness of the host bacteria.

Importantly, piPolB holds a great promise for developing novel biotechnological applications. For instance, in vitro activities of piPolB, namely strand displacement and faithful, processive DNA polymerization, can be harnessed for efficient primer-independent whole genome amplification, whereas the translesion synthesis can be useful for amplification of damaged or ancient DNA templates. Given that piPolBs do not display strong sequence requirement for replication initiation, replication origins may be selected in a random manner, a property useful for whole genome amplification. piPolB could become a single-enzyme solution to achieve the goal of whole genome amplification in single-cell genomics applications.

Figure 12:
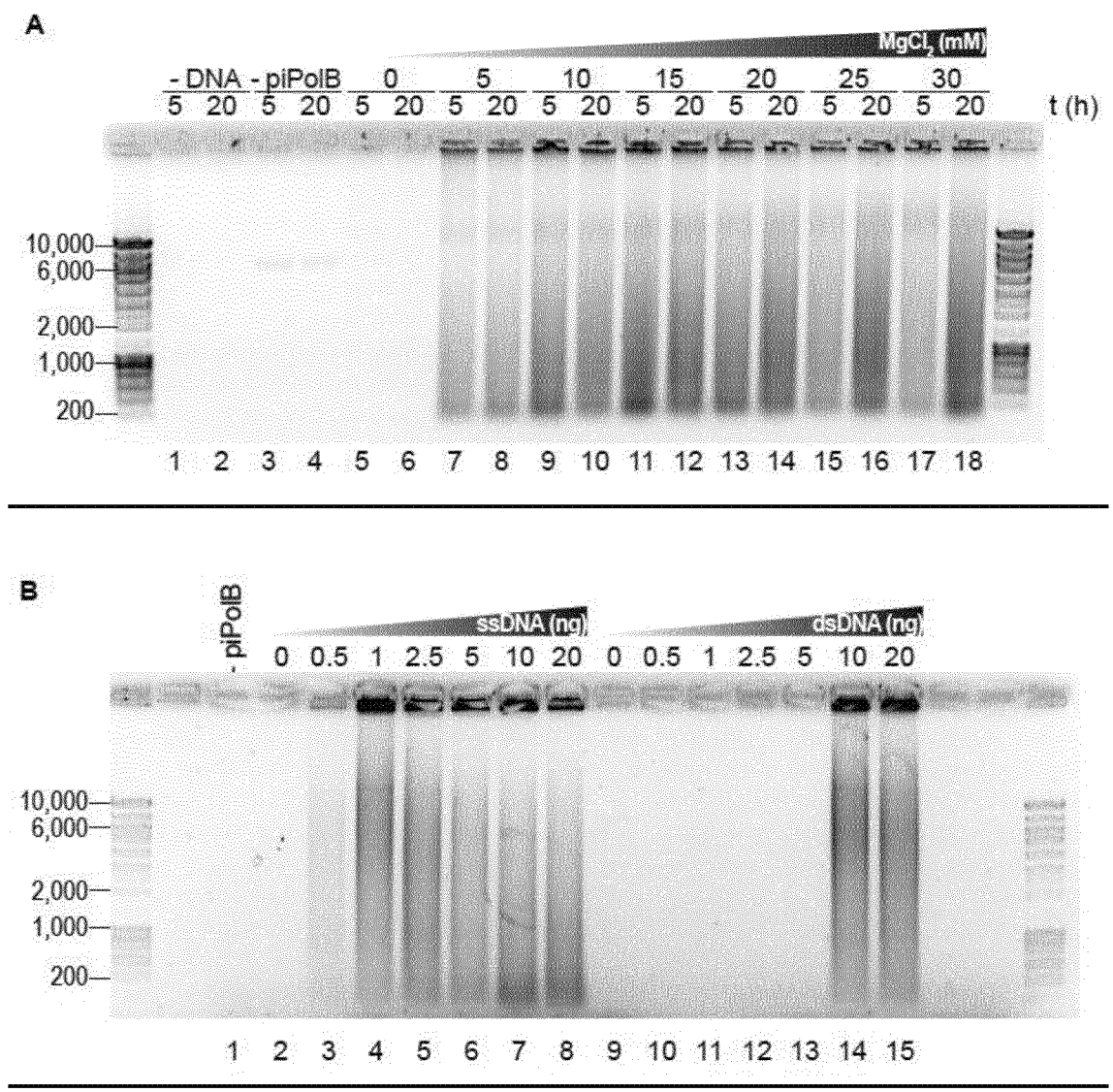
FIG. 12. Improved conditions for primer-independent DNA amplification. (A). Non-denaturing TAE agarose gel electrophoresis of M13 single-stranded DNA amplification by piPolB without the addition of external primers. Assays (final volume 10 μL) were made in the presence of 250 nM piPolB, 0.5 mM dNTPs, 10 mM ammonium sulfate, 20 ng DNA input and the indicated amount of $MgCl_2$. Lanes 1-4 contain 20 mM $MgCl_2$. Reactions were incubated at 30° C. for the indicated times and then piPolB was inactivated by incubation at 65° C. for 10 minutes and a sample (2 μL) was withdrawn and loaded into the gel. (B). Non-denaturing TAE agarose gel electrophoresis of single- and double-stranded M13 DNA amplification with limiting amounts of input DNA. Assays were carried out as above but with the indicated DNA input. A sample (2 μL) was withdrawn, digested with EcoRI and loaded into the gel.

Example 9. Amplification of Single- and Double-Stranded DNA by piPolB in the Absence of External Primers To further analyze the application of piPolB for amplification of DNA without the addition of external primers, an optimization of the reaction conditions was first carried out using increasing concentrations of MgCl$_2$ as divalent cofactor, different reaction incubation times and M13 ssDNA input amount (FIG. 12).

As shown in FIG. 12A, the reaction is dependent of the metal concentration, with an optimum concentration of magnesium chloride of 15-30 mM. Thus, a concentration of 20 mM MgCl$_2$ was selected for subsequent experiments.

Amplified DNA can be detected after 5 h of reaction, although it increases with longer incubation time. In agreement with previous results, reaction product appeared as a smear of amplified DNA of a wide range of size lengths. It was then performed amplification of M13 ssDNA and dsDNA forms, using limiting DNA input amount (FIG. 12B). Amplification of ssDNA could be detected with 1 ng DNA input (lane 4). Increasing DNA amount (lanes 5-8) gave rise to shorter DNA fragments, indicating distributive synthesis. Double-stranded DNA could be also amplified without any denaturing step, although it required higher amount of DNA input (lanes 14-15). Importantly, the reaction is highly specific, as no product is detected in the absence of DNA input (lanes 1-2, FIG. 12A and lanes 2 and 9, FIG. 12B) or without metal (lanes 5-6, FIG. 12A).

Samples in FIG. 12B were digested with EcoRI, a single-cut reaction enzyme, prior to electrophoretic analysis. However, the smeared pattern is the same as in FIG. 12A, indicating that the piPolB-generated DNA product would be mainly ssDNA. The use of ssDNA libraries has been successfully employed for amplification and subsequent sequencing of highly damaged ancient DNA. Furthermore, single-stranded library preparation can provide a higher yield and resolution level of DNA sequences from cell-free circulating DNA from blood and urine as well as DNA sequences from formalin-fixed, paraffin-embedded (FFPE) tissues. This, as well as the TLS of piPolB, suggest the potential application of primer-free amplification with piPolB for analysis of ancient and/or damaged DNA from a wide variety of sources.

Figure 13:
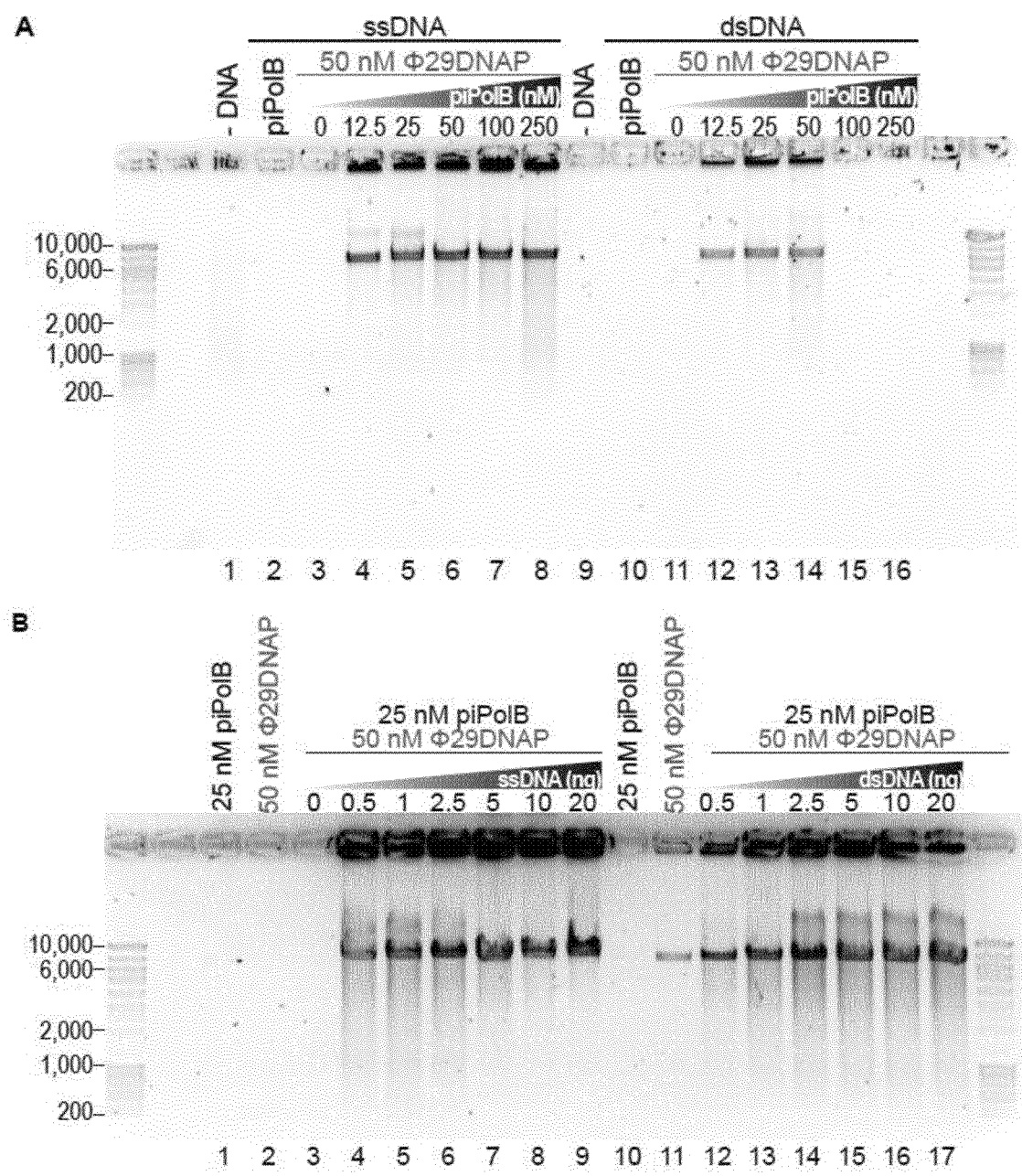
FIG. 13. Primer-free DNA amplification by the combination of piPolB and 429DNAP increased DNA amplification sensitivity. (A). Non-denaturing TAE agarose gel electrophoresis of M13 single-stranded DNA amplification with Φ29DNAP and increasing concentration of piPolB. Assays were made in the presence of 0.5 mM dNTPs, 10 mM ammonium sulfate, 20 mM $MgCl_2$, 20 ng DNA input, 50 nM Φ29DNAP and the indicated amount of piPolB. Lane 2 contains 25 nM piPolB. Reactions were incubated at 30° C. for 16 h and then DNAPs inactivated by incubation at 65° C. for 10 minutes. A sample (2 μL) was withdrawn, digested with EcoRI and loaded into the gel. (B). Non-denaturing TAE agarose gel electrophoresis of single- and double-stranded M13 DNA amplification with limiting amounts of input DNA. Assays were carried out as above but with 20 ng (lanes 1, 2, 10 and 11) or the indicated amount of DNA input (lanes 3-9 and 12-17).

As shown above, the reduced processivity of piPolB as compared with Φ29DNAP and other DNAPs, gives rise to a DNA amplified product that constitutes a DNA library of a wide range of length. Thus, we wondered if the joint use of piPolB and Φ29DNAP in the same reaction mixture would be able to produce a more homogeneous amplified product. As shown in FIG. 13A, using both ssDNA and dsDNA, the addition of low piPolB concentration (12.5 nM, lanes 4 and 12) to a fixed concentration of Φ29DNAP is enough to produce large DNA fragments that can be resolved in dsDNA monomers of unit length. Furthermore, as shown in FIG. 13B, the combined addition of piPolB and Φ29DNAP reduced the minimal input DNA required to 0.5 ng or below with either ssDNA and dsDNA.

Altogether, these results confirm the successful amplification of ssDNA and dsDNA, using piPolB in the absence of external primers, either by itself or together with another suitable DNAP, such as Φ29DNAP, and suggest multiple possible applications.

Example 10. Experimental Procedures 10.1. Bioinformatic Analyses.

Phylogenetic analysis. The non-redundant database of protein sequences at the NCBI was searched using the PSI-BLAST. For phylogenetic analyses protein sequences were aligned with the multiple sequence and structure alignment server PROMALS3D. Poorly aligned (low information content) positions were removed using the Gappyout function of Trimal. The dataset of viral, plasmid and polintons pDNAP sequences was collected previously (Krupovic, M., and Koonin, E. V., 2015, Nat Rev Microbiol, 13, 105-115). Maximum likelihood phylogenetic tree was constructed using the PhyML program the latest version of which includes automatic selection of the best-fit substitution model for a given alignment. The best model identified by PhyML was LG+G6+I+F (LG, Le-Gascuel matrix; G6, Gamma shape parameter: fixed, number of categories: 6; I, proportion of invariable sites: fixed; F, equilibrium frequencies: empirical).

Identification and annotation of integrated MGE. The pipolins' were identified thorough analysis of genomic neighborhoods of the piPolB-encoding genes. The precise boarders of integration were defined based on the presence of direct repeats corresponding to attachment sites. The repeats were searched for using Unipro UGENE. Pipolin genes were annotated based on the PSI-BLAST searches against the non-redundant protein database at NCBI and HHpred searches. Pipolins were compared to each other and visualized using the Genome Comparison Visualizer EASY-FIG.

10.2. Protein Expression and Purification.

Primer-independent DNA polymerase (piPolB) from *E. coli* 3-373-03_S1_C2 Pipolin (NCBI GI:693097161, SEQ ID NO: 2) was obtained from GeneScript into NdeI-XhoI sites of pET23a. A stop codon was included to obtain the untagged recombinant protein (SEQ ID NO: 45). Polymerase (D368A) and exonuclease (D59A/E61A) deficient proteins, as well as wild type, K613A, H614A, K623A and R625A his-tagged variants, were obtained by site directed mutagenesis (Table 1):

TABLE 1

Gene Sequence Information and mutagenesis primers. Oligonucleotide pairs used for site-directed mutagenesis

| piPolB variant | Sequence (5'-3') |
|---|---|
| D368A | CCCCGTCAGATCACTGGTATGATTACGCCCTGGCAGGCGC TTATACCACG (SEQ ID NO: 47) |
| | GCTGGTATAAGCGCCTGCCAGGGCGTAATCATACCAGTGA TCTGACGGGG (SEQ ID NO: 48) |
| D59A/ 61A | CCCTGCATATCGGTTTTGCCACGGCATACGTGTTCAACCC GGAAACCC (SEQ ID NO: 49) |
| | GGGTTTCCGGGTTGAACACGTATGCCGTGGCAAAACCGAT ATGCAGGG (SEQ ID NO: 50) |
| WTHis | CCTTTTGCCTGCCGGTTTTACTCGAGCACCACCACCACCA CCAC (SEQ ID NO: 51) |
| | GTGGTGGTGGTGGTGGTGCTCGAGTAAAACCGGCAGGCAA AAGG (SEQ ID NO: 52) |
| K613A | GGGTTCATCGATGCTGACCTGTGCACATGAAGTCTCTCAA CTGATCGC (SEQ ID NO: 53) |
| | GCGATCAGTTGAGAGACTTCATGTGCACAGGTCAGCATCG ATGAACCC (SEQ ID NO: 54) |
| H614A | GGGTTCATCGATGCTGACCTGTAAAGCTGAAGTCTCTCAA CTGATCGC (SEQ ID NO: 55) |
| | GCGATCAGTTGAGAGACTTCAGCTTTACAGGTCAGCATCG ATGAACCC (SEQ ID NO: 56) |
| K623A | GTCTCTCAACTGATCGCCATGGCAACCCGTGGTCAGCTGA CG (SEQ ID NO: 57) |
| | CGTCAGCTGACCACGGGTTGCCATGGCGATCAGTTGAGAG AC (SEQ ID NO: 58) |

TABLE 1-continued

Gene Sequence Information and mutagenesis primers. Oligonucleotide pairs used for site-directed mutagenesis

| piPolB variant | Sequence (5'-3') |
|---|---|
| R625A | GTCTCTCAACTGATCGCCATGAAAACCGCTGGTCAGCTGA CGTATAAAGC (SEQ ID NO: 59) |
| | GCTTTATACGTCAGCTGACCAGCGGTTTTCATGGCGATCA GTTGAGAGAC (SEQ ID NO: 60) |

Table 1. Gene Sequence Information and Mutagenesis Primers

All piPolB variants were expressed in B121(DE3) *E. coli* cells, using ZYM-5052 autoinduction medium in the presence of 100 mg/L ampicillin. Cultures were grown for 20 h at 28° C. For purification of untagged piPolB variants, cells were disrupted by grinding with alumina and suspended in buffer A (50 mM Tris-HCl, pH 7.5, 1 mM EDTA, 7 mM β-mercaptoethanol, 5% (v/v) glycerol) containing 1 M NaCl. Alumina and cell debris were removed by centrifugation, and absorbance at 260 nm was adjusted to 120 units/ml prior to DNA precipitation with 0.3% (w/v) polyethyleneimine. After centrifugation at 20,000×g for 20 min, ammonium sulfate was added to the supernatant to 69% saturation and centrifuged at 20,000×g for 30 min. The piPolB (wild type and mutants) containing pellet was resuspended in buffer A and applied to serial Q SEPHAROSE® FAST FLOW (GE Healthcare) anion exchange column and phosphocellulose (P11, Whatman) columns, at an ionic strength about 0.2 M NaCl. After extensive wash with increasing concentrations of NaCl in buffer A, purified DNA polymerase was eluted with 0.35 M NaCl and applied to Heparin-Sepharose® CL-6B affinity column (GE Healthcare), where, after washing with 0.35, 0.4 and 0.45 M NaCl, they were eluted at 1 M NaCl in buffer A.

Histidine-tagged variants were purified by standard method. Briefly, cells were resuspended in buffer C (50 mM phosphate buffer, pH 8, 7 mM β-mercaptoethanol, 5% (v/v) glycerol, 1 M NaCl, 5 mM imidazole) and incubated for 30 min at room temperature with 1 mg/mL lysozyme (Sigma) and 1 unit of benzonase (Sigma), prior to cell disruption by sonication. After centrifugation at 20,000×g for 30 min, the soluble fraction was applied to a Ni-NTA column (Qiagen). After extensive wash with 5, 10, 25 and 50 mM imidazole, the protein was eluted with 200 mM imidazole and subsequently applied to Heparin-Sepharose® CL-6B affinity column (GE Healthcare), where, after washing with 0.35, 0.4 and 0.45 M NaCl, it was eluted at 1 M NaCl in buffer A.

In all cases, pooled fractions containing pure piPolB variants were dyalized overnight against 500 volumes of buffer B (50 mM Tris-HCl, pH 7.5, 1 mM EDTA, 7 mM β-mercaptoethanol, 0.25 M NaCl and 50% (v/v) glycerol) and kept at −20° C., or at −70° C. for long storage. Final purity of the proteins was estimated to be >90% by SDS-PAGE followed by Coomassie blue staining.

10.3. Primer Extension Assays.

Oligonucleotides (Table 2) were purchased from Sigma in PAGE purification grade. To form a primer/template substrate as indicated in the top of each figure, the P15 oligonucleotide (Table 2) was 5'-labeled with [γ-$^{32}$P]ATP using T4 Polynucleotide Kinase and hybridized to 1.2-fold molar excess of complementary unlabeled template oligonucleotides (T33GTA, T33GTT or T33GFA, Table 2) in the presence of 50 mM NaCl and 50 mM Tris-HCl, pH 7.5.

TABLE 2

Sequences of oligonucleotides used in the examples.

| Name | Sequence (5'-3') |
| --- | --- |
| P4 | GATC (SEQ ID NO: 61) |
| P10 | GACTGCTTAC (SEQ ID NO: 62) |
| P15 | GATCACAGTGAGTAC (SEQ ID NO: 63) |
| T33GTA | ACTGGCCGTCGTTCTATTGTACTCACTGTGATC (SEQ ID NO: 64) |
| T33GTT | ACTGGCCGTCGTTCTAATGTACTCACTGTGATC (SEQ ID NO: 65) |
| T33GFT | ACTGGCCGTCGTTCTATFGTACTCACTGTGATC (SEQ ID NO: 66) |
| P20-33 | GAACGACGGCCAGT (SEQ ID NO: 67) |
| 33A | AAAAAAAAAAAAAAAAAAAAAAAAAAAAAAAAA (SEQ ID NO: 68) |
| 33T* | TTTTTTTTTTTTTTTTTTTTTTTTTTTTTTTT/invT/ (SEQ ID NO: 69) |
| CC31T* | CCTTTTTTTTTTTTTTTTTTTTTTTTTTTTTT/invT/ (SEQ ID NO: 70) |
| 15TCC16T* | TTTTTTTTTTTTTTCCTTTTTTTTTTTTTTTT/invT/ (SEQ ID NO: 71) |
| 15TC17T* | TTTTTTTTTTTTTTTCTTTTTTTTTTTTTTTTT/invT/ (SEQ ID NO: 72) |
| 15TA17T* | TTTTTTTTTTTTTTTATTTTTTTTTTTTTTTTT/invT/ (SEQ ID NO: 73) |
| M13 UP | GTAAAACGACGGCCAGT (SEQ ID NO: 74) |

F represents the THF abasic site analog. */invT/ stands for a last dTMP nucleotide linked by an inverted 3'-3' bond.

Assays were performed in 20 μL final volume containing 50 mM Tris-HCl, pH 7.5, 1 mM DTT, 4% (v/v) glycerol, 0.1 mg/ml BSA, 0.05% (v/v) polyethylene glycol sorbitan monolaurate (TWEEN® 20) and, unless otherwise stated, 1 nM of the indicated 5'-labeled primer/template duplex, 10 nM DNA polymerase and the indicated dNTPs concentration. Reactions were triggered by addition of either 10 mM $MgCl_2$ or 1 mM $MnCl_2$, as indicated and, after incubation for the indicated times at 30° C., the reactions were stopped by adding 10 μL of formamide loading buffer (98% formamide, 20 mM EDTA, 0.5% (w/v) bromophenol blue, and 0.5% (w/v) xylene cyanol). Samples were analyzed by 8 M urea-20% polyacrylamide gel electrophoresis (20×30×0.5 mm) in 1×TBE buffer. Gel bands were detected by an image analyzer either by autoradiography or phosphorimages (TYPHOON™ FLA 7000) and processed with IMAGE J SOFTWARE.

10.4. Replication of Single-Stranded DNA.

Genomic M13mp18 single-stranded circular DNA (laboratory stock) was diluted up to 50 ng/μL in a buffer containing 0.2 M NaCl and 60 mM Tris-HCl, pH 7.5 with or without M13 UP primer (Table 2), heated for 5 min at 65° C. and cooled slowly overnight to allow the annealing of the primer. Primed and non-primed M13 substrates were stored at −20° C. in small aliquots to minimize DNA nicking due to repetitive cycles of freeze-thaw.

The reaction mixture contained, in a final volume of 25 μL, 50 mM Tris-HCl, pH 7.5, 1 mM DTT, 4% (v/v) glycerol, 0.1 mg/ml BSA, 0.05% (w/v) polyethylene glycol sorbitan monolaurate (TWEEN® 20), 20 mM ammonium sulfate, 100 μM dNTPs, 0.5 μCi [α-$^{32}$P]dATP, 3.2 nM of primed or non-primed M13mp18 ssDNA, and the indicated concentrations of each DNA polymerase. Reactions were triggered by addition of either 10 mM $MgCl_2$ or 1 mM $MnCl_2$ and incubated for 20 min at 30° C. Reactions were then quenched by adding 5 μL of 250 mM EDTA, 5% (w/v) SDS and directly loaded in TAE1× non-denaturing agarose electrophoresis. For alkaline agarose electrophoresis, an aliquot (15 μL) was subjected to gel filtration through Sephadex® G-15 gel filtration spin columns containing 0.1% (w/v) SDS. Lambda DNA ladder used as a size marker was labeled by filling-in with Klenow fragment (New England Biolabs) in the presence of [α-$^{32}$P]dATP.

Replication of homopolymeric single stranded template was performed in similar conditions, using the 33-mer oligonucleotides (IDT) with the indicated sequences (Table 2), containing a terminal 3'-3' inverted 3'-3' inverted link to prevent both primer extension and exonucleolytic degradation. Oligonucleotide replication assays were performed in 20 μL final volume containing 50 mM Tris-HCl, pH 7.5, 1 mM DTT, 4% (v/v) glycerol, 0.1 mg/ml BSA, 0.05% (v/v) polyethylene glycol sorbitan monolaurate (TWEEN® 20), 1 μM oligonucleotide template, 100 μM dNTPs, 500 nM of the indicated piPolB variant and 0.5 μCi [α-$^{32}$P]dATP. After incubation for the indicated times at 30° C., the reactions were stopped by adding 10 μL of formamide loading buffer (98% formamide, 20 mM EDTA, 0.5% (w/v) bromophenol blue, and 0.5% (w/v) xylene cyanol). Samples were analyzed by 8 M urea-20% polyacrylamide analyzer either by autoradiography or phosphorimages (TYPHOON™ FLA 7000) and processed with IMAGE J SOFTWARE.

10.5. De Novo Primer Synthesis Detection.

To detect de novo primer synthesis [γ-$^{32}$P]ATP was used as the labeled nucleotide. M13 ssDNA (3.2 nM) was used as template. The reaction mixture contained, in a final volume of 25 L, 50 mM Tris-HCl, pH 7.5, 1 mM DTT, 4% (v/v) glycerol, 0.1 mg/ml BSA, 0.05% (v/v) polyethylene glycol sorbitan monolaurate (TWEEN® 20), 10 μM dNTPs, 0.5 μCi [γ-$^{32}$P]ATP, the indicated template and DNA polymerase (500 nM). Reactions were triggered by addition of either 10 mM $MgCl_2$ or 1 mM $MnCl_2$ and incubated for indicated times at 30° C. Then, the reactions were stopped by adding 10 μL of formamide loading buffer (98% formamide, 20 mM EDTA, 0.5% (w/v) bromophenol blue, and 0.5% (w/v) xylene cyanol). Samples were analyzed by 8 M urea-20% polyacrylamide gel electrophoresis (20×30×0.5 mm) in 1×TBE buffer. When indicated, high resolution gels (40 cm long) were used. Gel bands were detected by an image analyzer by phosphorimages (TYPHOON™ FLA 7000) and processed with IMAGE J SOFTWARE. The [γ$^{32}$P]ATP-(dGMP)n DNA ladder used as size marker, generated by human PrimPol, was a gift from Dr. Luis Blanco (CBMSO, Madrid).

10.6. DNA Amplification Assays.

The reaction mixture contained, in a final volume of 10 μL, 50 mM Tris-HCl, pH 7.5, 1 mM DTT, 4% (v/v) glycerol, 0.1 mg/ml BSA, 0.05% (w/v) polyethylene glycol sorbitan monolaurate (TWEEN® 20), 10 mM ammonium sulfate, 500 μM dNTPs and, except otherwise stated, 20 mM $MgCl_2$ and 20 ng of either M13mp18 ssDNA or the counterpart dsDNA replicative form (RFI, New England Biolabs). Reactions were triggered by addition of the indicated DNA polymerase and incubated for the indicated times at 30° C., followed by incubation at 65° C. for 10 minutes and stored at 4° C. until analysis. When indicated, an aliquot (2 μL) was withdrawn and digested with EcoRI (EcoRI-HF, New England Biolabs), under standard conditions prior to analysis by TAE1× non-denaturing 0.8% agarose gel electrophoresis. DNA bands were visualized by subsequent staining with ethidium bromide (0.2 μg/mL). NZYDNA Ladder III molecular weight marker (NZYTech) were loaded for reference at each side of the gel.

10.7. Survival of piPolB Expressing Bacteria Upon DNA Damaging Agents Challenges.

Starter cultures of *E. coli* B121(DE3) harboring pET23a::piPolB or pET23a::piPolB(D368A) plasmids were inoculated in LB media in the presence of ampicillin (150 μg/mL) and glucose (40 mM) and grown overnight shaking at 37° C. Saturated cultures were diluted (1:100) in fresh LB media with ampicillin and grown 1-2 h at 28° C. until DO600 nm=0.4. Recombinant protein expression was then induced by 0.5 mM IPTG during one hour prior to genotoxic challenge. At this point an aliquot was withdrawn to verify recombinant protein expression by SDS-PAGE (not shown). For MMC treatment, the indicated drug concentration was added directly into the cultures that were grown for an additional hour and then serial-diluted in fresh LB and plate onto LB-agar plates (without antibiotic). In the case of UV-exposure, the induced cultures were serial-diluted in sterile PBS and plated onto LB-agar plates prior to irradiation with the indicated UV-light intensity in a spectroline UV crosslinker SPECTROLINKER™ XL-1000, Spectronics Corporation).

Data analysis and representation was performed using R and R-Studio (Studio, Inc., Boston, MA), using packages Dplyr, Stats and Ggplot2, available from CRAN (The comprehensive R archive network). Based on Shapiro-Wilk normality tests, results from MMC and UV light challenges were analyzed by Paired T-test and Dependent 2-group Wilcoxon Signed Rank Test, respectively. P-values are indicated in the FIG. 6 as *p≤0.1, p≤0.05 and *p≤0.01.

The following references are incorporated herein by reference into the specification:

Krupovic and Koonin, 2016, Curr Opin Microbiol, 31, 25-33.
Krupovic, et al., 2014a, Biol Direct, 9, 6.
Krupovic, et al., 2014b, BMC biology, 12, 36.
Kapitonov, V. V., and Jurka, J., 2006, Proc Natl Acad Sci USA, 103, 4540-4545.
Gill, et al., 2014, Nucleic Acids Res, 42, 3707-3719.
Martinez-Jimenez, et al., 2015, DNA Repair (Amst), 29, 127-138.
Zhu, et al., 2017, Proc Natl Acad Sci USA, 114, E2310-E2318.
Beck, et al., 2010, Nucleic Acids Res, 38, 6707-6718.
Picher, et al., 2016, Nature communications, 7, 13296.
Higgins, 1989, CABIOS 5: 151-153.
Wilbury Lipman, 1983, *Proceedings of the National Academy of Science USA* 80: 726-730.
Devereux et al. 1984, *Nucleic Acids Research* 12: 287 Genetics Computer Group University of Wisconsin, Madison, 25 (WI).
Altschul et al. 1999, *J. Mol. Biol.* 215: 403-410.
Krupovic, M., and Koonin, E. V., 2015, Nat Rev Microbiol, 13, 105-115.

---

The invention claimed is:

1. A recombinant DNA polymerase enzyme comprising an amino acid sequence of a parental DNA polymerase of family B wherein the KxY motif has been substituted by a peptide consisting of the amino acid sequence SEQ ID NO: 1, wherein the recombinant DNA polymerase enzyme has DNA polymerase activity and primase activity, wherein the parental DNA polymerase of family B is a Bam35 DNA polymerase or a phi-29 DNA polymerase, and wherein the recombinant DNA polymerase enzyme comprises the amino acid sequence SEQ ID NO: 3 or SEQ ID NO: 4.

2. A nucleic acid molecule encoding the recombinant DNA polymerase enzyme according to claim 1.

3. A genetic construct comprising the nucleic acid molecule according to claim 2.

4. The genetic construct according to claim 3 which is an expression vector.

5. A host cell comprising the nucleic acid molecule according to claim 2 or a genetic construct comprising a nucleic acid sequence encoding a recombinant DNA polymerase enzyme comprising an amino acid sequence of a parental DNA polymerase of family B wherein the KxY motif has been substituted by the peptide consisting of the amino acid sequence SEQ ID NO: 1, wherein the recombinant DNA polymerase enzyme has DNA polymerase activity and primase activity, wherein the parental DNA polymerase of family B is a Bam35 DNA polymerase or a phi-29 DNA polymerase and wherein the recombinant DNA polymerase enzyme comprises the amino acid sequence SEQ ID NO: 3 or SEQ ID NO: 4.

6. A kit for amplifying a template DNA comprising the following elements:
   a. the recombinant DNA polymerase enzyme according to claim 1,
   b. at least one buffer,
   c. dNTPs, and
   d. magnesium or manganese ions.

7. A method for amplifying a template DNA comprising:
a. placing a template DNA in contact with a reaction mixture that comprises:
   the recombinant DNA polymerase enzyme according to claim 1,
   a buffer,
   magnesium or manganese ions, and
   dNTPs, and
b. incubating the template DNA with the reaction mixture under conditions that enable DNA amplification.

8. The method according to claim 7, wherein the template DNA is linear or circular and doubled or singled stranded.

9. The method according to claim 7, wherein if the template DNA is doubled stranded the method comprises denaturation of the template DNA prior to part a.

10. The method according to claim 7, wherein the amplification of the template DNA is performed by a technique selected from the list consisting of: polymerase chain reaction (PCR), multiple displacement isothermal amplification (MDA), rolling circle amplification (RCA), strand displacement amplification (SDA), nucleic acid sequence based amplification (NASBA), ligase chain reaction (LCR), helicase dependent amplification (HDA), ramification amplification method (RAM) and loop mediated amplification (LAMP).

11. The method according to claim 7, wherein the reaction mixture does not comprise oligonucleotides.

\* \* \* \* \*